United States Patent [19]

Meyerowitz et al.

[11] Patent Number: 5,824,868
[45] Date of Patent: Oct. 20, 1998

[54] PLANTS HAVING MODIFIED RESPONSE TO ETHYLENE

[75] Inventors: Elliot M. Meyerowitz; Caren Chang, both of Pasadena, Calif.; Anthony B. Bleecker, Madison, Wis.

[73] Assignee: California Institute of Technology, Pasadena, Calif.

[21] Appl. No.: 484,101

[22] Filed: Jun. 7, 1995

Related U.S. Application Data

[63] Continuation-in-part of Ser. No. 263,480, Jun. 28, 1994, abandoned, which is a continuation-in-part of Ser. No. 86,555, Jul. 1, 1993, abandoned.

[51] Int. Cl.$^6$ .............................. A01H 5/00; C12N 5/14; C12N 15/29; C12N 15/82
[52] U.S. Cl. .................. 800/205; 435/172.3; 435/320.1; 435/419; 536/23.6; 536/24.5
[58] Field of Search ................................ 435/69.1, 320.1, 435/172.3, 240.4, 419; 800/205, DIG. 15, DIG. 44; 536/23.6, 24.5

[56] References Cited

U.S. PATENT DOCUMENTS

| | | | |
|---|---|---|---|
| 4,743,548 | 5/1988 | Crossway et al. | 435/172.3 |
| 4,762,785 | 8/1988 | Comai | 435/172.3 |
| 4,769,061 | 9/1988 | Comai | 435/240.4 |
| 4,801,540 | 1/1989 | Hiatt et al. | 435/172.3 |
| 4,943,674 | 7/1990 | Houck et al. | 800/205 |
| 4,956,282 | 9/1990 | Goodman | 435/172.3 |
| 5,068,193 | 11/1991 | Comai | 435/252.3 |
| 5,106,739 | 4/1992 | Comai et al. | 435/172.3 |
| 5,107,065 | 4/1992 | Shewmaker et al. | 800/205 |
| 5,110,728 | 5/1992 | Kridl et al. | 435/69.1 |
| 5,147,792 | 9/1992 | Perchorowitcz et al. | 435/134 |
| 5,175,095 | 12/1992 | Martineau et al. | 435/69.1 |
| 5,177,011 | 1/1993 | Shewmaker et al. | 435/172.3 |
| 5,177,307 | 1/1993 | Houck et al. | 800/205 |

FOREIGN PATENT DOCUMENTS

| | | |
|---|---|---|
| 8912386 | 12/1989 | WIPO . |
| 9001260 | 2/1990 | WIPO . |
| 9101324 | 2/1991 | WIPO . |
| 9101373 | 2/1991 | WIPO . |
| 9211382 | 7/1992 | WIPO . |
| 9212249 | 7/1992 | WIPO . |
| 9307264 | 4/1993 | WIPO . |

OTHER PUBLICATIONS

Bleecker et al., "Insensitivity to Ethylene Conferred by a Cominant Mutation in *Arabidopsis thaliana*," *Science*, 241:1086–1089 (1988).

Guzman et al., "Exploiting the Triple Response of Arabidopsis to Identify Ethylene–Related Mutants," *The Plant Cell*, 2:513–523 (1990).

Kleber et al., "CTRI, a Negative Regulator of the Ethylene Response Pathway in Arabidopsis, Encodes a Member of the Raf Family of Protein Kinases," *Cell*, 72:427–441 (1993).

Harpman, et al., "The Effect of Ethylene on the Growth and Development of Wild–Type and Mutant *Arabidopsis thaliana* (L.) Heynh" *Annals of Botany*, 68:55–61 (1991).

Oeller et al., "Reversible Inhibition of Tomato Fruit Senescence by Antisense RNA," *Science*, 254:437–439 (1991).

*Ethylene in Plant Biology*, 2d ed., F.B. Abeles, P.W. Morgan and M.E., Saltveit Jr., Eds. (San Diego) Academic Press, Inc., pp. 242–263 (1992).

McCormick et al., "Leaf Disc Transformation of Cultivated Tomato (*L. Ezculentum*) Using *Agrobacterium tumefaciens*" *Plant Cell Reports*, 5:81–84 (1986).

Horsch et al., "A Simple and General Method for Tansferring Genes into Plants," *Science*, 227:1229 (1985).

Trolinder et al., "Somatic Embryogenesis and Plant Regeneration in Cotton (*Gossypium hirsutum* L.)," *Plant Cell Reports*,6:231–234 (1987).

Bollmann et al., "Allelic Interactions at the Nivea Locus of Antirrhinum," *The Plant Cell*, 3:1327–1336 (1991).

Matzke et al., "A Variety of Epistatic Interactions Can Occur Between Partially Homologous Transgene Loci Brought Together by Sexual Crossing," *Mol. Gen. Genet.*, 236:379–386 (1993).

McBride et al., "Improved Binary Vectors for Agrobacterium–Mediated Plant Transformation," *Plant Molecular Biology*, 14:269–276 (1990).

Jorgensen, R., "Beyond Antisense—How do Transgenes Interact with Homologous Plant Genes?" *Tibtech*, 9:266–267 (1991).

Chang et al., "Arabidopsis Ethykene–Response Gene ETR1: Similarity of Product of Two–Component Regulators," *Science*, 262:539–544 (1993).

Chang et al., "Eukaryotes Have Two–Component Signal Transducers," *Res. Microb.*, 1459:481–486 (1994).

Lawton et al., "Acquired–Resistance Signal–Transduction in Arabidopsis is Ethylene Independent," *Cell*, 6(5):581–588 (1994).

Chang et al., "Restriction Fragment Length Polymorphism Linkage Map for *Arabidopsis thaliana*," *PNAS USA*, 85:685–6860 (1988).

(List continued on next page.)

Primary Examiner—David T. Fox
Assistant Examiner—Amy J. Nelson
Attorney, Agent, or Firm—Flehr Hohbach Test Albritton & Herbert LLP; Richard F. Trecartin

[57] ABSTRACT

The invention includes transformed plants having at least one cell transformed with a modified ETR nucleic acid. Such plants have a phenotype characterized by a decrease in the response of at least one transformed plant cell to ethylene as compared to a plant not containing the transformed plant cell. Tissue and/or temporal specificity for expression of the modified ETR nucleic acid is controlled by selecting appropriate expression regulation sequences to target the location and/or time of expression of the transformed nucleic acid. The plants are made by transforming at least one plant cell with an appropriate modified ETR nucleic acid, regenerating plants from one or more of the transformed plant cells and selecting at least one plant having the desired phenotype.

14 Claims, 65 Drawing Sheets

OTHER PUBLICATIONS

Pickett et al., "Recessive Mutation at the ETR–2 Locus of *Arabidopsis thaliana* Confers Resistance to Some Effects of Ethylene Exposure," *J. Cell. Biochem.*, Supp. 0(13 part D)324 Symposium on Plant Gene Transfer, 18th Annual UCLA Symposium, Park City, Utah, USA: Apr. 1–7 (1989).

Matzke et al., "Differential Inactivation and Methylation of a Transgene in Plants by Two Suppressor Loci Containing Homologous Sequences," *Plant Molecular Biology*, 16:821–830 (1991).

Chang et al., "The TMKI Gene from Arabidopsis Codes for a Protein with Structural and Biochemical Characteristics of a Receptor Protein Kinase," *Plant Cell*, 4:1263 (1992).

Bleecker et al., "Genetic Analysis of Ethylene Responses in *Arabidopsis thaliana*," *Great Britain Society for Experimental Biology*, (1991).

Chang et al., "Molecular Cloning Approach for a Putative Ethylene Receptor Gene in Arabidopsis," *Biochem. Soc. Trans.*, 20:73–75 (1992).

Aroundel et al., Map–Based Cloning of a Gene Controlling Omega–3 Fatty Acid Desaturation in *Arabidopsis, Science*, 258:1353–1355 (1992).

Giraudat et al., "Isolation of the *Arabidopsis AB13* Gene by Positional Cloning," *Plant Cell*, 4:1251–1261 (1992).

Boswell et al., "Computational Molecular Biology Sources and Methods for Sequence Analysis," (Lest, ed.) Oxford University Press: Oxford (1989) pp. 170–171.

Chang et al (1994) Res. Microb. 1459:481.

| | | | | |
|---|---|---|---|---|
| AAAGATAGTA | TTTGTTGATA | AATATGGGGA | TATTTATCCT | ATATTATCTG | 50
| TATTTTTCTT | ACCATTTTTA | CTCTATTCCT | TTATCTACAT | TACGTCATTA | 100
| CACTATCATA | AGATATTTGA | ATGAACAAAT | TCATGCACCC | ACCAGCTATA | 150
| TTACCCTTTT | TTATTAAAAA | AAACATCTG | ATAATAATAA | CAAAAAAATT | 200
| AGAGAAATGA | CGTCGAAAAA | AAAGTAAGA | ACGAAGAAGA | AGTGTTAAAC | 250
| CCAACCAATT | TTGACTTGAA | AAAAGCTTC | AACGCTCCCC | TTTTCTCCTT | 300
| CTCCGTCGCT | CTCCGCCGCG | TCCCAAATCC | CCAATTCCTC | CTCTTCTCCG | 350
| ATCAATTCTT | CCCAAGTAAG | CTTCTTCTTC | CTCGATTCTC | TCCTCAGATT | 400
| GTTTCGTGAC | TTCTTTATAT | ATATTCTTCA | CTTCCACAGT | TTTCTTCTGT | 450
| TGTTGTCGTC | GATCTCAAAT | CATAGAGATT | GATTAACCTA | ATTGGTCTTT | 500
| ATCTAGTGTA | ATGCATCGTT | ATTAGGAACT | TTAAATTAAG | ATTTAATCGT | 550
| TAATTTCATG | ATTCGGATTC | GAATTTTACT | GTTCTCGAGA | CTGAAATATG | 600
| CAACCTATTT | TTTCGTAATC | GTTGTGATCG | AATTCGATTC | TTCAGAATTT | 650
| ATAGCAATTT | TGATGCTCAT | GATCTGTCTA | CGCTACGTTC | TCGTCGTAAA | 700
| TCGAAGTTGA | TAATGCTATG | TGTTTGTTAC | ACAGGTGTGT | GTATGTGTGA | 750
| GAGAGGAACT | ATAGTGTAAA | AAATTCATAA | TGGAAGTCTG | CAATTGTATT | 800
| GAACCGCAAT | GGCCAGCGGA | TGAATTGTTA | ATGAAATACC | AATACATCTC | 850
| CGATTTCTTC | ATTGCGATTG | CGTATTTTC | GATTCCTCTT | GAGTTGATTT | 900
| ACTTTGTGAA | GAAATCAGCC | GTGTTTCCGT | ATAGATGGGT | ACTTGTTCAG | 950
| TTTGGTGCTT | TTATCGTTCT | TTGTGGAGCA | ACTCATCTTA | TTAACTTATG | 1000
| GACTTTCACT | ACGCATTCGA | GAACCGTGGC | GCTTGTGATG | ACTACCGCGA | 1050
| AGGTGTTAAC | CGCTGTTGTC | TCGTGTGCTA | CTGCGTTGAT | GCTTGTTCAT | 1100
| ATTATTCCTG | ATCTTTTGAG | TGTTAAGACT | CGGGAGCTTT | TCTTGAAAAA | 1150
| TAAAGCTGCT | GAGCTCGATA | GAGAAATGGG | ATTGATTCGA | ACTCAGGAAG | 1200
| AAACCGGAAG | GCATGTGAGA | ATGTTGACTC | ATGAGATTAG | AAGCACTTTA | 1250
| GATAGACATA | CTATTTTAAA | GACTACACTT | GTTGAGCTTG | GTAGGACATT | 1300
| AGCTTTGGAG | GAGTGTGCAT | TGTGGATGCC | TACTAGAACT | GGGTTAGAGC | 1350
| TACAGCTTTC | TTATACACTT | CGTCATCAAC | ATCCCGTGGA | GTATACGGTT | 1400
| CCTATTCAAT | TACCGGTGAT | TAACCAAGTG | TTTGGTACTA | GTAGGGCTGT | 1450
| AAAAATATCT | CCTAATTCTC | CTGTGGCTAG | GTTGAGACCT | GTTTCTGGGA | 1500
| AATATATGCT | AGGGGAGGTG | GTCGCTGTGA | GGGTTCCGCT | TCTCCACCTT | 1550

*FIG. 2A*

| | | | | |
|---|---|---|---|---|
| TCTAATTTTC | AGATTAATGA | CTGGCCTGAG | CTTTCAACAA | AGAGATATGC | 1600
| TTTGATGGTT | TTGATGCTTC | CTTCAGATAG | TGCAAGGCAA | TGGCATGTCC | 1650
| ATGAGTTGGA | ACTCGTTGAA | GTCGTCGCTG | ATCAGGTTTT | ACATTGCTGA | 1700
| GAATTTCTCT | TCTTTGCTAT | GTTCATGATC | TTGTCTATAA | CTTTTCTTCT | 1750
| CTTATTATAG | GTGGCTGTAG | CTCTCTCACA | TGCTGCGATC | CTAGAAGAGT | 1800
| CGATGCGAGC | TAGGGACCTT | CTCATGGAGC | AGAATGTTGC | TCTTGATCTA | 1850
| GCTAGACGAG | AAGCAGAAAC | AGCAATCCGT | GCCCGCAATG | ATTTCCTAGC | 1900
| GGTTATGAAC | CATGAAATGC | GAACACCGAT | GCATGCGATT | ATTGCACTCT | 1950
| CTTCCTTACT | CCAAGAAACG | GAACTAACCC | CTGAACAAAG | ACTGATGGTG | 2000
| GAAACAATAC | TTAAAAGTAG | TAACCTTTTG | GCAACTTTGA | TGAATGATGT | 2050
| CTTAGATCTT | TCAAGGTTAG | AAGATGGAAG | TCTTCAACTT | GAACTTGGGA | 2100
| CATTCAATCT | TCATACATTA | TTTAGAGAGG | TAACTTTTGA | ACAGCTCTAT | 2150
| GTTTCATAAG | TTTATACTAT | TTGTGTACTT | GATTGTCATA | TTGAATCTTG | 2200
| TTGCAGGTCC | TCAATCTGAT | AAAGCCTATA | GCGGTTGTTA | AGAAATTACC | 2250
| CATCACACTA | AATCTTGCAC | CAGATTTGCC | AGAATTTGTT | GTTGGGGATG | 2300
| AGAAACGGCT | AATGCAGATA | ATATTAAATA | TAGTTGGTAA | TGCTGTGAAA | 2350
| TTCTCCAAAC | AAGGTAGTAT | CTCCGTAACC | GCTCTTGTCA | CCAAGTCAGA | 2400
| CACACGAGCT | GCTGACTTTT | TTGTCGTGCC | AACTGGGAGT | CATTTCTACT | 2450
| TGAGAGTGAA | GGTTATTATC | TTGTATCTTG | GGATCTTATA | CCATAGCTGA | 2500
| AAGTATTTCT | TAGGTCTTAA | TTTTGATGAT | TATTCAAATA | TAGGTAAAAG | 2550
| ACTCTGGAGC | AGGAATAAAT | CCTCAAGACA | TTCCAAAGAT | TTTCACTAAA | 2600
| TTTGCTCAAA | CACAATCTTT | AGCGACGAGA | AGCTCGGGTG | GTAGTGGGCT | 2650
| TGGCCTCGCC | ATCTCCAAGA | GGTTTGAGCC | TTATTAAAAG | ACGTTTTTTT | 2700
| CCAACTTTTT | CTTGTCTTCT | GTGTTGTTAA | AAGTTTACTC | ATAAGCGTTT | 2750
| AATATGACAA | GGTTTGTGAA | TCTGATGGAG | GGTAACATTT | GGATTGAGAG | 2800
| CGATGGTCTT | GGAAAAGGAT | GCACGGCTAT | CTTTGATGTT | AAACTTGGGA | 2850
| TCTCAGAACG | TTCAAACGAA | TCTAAACAGT | CGGGCATACC | GAAAGTTCCA | 2900
| GCCATTCCCC | GACATTCAAA | TTTCACTGGA | CTTAAGGTTC | TTGTCATGGA | 2950
| TGAGAACGGG | TTAGTATAAG | CTTCTCACCT | TTCTCTTTGC | AAAATCTCTC | 3000
| GCCTTACTTC | TTGCAAATGC | AGATATTGGC | GTTTAGAAAA | AACGCAAATT | 3050
| TAATCTTATG | AGAAACCGAT | GATTATTTTG | GTTGCAGGGT | AAGTAGAATG | 3100

*FIG. 2B*

```
GTGACGAAGG GACTTCTTGT ACACCTTGGG TGCGAAGTGA CCACGGTGAG    3150
TTCAAACGAG GAGTGTCTCC GAGTTGTGTC CCATGAGCAC AAAGTGGTCT    3200
TCATGGACGT GTGCATGCCC GGGGTCGAAA ACTACCAAAT CGCTCTCCGT    3250
ATTCACGAGA AATTCACAAA ACAACGCCAC CAACGGCCAC TACTTGTGGC    3300
ACTCAGTGGT AACACTGACA AATCCACAAA AGAGAAATGC ATGAGCTTTG    3350
GTCTAGACGG TGTGTTGCTC AAACCCGTAT CACTAGACAA CATAAGAGAT    3400
GTTCTGTCTG ATCTTCTCGA GCCCCGGGTA CTGTACGAGG GCATGTAAAG    3450
GCGATGGATG CCCCATGCCC CAGAGGAGTA ATTCCGCTCC CGCCTTCTTC    3500
TCCCGTAAAA CATCGGAAGC TGATGTTCTC TGGTTTAATT GTGTACATAT    3550
CAGAGATTGT CGGAGCGTTT TGGATGATAT CTTAAAACAG AAAGGGAATA    3600
ACAAAATAGA AACTCTAAAC CGGTATGTGT CCGTGGCGAT TTCGGTTATA    3650
GAGGAACAAG ATGGTGGTGG TATAATCATA CCATTTCAGA TTACATGTTT    3700
GACTAATGTT GTATCCTTAT ATATGTAGTT ACATTCTTAT AAGAATTTGG    3750
ATCGAGTTAT GGATGCTTGT TGCGTGCATG TATGACATTG ATGCAGTATT    3800
ATGGCGTCAG CTTTGCGCCG CTTAGTAGAA CAACAACAAT GGCGTTACTT    3850
AGTTTCTCAA TCAACCCGAT CTCCAAAAC                           3879
```

FIG. 2C

| | |
|---|---:|
| AGTAAGAACG AAGAAGAAGT GTTAAACCCA ACCAATTTTG ACTTGAAAAA | 50 |
| AAGCTTCAAC GCTCCCCTTT TCTCCTTCTC CGTCGCTCTC CGCCGCGTCC | 100 |
| CAAATCCCCA ATTCCTCCTC TTCTCCGATC AATTCTTCCC AAGTGTGTGT | 150 |
| ATGTGTGAGA GAGGAACTAT AGTGTAAAAA ATTCATA ATG GAA GTC TGC | 199 |

```
                                            Met Glu Val Cys
                                             1
AAT TGT ATT GAA CCG CAA TGG CCA GCG GAT GAA TTG TTA ATG    241
Asn Cys Ile Glu Pro Gln Trp Pro Ala Asp Glu Leu Leu Met
 5               10                  15
AAA TAC CAA TAC ATC TCC GAT TTC TTC ATT GCG ATT GCG TAT    283
Lys Tyr Gln Tyr Ile Ser Asp Phe Phe Ile Ala Ile Ala Tyr
     20                  25                  30
TTT TCG ATT CCT CTT GAG TTG ATT TAC TTT GTG AAG AAA TCA    325
Phe Ser Ile Pro Leu Glu Leu Ile Tyr Phe Val Lys Lys Ser
         35                  40                  45
GCC GTG TTT CCG TAT AGA TGG GTA CTT GTT CAG TTT GGT GCT    367
Ala Val Phe Pro Tyr Arg Trp Val Leu Val Gln Phe Gly Ala
             50                  55                  60
TTT ATC GTT CTT TGT GGA GCA ACT CAT CTT ATT AAC TTA TGG    409
Phe Ile Val Leu Cys Gly Ala Thr His Leu Ile Asn Leu Trp
                 65                  70
ACT TTC ACT ACG CAT TCG AGA ACC GTG GCG CTT GTG ATG ACT    451
Thr Phe Thr Thr His Ser Arg Thr Val Ala Leu Val Met Thr
75                  80                  85
ACC GCG AAG GTG TTA ACC GCT GTT GTC TCG TGT GCT ACT GCG    493
Thr Ala Lys Val Leu Thr Ala Val Val Ser Cys Ala Thr Ala
     90                  95                 100
TTG ATG CTT GTT CAT ATT ATT CCT GAT CTT TTG AGT GTT AAG    535
Leu Met Leu Val His Ile Ile Pro Asp Leu Leu Ser Val Lys
        105                 110                 115
ACT CGG GAG CTT TTC TTG AAA AAT AAA GCT GCT GAG CTC GAT    577
Thr Arg Glu Leu Phe Leu Lys Asn Lys Ala Ala Glu Leu Asp
            120                 125                 130
AGA GAA ATG GGA TTG ATT CGA ACT CAG GAA GAA ACC GGA AGG    619
Arg Glu Met Gly Leu Ile Arg Thr Gln Glu Glu Thr Gly Arg
                135                 140
CAT GTG AGA ATG TTG ACT CAT GAG ATT AGA AGC ACT TTA GAT    661
His Val Arg Met Leu Thr His Glu Ile Arg Ser Thr Leu Asp
145                 150                 155
AGA CAT ACT ATT TTA AAG ACT ACA CTT GTT GAG CTT GGT AGG    703
Arg His Thr Ile Leu Lys Thr Thr Leu Val Glu Leu Gly Arg
        160                 165                 170
ACA TTA GCT TTG GAG GAG TGT GCA TTG TGG ATG CCT ACT AGA    745
Thr Leu Ala Leu Glu Glu Cys Ala Leu Trp Met Pro Thr Arg
            175                 180                 185
```

*FIG. 3A*

| | | | | | | | | | | | | | |
|---|---|---|---|---|---|---|---|---|---|---|---|---|---|
| ACT | GGG | TTA | GAG | CTA | CAG | CTT | TCT | TAT | ACA | CTT | CGT | CAT | CAA | 787 |
| Thr | Gly | Leu | Glu | Leu | Gln | Leu | Ser | Tyr | Thr | Leu | Arg | His | Gln | |
| | | | 190 | | | | 195 | | | | | | 200 | |
| CAT | CCC | GTG | GAG | TAT | ACG | GTT | CCT | ATT | CAA | TTA | CCG | GTG | ATT | 829 |
| His | Pro | Val | Glu | Tyr | Thr | Val | Pro | Ile | Gln | Leu | Pro | Val | Ile | |
| | | | | 205 | | | | | 210 | | | | | |
| AAC | CAA | GTG | TTT | GGT | ACT | AGT | AGG | GCT | GTA | AAA | ATA | TCT | CCT | 871 |
| Asn | Gln | Val | Phe | Gly | Thr | Ser | Arg | Ala | Val | Lys | Ile | Ser | Pro | |
| 215 | | | | | 220 | | | | | 225 | | | | |
| AAT | TCT | CCT | GTG | GCT | AGG | TTG | AGA | CCT | GTT | TCT | GGG | AAA | TAT | 913 |
| Asn | Ser | Pro | Val | Ala | Arg | Leu | Arg | Pro | Val | Ser | Gly | Lys | Tyr | |
| | 230 | | | | | 235 | | | | | 240 | | | |
| ATG | CTA | GGG | GAG | GTG | GTC | GCT | GTG | AGG | GTT | CCG | CTT | CTC | CAC | 955 |
| Met | Leu | Gly | Glu | Val | Val | Ala | Val | Arg | Val | Pro | Leu | Leu | His | |
| | | 245 | | | | | 250 | | | | | 255 | | |
| CTT | TCT | AAT | TTT | CAG | ATT | AAT | GAC | TGG | CCT | GAG | CTT | TCA | ACA | 997 |
| Leu | Ser | Asn | Phe | Gln | Ile | Asn | Asp | Trp | Pro | Glu | Leu | Ser | Thr | |
| | | | 260 | | | | | 265 | | | | | 270 | |
| AAG | AGA | TAT | GCT | TTG | ATG | GTT | TTG | ATG | CTT | CCT | TCA | GAT | AGT | 1039 |
| Lys | Arg | Tyr | Ala | Leu | Met | Val | Leu | Met | Leu | Pro | Ser | Asp | Ser | |
| | | | | 275 | | | | | 280 | | | | | |
| GCA | AGG | CAA | TGG | CAT | GTC | CAT | GAG | TTG | GAA | CTC | GTT | GAA | GTC | 1081 |
| Ala | Arg | Gln | Trp | His | Val | His | Glu | Leu | Glu | Leu | Val | Glu | Val | |
| 285 | | | | | 290 | | | | | 295 | | | | |
| GTC | GCT | GAT | CAG | GTG | GCT | GTA | GCT | CTC | TCA | CAT | GCT | GCG | ATC | 1123 |
| Val | Ala | Asp | Gln | Val | Ala | Val | Ala | Leu | Ser | His | Ala | Ala | Ile | |
| | | 300 | | | | | 305 | | | | | 310 | | |
| CTA | GAA | GAG | TCG | ATG | CGA | GCT | AGG | GAC | CTT | CTC | ATG | GAG | CAG | 1165 |
| Leu | Glu | Glu | Ser | Met | Arg | Ala | Arg | Asp | Leu | Leu | Met | Glu | Gln | |
| | | 315 | | | | | 320 | | | | | 325 | | |
| AAT | GTT | GCT | CTT | GAT | CTA | GCT | AGA | CGA | GAA | GCA | GAA | ACA | GCA | 1207 |
| Asn | Val | Ala | Leu | Asp | Leu | Ala | Arg | Arg | Glu | Ala | Glu | Thr | Ala | |
| | | | 330 | | | | | 335 | | | | | 340 | |
| ATC | CGT | GCC | CGC | AAT | GAT | TTC | CTA | GCG | GTT | ATG | AAC | CAT | GAA | 1249 |
| Ile | Arg | Ala | Arg | Asn | Asp | Phe | Leu | Ala | Val | Met | Asn | His | Glu | |
| | | | | 345 | | | | | 350 | | | | | |
| ATG | CGA | ACA | CCG | ATG | CAT | GCG | ATT | ATT | GCA | CTC | TCT | TCC | TTA | 1291 |
| Met | Arg | Thr | Pro | Met | His | Ala | Ile | Ile | Ala | Leu | Ser | Ser | Leu | |
| 355 | | | | | 360 | | | | | 365 | | | | |
| CTC | CAA | GAA | ACG | GAA | CTA | ACC | CCT | GAA | CAA | AGA | CTG | ATG | GTG | 1333 |
| Leu | Gln | Glu | Thr | Glu | Leu | Thr | Pro | Glu | Gln | Arg | Leu | Met | Val | |
| | 370 | | | | | 375 | | | | | 380 | | | |
| GAA | ACA | ATA | CTT | AAA | AGT | AGT | AAC | CTT | TTG | GCA | ACT | TTG | ATG | 1375 |
| Glu | Thr | Ile | Leu | Lys | Ser | Ser | Asn | Leu | Leu | Ala | Thr | Leu | Met | |
| | | 385 | | | | | 390 | | | | | 395 | | |

*FIG. 3B*

| | | | | | | | | | | | | |
|---|---|---|---|---|---|---|---|---|---|---|---|---|
| AAT | GAT | GTC | TTA | GAT | CTT | TCA | AGG | TTA | GAA | GAT | GGA | AGT | CTT | 1417 |
| Asn | Asp | Val | Leu | Asp | Leu | Ser | Arg | Leu | Glu | Asp | Gly | Ser | Leu | |
| | | | 400 | | | | 405 | | | | | | 410 | |

```
AAT GAT GTC TTA GAT CTT TCA AGG TTA GAA GAT GGA AGT CTT       1417
Asn Asp Val Leu Asp Leu Ser Arg Leu Glu Asp Gly Ser Leu
            400             405                     410

CAA CTT GAA CTT GGG ACA TTC AAT CTT CAT ACA TTA TTT AGA       1459
Gln Leu Glu Leu Gly Thr Phe Asn Leu His Thr Leu Phe Arg
                415             420

GAG GTC CTC AAT CTG ATA AAG CCT ATA GCG GTT GTT AAG AAA       1501
Glu Val Leu Asn Leu Ile Lys Pro Ile Ala Val Val Lys Lys
425                 430             435

TTA CCC ATC ACA CTA AAT CTT GCA CCA GAT TTG CCA GAA TTT       1543
Leu Pro Ile Thr Leu Asn Leu Ala Pro Asp Leu Pro Glu Phe
    440             445             450

GTT GTT GGG GAT GAG AAA CGG CTA ATG CAG ATA ATA TTA AAT       1585
Val Val Gly Asp Glu Lys Arg Leu Met Gln Ile Ile Leu Asn
            455             460                 465

ATA GTT GGT AAT GCT GTG AAA TTC TCC AAA CAA GGT AGT ATC       1621
Ile Val Gly Asn Ala Val Lys Phe Ser Lys Gln Gly Ser Ile
                470             475                 480

TCC GTA ACC GCT CTT GTC ACC AAG TCA GAC ACA CGA GCT GCT       1669
Ser Val Thr Ala Leu Val Thr Lys Ser Asp Thr Arg Ala Ala
                    485             490

GAC TTT TTT GTC GTG CCA ACT GGG AGT CAT TTC TAC TTG AGA       1711
Asp Phe Phe Val Val Pro Thr Gly Ser His Phe Tyr Leu Arg
495                 500             505

GTG AAG GTA AAA GAC TCT GGA GCA GGA ATA AAT CCT CAA GAC       1753
Val Lys Val Lys Asp Ser Gly Ala Gly Ile Asn Pro Gln Asp
    510             515                 520

ATT CCA AAG ATT TTC ACT AAA TTT GCT CAA ACA CAA TCT TTA       1795
Ile Pro Lys Ile Phe Thr Lys Phe Ala Gln Thr Gln Ser Leu
        525             530                 535

GCG ACG AGA AGC TCG GGT GGT AGT GGG CTT GGC CTC GCC ATC       1837
Ala Thr Arg Ser Ser Gly Gly Ser Gly Leu Gly Leu Ala Ile
            540             545                 550

TCC AAG AGG TTT GTG AAT CTG ATG GAG GGT AAC ATT TGG ATT       1879
Ser Lys Arg Phe Val Asn Leu Met Glu Gly Asn Ile Trp Ile
                555             560

GAG AGC GAT GGT CTT GGA AAA GGA TGC ACG GCT ATC TTT GAT       1921
Glu Ser Asp Gly Leu Gly Lys Gly Cys Thr Ala Ile Phe Asp
565             570                 575

GTT AAA CTT GGG ATC TCA GAA CGT TCA AAC GAA TCT AAA CAG       1963
Val Lys Leu Gly Ile Ser Glu Arg Ser Asn Glu Ser Lys Gln
    580             585                 590

TCG GGC ATA CCG AAA GTT CCA GCC ATT CCC CGA CAT TCA AAT       2005
Ser Gly Ile Pro Lys Val Pro Ala Ile Pro Arg His Ser Asn
        595             600                 605
```

FIG. 3C

```
TTC ACT GGA CTT AAG GTT CTT GTC ATG GAT GAG AAC GGG GTA        2047
Phe Thr Gly Leu Lys Val Leu Val Met Asp Glu Asn Gly Val
            610             615                     620

AGT AGA ATG GTG ACG AAG GGA CTT CTT GTA CAC CTT GGG TGC        2089
Ser Arg Met Val Thr Lys Gly Leu Leu Val His Leu Gly Cys
                625                 630

GAA GTG ACC ACG GTG AGT TCA AAC GAG GAG TGT CTC CGA GTT        2131
Glu Val Thr Thr Val Ser Ser Asn Glu Glu Cys Leu Arg Val
635                 640                 645

GTG TCC CAT GAG CAC AAA GTG GTC TTC ATG GAC GTG TGC ATG        2173
Val Ser His Glu His Lys Val Val Phe Met Asp Val Cys Met
        650             655             660

CCC GGG GTC GAA AAC TAC CAA ATC GCT CTC CGT ATT CAC GAG        2215
Pro Gly Val Glu Asn Tyr Gln Ile Ala Leu Arg Ile His Glu
            665             670             675

AAA TTC ACA AAA CAA CGC CAC CAA CGG CCA CTA CTT GTG GCA        2257
Lys Phe Thr Lys Gln Arg His Gln Arg Pro Leu Leu Val Ala
                680             685                 690

CTC AGT GGT AAC ACT GAC AAA TCC ACA AAA GAG AAA TGC ATG        2299
Leu Ser Gly Asn Thr Asp Lys Ser Thr Lys Glu Lys Cys Met
                    695             700

AGC TTT GGT CTA GAC GGT GTG TTG CTC AAA CCC GTA TCA CTA        2341
Ser Phe Gly Leu Asp Gly Val Leu Leu Lys Pro Val Ser Leu
705                     710             715

GAC AAC ATA AGA GAT GTT CTG TCT GAT CTT CTC GAG CCC CGG        2383
Asp Asn Ile Arg Asp Val Leu Ser Asp Leu Leu Glu Pro Arg
        720             725             730

GTA CTG TAC GAG GGC ATG TAAAGGCGAT GGATGCCCCA                  2421
Val Leu Tyr Glu Gly Met
            735

TGCCCCAGAG GAGTAATTCC GCTCCCGCCT TCTTCTCCCG TAAAACATCG         2471

GAAGCTGATG TTCTCTGGTT TAATTGTGTA CATATCAGAG ATTGTCGGAG         2521

CGTTTTGGAT GATATCTTAA AACAGAAAGG GAATAACAAA ATAGAAACTC         2571

TAAACCGGTA TGTGTCCGTG GCGATTTCGG TTATAGAGGA ACAAGATGGT         2621

GGTGGTATAA TCATACCATT TCAGATTACA TGTTTGACTA ATGTTGTATC         2671

CTTATATATG TAGTTACATT CTTATAAGAA TTTGGATCGA GTTATGGATG         2721

CTTGTTGCGT GCATGTATGA CATTGATGCA GTATTATGGC GTCAGCTTTG         2771

CGCCGCTTAG TAGAAC                                              2787
```

FIG. 3D

```
AGTAAGAACG AAGAAGAAGT GTTAAACCCA ACCAATTTTG ACTTGAAAAA            50

AAGCTTCAAC GCTCCCCTTT TCTCCTTCTC CGTCGCTCTC CGCCGCGTCC           100

CAAATCCCCA ATTCCTCCTC TTCTCCGATC AATTCTTCCC AAGTGTGTGT           150

ATGTGTGAGA GAGGAACTAT AGTGTAAAAA ATTCATA ATG GAA GTC TGC         199
                                         Met Glu Val Cys
                                          1
```

| | | | | | | | | | | | | | |
|---|---|---|---|---|---|---|---|---|---|---|---|---|---|
| AAT | TGT | ATT | GAA | CCG | CAA | TGG | CCA | GCG | GAT | GAA | TTG | TTA | ATG | 241
| Asn | Cys | Ile | Glu | Pro | Gln | Trp | Pro | Ala | Asp | Glu | Leu | Leu | Met |
| 5 | | | | 10 | | | | | 15 | | | | |
| AAA | TAC | CAA | TAC | ATC | TCC | GAT | TTC | TTC | ATT | GCG | ATT | GTG | TAT | 283
| Lys | Tyr | Gln | Tyr | Ile | Ser | Asp | Phe | Phe | Ile | Ala | Ile | Val | Tyr |
| | 20 | | | | 25 | | | | 30 | | | | |
| TTT | TCG | ATT | CCT | CTT | GAG | TTG | ATT | TAC | TTT | GTG | AAG | AAA | TCA | 325
| Phe | Ser | Ile | Pro | Leu | Glu | Leu | Ile | Tyr | Phe | Val | Lys | Lys | Ser |
| | | 35 | | | | 40 | | | | | 45 | | |
| GCC | GTG | TTT | CCG | TAT | AGA | TGG | GTA | CTT | GTT | CAG | TTT | GGT | GCT | 367
| Ala | Val | Phe | Pro | Tyr | Arg | Trp | Val | Leu | Val | Gln | Phe | Gly | Ala |
| | | | 50 | | | | 55 | | | | | | 60 |
| TTT | ATC | GTT | CTT | TGT | GGA | GCA | ACT | CAT | CTT | ATT | AAC | TTA | TGG | 409
| Phe | Ile | Val | Leu | Cys | Gly | Ala | Thr | His | Leu | Ile | Asn | Leu | Trp |
| | | | | 65 | | | | 70 | | | | | |
| ACT | TTC | ACT | ACG | CAT | TCG | AGA | ACC | GTG | GCG | CTT | GTG | ATG | ACT | 451
| Thr | Phe | Thr | Thr | His | Ser | Arg | Thr | Val | Ala | Leu | Val | Met | Thr |
| 75 | | | | | 80 | | | | | 85 | | | |
| ACC | GCG | AAG | GTG | TTA | ACC | GCT | GTT | GTC | TCG | TGT | GCT | ACT | GCG | 493
| Thr | Ala | Lys | Val | Leu | Thr | Ala | Val | Val | Ser | Cys | Ala | Thr | Ala |
| | 90 | | | | | 95 | | | | 100 | | | |
| TTG | ATG | CTT | GTT | CAT | ATT | ATT | CCT | GAT | CTT | TTG | AGT | GTT | AAG | 535
| Leu | Met | Leu | Val | His | Ile | Ile | Pro | Asp | Leu | Leu | Ser | Val | Lys |
| | | 105 | | | | 110 | | | | | 115 | | |
| ACT | CGG | GAG | CTT | TTC | TTG | AAA | AAT | AAA | GCT | GCT | GAG | CTC | GAT | 577
| Thr | Arg | Glu | Leu | Phe | Leu | Lys | Asn | Lys | Ala | Ala | Glu | Leu | Asp |
| | | | 120 | | | | 125 | | | | | 130 | |
| AGA | GAA | ATG | GGA | TTG | ATT | CGA | ACT | CAG | GAA | GAA | ACC | GGA | AGG | 619
| Arg | Glu | Met | Gly | Leu | Ile | Arg | Thr | Gln | Glu | Glu | Thr | Gly | Arg |
| | | | | 135 | | | | 140 | | | | | |
| CAT | GTG | AGA | ATG | TTG | ACT | CAT | GAG | ATT | AGA | AGC | ACT | TTA | GAT | 661
| His | Val | Arg | Met | Leu | Thr | His | Glu | Ile | Arg | Ser | Thr | Leu | Asp |
| 145 | | | | | 150 | | | | | 155 | | | |
| AGA | CAT | ACT | ATT | TTA | AAG | ACT | ACA | CTT | GTT | GAG | CTT | GGT | AGG | 703
| Arg | His | Thr | Ile | Leu | Lys | Thr | Thr | Leu | Val | Glu | Leu | Gly | Arg |
| | 160 | | | | | 165 | | | | | 170 | | |
| ACA | TTA | GCT | TTG | GAG | GAG | TGT | GCA | TTG | TGG | ATG | CCT | ACT | AGA | 745
| Thr | Leu | Ala | Leu | Glu | Glu | Cys | Ala | Leu | Trp | Met | Pro | Thr | Arg |
| | | 175 | | | | 180 | | | | | 185 | | |

*FIG. 4A*

```
ACT GGG TTA GAG CTA CAG CTT TCT TAT ACA CTT CGT CAT CAA     787
Thr Gly Leu Glu Leu Gln Leu Ser Tyr Thr Leu Arg His Gln
            190             195                     200

CAT CCC GTG GAG TAT ACG GTT CCT ATT CAA TTA CCG GTG ATT     829
His Pro Val Glu Tyr Thr Val Pro Ile Gln Leu Pro Val Ile
                205                 210

AAC CAA GTG TTT GGT ACT AGT AGG GCT GTA AAA ATA TCT CCT     871
Asn Gln Val Phe Gly Thr Ser Arg Ala Val Lys Ile Ser Pro
215             220                 225

AAT TCT CCT GTG GCT AGG TTG AGA CCT GTT TCT GGG AAA TAT     913
Asn Ser Pro Val Ala Arg Leu Arg Pro Val Ser Gly Lys Tyr
    230             235                 240

ATG CTA GGG GAG GTG GTC GCT GTG AGG GTT CCG CTT CTC CAC     955
Met Leu Gly Glu Val Val Ala Val Arg Val Pro Leu Leu His
        245                 250             255

CTT TCT AAT TTT CAG ATT AAT GAC TGG CCT GAG CTT TCA ACA     997
Leu Ser Asn Phe Gln Ile Asn Asp Trp Pro Glu Leu Ser Thr
            260             265                 270

AAG AGA TAT GCT TTG ATG GTT TTG ATG CTT CCT TCA GAT AGT     1039
Lys Arg Tyr Ala Leu Met Val Leu Met Leu Pro Ser Asp Ser
                275             280

GCA AGG CAA TGG CAT GTC CAT GAG TTG GAA CTC GTT GAA GTC     1081
Ala Arg Gln Trp His Val His Glu Leu Glu Leu Val Glu Val
285             290                 295

GTC GCT GAT CAG GTG GCT GTA GCT CTC TCA CAT GCT GCG ATC     1123
Val Ala Asp Gln Val Ala Val Ala Leu Ser His Ala Ala Ile
        300                 305             310

CTA GAA GAG TCG ATG CGA GCT AGG GAC CTT CTC ATG GAG CAG     1165
Leu Glu Glu Ser Met Arg Ala Arg Asp Leu Leu Met Glu Gln
            315             320                 325

AAT GTT GCT CTT GAT CTA GCT AGA CGA GAA GCA GAA ACA GCA     1207
Asn Val Ala Leu Asp Leu Ala Arg Arg Glu Ala Glu Thr Ala
                330             335                 340

ATC CGT GCC CGC AAT GAT TTC CTA GCG GTT ATG AAC CAT GAA     1249
Ile Arg Ala Arg Asn Asp Phe Leu Ala Val Met Asn His Glu
                345                 350

ATG CGA ACA CCG ATG CAT GCG ATT ATT GCA CTC TCT TCC TTA     1291
Met Arg Thr Pro Met His Ala Ile Ile Ala Leu Ser Ser Leu
355             360                 365

CTC CAA GAA ACG GAA CTA ACC CCT GAA CAA AGA CTG ATG GTG     1333
Leu Gln Glu Thr Glu Leu Thr Pro Glu Gln Arg Leu Met Val
    370                 375                 380

GAA ACA ATA CTT AAA AGT AGT AAC CTT TTG GCA ACT TTG ATG     1375
Glu Thr Ile Leu Lys Ser Ser Asn Leu Leu Ala Thr Leu Met
            385                 390                 395
```

FIG. 4B

```
AAT GAT GTC TTA GAT CTT TCA AGG TTA GAA GAT GGA AGT CTT      1417
Asn Asp Val Leu Asp Leu Ser Arg Leu Glu Asp Gly Ser Leu
            400             405                     410

CAA CTT GAA CTT GGG ACA TTC AAT CTT CAT ACA TTA TTT AGA      1459
Gln Leu Glu Leu Gly Thr Phe Asn Leu His Thr Leu Phe Arg
                415             420

GAG GTC CTC AAT CTG ATA AAG CCT ATA GCG GTT GTT AAG AAA      1501
Glu Val Leu Asn Leu Ile Lys Pro Ile Ala Val Val Lys Lys
425                 430             435

TTA CCC ATC ACA CTA AAT CTT GCA CCA GAT TTG CCA GAA TTT      1543
Leu Pro Ile Thr Leu Asn Leu Ala Pro Asp Leu Pro Glu Phe
    440             445             450

GTT GTT GGG GAT GAG AAA CGG CTA ATG CAG ATA ATA TTA AAT      1585
Val Val Gly Asp Glu Lys Arg Leu Met Gln Ile Ile Leu Asn
        455             460             465

ATA GTT GGT AAT GCT GTG AAA TTC TCC AAA CAA GGT AGT ATC      1627
Ile Val Gly Asn Ala Val Lys Phe Ser Lys Gln Gly Ser Ile
            470             475             480

TCC GTA ACC GCT CTT GTC ACC AAG TCA GAC ACA CGA GCT GCT      1669
Ser Val Thr Ala Leu Val Thr Lys Ser Asp Thr Arg Ala Ala
                485             490

GAC TTT TTT GTC GTG CCA ACT GGG AGT CAT TTC TAC TTG AGA      1711
Asp Phe Phe Val Val Pro Thr Gly Ser His Phe Tyr Leu Arg
495             500             505

GTG AAG GTA AAA GAC TCT GGA GCA GGA ATA AAT CCT CAA GAC      1753
Val Lys Val Lys Asp Ser Gly Ala Gly Ile Asn Pro Gln Asp
    510             515             520

ATT CCA AAG ATT TTC ACT AAA TTT GCT CAA ACA CAA TCT TTA      1795
Ile Pro Lys Ile Phe Thr Lys Phe Ala Gln Thr Gln Ser Leu
        525             530             535

GCG ACG AGA AGC TCG GGT GGT AGT GGG CTT GGC CTC GCC ATC      1837
Ala Thr Arg Ser Ser Gly Gly Ser Gly Leu Gly Leu Ala Ile
            540             545             550

TCC AAG AGG TTT GTG AAT CTG ATG GAG GGT AAC ATT TGG ATT      1879
Ser Lys Arg Phe Val Asn Leu Met Glu Gly Asn Ile Trp Ile
                555             560

GAG AGC GAT GGT CTT GGA AAA GGA TGC ACG GCT ATC TTT GAT      1921
Glu Ser Asp Gly Leu Gly Lys Gly Cys Thr Ala Ile Phe Asp
565             570             575

GTT AAA CTT GGG ATC TCA GAA CGT TCA AAC GAA TCT AAA CAG      1963
Val Lys Leu Gly Ile Ser Glu Arg Ser Asn Glu Ser Lys Gln
    580             585             590

TCG GGC ATA CCG AAA GTT CCA GCC ATT CCC CGA CAT TCA AAT      2005
Ser Gly Ile Pro Lys Val Pro Ala Ile Pro Arg His Ser Asn
        595             600             605
```

*FIG. 4C*

```
TTC ACT GGA CTT AAG GTT CTT GTC ATG GAT GAG AAC GGG GTA        2047
Phe Thr Gly Leu Lys Val Leu Val Met Asp Glu Asn Gly Val
            610             615                     620

AGT AGA ATG GTG ACG AAG GGA CTT CTT GTA CAC CTT GGG TGC        2089
Ser Arg Met Val Thr Lys Gly Leu Leu Val His Leu Gly Cys
                625             630

GAA GTG ACC ACG GTG AGT TCA AAC GAG GAG TGT CTC CGA GTT        2131
Glu Val Thr Thr Val Ser Ser Asn Glu Glu Cys Leu Arg Val
635                     640             645

GTG TCC CAT GAG CAC AAA GTG GTC TTC ATG GAC GTG TGC ATG        2173
Val Ser His Glu His Lys Val Val Phe Met Asp Val Cys Met
        650             655             660

CCC GGG GTC GAA AAC TAC CAA ATC GCT CTC CGT ATT CAC GAG        2215
Pro Gly Val Glu Asn Tyr Gln Ile Ala Leu Arg Ile His Glu
            665             670             675

AAA TTC ACA AAA CAA CGC CAC CAA CGG CCA CTA CTT GTG GCA        2257
Lys Phe Thr Lys Gln Arg His Gln Arg Pro Leu Leu Val Ala
            680             685                     690

CTC AGT GGT AAC ACT GAC AAA TCC ACA AAA GAG AAA TGC ATG        2299
Leu Ser Gly Asn Thr Asp Lys Ser Thr Lys Glu Lys Cys Met
                695             700

AGC TTT GGT CTA GAC GGT GTG TTG CTC AAA CCC GTA TCA CTA        2341
Ser Phe Gly Leu Asp Gly Val Leu Leu Lys Pro Val Ser Leu
705             710             715

GAC AAC ATA AGA GAT GTT CTG TCT GAT CTT CTC GAG CCC CGG        2383
Asp Asn Ile Arg Asp Val Leu Ser Asp Leu Leu Glu Pro Arg
    720             725             730

GTA CTG TAC GAG GGC ATG TAAAGGCGAT GGATGCCCCA                  2421
Val Leu Tyr Glu Gly Met
            735

TGCCCCAGAG GAGTAATTCC GCTCCCGCCT TCTTCTCCCG TAAAACATCG         2471

GAAGCTGATG TTCTCTGGTT TAATTGTGTA CATATCAGAG ATTGTCGGAG         2521

CGTTTTGGAT GATATCTTAA AACAGAAAGG GAATAACAAA ATAGAAACTC         2571

TAAACCGGTA TGTGTCCGTG GCGATTTCGG TTATAGAGGA ACAAGATGGT         2621

GGTGGTATAA TCATACCATT TCAGATTACA TGTTTGACTA ATGTTGTATC         2671

CTTATATATG TAGTTACATT CTTATAAGAA TTTGGATCGA GTTATGGATG         2721

CTTGTTGCGT GCATGTATGA CATTGATGCA GTATTATGGC GTCAGCTTTG         2771

CGCCGCTTAG TAGAAC                                              2787
```

FIG. 4D

| Sequence | Position |
|---|---|
| AGTAAGAACG AAGAAGAAGT GTTAAACCCA ACCAATTTTG ACTTGAAAAA | 50 |
| AAGCTTCAAC GCTCCCCTTT TCTCCTTCTC CGTCGCTCTC CGCCGCGTCC | 100 |
| CAAATCCCCA ATTCCTCCTC TTCTCCGATC AATTCTTCCC AAGTGTGTGT | 150 |
| ATGTGTGAGA GAGGAACTAT AGTGTAAAAA ATTCATA ATG GAA GTC TGC | 199 |

```
                                            Met Glu Val Cys
                                             1
AAT TGT ATT GAA CCG CAA TGG CCA GCG GAT GAA TTG TTA ATG      241
Asn Cys Ile Glu Pro Gln Trp Pro Ala Asp Glu Leu Leu Met
 5              10                  15
AAA TAC CAA TAC ATC TCC GAT TTC TTC ATT GCG ATT GCG TAT      283
Lys Tyr Gln Tyr Ile Ser Asp Phe Phe Ile Ala Ile Ala Tyr
    20              25                  30
TTT TCG ATT CCT CTT GAG TTG ATT TAC TTT GTG AAG AAA TCA      325
Phe Ser Ile Pro Leu Glu Leu Ile Tyr Phe Val Lys Lys Ser
        35              40                  45
GCC GTG TTT CCG TAT AGA TGG GTA CTT GTT CAG TTT GGT GCT      367
Ala Val Phe Pro Tyr Arg Trp Val Leu Val Gln Phe Gly Ala
            50              55                  60
TTT TTC GTT CTT TGT GGA GCA ACT CAT CTT ATT AAC TTA TGG      409
Phe Phe Val Leu Cys Gly Ala Thr His Leu Ile Asn Leu Trp
                65              70
ACT TTC ACT ACG CAT TCG AGA ACC GTG GCG CTT GTG ATG ACT      451
Thr Phe Thr Thr His Ser Arg Thr Val Ala Leu Val Met Thr
 75              80                  85
ACC GCG AAG GTG TTA ACC GCT GTT GTC TCG TGT GCT ACT GCG      493
Thr Ala Lys Val Leu Thr Ala Val Val Ser Cys Ala Thr Ala
    90              95                 100
TTG ATG CTT GTT CAT ATT ATT CCT GAT CTT TTG AGT GTT AAG      535
Leu Met Leu Val His Ile Ile Pro Asp Leu Leu Ser Val Lys
        105             110                 115
ACT CGG GAG CTT TTC TTG AAA AAT AAA GCT GCT GAG CTC GAT      577
Thr Arg Glu Leu Phe Leu Lys Asn Lys Ala Ala Glu Leu Asp
            120             125                 130
AGA GAA ATG GGA TTG ATT CGA ACT CAG GAA GAA ACC GGA AGG      619
Arg Glu Met Gly Leu Ile Arg Thr Gln Glu Glu Thr Gly Arg
                135             140
CAT GTG AGA ATG TTG ACT CAT GAG ATT AGA AGC ACT TTA GAT      661
His Val Arg Met Leu Thr His Glu Ile Arg Ser Thr Leu Asp
145             150                 155
AGA CAT ACT ATT TTA AAG ACT ACA CTT GTT GAG CTT GGT AGG      703
Arg His Thr Ile Leu Lys Thr Thr Leu Val Glu Leu Gly Arg
    160             165                 170
ACA TTA GCT TTG GAG GAG TGT GCA TTG TGG ATG CCT ACT AGA      745
Thr Leu Ala Leu Glu Glu Cys Ala Leu Trp Met Pro Thr Arg
        175             180                 185
```

*FIG. 5A*

```
ACT GGG TTA GAG CTA CAG CTT TCT TAT ACA CTT CGT CAT CAA    787
Thr Gly Leu Glu Leu Gln Leu Ser Tyr Thr Leu Arg His Gln
            190                 195                 200

CAT CCC GTG GAG TAT ACG GTT CCT ATT CAA TTA CCG GTG ATT    829
His Pro Val Glu Tyr Thr Val Pro Ile Gln Leu Pro Val Ile
                205                 210

AAC CAA GTG TTT GGT ACT AGT AGG GCT GTA AAA ATA TCT CCT    871
Asn Gln Val Phe Gly Thr Ser Arg Ala Val Lys Ile Ser Pro
215                 220                 225

AAT TCT CCT GTG GCT AGG TTG AGA CCT GTT TCT GGG AAA TAT    913
Asn Ser Pro Val Ala Arg Leu Arg Pro Val Ser Gly Lys Tyr
    230                 235                 240

ATG CTA GGG GAG GTG GTC GCT GTG AGG GTT CCG CTT CTC CAC    955
Met Leu Gly Glu Val Val Ala Val Arg Val Pro Leu Leu His
            245                 250                 255

CTT TCT AAT TTT CAG ATT AAT GAC TGG CCT GAG CTT TCA ACA    997
Leu Ser Asn Phe Gln Ile Asn Asp Trp Pro Glu Leu Ser Thr
                260                 265                 270

AAG AGA TAT GCT TTG ATG GTT TTG ATG CTT CCT TCA GAT AGT    1039
Lys Arg Tyr Ala Leu Met Val Leu Met Leu Pro Ser Asp Ser
                    275                 280

GCA AGG CAA TGG CAT GTC CAT GAG TTG GAA CTC GTT GAA GTC    1081
Ala Arg Gln Trp His Val His Glu Leu Glu Leu Val Glu Val
285                 290                 295

GTC GCT GAT CAG GTG GCT GTA GCT CTC TCA CAT GCT GCG ATC    1123
Val Ala Asp Gln Val Ala Val Ala Leu Ser His Ala Ala Ile
        300                 305                 310

CTA GAA GAG TCG ATG CGA GCT AGG GAC CTT CTC ATG GAG CAG    1165
Leu Glu Glu Ser Met Arg Ala Arg Asp Leu Leu Met Glu Gln
            315                 320                 325

AAT GTT GCT CTT GAT CTA GCT AGA CGA GAA GCA GAA ACA GCA    1207
Asn Val Ala Leu Asp Leu Ala Arg Arg Glu Ala Glu Thr Ala
                330                 335                 340

ATC CGT GCC CGC AAT GAT TTC CTA GCG GTT ATG AAC CAT GAA    1249
Ile Arg Ala Arg Asn Asp Phe Leu Ala Val Met Asn His Glu
                    345                 350

ATG CGA ACA CCG ATG CAT GCG ATT ATT GCA CTC TCT TCC TTA    1291
Met Arg Thr Pro Met His Ala Ile Ile Ala Leu Ser Ser Leu
355                 360                 365

CTC CAA GAA ACG GAA CTA ACC CCT GAA CAA AGA CTG ATG GTG    1333
Leu Gln Glu Thr Glu Leu Thr Pro Glu Gln Arg Leu Met Val
    370                 375                 380

GAA ACA ATA CTT AAA AGT AGT AAC CTT TTG GCA ACT TTG ATG    1375
Glu Thr Ile Leu Lys Ser Ser Asn Leu Leu Ala Thr Leu Met
            385                 390                 395
```

FIG. 5B

```
AAT GAT GTC TTA GAT CTT TCA AGG TTA GAA GAT GGA AGT CTT    1417
Asn Asp Val Leu Asp Leu Ser Arg Leu Glu Asp Gly Ser Leu
            400             405                     410

CAA CTT GAA CTT GGG ACA TTC AAT CTT CAT ACA TTA TTT AGA    1459
Gln Leu Glu Leu Gly Thr Phe Asn Leu His Thr Leu Phe Arg
                415                 420

GAG GTC CTC AAT CTG ATA AAG CCT ATA GCG GTT GTT AAG AAA    1501
Glu Val Leu Asn Leu Ile Lys Pro Ile Ala Val Val Lys Lys
425                     430                 435

TTA CCC ATC ACA CTA AAT CTT GCA CCA GAT TTG CCA GAA TTT    1543
Leu Pro Ile Thr Leu Asn Leu Ala Pro Asp Leu Pro Glu Phe
    440                 445                 450

GTT GTT GGG GAT GAG AAA CGG CTA ATG CAG ATA ATA TTA AAT    1585
Val Val Gly Asp Glu Lys Arg Leu Met Gln Ile Ile Leu Asn
            455                 460                 465

ATA GTT GGT AAT GCT GTG AAA TTC TCC AAA CAA GGT AGT ATC    1627
Ile Val Gly Asn Ala Val Lys Phe Ser Lys Gln Gly Ser Ile
            470                 475                 480

TCC GTA ACC GCT CTT GTC ACC AAG TCA GAC ACA CGA GCT GCT    1669
Ser Val Thr Ala Leu Val Thr Lys Ser Asp Thr Arg Ala Ala
                485                 490

GAC TTT TTT GTC GTG CCA ACT GGG AGT CAT TTC TAC TTG AGA    1711
Asp Phe Phe Val Val Pro Thr Gly Ser His Phe Tyr Leu Arg
495                 500                 505

GTG AAG GTA AAA GAC TCT GGA GCA GGA ATA AAT CCT CAA GAC    1753
Val Lys Val Lys Asp Ser Gly Ala Gly Ile Asn Pro Gln Asp
    510                 515                 520

ATT CCA AAG ATT TTC ACT AAA TTT GCT CAA ACA CAA TCT TTA    1795
Ile Pro Lys Ile Phe Thr Lys Phe Ala Gln Thr Gln Ser Leu
        525                 530                 535

GCG ACG AGA AGC TCG GGT GGT AGT GGG CTT GGC CTC GCC ATC    1837
Ala Thr Arg Ser Ser Gly Gly Ser Gly Leu Gly Leu Ala Ile
                540                 545                 550

TCC AAG AGG TTT GTG AAT CTG ATG GAG GGT AAC ATT TGG ATT    1879
Ser Lys Arg Phe Val Asn Leu Met Glu Gly Asn Ile Trp Ile
                    555                 560

GAG AGC GAT GGT CTT GGA AAA GGA TGC ACG GCT ATC TTT GAT    1921
Glu Ser Asp Gly Leu Gly Lys Gly Cys Thr Ala Ile Phe Asp
565             570                 575

GTT AAA CTT GGG ATC TCA GAA CGT TCA AAC GAA TCT AAA CAG    1963
Val Lys Leu Gly Ile Ser Glu Arg Ser Asn Glu Ser Lys Gln
    580                 585                 590

TCG GGC ATA CCG AAA GTT CCA GCC ATT CCC CGA CAT TCA AAT    2005
Ser Gly Ile Pro Lys Val Pro Ala Ile Pro Arg His Ser Asn
        595                 600                 605
```

*FIG. 5C*

```
TTC ACT GGA CTT AAG GTT CTT GTC ATG GAT GAG AAC GGG GTA    2047
Phe Thr Gly Leu Lys Val Leu Val Met Asp Glu Asn Gly Val
            610                 615                 620

AGT AGA ATG GTG ACG AAG GGA CTT CTT GTA CAC CTT GGG TGC    2089
Ser Arg Met Val Thr Lys Gly Leu Leu Val His Leu Gly Cys
            625                 630

GAA GTG ACC ACG GTG AGT TCA AAC GAG GAG TGT CTC CGA GTT    2131
Glu Val Thr Thr Val Ser Ser Asn Glu Glu Cys Leu Arg Val
635                 640                 645

GTG TCC CAT GAG CAC AAA GTG GTC TTC ATG GAC GTG TGC ATG    2173
Val Ser His Glu His Lys Val Val Phe Met Asp Val Cys Met
    650                 655                 660

CCC GGG GTC GAA AAC TAC CAA ATC GCT CTC CGT ATT CAC GAG    2215
Pro Gly Val Glu Asn Tyr Gln Ile Ala Leu Arg Ile His Glu
            665                 670                 675

AAA TTC ACA AAA CAA CGC CAC CAA CGG CCA CTA CTT GTG GCA    2257
Lys Phe Thr Lys Gln Arg His Gln Arg Pro Leu Leu Val Ala
            680                 685                 690

CTC AGT GGT AAC ACT GAC AAA TCC ACA AAA GAG AAA TGC ATG    2299
Leu Ser Gly Asn Thr Asp Lys Ser Thr Lys Glu Lys Cys Met
            695                 700

AGC TTT GGT CTA GAC GGT GTG TTG CTC AAA CCC GTA TCA CTA    2341
Ser Phe Gly Leu Asp Gly Val Leu Leu Lys Pro Val Ser Leu
705                 710                 715

GAC AAC ATA AGA GAT GTT CTG TCT GAT CTT CTC GAG CCC CGG    2383
Asp Asn Ile Arg Asp Val Leu Ser Asp Leu Leu Glu Pro Arg
            720                 725                 730

GTA CTG TAC GAG GGC ATG TAAAGGCGAT GGATGCCCCA              2421
Val Leu Tyr Glu Gly Met
            735

TGCCCCAGAG GAGTAATTCC GCTCCCGCCT TCTTCTCCCG TAAAACATCG     2471

GAAGCTGATG TTCTCTGGTT TAATTGTGTA CATATCAGAG ATTGTCGGAG     2521

CGTTTTGGAT GATATCTTAA AACAGAAAGG GAATAACAAA ATAGAAACTC     2571

TAAACCGGTA TGTGTCCGTG GCGATTTCGG TTATAGAGGA ACAAGATGGT    2621

GGTGGTATAA TCATACCATT TCAGATTACA TGTTTGACTA ATGTTGTATC     2671

CTTATATATG TAGTTACATT CTTATAAGAA TTTGGATCGA GTTATGGATG     2721

CTTGTTGCGT GCATGTATGA CATTGATGCA GTATTATGGC GTCAGCTTTG .   2771

CGCCGCTTAG TAGAAC                                          2787
```

FIG. 5D

| | |
|---|---|
| AGTAAGAACG AAGAAGAAGT GTTAAACCCA ACCAATTTTG ACTTGAAAAA | 50 |
| AAGCTTCAAC GCTCCCCTTT TCTCCTTCTC CGTCGCTCTC CGCCGCGTCC | 100 |
| CAAATCCCCA ATTCCTCCTC TTCTCCGATC AATTCTTCCC AAGTGTGTGT | 150 |
| ATGTGTGAGA GAGGAACTAT AGTGTAAAAA ATTCATA ATG GAA GTC TGC | 199 |

```
                                               Met Glu Val Cys
                                                 1
AAT TGT ATT GAA CCG CAA TGG CCA GCG GAT GAA TTG TTA ATG       241
Asn Cys Ile Glu Pro Gln Trp Pro Ala Asp Glu Leu Leu Met
  5          10                   15

AAA TAC CAA TAC ATC TCC GAT TTC TTC ATT GCG ATT GCG TAT       283
Lys Tyr Gln Tyr Ile Ser Asp Phe Phe Ile Ala Ile Ala Tyr
     20              25                   30

TTT TCG ATT CCT CTT GAG TTG ATT TAC TTT GTG AAG AAA TCA       325
Phe Ser Ile Pro Leu Glu Leu Ile Tyr Phe Val Lys Lys Ser
         35              40                   45

GCC GTG TTT CCG TAT AGA TGG GTA CTT GTT CAG TTT GGT GCT       367
Ala Val Phe Pro Tyr Arg Trp Val Leu Val Gln Phe Gly Ala
             50              55                   60

TTT ATC GTT CTT TAT GGA GCA ACT CAT CTT ATT AAC TTA TGG       409
Phe Ile Val Leu Tyr Gly Ala Thr His Leu Ile Asn Leu Trp
                 65              70

ACT TTC ACT ACG CAT TCG AGA ACC GTG GCG CTT GTG ATG ACT       451
Thr Phe Thr Thr His Ser Arg Thr Val Ala Leu Val Met Thr
75              80                   85

ACC GCG AAG GTG TTA ACC GCT GTT GTC TCG TGT GCT ACT GCG       493
Thr Ala Lys Val Leu Thr Ala Val Val Ser Cys Ala Thr Ala
     90              95                  100

TTG ATG CTT GTT CAT ATT ATT CCT GAT CTT TTG AGT GTT AAG       535
Leu Met Leu Val His Ile Ile Pro Asp Leu Leu Ser Val Lys
        105              110                  115

ACT CGG GAG CTT TTC TTG AAA AAT AAA GCT GCT GAG CTC GAT       577
Thr Arg Glu Leu Phe Leu Lys Asn Lys Ala Ala Glu Leu Asp
            120              125                  130

AGA GAA ATG GGA TTG ATT CGA ACT CAG GAA GAA ACC GGA AGG       619
Arg Glu Met Gly Leu Ile Arg Thr Gln Glu Glu Thr Gly Arg
                135              140

CAT GTG AGA ATG TTG ACT CAT GAG ATT AGA AGC ACT TTA GAT       661
His Val Arg Met Leu Thr His Glu Ile Arg Ser Thr Leu Asp
145              150                  155

AGA CAT ACT ATT TTA AAG ACT ACA CTT GTT GAG CTT GGT AGG       703
Arg His Thr Ile Leu Lys Thr Thr Leu Val Glu Leu Gly Arg
        160              165                  170

ACA TTA GCT TTG GAG GAG TGT GCA TTG TGG ATG CCT ACT AGA       745
Thr Leu Ala Leu Glu Glu Cys Ala Leu Trp Met Pro Thr Arg
            175              180                  185
```

*FIG. 6A*

```
ACT GGG TTA GAG CTA CAG CTT TCT TAT ACA CTT CGT CAT CAA      787
Thr Gly Leu Glu Leu Gln Leu Ser Tyr Thr Leu Arg His Gln
            190                 195                 200

CAT CCC GTG GAG TAT ACG GTT CCT ATT CAA TTA CCG GTG ATT      829
His Pro Val Glu Tyr Thr Val Pro Ile Gln Leu Pro Val Ile
                205                 210

AAC CAA GTG TTT GGT ACT AGT AGG GCT GTA AAA ATA TCT CCT      871
Asn Gln Val Phe Gly Thr Ser Arg Ala Val Lys Ile Ser Pro
215                 220                 225

AAT TCT CCT GTG GCT AGG TTG AGA CCT GTT TCT GGG AAA TAT      913
Asn Ser Pro Val Ala Arg Leu Arg Pro Val Ser Gly Lys Tyr
    230                 235                 240

ATG CTA GGG GAG GTG GTC GCT GTG AGG GTT CCG CTT CTC CAC      955
Met Leu Gly Glu Val Val Ala Val Arg Val Pro Leu Leu His
        245                 250                 255

CTT TCT AAT TTT CAG ATT AAT GAC TGG CCT GAG CTT TCA ACA      997
Leu Ser Asn Phe Gln Ile Asn Asp Trp Pro Glu Leu Ser Thr
            260                 265                 270

AAG AGA TAT GCT TTG ATG GTT TTG ATG CTT CCT TCA GAT AGT      1039
Lys Arg Tyr Ala Leu Met Val Leu Met Leu Pro Ser Asp Ser
                275                 280

GCA AGG CAA TGG CAT GTC CAT GAG TTG GAA CTC GTT GAA GTC      1081
Ala Arg Gln Trp His Val His Glu Leu Glu Leu Val Glu Val
285                 290                 295

GTC GCT GAT CAG GTG GCT GTA GCT CTC TCA CAT GCT GCG ATC      1123
Val Ala Asp Gln Val Ala Val Ala Leu Ser His Ala Ala Ile
    300                 305                 310

CTA GAA GAG TCG ATG CGA GCT AGG GAC CTT CTC ATG GAG CAG      1165
Leu Glu Glu Ser Met Arg Ala Arg Asp Leu Leu Met Glu Gln
        315                 320                 325

AAT GTT GCT CTT GAT CTA GCT AGA CGA GAA GCA GAA ACA GCA      1207
Asn Val Ala Leu Asp Leu Ala Arg Arg Glu Ala Glu Thr Ala
            330                 335                 340

ATC CGT GCC CGC AAT GAT TTC CTA GCG GTT ATG AAC CAT GAA      1249
Ile Arg Ala Arg Asn Asp Phe Leu Ala Val Met Asn His Glu
                345                 350

ATG CGA ACA CCG ATG CAT GCG ATT ATT GCA CTC TCT TCC TTA      1291
Met Arg Thr Pro Met His Ala Ile Ile Ala Leu Ser Ser Leu
355                 360                 365

CTC CAA GAA ACG GAA CTA ACC CCT GAA CAA AGA CTG ATG GTG      1333
Leu Gln Glu Thr Glu Leu Thr Pro Glu Gln Arg Leu Met Val
    370                 375                 380

GAA ACA ATA CTT AAA AGT AGT AAC CTT TTG GCA ACT TTG ATG      1375
Glu Thr Ile Leu Lys Ser Ser Asn Leu Leu Ala Thr Leu Met
        385                 390                 395
```

*FIG. 6B*

```
AAT GAT GTC TTA GAT CTT TCA AGG TTA GAA GAT GGA AGT CTT    1417
Asn Asp Val Leu Asp Leu Ser Arg Leu Glu Asp Gly Ser Leu
            400             405                     410

CAA CTT GAA CTT GGG ACA TTC AAT CTT CAT ACA TTA TTT AGA    1459
Gln Leu Glu Leu Gly Thr Phe Asn Leu His Thr Leu Phe Arg
                415                 420

GAG GTC CTC AAT CTG ATA AAG CCT ATA GCG GTT GTT AAG AAA    1501
Glu Val Leu Asn Leu Ile Lys Pro Ile Ala Val Val Lys Lys
425                 430                 435

TTA CCC ATC ACA CTA AAT CTT GCA CCA GAT TTG CCA GAA TTT    1543
Leu Pro Ile Thr Leu Asn Leu Ala Pro Asp Leu Pro Glu Phe
    440                 445                 450

GTT GTT GGG GAT GAG AAA CGG CTA ATG CAG ATA ATA TTA AAT    1585
Val Val Gly Asp Glu Lys Arg Leu Met Gln Ile Ile Leu Asn
            455                 460                 465

ATA GTT GGT AAT GCT GTG AAA TTC TCC AAA CAA GGT AGT ATC    1627
Ile Val Gly Asn Ala Val Lys Phe Ser Lys Gln Gly Ser Ile
            470                 475                 480

TCC GTA ACC GCT CTT GTC ACC AAG TCA GAC ACA CGA GCT GCT    1669
Ser Val Thr Ala Leu Val Thr Lys Ser Asp Thr Arg Ala Ala
                485                 490

GAC TTT TTT GTC GTG CCA ACT GGG AGT CAT TTC TAC TTG AGA    1711
Asp Phe Phe Val Val Pro Thr Gly Ser His Phe Tyr Leu Arg
495                 500                 505

GTG AAG GTA AAA GAC TCT GGA GCA GGA ATA AAT CCT CAA GAC    1753
Val Lys Val Lys Asp Ser Gly Ala Gly Ile Asn Pro Gln Asp
    510                 515                 520

ATT CCA AAG ATT TTC ACT AAA TTT GCT CAA ACA CAA TCT TTA    1795
Ile Pro Lys Ile Phe Thr Lys Phe Ala Gln Thr Gln Ser Leu
        525                 530                 535

GCG ACG AGA AGC TCG GGT GGT AGT GGG CTT GGC CTC GCC ATC    1837
Ala Thr Arg Ser Ser Gly Gly Ser Gly Leu Gly Leu Ala Ile
                540                 545                 550

TCC AAG AGG TTT GTG AAT CTG ATG GAG GGT AAC ATT TGG ATT    1879
Ser Lys Arg Phe Val Asn Leu Met Glu Gly Asn Ile Trp Ile
                    555                 560

GAG AGC GAT GGT CTT GGA AAA GGA TGC ACG GCT ATC TTT GAT    1921
Glu Ser Asp Gly Leu Gly Lys Gly Cys Thr Ala Ile Phe Asp
565             570                 575

GTT AAA CTT GGG ATC TCA GAA CGT TCA AAC GAA TCT AAA CAG    1963
Val Lys Leu Gly Ile Ser Glu Arg Ser Asn Glu Ser Lys Gln
    580                 585                 590

TCG GGC ATA CCG AAA GTT CCA GCC ATT CCC CGA CAT TCA AAT    2005
Ser Gly Ile Pro Lys Val Pro Ala Ile Pro Arg His Ser Asn
        595                 600                 605
```

*FIG. 6C*

```
TTC ACT GGA CTT AAG GTT CTT GTC ATG GAT GAG AAC GGG GTA      2047
Phe Thr Gly Leu Lys Val Leu Val Met Asp Glu Asn Gly Val
            610                 615                 620

AGT AGA ATG GTG ACG AAG GGA CTT CTT GTA CAC CTT GGG TGC      2089
Ser Arg Met Val Thr Lys Gly Leu Leu Val His Leu Gly Cys
                    625                 630

GAA GTG ACC ACG GTG AGT TCA AAC GAG GAG TGT CTC CGA GTT      2131
Glu Val Thr Thr Val Ser Ser Asn Glu Glu Cys Leu Arg Val
635                     640                 645

GTG TCC CAT GAG CAC AAA GTG GTC TTC ATG GAC GTG TGC ATG      2173
Val Ser His Glu His Lys Val Val Phe Met Asp Val Cys Met
        650                 655                 660

CCC GGG GTC GAA AAC TAC CAA ATC GCT CTC CGT ATT CAC GAG      2215
Pro Gly Val Glu Asn Tyr Gln Ile Ala Leu Arg Ile His Glu
            665                 670                 675

AAA TTC ACA AAA CAA CGC CAC CAA CGG CCA CTA CTT GTG GCA      2257
Lys Phe Thr Lys Gln Arg His Gln Arg Pro Leu Leu Val Ala
                680                 685                 690

CTC AGT GGT AAC ACT GAC AAA TCC ACA AAA GAG AAA TGC ATG      2299
Leu Ser Gly Asn Thr Asp Lys Ser Thr Lys Glu Lys Cys Met
                    695                 700

AGC TTT GGT CTA GAC GGT GTG TTG CTC AAA CCC GTA TCA CTA      2341
Ser Phe Gly Leu Asp Gly Val Leu Leu Lys Pro Val Ser Leu
705                     710                 715

GAC AAC ATA AGA GAT GTT CTG TCT GAT CTT CTC GAG CCC CGG      2383
Asp Asn Ile Arg Asp Val Leu Ser Asp Leu Leu Glu Pro Arg
        720                 725                 730

GTA CTG TAC GAG GGC ATG TAAAGGCGAT GGATGCCCCA TGCCCCAGAG     2431
Val Leu Tyr Glu Gly Met
            735

GAGTAATTCC GCTCCCGCCT TCTTCTCCCG TAAAACATCG GAAGCTGATG       2481

TTCTCTGGTT TAATTGTGTA CATATCAGAG ATTGTCGGAG CGTTTTGGAT       2531

GATATCTTAA AACAGAAAGG GAATAACAAA ATAGAAACTC TAAACCGGTA       2581

TGTGTCCGTG GCGATTTCGG TTATAGAGGA ACAAGATGGT GGTGGTATAA       2631

TCATACCATT TCAGATTACA TGTTTGACTA ATGTTGTATC CTTATATATG       2681

TAGTTACATT CTTATAAGAA TTTGGATCGA GTTATGGATG CTTGTTGCGT       2731

GCATGTATGA CATTGATGCA GTATTATGGC GTCAGCTTTG CGCCGCTTAG       2781

TAGAAC                                                       2787
```

FIG. 6D

```
AGTAAGAACG AAGAAGAAGT GTTAAACCCA ACCAATTTTG ACTTGAAAAA         50
AAGCTTCAAC GCTCCCCTTT TCTCCTTCTC CGTCGCTCTC CGCCGCGTCC        100
CAAATCCCCA ATTCCTCCTC TTCTCCGATC AATTCTTCCC AAGTGTGTGT        150
ATGTGTGAGA GAGGAACTAT AGTGTAAAAA ATTCATA ATG GAA GTC TGC      199
                                         Met Glu Val Cys
                                           1
```

```
AAT TGT ATT GAA CCG CAA TGG CCA GCG GAT GAA TTG TTA ATG       241
Asn Cys Ile Glu Pro Gln Trp Pro Ala Asp Glu Leu Leu Met
 5              10                  15

AAA TAC CAA TAC ATC TCC GAT TTC TTC ATT GCG ATT GCG TAT       283
Lys Tyr Gln Tyr Ile Ser Asp Phe Phe Ile Ala Ile Ala Tyr
        20              25                  30

TTT TCG ATT CCT CTT GAG TTG ATT TAC TTT GTG AAG AAA TCA       325
Phe Ser Ile Pro Leu Glu Leu Ile Tyr Phe Val Lys Lys Ser
            35              40                  45

GCC GTG TTT CCG TAT AGA TGG GTA CTT GTT CAG TTT GGT GCT       367
Ala Val Phe Pro Tyr Arg Trp Val Leu Val Gln Phe Gly Ala
                50              55                  60

TTT ATC GTT CTT TGT GGA GCA ACT CAT CTT ATT AAC TTA TGG       409
Phe Ile Val Leu Cys Gly Ala Thr His Leu Ile Asn Leu Trp
                    65              70

ACT TTC ACT ACG CAT TCG AGA ACC GTG GCG CTT GTG ATG ACT       451
Thr Phe Thr Thr His Ser Arg Thr Val Ala Leu Val Met Thr
 75              80                  85

ACC GCG AAG GTG TTA ACC GCT GTT GTC TCG TGT GCT ACT ACG       493
Thr Ala Lys Val Leu Thr Ala Val Val Ser Cys Ala Thr Thr
        90              95                  100

TTG ATG CTT GTT CAT ATT ATT CCT GAT CTT TTG AGT GTT AAG       535
Leu Met Leu Val His Ile Ile Pro Asp Leu Leu Ser Val Lys
            105             110                 115

ACT CGG GAG CTT TTC TTG AAA AAT AAA GCT GCT GAG CTC GAT       577
Thr Arg Glu Leu Phe Leu Lys Asn Lys Ala Ala Glu Leu Asp
                120             125                 130

AGA GAA ATG GGA TTG ATT CGA ACT CAG GAA GAA ACC GGA AGG       619
Arg Glu Met Gly Leu Ile Arg Thr Gln Glu Glu Thr Gly Arg
                    135             140

CAT GTG AGA ATG TTG ACT CAT GAG ATT AGA AGC ACT TTA GAT       661
His Val Arg Met Leu Thr His Glu Ile Arg Ser Thr Leu Asp
145             150                 155

AGA CAT ACT ATT TTA AAG ACT ACA CTT GTT GAG CTT GGT AGG       703
Arg His Thr Ile Leu Lys Thr Thr Leu Val Glu Leu Gly Arg
        160             165                 170

ACA TTA GCT TTG GAG GAG TGT GCA TTG TGG ATG CCT ACT AGA       745
Thr Leu Ala Leu Glu Glu Cys Ala Leu Trp Met Pro Thr Arg
            175             180                 185
```

FIG. 7A

| | | | | | | | | | | | | | |
|---|---|---|---|---|---|---|---|---|---|---|---|---|---|
| ACT | GGG | TTA | GAG | CTA | CAG | CTT | TCT | TAT | ACA | CTT | CGT | CAT | CAA | 787
| Thr | Gly | Leu | Glu | Leu | Gln | Leu | Ser | Tyr | Thr | Leu | Arg | His | Gln |
| | | | 190 | | | | | 195 | | | | | 200 |

| CAT | CCC | GTG | GAG | TAT | ACG | GTT | CCT | ATT | CAA | TTA | CCG | GTG | ATT | 829
| His | Pro | Val | Glu | Tyr | Thr | Val | Pro | Ile | Gln | Leu | Pro | Val | Ile |
| | | | | 205 | | | | | 210 | | | | |

| AAC | CAA | GTG | TTT | GGT | ACT | AGT | AGG | GCT | GTA | AAA | ATA | TCT | CCT | 871
| Asn | Gln | Val | Phe | Gly | Thr | Ser | Arg | Ala | Val | Lys | Ile | Ser | Pro |
| 215 | | | | | 220 | | | | | 225 | | | |

| AAT | TCT | CCT | GTG | GCT | AGG | TTG | AGA | CCT | GTT | TCT | GGG | AAA | TAT | 913
| Asn | Ser | Pro | Val | Ala | Arg | Leu | Arg | Pro | Val | Ser | Gly | Lys | Tyr |
| | 230 | | | | | 235 | | | | | 240 | | |

| ATG | CTA | GGG | GAG | GTG | GTC | GCT | GTG | AGG | GTT | CCG | CTT | CTC | CAC | 955
| Met | Leu | Gly | Glu | Val | Val | Ala | Val | Arg | Val | Pro | Leu | Leu | His |
| | | 245 | | | | | 250 | | | | | 255 | |

| CTT | TCT | AAT | TTT | CAG | ATT | AAT | GAC | TGG | CCT | GAG | CTT | TCA | ACA | 997
| Leu | Ser | Asn | Phe | Gln | Ile | Asn | Asp | Trp | Pro | Glu | Leu | Ser | Thr |
| | | | 260 | | | | | 265 | | | | | 270 |

| AAG | AGA | TAT | GCT | TTG | ATG | GTT | TTG | ATG | CTT | CCT | TCA | GAT | AGT | 1039
| Lys | Arg | Tyr | Ala | Leu | Met | Val | Leu | Met | Leu | Pro | Ser | Asp | Ser |
| | | | | 275 | | | | | 280 | | | | |

| GCA | AGG | CAA | TGG | CAT | GTC | CAT | GAG | TTG | GAA | CTC | GTT | GAA | GTC | 1081
| Ala | Arg | Gln | Trp | His | Val | His | Glu | Leu | Glu | Leu | Val | Glu | Val |
| 285 | | | | | 290 | | | | | 295 | | | |

| GTC | GCT | GAT | CAG | GTG | GCT | GTA | GCT | CTC | TCA | CAT | GCT | GCG | ATC | 1123
| Val | Ala | Asp | Gln | Val | Ala | Val | Ala | Leu | Ser | His | Ala | Ala | Ile |
| | 300 | | | | | 305 | | | | | 310 | | |

| CTA | GAA | GAG | TCG | ATG | CGA | GCT | AGG | GAC | CTT | CTC | ATG | GAG | CAG | 1165
| Leu | Glu | Glu | Ser | Met | Arg | Ala | Arg | Asp | Leu | Leu | Met | Glu | Gln |
| | | 315 | | | | | 320 | | | | | 325 | |

| AAT | GTT | GCT | CTT | GAT | CTA | GCT | AGA | CGA | GAA | GCA | GAA | ACA | GCA | 1207
| Asn | Val | Ala | Leu | Asp | Leu | Ala | Arg | Arg | Glu | Ala | Glu | Thr | Ala |
| | | | 330 | | | | | 335 | | | | | 340 |

| ATC | CGT | GCC | CGC | AAT | GAT | TTC | CTA | GCG | GTT | ATG | AAC | CAT | GAA | 1249
| Ile | Arg | Ala | Arg | Asn | Asp | Phe | Leu | Ala | Val | Met | Asn | His | Glu |
| | | | | 345 | | | | | 350 | | | | |

| ATG | CGA | ACA | CCG | ATG | CAT | GCG | ATT | ATT | GCA | CTC | TCT | TCC | TTA | 1291
| Met | Arg | Thr | Pro | Met | His | Ala | Ile | Ile | Ala | Leu | Ser | Ser | Leu |
| 355 | | | | | 360 | | | | | 365 | | | |

| CTC | CAA | GAA | ACG | GAA | CTA | ACC | CCT | GAA | CAA | AGA | CTG | ATG | GTG | 1333
| Leu | Gln | Glu | Thr | Glu | Leu | Thr | Pro | Glu | Gln | Arg | Leu | Met | Val |
| | 370 | | | | | 375 | | | | | 380 | | |

| GAA | ACA | ATA | CTT | AAA | AGT | AGT | AAC | CTT | TTG | GCA | ACT | TTG | ATG | 1375
| Glu | Thr | Ile | Leu | Lys | Ser | Ser | Asn | Leu | Leu | Ala | Thr | Leu | Met |
| | | 385 | | | | | 390 | | | | | 395 | |

*FIG. 7B*

```
AAT GAT GTC TTA GAT CTT TCA AGG TTA GAA GAT GGA AGT CTT    1417
Asn Asp Val Leu Asp Leu Ser Arg Leu Glu Asp Gly Ser Leu
            400             405                     410

CAA CTT GAA CTT GGG ACA TTC AAT CTT CAT ACA TTA TTT AGA    1459
Gln Leu Glu Leu Gly Thr Phe Asn Leu His Thr Leu Phe Arg
                415                 420

GAG GTC CTC AAT CTG ATA AAG CCT ATA GCG GTT GTT AAG AAA    1501
Glu Val Leu Asn Leu Ile Lys Pro Ile Ala Val Val Lys Lys
425                     430                 435

TTA CCC ATC ACA CTA AAT CTT GCA CCA GAT TTG CCA GAA TTT    1543
Leu Pro Ile Thr Leu Asn Leu Ala Pro Asp Leu Pro Glu Phe
    440                     445                 450

GTT GTT GGG GAT GAG AAA CGG CTA ATG CAG ATA ATA TTA AAT    1585
Val Val Gly Asp Glu Lys Arg Leu Met Gln Ile Ile Leu Asn
            455                     460             465

ATA GTT GGT AAT GCT GTG AAA TTC TCC AAA CAA GGT AGT ATC    1627
Ile Val Gly Asn Ala Val Lys Phe Ser Lys Gln Gly Ser Ile
                470                 475                 480

TCC GTA ACC GCT CTT GTC ACC AAG TCA GAC ACA CGA GCT GCT    1669
Ser Val Thr Ala Leu Val Thr Lys Ser Asp Thr Arg Ala Ala
                    485                 490

GAC TTT TTT GTC GTG CCA ACT GGG AGT CAT TTC TAC TTG AGA    1711
Asp Phe Phe Val Val Pro Thr Gly Ser His Phe Tyr Leu Arg
495                     500                 505

GTG AAG GTA AAA GAC TCT GGA GCA GGA ATA AAT CCT CAA GAC    1753
Val Lys Val Lys Asp Ser Gly Ala Gly Ile Asn Pro Gln Asp
    510                     515                 520

ATT CCA AAG ATT TTC ACT AAA TTT GCT CAA ACA CAA TCT TTA    1795
Ile Pro Lys Ile Phe Thr Lys Phe Ala Gln Thr Gln Ser Leu
            525                     530             535

GCG ACG AGA AGC TCG GGT GGT AGT GGG CTT GGC CTC GCC ATC    1837
Ala Thr Arg Ser Ser Gly Gly Ser Gly Leu Gly Leu Ala Ile
                540                     545             550

TCC AAG AGG TTT GTG AAT CTG ATG GAG GGT AAC ATT TGG ATT    1879
Ser Lys Arg Phe Val Asn Leu Met Glu Gly Asn Ile Trp Ile
                    555                     560

GAG AGC GAT GGT CTT GGA AAA GGA TGC ACG GCT ATC TTT GAT    1921
Glu Ser Asp Gly Leu Gly Lys Gly Cys Thr Ala Ile Phe Asp
565                     570                 575

GTT AAA CTT GGG ATC TCA GAA CGT TCA AAC GAA TCT AAA CAG    1963
Val Lys Leu Gly Ile Ser Glu Arg Ser Asn Glu Ser Lys Gln
    580                     585                 590

TCG GGC ATA CCG AAA GTT CCA GCC ATT CCC CGA CAT TCA AAT    2005
Ser Gly Ile Pro Lys Val Pro Ala Ile Pro Arg His Ser Asn
            595                     600             605
```

FIG. 7C

```
TTC ACT GGA CTT AAG GTT CTT GTC ATG GAT GAG AAC GGG GTA          2047
Phe Thr Gly Leu Lys Val Leu Val Met Asp Glu Asn Gly Val
        610                 615                     620

AGT AGA ATG GTG ACG AAG GGA CTT CTT GTA CAC CTT GGG TGC          2089
Ser Arg Met Val Thr Lys Gly Leu Leu Val His Leu Gly Cys
                625                 630

GAA GTG ACC ACG GTG AGT TCA AAC GAG GAG TGT CTC CGA GTT          2131
Glu Val Thr Thr Val Ser Ser Asn Glu Glu Cys Leu Arg Val
635                     640                 645

GTG TCC CAT GAG CAC AAA GTG GTC TTC ATG GAC GTG TGC ATG          2173
Val Ser His Glu His Lys Val Val Phe Met Asp Val Cys Met
        650                 655                     660

CCC GGG GTC GAA AAC TAC CAA ATC GCT CTC CGT ATT CAC GAG          2215
Pro Gly Val Glu Asn Tyr Gln Ile Ala Leu Arg Ile His Glu
                665                 670                 675

AAA TTC ACA AAA CAA CGC CAC CAA CGG CCA CTA CTT GTG GCA          2257
Lys Phe Thr Lys Gln Arg His Gln Arg Pro Leu Leu Val Ala
                680                 685                     690

CTC AGT GGT AAC ACT GAC AAA TCC ACA AAA GAG AAA TGC ATG          2299
Leu Ser Gly Asn Thr Asp Lys Ser Thr Lys Glu Lys Cys Met
                    695                 700

AGC TTT GGT CTA GAC GGT GTG TTG CTC AAA CCC GTA TCA CTA          2341
Ser Phe Gly Leu Asp Gly Val Leu Leu Lys Pro Val Ser Leu
705                     710                 715

GAC AAC ATA AGA GAT GTT CTG TCT GAT CTT CTC GAG CCC CGG          2383
Asp Asn Ile Arg Asp Val Leu Ser Asp Leu Leu Glu Pro Arg
        720                 725                 730

GTA CTG TAC GAG GGC ATG TAAAGGCGAT GGATGCCCCA TGCCCCAGAG         2431
Val Leu Tyr Glu Gly Met
            735

GAGTAATTCC GCTCCCGCCT TCTTCTCCCG TAAAACATCG GAAGCTGATG           2481

TTCTCTGGTT TAATTGTGTA CATATCAGAG ATTGTCGGAG CGTTTTGGAT           2531

GATATCTTAA AACAGAAAGG GAATAACAAA ATAGAAACTC TAAACCGGTA           2581

TGTGTCCGTG GCGATTTCGG TTATAGAGGA ACAAGATGGT GGTGGTATAA           2631

TCATACCATT TCAGATTACA TGTTTGACTA ATGTTGTATC CTTATATATG           2681

TAGTTACATT CTTATAAGAA TTTGGATCGA GTTATGGATG CTTGTTGCGT           2731

GCATGTATGA CATTGATGCA GTATTATGGC GTCAGCTTTG CGCCGCTTAG           2781

TAGAAC                                                          2787
```

```
ETR1   QNVALDLARREAETAIRARNDFLAV  MNHEMRTPM  HAIIALSLLQETELTPEQRL  380
BARA   QNVELDLAKKRAQEAARIKSEFLAN  MSHELRTPL  NGVIGFTRLTLKTELTPTQRD 329
LEMA   QNIELDLARKEALEASRIKSEFLAN  MSHEIRTPL  NGILGFTHLLQKSELTPRQFD 311
RPFC                RAVREARHANQAKSRFLAN  MSHEFRTPL  NGLSGMTEVLATTRLDAEQKE 176

ETR1   MVETILKSSNLLATLMNDVLDLSRLEDGSLQLELGTFNLHTLFREVLNLIKPIAVV     436
BARA   HLNTIERSANNLLAIINDVLDFSKLEAGKLILESIPFLRSTLDEVVTLLAHSSHD     385
LEMA   YLGTIEKSADNLLSIINEILDFSKIEAGKLVLDNIPFNLRDLLQDTLTILAPAAHA     367
RPFC   CLNTIQASARSLLSLVEEVLDISAIEAGKIRIDRDFSLREMIGSVNLILQPQARG     232

ETR1   KKLPITLNLAPDLPEFVVGDEKR   LMQIILNIVGNA   VKFSKQGSI (26) LRVK  510
BARA   KGLELTLNIKSDVPDNVIGDPLR   LQQIITNLVGNA   IKFTENGNI (15) IEVQ  448
LEMA   KQLELVSLVYRDTPLALSGDPLR   LRQILTNLVSNA   IKFTREGTI (15) LRIS  430
RPFC   RRLEYGTQVADDVPLLLKGDTAH   LRQVLLNLVGNA   VKFTEHGHV (16) LRFD  296

ETR1   VKDSGAGIN  PQDIPK  IFTKF  AQTQSLATRSSG  GSGLGL  AISKRFVNLMEGNI  562
BARA   IRDTGIGIP  ERDQSR  LFQAF  RQADASISRRHG  GTGLGL  VITQKLVNEMGGDI  500
LEMA   VQDTGIGLS  SQDVRA  LFQAF  SQADNSLSRQPG  GTGLGL  VISKRLIEQMGGEI  482
RPFC   VEDTGIGVP  MDMRPR  LFEAF  EQADVGLSRRYE  GTGLGT  TIAKGLVEAMGGSI  348
```

FIG. 9B

```
ETR1   LKVLVM  DE  NGVSRMVTKGLLVHLGCEVTTVSSNEECLRV       648
BVGS   LRVLVV  DD  HKPNLMLLRQQLDYLGQRVVAADSGEAALAL     1011
RCSC   MMILVV  DD  HPINRRLLADQLGSLGYQCKTANDGVDALNV      847
LEMA   PRVLCV  DD  NPANLLIVQTLLEDMGAEVVAVEGGYAAVNA      695

ETR1   VSHEH-KVVFM  D  VCMPGVENYQIALRIH (10) PLLVA       690
BVGS   WHEHAFDVVIT  D  CNMPGINGYELARRIR (12) CILFG      1056
RCSC   LSKNHIDIVLS  D  VNMPNMDGYRLTQRIR  (5) LPVIG       885
LEMA   VQQEAFDLVLM  D  VQMPGMDGRQATEAIR (10) LPIVA       738

ETR1   LSGNTDKSTKEKCMSFGLDGVLL  K  PVSLDNIRDVLSDLL        729
BVGS   FTASAQMDEAHACRAAGMDDCLF  K  PIGVDALRQRLNEAA       1095
RCSC   VTANALAEEKQRCLESGMDSCLS  K  PVTLDVIKQSLTLYA        924
LEMA   LTAHAMANEKRSLLQSGMDDYLT  K  PISERQLAQVVLKWT        777
```

```
TOMATO       1 ATGGAATCCTGTGATTGCATTGAGGCTTTACTGCCAACTGGTGACCTGCT  50
               |||||| ||||||| |||||||||   |||| ||||| |||  || ||
ARABIDOPSIS 157 ATGGAAGTCTGCAATTGTATTGAACCGCAATGGCCAGCGGATGAATTGTT 206

51 GGTTAAATACCAATACCCTCTCAGATTTCTTCATTGCTGTAGCCTACTTTT 100
                ||| |||||||||||| |||||||||||||||||||||||  ||| ||||
            207 AATGAAATACCAATACATCTCCGATTTCTTCATTGCGATTGCCGTATTTTT 256

101 CCATTCCGTTGGAGCTTATTATTTGTCCACAAATCTGCATGCTTCCCA 150
                ||||||||||| |||||| | |  || || ||||| |||| |   ||
            257 CGATTCCTCTCTGAGTTGATTACTTTGTTCAGTTTGGTGCTTTTGTGGAGC 306

151 TACAGATGGGTCCTCATGCAATTTGGTGCTTTTATTGTGCTCTGCGAGC 200
                ||| || || |||  | || ||||  || |||| ||||||| ||| |||
            307 TATAGATGGGTACTTGTTCAGTTTGGCTGCTTTTATCGTTCTTGTGGAGC 356

201 AACACACTTTATTAGCTTGTGGACCCTTCTTTATGCACTCTAAGACGGTCG 250
                || || ||||||| ||| ||||  |||   ||||| || ||| | |||
            357 AACTCATCTTATTAACTTATGGACTTTCACTACGCATTCGAGAACCGTGG 406

251 CTGTGGGTTATGACCATATATCAAAAATGTTGACAGCTGCCGTGTCCTGTATC 300
                | ||| || || ||| || | || ||||||| || |||    ||||| |
            407 CGCTTGTGATGACTACCGCGAAGGTGTGTTAACCGCTGTGTCTCGTGTGCT 456

301 ACAGCTTTGATGCTTGTTCACATTATTCCTGATTGCTAAGTGTTAAAAC 350
                || ||||| || ||||| |||| |||||| |||     |||| ||| ||
            457 ACTGCGTTGATGCTTGTTCATATATTATTCCTGATCTTTTTGAGTGTTAAGAC 506

351 GCGAGAGTTGTTCTTGAAA 369
                | |||||  |||| |||||
            507 TCGGGAGCTTTTCTTGAAA 525
                                Lys
                                123
```

FIG. 10A

```
              Ala
              306
TOMATO      1 GCTCTTTCACATGCTGCAATTTTAGAAGATTCCATGCGAGCCCATGATCA    50
              ||||||||||||||||||||  ||||||| ||||| |||||||||||||||
ARABIDOPSIS 1072 GCTCTCTCACATGCTGCGATCCTAGAAGAGTCGATGCGAGCTAGGACCT 1121

51 GCTCATGGAACAGAATATTGCTTTTGGATGTAGCTCGACAAGAAGCAGAGA  100
              |||||||||| ||||||| |||| |||| |||||| ||||  ||||||||
          1122 TCTCATGGAGCAGAATGTTGCTCTTGATCTAGCTAGACGAGAAGCAGAAA 1171

101 TGGCCATCCGTGCACGTAACGACTTCCTTGCTGTGATGAACCATGAAATG  150
              ||||||||||| ||  |  ||| |||||||| || | |||||||||||||
          1172 CAGCAATCCGTGCCCGCAATGATTTCCTAGCGGTTATGAACCATGAAATG 1221

151 AGAACGCCCATGCATGCAGTTATTGCTCTCTGTGCTCTCTGCTTTTAGAAAC  200
              ||||| ||||||  ||||  |||||  |  || |||| ||| |  |||||
          1222 CGAACACCGATGCATGCCATTATTGCACTCTCTTCCTTACTCCAAGAAAC 1271

201 AGACTTAACTCCAGAGAGCAGAGAGTTATGATTGAGACCATATTGAAGAGCA  250
              |||||||||||  ||||  ||||||| || ||||| ||  | ||||||||
          1272 AGAACTAACCCCCTGAACAAAGACTGATGGTGAAACAATACTTAAAAGTA 1321

251 GCAATCTTCTTGCAACACTGATAAATGATGTTCTAGATCTTTTCTAG    296
              | ||||| || ||  ||| |||||| |||| ||||||||| | ||| 
          1322 GTAACCTTTTGGCAACTTTGATGAATGATGTCTTAGATCTTTTTCAAG 1367
                                                               Ser
                                                               403
```

*FIG. 10B*

```
TOMATO      1 MESCDCIEALLPTGDLLVKYQYLSDFFIAVAYFSIPLELIYFVHKSACFP  50
              || :|:|||  :| :|:|| ||:|||||:|||||||||||||| :|||
ARABIDOPSIS 1 MEVCNCIEPQWPADELLMKYQYISDFFIAIAYFSIPLELIYFVKKSAVFP  50

51 YRWVLMQFGAFIVLCGATHFISLWTFFMHSKTVAVVMTISKMLTAAVSCI 100
              |||||:|||||||||||||||:| |||| |||||||||:|::| |||| |
           51 YRWVLVQFGAFIVLCGATHLINLWTFTTHSRTVALVMTTAKVLTAVVSCA 100

101 TALMLVHIIPDLLSVKTRELFLK 123
              |||||||||||||||||||||||
          101 TALMLVHIIPDLLSVKTRELFLK 123
```

FIG. 11A

```
ARABIDOPSIS 306 ALSHAAILEESMRARDLLMEQNVALDLARREAETAIRARNDFLAVMNHEM 355
                ||||||||| ||||||:|||||:| ||  |:|| |||||||||||||||
TOMATO      1   ALSHAAILEDSMRAHDQLMEQNIALDVARQEAEMAIRARNDFLAVMNHEM  50

356 RTPMHAIIAISSLLQETELTPEQRLMVETILKSSNLLATLMNDVLDLS   403
                ||||||::||  ||| |:|:|||:|:|||||||||||||:|||:|||:
            51  RTPMHAVIALCSLLLETDLTPEQRVMIETILKSSNLLATLINDVLDLS    93
```

FIG. 11B

| | | |
|---|---|---|
| ACTTTTAAAA TTTCTTTATT TCATTGTCAG AAAAAGAGAG CTAATAATAT | | 50 |
| TATTATTTAA ATGTAACAAG TAGGCCTATA ACACGTGAAC TTCCCTCTTT | | 100 |
| GCAAAAAAAA AATCATCAAA AACTTTTACC TCTCATTGGT TTCTTCTTTA | | 150 |
| TCACACTGTT ACGCTTGGAT TCTCATTTCT TCAAGTTCAT AACGCTCGGA | | 200 |
| TCAATCAGGA AGACGAACTT GAACTTTCTT TTTTTCATCA TTACCCAAAG | | 250 |
| CTATGAGGCT CACACCACCA ATACGTCCGC CGTCATGAAT CCTTCTCTTC | | 300 |
| CAGGTACTGT GCCGTCTCGG GATAACAAAC TTTCTATTTA TTCTCTTCTG | | 350 |
| ATCGGATCTA TCTATCGATG AAGATTGATT TCACTACTTT AGTAACATTT | | 400 |
| CATCTGATCG ATCTGTGTTG TGTTATCGAG GAATCAATCT CATTTGTAG | | 450 |
| ATTCAATTTT CTGGATAGAT TTTGTATCTC TTTTCCATAG CTCTAGTCCA | | 500 |
| AATCTAGTCT CCACTGATAT CTGAGTTTTG TTGACCAGGT CAACACAAGT | | 550 |

```
CAGAGCTCCA AAA ATG GAG TCA TGC GAT TGT TTT GAG ACG CAT        593
         Met Glu Ser Cys Asp Cys Phe Glu Thr His
          1           5                    10

GTG AAT CAA GAT GAT CTG TTA GTG AAG TAC CAA TAC ATC TCA        635
Val Asn Gln Asp Asp Leu Leu Val Lys Tyr Gln Tyr Ile Ser
               15                    20

GAT GCG TTG ATT GCT CTT GCA TAC TTC TCA ATC CCA CTC GAG        677
Asp Ala Leu Ile Ala Leu Ala Tyr Phe Ser Ile Pro Leu Glu
25                  30                    35

CTT ATC TAT TTC GTG CAA AAG TCT GCT TTC TTC CCT TAC AAA        719
Leu Ile Tyr Phe Val Gln Lys Ser Ala Phe Phe Pro Tyr Lys
    40                  45                    50

TGG GTG CTT ATG CAG TTT GGA GCC TTT ATC ATT CTC TGT GGA        761
Trp Val Leu Met Gln Phe Gly Ala Phe Ile Ile Leu Cys Gly
        55                  60                    65

GCT ACG CAT TTC ATC AAC CTA TGG ATG TTC TTC ATG CAT TCC        803
Ala Thr His Phe Ile Asn Leu Trp Met Phe Phe Met His Ser
            70                  75                    80

AAA GCC GTT GCC ATT GTC ATG ACT ATT GCT AAA GTC TCT TGC        845
Lys Ala Val Ala Ile Val Met Thr Ile Ala Lys Val Ser Cys
                85                  90

GCG GTT GTG TCG TGT GCT ACC GCG TTG ATG TTG GTT CAT ATT        887
Ala Val Val Ser Cys Ala Thr Ala Leu Met Leu Val His Ile
95                  100                   105

ATT CCT GAT CTT CTC AGT GTT AAG AAC AGG GAA TTG TTT CTC        929
Ile Pro Asp Leu Leu Ser Val Lys Asn Arg Glu Leu Phe Leu
    110                 115                   120

AAG AAG AAA GCT GAT GAG TTA GAT AGA GAA ATG GGT CTT ATT        971
Lys Lys Lys Ala Asp Glu Leu Asp Arg Glu Met Gly Leu Ile
        125                 130                   135
```

FIG. 12A

| | |
|---|---|
| TTA ACA CAA GAG GAG ACT GGT AGG CAT GTT AGG ATG CTT ACT<br>Leu Thr Gln Glu Glu Thr Gly Arg His Val Arg Met Leu Thr<br>            140                    145                  150 | 1013 |
| CAT GGA ATT AGA AGA ACT CTT GAT AGG CAT ACT ATT TTA AGA<br>His Gly Ile Arg Arg Thr Leu Asp Arg His Thr Ile Leu Arg<br>                    155                        160 | 1055 |
| ACC ACT CTT GTT GAG CTT GGT AAA ACT CTT TGT CTT GAG GAA<br>Thr Thr Leu Val Glu Leu Gly Lys Thr Leu Cys Leu Glu Glu<br>165                    170                    175 | 1097 |
| TGT GCG TTG TGG ATG CCT TCT CAA AGT GGT TTA TAT TTG CAG<br>Cys Ala Leu Trp Met Pro Ser Gln Ser Gly Leu Tyr Leu Gln<br>            180                    185                  190 | 1139 |
| CTT TCT CAT ACT TTG AGT CAT AAA ATA CAA GTT GGA AGC AGT<br>Leu Ser His Thr Leu Ser His Lys Ile Gln Val Gly Ser Ser<br>              195                    200               205 | 1181 |
| GTG CCG ATA AAT CTC CCG ATT ATT AAT GAA CTC TTC AAT AGC<br>Val Pro Ile Asn Leu Pro Ile Ile Asn Glu Leu Phe Asn Ser<br>                    210                    215               220 | 1223 |
| GCT CAA GCT ATG CAC ATA CCT CAT TCT TGT CCT TTG GCT AAG<br>Ala Gln Ala Met His Ile Pro His Ser Cys Pro Leu Ala Lys<br>                  225                      230 | 1265 |
| ATT GGG CCT CCG GTT GGG AGA TAT TCA CCT CCT GAG GTT GTT<br>Ile Gly Pro Pro Val Gly Arg Tyr Ser Pro Pro Glu Val Val<br>235                    240                    245 | 1307 |
| TCT GTC CGT GTT CCT CTT TTA CAT CTC TCT AAT TTC CAA GGC<br>Ser Val Arg Val Pro Leu Leu His Leu Ser Asn Phe Gln Gly<br>            250                    255               260 | 1349 |
| AGT GAC TGG TCG GAT CTC TCT GGC AAA GGT TAC GCT ATC ATG<br>Ser Asp Trp Ser Asp Leu Ser Gly Lys Gly Tyr Ala Ile Met<br>              265                    270               275 | 1391 |
| GTC CTG ATT CTC CCA ACC GAT GGT GCA AGA AAA TGG AGA GAC<br>Val Leu Ile Leu Pro Thr Asp Gly Ala Arg Lys Trp Arg Asp<br>                    280                      285               290 | 1433 |
| CAT GAG TTA GAG CTT GTA GAA AAC GTG GCG GAT CAG<br>His Glu Leu Glu Leu Val Glu Asn Val Ala Asp Gln<br>                        295                      300 | 1469 |
| GTCCATCTCT TTACTTGTAT ATGTTTGGTT GTGTGTCAAG TTGCTTTACC | 1519 |
| AGCTTTTAGT GTTTTGTTTT GTCCCTGAC TCTCACTTCA TTCAG | 1564 |
| GTG GCT GTG GCT CTC TCA CAT GCT GCA ATT TTG GAA GAA TCC<br>Val Ala Val Ala Leu Ser His Ala Ala Ile Leu Glu Glu Ser<br>            305                    310               315 | 1606 |
| ATG CAC GCT CGT GAC CAG CTT ATG GAG CAG AAT TTT GCT TTA<br>Met His Ala Arg Asp Gln Leu Met Glu Gln Asn Phe Ala Leu<br>                  320                    325               330 | 1648 |
| GAC AAG GCT CGT CAA GAG GCT GAG ATG GCA GTA CAT GCT CGA<br>Asp Lys Ala Arg Gln Glu Ala Glu Met Ala Val His Ala Arg<br>                  335                    340 | 1690 |

FIG. 12B

```
AAT GAT TTC CTA GCT GTT ATG AAC CAC GAG ATG AGG ACA CCG    1732
Asn Asp Phe Leu Ala Val Met Asn His Glu Met Arg Thr Pro
345                 350                 355

ATG CAT GCC ATC ATC TCT CTT TCT TCT CTT CTC CTT GAG ACT    1774
Met His Ala Ile Ile Ser Leu Ser Ser Leu Leu Leu Glu Thr
360                 365                 370

GAG CTG TCT CCA GAG CAA AGA GTT ATG ATC GAG ACA ATA CTG    1816
Glu Leu Ser Pro Glu Gln Arg Val Met Ile Glu Thr Ile Leu
    375                 380                 385

AAA AGC AGC AAT CTT GTG GCT ACA CTA ATC AGC GAC GTT CTG    1858
Lys Ser Ser Asn Leu Val Ala Thr Leu Ile Ser Asp Val Leu
                390                 395                 400

GAT CTT TCG AGA TTG GAA GAT GGG AGC TTA CTC TTG GAA AAT    1900
Asp Leu Ser Arg Leu Glu Asp Gly Ser Leu Leu Leu Glu Asn
                405                 410

GAA CCA TTC AGT CTA CAA GCG ATC TTT GAA GAG GTAACTAAAT    1943
Glu Pro Phe Ser Leu Gln Ala Ile Phe Glu Glu
415                 420                 425

CCCCCTGATT AACCAGTGAA GTCCATTATA TATGTCTTAC ATGAATAACA    1993

TGGGCGCTTT GAATCTGCAG GTC ATC TCT TTG ATA AAG CCA ATC    2037
                      Val Ile Ser Leu Ile Lys Pro Ile
                                          430

GCA TCA GTG AAG AAA CTA TCA ACG AAT CTG ATT CTG TCT GCA    2079
Ala Ser Val Lys Lys Leu Ser Thr Asn Leu Ile Leu Ser Ala
    435                 440                 445

GAC TTA CCA ACT TAT GCT ATT GGT GAT GAG AAA CGT CTG ATG    2121
Asp Leu Pro Thr Tyr Ala Ile Gly Asp Glu Lys Arg Leu Met
        450                 455                 460

CAA ACA ATT CTT AAC ATC ATG GGC AAC GCT GTG AAA TTT ACT    2163
Gln Thr Ile Leu Asn Ile Met Gly Asn Ala Val Lys Phe Thr
                465                 470                 475

AAG GAA GGC TAC ATC TCC ATA ATA GCC TCT ATC ATG AAA CCC    2205
Lys Glu Gly Tyr Ile Ser Ile Ile Ala Ser Ile Met Lys Pro
                    480                 485

GAG TCC TTA CAA GAA TTA CCA TCT CCA GAA TTT TTT CCA GTT    2247
Glu Ser Leu Gln Glu Leu Pro Ser Pro Glu Phe Phe Pro Val
490                 495                 500

CTC AGT GAC AGT CAC TTC TAC CTA TGT GTG CAG GTTAGACCCA    2290
Leu Ser Asp Ser His Phe Tyr Leu Cys Val Gln
    505                 510

ATCTACAAAT TACTAAACTA CAAAGTTAAG CTTCTTACTG TGTTCTTACT    2340

GTTATAATCA TGGTGCAG GTG AAG GAC ACA GGG TGT GGA ATT CAC    2385
                    Val Lys Asp Thr Gly Cys Gly Ile His
                        515                 520

ACA CAA GAC ATT CCT TTG CTC TTT ACC AAA TTT GTA CAG CCT    2427
Thr Gln Asp Ile Pro Leu Leu Phe Thr Lys Phe Val Gln Pro
525                 530                 535
```

FIG. 12C

| | |
|---|---|
| CGG ACC GGA ACT CAG AGG AAC CAT TCC GGT GGA GGA CTC GGG<br>Arg Thr Gly Thr Gln Arg Asn His Ser Gly Gly Gly Leu Gly<br>540                      545                  550 | 2469 |
| CTA GCT CTC TGT AAA CGG TAACAACCC AAAAGTATAT ATAAGTTATA<br>Leu Ala Leu Cys Lys Arg<br>555 | 2516 |
| AGCAGATGGT GTTACAAATA GCTAAAAGGC AAGTTTCTGT TGATGGATGT | 2566 |
| CTCTGGTTAG G TTT GTC GGG CTA ATG GGA GGA TAC ATG TGG<br>              Phe Val Gly Leu Met Gly Gly Tyr Met Trp<br>                      560                  565 | 2607 |
| ATA GAA AGT GAA GGC CTA GAG AAA GGC TGC ACA GCT TCG TTC<br>Ile Glu Ser Glu Gly Leu Glu Lys Gly Cys Thr Ala Ser Phe<br>570                      575                  580 | 2649 |
| ATC ATC AGG CTT GGT ATC TGC AAC GGT CCA AGC AGT AGC AGT<br>Ile Ile Arg Leu Gly Ile Cys Asn Gly Pro Ser Ser Ser Ser<br>            585                  590                  595 | 2691 |
| GGT TCA ATG GCG CTA CAT CTT GCA GCT AAA TCA CAA ACC AGA<br>Gly Ser Met Ala Leu His Leu Ala Ala Lys Ser Gln Thr Arg<br>                600                      605 | 2733 |
| CCG TGG AAC TGG TGATACTTAC GTTGGAAAGA CTTGTATTGA<br>Pro Trp Asn Trp<br>610 | 2775 |
| GGTGAGACTT TTTAACTACA CAGCAGCAAG AGAAAGAAGA AAATACATGA | 2825 |
| CCGGACGGTG TGATCTAACT TATTGGATTT TGTTGGATGT AATATGTAAA | 2875 |
| ATAAAAATCC TATATACGGG GAGAGGTACC TTATCTGTTC TCACTATATT | 2925 |
| TTATTGAACA TTACTTTAGA GAATATGTTT TGGAATTCAC TACTAAATAA | 2975 |
| ACGATATAAA TCTTCACGAA AAGAGCAACA TTTT | 3009 |

FIG. 12D

```
AAAAAAATCA TCAAAAACTT TTACCTCTCA TTGGTTTCTT CTTTATCACA                                    50

CTGTTACGCT TGGATTCTCA TTTCTTCAAG TTCATAACGC TCGGATCAAT                                   100

CAGGAAGACG AACTTGAACT TTCTTTTTTT CATCATTACC CAAAGCTATG                                   150

AGGCTCACAC CACCAATACG TCCGCCGTCA TGAATCCTTC TCTTCCAGGT                                   200

CAACACAAGT CAGAGCTCCA AAA ATG GAG TCA TGC GAT TGT TTT                                    244
                         Met Glu Ser Cys Asp Cys Phe
                          1                   5

GAG ACG CAT GTG AAT CAA GAT GAT CTG TTA GTG AAG TAC CAA                                  286
Glu Thr His Val Asn Gln Asp Asp Leu Leu Val Lys Tyr Gln
             10              15                  20

TAC ATC TCA GAT GCG TTG ATT GCT CTT GCA TAC TTC TCA ATC                                  328
Tyr Ile Ser Asp Ala Leu Ile Ala Leu Ala Tyr Phe Ser Ile
             25              30                  35

CCA CTC GAG CTT ATC TAT TTC GTG CAA AAG TCT GCT TTC TTC                                  370
Pro Leu Glu Leu Ile Tyr Phe Val Gln Lys Ser Ala Phe Phe
             40              45

CCT TAC AAA TGG GTG CTT ATG CAG TTT GGA GCC TTT ATC ATT                                  412
Pro Tyr Lys Trp Val Leu Met Gln Phe Gly Ala Phe Ile Ile
 50              55              60

CTC TGT GGA GCT ACG CAT TTC ATC AAC CTA TGG ATG TTC TTC                                  454
Leu Cys Gly Ala Thr His Phe Ile Asn Leu Trp Met Phe Phe
     65              70                  75

ATG CAT TCC AAA GCC GTT GCC ATT GTC ATG ACT ATT GCT AAA                                  496
Met His Ser Lys Ala Val Ala Ile Val Met Thr Ile Ala Lys
             80              85                  90

GTC TCT TGC GCG GTT GTG TCG TGT GCT ACC GCG TTG ATG TTG                                  538
Val Ser Cys Ala Val Val Ser Cys Ala Thr Ala Leu Met Leu
             95              100                 105

GTT CAT ATT ATT CCT GAT CTT CTC AGT GTT AAG AAC AGG GAA                                  580
Val His Ile Ile Pro Asp Leu Leu Ser Val Lys Asn Arg Glu
                 110             115

TTG TTT CTC AAG AAG AAA GCT GAT GAG TTA GAT AGA GAA ATG                                  622
Leu Phe Leu Lys Lys Lys Ala Asp Glu Leu Asp Arg Glu Met
120             125                 130

GGT CTT ATT TTA ACA CAA GAG GAG ACT GGT AGG CAT GTT AGG                                  664
Gly Leu Ile Leu Thr Gln Glu Glu Thr Gly Arg His Val Arg
    135                 140             145

ATG CTT ACT CAT GGA ATT AGA AGA ACT CTT GAT AGG CAT ACT                                  706
Met Leu Thr His Gly Ile Arg Arg Thr Leu Asp Arg His Thr
            150             155             160

ATT TTA AGA ACC ACT CTT GTT GAG CTT GGT AAA ACT CTT TGT                                  748
Ile Leu Arg Thr Thr Leu Val Glu Leu Gly Lys Thr Leu Cys
                165             170                 175
```

FIG. 13A

| | | | | | | | | | | | | | |
|---|---|---|---|---|---|---|---|---|---|---|---|---|---|
| CTT | GAG | GAA | TGT | GCG | TTG | TGG | ATG | CCT | TCT | CAA | AGT | GGT | TTA | 790 |
| Leu | Glu | Glu | Cys | Ala | Leu | Trp | Met | Pro | Ser | Gln | Ser | Gly | Leu | |
| | | | 180 | | | | | | 185 | | | | | |

```
CTT GAG GAA TGT GCG TTG TGG ATG CCT TCT CAA AGT GGT TTA    790
Leu Glu Glu Cys Ala Leu Trp Met Pro Ser Gln Ser Gly Leu
            180                     185

TAT TTG CAG CTT TCT CAT ACT TTG AGT CAT AAA ATA CAA GTT    832
Tyr Leu Gln Leu Ser His Thr Leu Ser His Lys Ile Gln Val
190                 195                 200

GGA AGC AGT GTG CCG ATA AAT CTC CCG ATT ATT AAT GAA CTC    874
Gly Ser Ser Val Pro Ile Asn Leu Pro Ile Ile Asn Glu Leu
        205                 210                 215

TTC AAT AGC GCT CAA GCT ATG CAC ATA CCT CAT TCT TGT CCT    916
Phe Asn Ser Ala Gln Ala Met His Ile Pro His Ser Cys Pro
            220                 225                 230

TTG GCT AAG ATT GGG CCT CCG GTT GGG AGA TAT TCA CCT CCT    958
Leu Ala Lys Ile Gly Pro Pro Val Gly Arg Tyr Ser Pro Pro
                235                 240                 245

GAG GTT GTT TCT GTC CGT GTT CCT CTT TTA CAT CTC TCT AAT   1000
Glu Val Val Ser Val Arg Val Pro Leu Leu His Leu Ser Asn
                250                 255

TTC CAA GGC AGT GAC TGG TCG GAT CTC TCT GGC AAA GGT TAC   1042
Phe Gln Gly Ser Asp Trp Ser Asp Leu Ser Gly Lys Gly Tyr
260                 265                 270

GCT ATC ATG GTC CTG ATT CTC CCA ACC GAT GGT GCA AGA AAA   1084
Ala Ile Met Val Leu Ile Leu Pro Thr Asp Gly Ala Arg Lys
    275                 280                 285

TGG AGA GAC CAT GAG TTA GAG CTT GTA GAA AAC GTG GCG GAT   1126
Trp Arg Asp His Glu Leu Glu Leu Val Glu Asn Val Ala Asp
        290                 295                 300

CAG GTG GCT GTG GCT CTC TCA CAT GCT GCA ATT TTG GAA GAA   1168
Gln Val Ala Val Ala Leu Ser His Ala Ala Ile Leu Glu Glu
            305                 310                 315

TCC ATG CAC GCT CGT GAC CAG CTT ATG GAG CAG AAT TTT GCT   1210
Ser Met His Ala Arg Asp Gln Leu Met Glu Gln Asn Phe Ala
                320                 325

TTA GAC AAG GCT CGT CAA GAG GCT GAG ATG GCA GTA CAT GCT   1252
Leu Asp Lys Ala Arg Gln Glu Ala Glu Met Ala Val His Ala
330                 335                 340

CGA AAT GAT TTC CTA GCT GTT ATG AAC CAC GAG ATG AGG ACA   1294
Arg Asn Asp Phe Leu Ala Val Met Asn His Glu Met Arg Thr
    345                 350                 355

CCG ATG CAT GCC ATC ATC TCT CTT TCT TCT CTT CTT CTT GAG   1336
Pro Met His Ala Ile Ile Ser Leu Ser Ser Leu Leu Leu Glu
        360                 365                 370

ACT GAG CTG TCT CCA GAG CAA AGA GTT ATG ATC GAG ACA ATA   1378
Thr Glu Leu Ser Pro Glu Gln Arg Val Met Ile Glu Thr Ile
            375                 380                 385
```

*FIG. 13B*

```
CTG AAA AGC AGC AAT CTT GTG GCT ACA CTA ATC AGC GAC GTT       1420
Leu Lys Ser Ser Asn Leu Val Ala Thr Leu Ile Ser Asp Val
            390                 395

CTG GAT CTT TCG AGA TTG GAA GAT GGG AGC TTA CTC TTG GAA       1462
Leu Asp Leu Ser Arg Leu Glu Asp Gly Ser Leu Leu Leu Glu
400             405                 410

AAT GAA CCA TTC AGT CTA CAA GCG ATC TTT GAA GAG GTC ATC       1504
Asn Glu Pro Phe Ser Leu Gln Ala Ile Phe Glu Glu Val Ile
        415                 420             425

TCT TTG ATA AAG CCA ATC GCA TCA GTG AAG AAA CTA TCA ACG       1546
Ser Leu Ile Lys Pro Ile Ala Ser Val Lys Lys Leu Ser Thr
            430                 435             440

AAT CTG ATT CTG TCT GCA GAC TTA CCA ACT TAT GCT ATT GGT       1588
Asn Leu Ile Leu Ser Ala Asp Leu Pro Thr Tyr Ala Ile Gly
                445                 450                 455

GAT GAG AAA CGT CTG ATG CAA ACA ATT CTT AAC ATC ATG GGC       1630
Asp Glu Lys Arg Leu Met Gln Thr Ile Leu Asn Ile Met Gly
                    460                 465

AAC GCT GTG AAA TTT ACT AAG GAA GGC TAC ATC TCC ATA ATA       1672
Asn Ala Val Lys Phe Thr Lys Glu Gly Tyr Ile Ser Ile Ile
470             475                 480

GCC TCT ATC ATG AAA CCC GAG TCC TTA CAA GAA TTA CCA TCT       1714
Ala Ser Ile Met Lys Pro Glu Ser Leu Gln Glu Leu Pro Ser
        485                 490                 495

CCA GAA TTT TTT CCA GTT CTC AGT GAC AGT CAC TTC TAC CTA       1756
Pro Glu Phe Phe Pro Val Leu Ser Asp Ser His Phe Tyr Leu
            500                 505                 510

TGT GTG CAG GTG AAG GAC ACA GGG TGT GGA ATT CAC ACA CAA       1798
Cys Val Gln Val Lys Asp Thr Gly Cys Gly Ile His Thr Gln
                515                 520                 525

GAC ATT CCT TTG CTC TTT ACC AAA TTT GTA CAG CCT CGG ACC       1840
Asp Ile Pro Leu Leu Phe Thr Lys Phe Val Gln Pro Arg Thr
                    530                 535

GGA ACT CAG AGG AAC CAT TCC GGT GGA GGA CTC GGG CTA GCT       1882
Gly Thr Gln Arg Asn His Ser Gly Gly Gly Leu Gly Leu Ala
540             545                 550

CTC TGT AAA CGG TTT GTC GGG CTA ATG GGA GGA TAC ATG TGG       1924
Leu Cys Lys Arg Phe Val Gly Leu Met Gly Gly Tyr Met Trp
    555                 560                 565

ATA GAA AGT GAA GGC CTA GAG AAA GGC TGC ACA GCT TCG TTC       1966
Ile Glu Ser Glu Gly Leu Glu Lys Gly Cys Thr Ala Ser Phe
        570                 575                 580

ATC ATC AGG CTT GGT ATC TGC AAC GGT CCA AGC AGT AGC AGT       2008
Ile Ile Arg Leu Gly Ile Cys Asn Gly Pro Ser Ser Ser Ser
            585                 590                 595
```

FIG. 13C

```
GGT TCA ATG GCG CTA CAT CTT GCA GCT AAA TCA CAA ACC AGA              2050
Gly Ser Met Ala Leu His Leu Ala Ala Lys Ser Gln Thr Arg
                600                 605
CCG TGG AAC TGG TGATACTTAC GTTGGAAAGA CTTGTATTGA                     2092
Pro Trp Asn Trp
610

GGTGAGACTT TTTAACTACA CAGCAGCAAG AGAAAGAAGA AAATACATGA               2142

CCGGACGGTG TGATCTAACT TATTGGATTT TGTTGGATGT AATATGTAAA               2192

ATAAAAATCC TATATACGGG GAGAGGTACC TTATCTGTTC TCACTATATT               2242

TTATTGAACA TTACTTTAGA GAATATGTTT TGGAATTCAC TACTAAATAA               2292

ACGATATAAA TCTTCACGAA AA                                             2314
```

FIG. 13D

```
GAATTCGAAC TGCAATGGGA TAAACATTAT ATGCGTTTTA ATAATAGGTT      50
GGTGAAGTTT ATAATTTACA CCATTTGAAA AGCCTTCCAA ATTTAGAAAC     100
TACATTTTTG CAGACCCATG TGAGCTCATA TGAATCAATC ATAGCCTTGA     150
TGTTGTAAAA CAAATTATGA TTATAAAAAT GTGATAGTAT ATTACATGCA     200
TAAAAAATAA AGGAGAGTAA ATGAAAGTCA AATCTGGGTT TTATGAACTG     250
AAAGTTGAAG TTTAGAAGTA GAAGTAGCGA TCAAAGTATG ACCAGTTAAA     300
AGGCCCAATA TCATTTGGAG GTTTGATTTT TGGGTTCGTA AATTTCAAGA     350
GCCAGATTAT GATTTGCTGG GCTTAAAAAT CATGGAAAAA TTGAAATGAC     400
GGTGTTAAAA TATATAACTC AAATTAAAGA TTTTAATTGG GTGTAGTAGG     450
CTGATTTTTT TATAAGAATC TTGTCTATAG ATGCTTCAAG GTTATGCCTT     500
ATAGTACTGG TTGTAAAACA CCACTATCTA ATTTTGAAGC TGGTCAGAAC     550
TATAAGGTAT GTTGTTGTTC GCCTTGTTGC TAATGAAGAT TATAACATTC     600
TGTTGTTGCA TTTTTTTTTT TTTTTTGTG TTAAATATAT ATATTTTTT      650
TGCATATTTA TTGTTGCATA TTGTGTTGCA TATTTAGTAA TGGTTACATT     700
CCCTGTTATC GGAGACCAAG ATAATACGGC TCTGTGGCAT GGACTACTAC     750
TCCATGGATT CTTCCAAGTA ATCTTGCTTT GTGTGTCAAT GCAAAGTTTG     800
TTTATCTTAA GGTTCGTCAA CAACACTGGA AAAGTCTACA TTGTTGCTGA     850
ATCTCGGTTG TCATCGCTTC CTAGTGATAA GCCTAAGGCC GGCTTAACTA     900
ATGGAACTTA CTAGTGATAC CATAATGCGA AAGGTGCTAA TTAAGCTTGA     950
CAGTGAAGAG GATTCTTATC AAGTTTTGGA AAATTTTAAT GGAGATTCCT    1000
TGGTTGGGAA GAAGTATGAA CCTTGTTTG ATTACTTTTA GCGATTTCTC    1050
AAGTGTGACT TTTCGACTAG TAGCAGATGA TTATGTCATG AATGATAGTG    1100
GTACTGGTAT TGTCCATTGT GCTCCTGTCT TTGGTGCAGA TGACTATCGT    1150
GTTTGTCTTG AGAACGAGAT AATTAAGAAG GTTAGATTTG ACAACATCTT    1200
CCTTATATCA CCACCTTTAA CATTAAGTTT ATTTCTTTC TTGTTTAAGT    1250
TTACAGTATC TTCAAGAACC CATGTTCATG ACACATTTTG TTCATGTGTT    1300
GTTTAGATTG TCAGAGATTT CAAACGTCCA GATGGTTTGA AAGATACAGA    1350
GATTGATGCA GCTGTAGATA GTACATATCT TAATTAAAAA TACCACTTCT    1400
CTATGCTCTA TTGTTGAGGA AACATATAAT ATTTGCATTC GTTCATGGTT    1450
CAGATATGAT GTTATGGTAA TTCTTGATCT ACGAGAAGAT GAATCTTTGA    1500
AAAACGAAGG TGTTGCCCGT GAGGTAAATA AATGTAACCG AAGCGATTAA    1550
TGGTCATATA TAAGTTGTAT ATTTGATATA TGGGTTTCCT TCTCATTGTG    1600
```

*FIG. 14A*

| | | | | | |
|---|---|---|---|---|---|
| CTCATGCATT | GAAAAGCACC | CTGTTATGAC | TGTGGTTCTA | GGAGAACATT | 1650 |
| TGCATTTGAC | AGTCGGTGAC | TAATTGTTAA | GCAAGAAGAA | CGCATGAGAG | 1700 |
| CCTTTTAAAG | TGTTTTCTTC | TAGATCGTTG | CAAAAAGTTA | AATGTCTCTT | 1750 |
| GAGACTTTGT | ACTCATTCTA | TAGATAAAGA | TGGGATTTAT | TACAAAAACA | 1800 |
| ACAAGAAACT | TGTTACTTG | TGGAAATTCA | AAATTATCCG | AACTAGCTTC | 1850 |
| ACAAAATATG | CTCAAGAGTT | TCAATGTATT | TTTTTTTGTT | CTGTAATTGT | 1900 |
| ATGACTCCGT | TGAAGCATC | AAGATTATGG | TTATAGGTAG | TGATGCTAAA | 1950 |
| ACTCTCTGTT | GTTACAGTGA | CCACTAAAAA | CACCAACAAA | AAAAACTTAG | 2000 |
| GTAACGTGTC | GTCTAAAAAC | TTCTAGGTTC | AATTTCTTTA | GATAGTACTA | 2050 |
| TCAATAAATA | AAATAAATAT | GTACAAAGGC | TTTAAACAAT | GATGTTTTTC | 2100 |
| AAAGATGATT | GGTAGATACT | AATTAGAGCT | TCAATATAAA | AGAACACATG | 2150 |
| CGATTCTGAC | ATTCTGTGGT | CTAACATGGT | TTCTTCTAGA | GTCAAAACCA | 2200 |
| TACAATTAAA | AGTTAGGAAA | GTAATAGCAA | TGTGGTTTCA | AATATATACT | 2250 |
| CATTACTCTT | TAGATTCATG | TATGGTGAAG | GAAACATTAT | AATAAAATCA | 2300 |
| AAGATCACAG | TTTTGTAGGT | CCCTCATATT | AATCAACATC | TTAAGGCGTT | 2350 |
| ATACATATCT | TCTTTTTGTA | AATATTTGAC | TAATTAAAAT | ATCTAATTAG | 2400 |
| AGTATTAGAC | TAATCTCATC | AAATATCCGA | CTACTTGTGT | CAGTTCAAAA | 2450 |
| CACAGTGATT | ACGTTAGATT | TTGTGCTCTT | TTGTTTATAA | ACAAAGCTAA | 2500 |
| TTTAAGAAAT | ATATGATCTA | TTTGCCTCCT | TGGTCTTAAT | TTTATACTTT | 2550 |
| CTTGGAATAA | AACACATTTA | TTAAAATAAT | TTTTAGGGTC | CTAGATTCAT | 2600 |
| GTCATGTGGC | TTGATAGTTT | CCAACAATTA | TACCAATATT | TTACTCATTC | 2650 |
| ATATACAAAT | AAACAAGCTT | TATTCTATTC | TTCAGTCTCA | TGATATACGG | 2700 |
| GATTTTGATA | AAATTCAGAG | TACCCATTAA | TTATTCTATG | TTACAGCTTG | 2750 |
| TAATAAGTTA | AATTTATAAA | ACGTACAAGT | TGAGGAAATA | ACAAATGTTT | 2800 |
| TCAATATTAA | ATGATTTATT | AATACATTAG | TGACCAAAAA | ATTATTAAGT | 2850 |
| GTAAGAAAAA | AAACACAACT | CAGAAAAAAT | TCAAAAGACC | GTCTAAGTTC | 2900 |
| GGTTCATGTA | AGAACAAGTG | GGACCTCTTT | AAGTTTCTAA | ATCAGAGAAT | 2950 |
| AAAGAAGAAG | AAAAAATCTC | AAAACCTTCC | TCTAAAACCA | ACGGCTCCTA | 3000 |
| CCTTTACTTA | CACCCTATAC | ATACACTTCT | CTTTTTATCC | TCCATCGGCG | 3050 |
| GCTTATGGCG | GTTTTCCGGC | ACTAATCATC | TCCGGCATAT | ATAAATAAAC | 3100 |
| GTACTTCACG | TTTTTTTATA | TAACTTCAAA | GTAGTTTCAG | ATTTGTCTCT | 3150 |
| ATCTCTTCAC | TTTTAAGTCT | TCTGGTTTTG | TCATCACCAG | CTTTTTTTGT | 3200 |
| TCTCTCTCTG | TCTCTGTCTC | TGTCTTTCTC | TTTGTGTATT | TTATTCTCG | 3250 |

*FIG. 14B*

```
TCATCGTTGT TCTTCTATGA GAGGAAGATC GGAATGTCGA AGAGAATTAG      3300

AAGATTCTCG TACATCACTT CGTTGGAATT TCACAGGTCG ATGAGAGATC      3350

TGAGAACTGT TTCATTTTGA TCCAAACTCA TCTCTTTCAG GTATTCCAAA      3400

TTTGTCTTTC TCTGTTCTTT CTACTATTAC CCAAATTAAA GTTTTGATTT      3450

TTATTTCTCA CTCTGTTTCT TGTTTTTCTA ATTGCAGAGT ATAATGGACT      3500

AAGCATTTTT TTTCTCCGAA G ATG GTT AAA GAA ATA GCT TCT TGG     3545
                        Met Val Lys Glu Ile Ala Ser Trp
                         1               5

TTA TTG ATA CTA TCA ATG GTG GTG TTT GTT TCT CCG GTT TTA     3587
Leu Leu Ile Leu Ser Met Val Val Phe Val Ser Pro Val Leu
         10              15                  20

GCT ATA AAC GGC GGT GGT TAT CCA CGA TGT AAC TGC GAA GAC     3629
Ala Ile Asn Gly Gly Gly Tyr Pro Arg Cys Asn Cys Glu Asp
             25              30                  35

GAA GGA AAC AGT TTC TGG AGT ACA GAG AAC ATT CTA GAA ACT     3671
Glu Gly Asn Ser Phe Trp Ser Thr Glu Asn Ile Leu Glu Thr
             40              45                  50

CAA AGA GTA AGC GAT TTC TTA ATC GCA GTA GCT TAT TTC TCA     3713
Gln Arg Val Ser Asp Phe Leu Ile Ala Val Ala Tyr Phe Ser
             55              60

ATC CCT ATT GAG TTA CTT TAC TTC GTG AGT TGT TCC AAT GTT     3755
Ile Pro Ile Glu Leu Leu Tyr Phe Val Ser Cys Ser Asn Val
65              70              75

CCA TTC AAA TGG GTT CTC TTT GAG TTT ATC GCC TTC ATT GTT     3797
Pro Phe Lys Trp Val Leu Phe Glu Phe Ile Ala Phe Ile Val
         80              85                  90

CTT TGT GGT ATG ACT CAT CTT CTT CAT GGT TGG ACT TAC TCT     3839
Leu Cys Gly Met Thr His Leu Leu His Gly Trp Thr Tyr Ser
             95              100                 105

GCT CAT CCA TTT AGA TTA ATG ATG GCG TTT ACT GTT TTC AAG     3881
Ala His Pro Phe Arg Leu Met Met Ala Phe Thr Val Phe Lys
             110             115                 120

ATG TTG ACT GCT TTA GTC TCT TGT GCT ACT GCG ATT ACG CTT     3923
Met Leu Thr Ala Leu Val Ser Cys Ala Thr Ala Ile Thr Leu
             125             130

ATT ACT TTG ATT CCT CTG CTT TTG AAA GTT AAA GTT AGA GAG     3965
Ile Thr Leu Ile Pro Leu Leu Leu Lys Val Lys Val Arg Glu
135             140             145

TTT ATG CTT AAG AAG AAA GCT CAT GAG CTT GGT CGT GAA GTT     4007
Phe Met Leu Lys Lys Lys Ala His Glu Leu Gly Arg Glu Val
         150             155             160

GGT TTG ATT TTG ATT AAG AAA GAG ACT GGC TTT CAT GTT CGT     4049
Gly Leu Ile Leu Ile Lys Lys Glu Thr Gly Phe His Val Arg
             165             170             175
```

*FIG. 14C*

```
ATG CTT ACT CAA GAG ATT CGT AAG TCT TTG GAT CGT CAT ACG    4091
Met Leu Thr Gln Glu Ile Arg Lys Ser Leu Asp Arg His Thr
            180                 185                 190

ATT CTT TAT ACT ACT TTG GTT GAG CTT TCG AAG ACT TTA GGG    4133
Ile Leu Tyr Thr Thr Leu Val Glu Leu Ser Lys Thr Leu Gly
                195                 200

TTG CAG AAT TGT GCG GTT TGG ATG CCG AAT GAC GGT GGA ACG    4175
Leu Gln Asn Cys Ala Val Trp Met Pro Asn Asp Gly Gly Thr
205                     210                 215

GAG ATG GAT TTG ACT CAT GAG TTG AGA GGG AGA GGT GGT TAT    4217
Glu Met Asp Leu Thr His Glu Leu Arg Gly Arg Gly Gly Tyr
    220                 225                 230

GGT GGT TGT TCT GTT TCT ATG GAG GAT TTG GAT GTT GTT AGG    4259
Gly Gly Cys Ser Val Ser Met Glu Asp Leu Asp Val Val Arg
        235                 240                 245

ATT AGG GAG AGT GAT GAA GTG AAT GTG TTG AGT GTT GAC TCG    4301
Ile Arg Glu Ser Asp Glu Val Asn Val Leu Ser Val Asp Ser
            250                 255                 260

TCC ATT GCT CGA GCT AGT GGT GGT GGT GGG GAT GTT AGT GAG    4343
Ser Ile Ala Arg Ala Ser Gly Gly Gly Gly Asp Val Ser Glu
                265                 270

ATT GGT GCC GTG GCT GCT ATT AGA ATG CCG ATG CTT CGT GTT    4385
Ile Gly Ala Val Ala Ala Ile Arg Met Pro Met Leu Arg Val
275                     280                 285

TCG GAT TTT AAT GGA GAG CTA AGT TAT GCG ATA CTT GTT TGT    4427
Ser Asp Phe Asn Gly Glu Leu Ser Tyr Ala Ile Leu Val Cys
    290                 295                 300

GTT TTA CCG GGC GGG ACC CGT CGG GAT TGG ACT TAT CAG GAG    4469
Val Leu Pro Gly Gly Thr Arg Arg Asp Trp Thr Tyr Gln Glu
        305                 310                 315

ATT GAG ATT GTT AAA GTT GTG GCG GAT CAA GTA ACC GTT GCG    4511
Ile Glu Ile Val Lys Val Val Ala Asp Gln Val Thr Val Ala
            320                 325                 330

TTA GAT CAT GCA GCG GTT CTT GAA GAG TCT CAG CTT ATG AGG    4553
Leu Asp His Ala Ala Val Leu Glu Glu Ser Gln Leu Met Arg
                335                 340

GAG AAG CTG GCG GAA CAG AAC AGG GCG TTG CAG ATG GCG AAG    4595
Glu Lys Leu Ala Glu Gln Asn Arg Ala Leu Gln Met Ala Lys
345                     350                 355

AGA GAC GCG TTG AGA GCG AGC CAA GCG AGG AAT GCG TTT CAG    4637
Arg Asp Ala Leu Arg Ala Ser Gln Ala Arg Asn Ala Phe Gln
    360                 365                 370

AAA ACG ATG AGC GAA GGG ATG AGG CGT CCT ATG CAT TCG ATA    4679
Lys Thr Met Ser Glu Gly Met Arg Arg Pro Met His Ser Ile
        375                 380                 385

CTC GGT CTT TTG TCG ATG ATT CAG GAC GAG AAG TTG AGT GAC    4721
Leu Gly Leu Leu Ser Met Ile Gln Asp Glu Lys Leu Ser Asp
            390                 395                 400
```

FIG. 14D

```
GAG CAG AAA ATG ATT GTT GAT ACG ATG GTT AAA ACA GGG AAT    4763
Glu Gln Lys Met Ile Val Asp Thr Met Val Lys Thr Gly Asn
            405             410

GTT ATG TCG AAT TTG GTG GGG GAC TCT ATG GAT GTG CCT GAC    4805
Val Met Ser Asn Leu Val Gly Asp Ser Met Asp Val Pro Asp
415             420             425

GGT AGA TTT GGT ACG GAG ATG AAA CCG TTT AGT CTG CAT CGT    4847
Gly Arg Phe Gly Thr Glu Met Lys Pro Phe Ser Leu His Arg
        430             435             440

ACG ATC CAT GAA GCA GCT TGT ATG GCG AGA TGT TTG TGT CTA    4889
Thr Ile His Glu Ala Ala Cys Met Ala Arg Cys Leu Cys Leu
            445             450             455

TGC AAT GGA ATT AGG TTC TTG GTT GAC GCG GAG AAG TCT CTA    4931
Cys Asn Gly Ile Arg Phe Leu Val Asp Ala Glu Lys Ser Leu
            460             465             470

CCT GAT AAT GTA GTA GGT GAT GAA AGA AGG GTC TTT CAA GTG    4973
Pro Asp Asn Val Val Gly Asp Glu Arg Arg Val Phe Gln Val
            475             480

ATA CTT CAT ATG GTT GGT AGT TTA GTA AAG CCT AGA AAA CGT    5015
Ile Leu His Met Val Gly Ser Leu Val Lys Pro Arg Lys Arg
485             490             495

CAA GAA GGA TCT TCA TTG ATG TTT AAG GTT TTG AAA GAA AGA    5057
Gln Glu Gly Ser Ser Leu Met Phe Lys Val Leu Lys Glu Arg
    500             505             510

GGA AGC TTG GAT AGG AGT GAT CAT AGA TGG GCT GCT TGG AGA    5099
Gly Ser Leu Asp Arg Ser Asp His Arg Trp Ala Ala Trp Arg
        515             520             525

TCA CCG GCT TCT TCA GCA GAT GGA GAT GTG TAT ATA AGA TTT    5141
Ser Pro Ala Ser Ser Ala Asp Gly Asp Val Tyr Ile Arg Phe
            530             535             540

GAA ATG AAT GTA GAG AAT GAT GAT TCA AGT TCT CAA TCA TTT    5183
Glu Met Asn Val Glu Asn Asp Asp Ser Ser Ser Gln Ser Phe
            545             550

GCT TCT GTT TCC TCC AGA GAT CAA GAA GTT GGT GAT GTT AGA    5225
Ala Ser Val Ser Ser Arg Asp Gln Glu Val Gly Asp Val Arg
555             560             565

TTC TCC GGC GGC TAT GGG TTA GGA CAA GAT CTA AGC TTT GGT    5266
Phe Ser Gly Gly Tyr Gly Leu Gly Gln Asp Leu Ser Phe Gly
    570             575             580

GTT TGT AAG AAA GTG GTG CAG GTGAGTTTCC TTACATATCT          5316
Val Cys Lys Lys Val Val Gln
            585

CTTTCTAAAG TTCCTGTCAT TAGTCTGAGT TTCTGTTTAG GAGTTCTTTG     5359
```

FIG. 14E

```
ATAATGTGTG CAG TTG ATT CAT GGG AAT ATC TCG GTG GTC CCT          5401
           Leu Ile His Gly Asn Ile Ser Val Val Pro
           590                 595

GGC TCG GAT GGT TCA CCG GAG ACC ATG TCG TTG CTC CTT CGG          5443
Gly Ser Asp Gly Ser Pro Glu Thr Met Ser Leu Leu Leu Arg
600             605                 610

TTT CGA CGT AGA CCC TCC ATA TCT GTC CAT GGA TCC AGC GAG          5485
Phe Arg Arg Arg Pro Ser Ile Ser Val His Gly Ser Ser Glu
    615             620                 625

TCG CCA GCT CCT GAC CAC CAC GCT CAC CCA CAT TCG AAT TCT          5527
Ser Pro Ala Pro Asp His His Ala His Pro His Ser Asn Ser
        630             635                 640

CTG TTA CGT GGC TTA CAA GTT TTA TTG GTA GAC ACC AAC GAT          5569
Leu Leu Arg Gly Leu Gln Val Leu Leu Val Asp Thr Asn Asp
            645             650                 655

TCG AAC CGG GCA GTT ACA CGT AAA CTC TTA GAG AAA CTC GGG          5611
Ser Asn Arg Ala Val Thr Arg Lys Leu Leu Glu Lys Leu Gly
                660             665

TGC GAT GTA ACC GCG GTT TCC TCT GGA TTC GAT TGC CTT ACC          5653
Cys Asp Val Thr Ala Val Ser Ser Gly Phe Asp Cys Leu Thr
670             675                 680

GCC ATT GCT CCC GGC TCG TCC TCG CCT TCT ACT TCG TTT CAA          5695
Ala Ile Ala Pro Gly Ser Ser Ser Pro Ser Thr Ser Phe Gln
    685             690                 695

GTG GTG GTG CTT GAT CTT CAA ATG GCA GAG ATG GAC GGT TAT          5737
Val Val Val Leu Asp Leu Gln Met Ala Glu Met Asp Gly Tyr
        700             705                 710

GAA GTG GCC ATG AGG ATC AGG AGT CGA TCT TGG CCG TTG ATT          5779
Glu Val Ala Met Arg Ile Arg Ser Arg Ser Trp Pro Leu Ile
            715             720                 725

GTG GCG ACG ACA GTG AGC TTG GAT GAA GAA ATG TGG GAC AAG          5821
Val Ala Thr Thr Val Ser Leu Asp Glu Glu Met Trp Asp Lys
                730             735

TGT GCA CAG ATT GGA ATC AAT GGA GTT GTG AGA AAG CCA GTG          5863
Cys Ala Gln Ile Gly Ile Asn Gly Val Val Arg Lys Pro Val
740             745                 750

GTG TTA AGA GCT ATG GAG AGT GAG CTC CGA AGA GTA TTG TTG          5905
Val Leu Arg Ala Met Glu Ser Glu Leu Arg Arg Val Leu Leu
    755             760                 765

CAA GCT GAC CAA CTT CTC TAAGTTGTTA TCTCAACTTC TCTTCTACAT         5953
Gln Ala Asp Gln Leu Leu
        770

TCAAAATTTT TACACCATAG ATTTATGTCA AATATATCAA AATGAAATTT           6003

CGAAATTGTT ATTATATATA CCACCCATAT CTCTATGATT TGTACATCCT           6053

GTTTTTTTTT GTTCTTTTTC TCATTTTGAA CCCCACGAAA TTGCATTGAA           6103

TCTTAGTATT TCGTAGGGTC AAGAAGGAGT CAGTTTCGTA GTTTTTTGTT           6153

TTCTTTATGT TACGAACTTA CGAAACTGAA TATGGCATTA TAGAGTTTT            6202
```

*FIG. 14F*

```
ATG GTT AAA GAA ATA GCT TCT TGG TTA TTG ATA CTA TCA ATG        42
Met Val Lys Glu Ile Ala Ser Trp Leu Leu Ile Leu Ser Met
 1           5                   10

GTG GTG TTT GTT TCT CCG GTT TTA GCT ATA AAC GGC GGT GGT        84
Val Val Phe Val Ser Pro Val Leu Ala Ile Asn Gly Gly Gly
15              20                  25

TAT CCA CGA TGT AAC TGC GAA GAC GAA GGA AAC AGT TTC TGG       126
Tyr Pro Arg Cys Asn Cys Glu Asp Glu Gly Asn Ser Phe Trp
         30                  35                  40

AGT ACA GAG AAC ATT CTA GAA ACT CAA AGA GTA AGC GAT TTC       168
Ser Thr Glu Asn Ile Leu Glu Thr Gln Arg Val Ser Asp Phe
             45                  50                  55

TTA ATC GCA GTA GCT TAT TTC TCA ATC CCT ATT GAG TTA CTT       210
Leu Ile Ala Val Ala Tyr Phe Ser Ile Pro Ile Glu Leu Leu
                 60                  65                  70

TAC TTC GTG AGT TGT TCC AAT GTT CCA TTC AAA TGG GTT CTC       252
Tyr Phe Val Ser Cys Ser Asn Val Pro Phe Lys Trp Val Leu
                 75                  80

TTT GAG TTT ATC GCC TTC ATT GTT CTT TGT GGT ATG ACT CAT       294
Phe Glu Phe Ile Ala Phe Ile Val Leu Cys Gly Met Thr His
 85                  90                  95

CTT CTT CAT GGT TGG ACT TAC TCT GCT CAT CCA TTT AGA TTA       336
Leu Leu His Gly Trp Thr Tyr Ser Ala His Pro Phe Arg Leu
    100                 105                 110

ATG ATG GCG TTT ACT GTT TTC AAG ATG TTG ACT GCT TTA GTC       378
Met Met Ala Phe Thr Val Phe Lys Met Leu Thr Ala Leu Val
        115                 120                 125

TCT TGT GCT ACT GCG ATT ACG CTT ATT ACT TTG ATT CCT CTG       420
Ser Cys Ala Thr Ala Ile Thr Leu Ile Thr Leu Ile Pro Leu
            130                 135                 140

CTT TTG AAA GTT AAA GTT AGA GAG TTT ATG CTT AAG AAG AAA       462
Leu Leu Lys Val Lys Val Arg Glu Phe Met Leu Lys Lys Lys
                145                 150

GCT CAT GAG CTT GGT CGT GAA GTT GGT TTG ATT TTG ATT AAG       504
Ala His Glu Leu Gly Arg Glu Val Gly Leu Ile Leu Ile Lys
155                 160                 165

AAA GAG ACT GGC TTT CAT GTT CGT ATG CTT ACT CAA GAG ATT       546
Lys Glu Thr Gly Phe His Val Arg Met Leu Thr Gln Glu Ile
    170                 175                 180

CGT AAG TCT TTG GAT CGT CAT ACG ATT CTT TAT ACT ACT TTG       588
Arg Lys Ser Leu Asp Arg His Thr Ile Leu Tyr Thr Thr Leu
        185                 190                 195

GTT GAG CTT TCG AAG ACT TTA GGG TTG CAG AAT TGT GCG GTT       630
Val Glu Leu Ser Lys Thr Leu Gly Leu Gln Asn Cys Ala Val
            200                 205                 210

TGG ATG CCG AAT GAC GGT GGA ACG GAG ATG GAT TTG ACT CAT       672
Trp Met Pro Asn Asp Gly Gly Thr Glu Met Asp Leu Thr His
                215                 220
```

FIG. 15A

```
GAG TTG AGA GGG AGA GGT GGT TAT GGT GGT TGT TCT GTT TCT           714
Glu Leu Arg Gly Arg Gly Gly Tyr Gly Gly Cys Ser Val Ser
225             230                 235

ATG GAG GAT TTG GAT GTT GTT AGG ATT AGG GAG AGT GAT GAA           756
Met Glu Asp Leu Asp Val Val Arg Ile Arg Glu Ser Asp Glu
    240                 245                 250

GTG AAT GTG TTG AGT GTT GAC TCG TCC ATT GCT CGA GCT AGT           798
Val Asn Val Leu Ser Val Asp Ser Ser Ile Ala Arg Ala Ser
        255                 260                 265

GGT GGT GGT GGG GAT GTT AGT GAG ATT GGT GCC GTG GCT GCT           840
Gly Gly Gly Gly Asp Val Ser Glu Ile Gly Ala Val Ala Ala
            270                 275                 280

ATT AGA ATG CCG ATG CTT CGT GTT TCG GAT TTT AAT GGA GAG           882
Ile Arg Met Pro Met Leu Arg Val Ser Asp Phe Asn Gly Glu
                285                 290

CTA AGT TAT GCG ATA CTT GTT TGT GTT TTA CCG GGC GGG ACC           924
Leu Ser Tyr Ala Ile Leu Val Cys Val Leu Pro Gly Gly Thr
295             300                 305

CGT CGG GAT TGG ACT TAT CAG GAG ATT GAG ATT GTT AAA GTT           966
Arg Arg Asp Trp Thr Tyr Gln Glu Ile Glu Ile Val Lys Val
    310                 315                 320

GTG GCG GAT CAA GTA ACC GTT GCG TTA GAT CAT GCA GCG GTT          1008
Val Ala Asp Gln Val Thr Val Ala Leu Asp His Ala Ala Val
        325                 330                 335

CTT GAA GAG TCT CAG CTT ATG AGG GAG AAG CTG GCG GAA CAG          1050
Leu Glu Glu Ser Gln Leu Met Arg Glu Lys Leu Ala Glu Gln
            340                 345                 350

AAC AGG GCG TTG CAG ATG GCG AAG AGA GAC GCG TTG AGA GCG          1092
Asn Arg Ala Leu Gln Met Ala Lys Arg Asp Ala Leu Arg Ala
                355                 360

AGC CAA GCG AGG AAT GCG TTT CAG AAA ACG ATG AGC GAA GGG          1134
Ser Gln Ala Arg Asn Ala Phe Gln Lys Thr Met Ser Glu Gly
365             370                 375

ATG AGG CGT CCT ATG CAT TCG ATA CTC GGT CTT TTG TCG ATG          1176
Met Arg Arg Pro Met His Ser Ile Leu Gly Leu Leu Ser Met
    380                 385                 390

ATT CAG GAC GAG AAG TTG AGT GAC GAG CAG AAA ATG ATT GTT          1218
Ile Gln Asp Glu Lys Leu Ser Asp Glu Gln Lys Met Ile Val
        395                 400                 405

GAT ACG ATG GTT AAA ACA GGG AAT GTT ATG TCG AAT TTG GTG          1260
Asp Thr Met Val Lys Thr Gly Asn Val Met Ser Asn Leu Val
            410                 415                 420

GGG GAC TCT ATG GAT GTG CCT GAC GGT AGA TTT GGT ACG GAG          1302
Gly Asp Ser Met Asp Val Pro Asp Gly Arg Phe Gly Thr Glu
                425                 430

ATG AAA CCG TTT AGT CTG CAT CGT ACG ATC CAT GAA GCA GCT          1344
Met Lys Pro Phe Ser Leu His Arg Thr Ile His Glu Ala Ala
435             440                 445
```

FIG. 15B

```
TGT ATG GCG AGA TGT TTG TGT CTA TGC AAT GGA ATT AGG TTC    1386
Cys Met Ala Arg Cys Leu Cys Leu Cys Asn Gly Ile Arg Phe
    450             455                 460

TTG GTT GAC GCG GAG AAG TCT CTA CCT GAT AAT GTA GTA GGT    1428
Leu Val Asp Ala Glu Lys Ser Leu Pro Asp Asn Val Val Gly
        465             470                 475

GAT GAA AGA AGG GTC TTT CAA GTG ATA CTT CAT ATG GTT GGT    1470
Asp Glu Arg Arg Val Phe Gln Val Ile Leu His Met Val Gly
            480             485                 490

AGT TTA GTA AAG CCT AGA AAA CGT CAA GAA GGA TCT TCA TTG    1512
Ser Leu Val Lys Pro Arg Lys Arg Gln Glu Gly Ser Ser Leu
                495             500

ATG TTT AAG GTT TTG AAA GAA AGA GGA AGC TTG GAT AGG AGT    1554
Met Phe Lys Val Leu Lys Glu Arg Gly Ser Leu Asp Arg Ser
505                 510                 515

GAT CAT AGA TGG GCT GCT TGG AGA TCA CCG GCT TCT TCA GCA    1596
Asp His Arg Trp Ala Ala Trp Arg Ser Pro Ala Ser Ser Ala
        520             525                 530

GAT GGA GAT GTG TAT ATA AGA TTT GAA ATG AAT GTA GAG AAT    1636
Asp Gly Asp Val Tyr Ile Arg Phe Glu Met Asn Val Glu Asn
            535             540                 545

GAT GAT TCA AGT TCT CAA TCA TTT GCT TCT GTT TCC TCC AGA    1680
Asp Asp Ser Ser Ser Gln Ser Phe Ala Ser Val Ser Ser Arg
                550             555                 560

GAT CAA GAA GTT GGT GAT GTT AGA TTC TCC GGC GGC TAT GGG    1722
Asp Gln Glu Val Gly Asp Val Arg Phe Ser Gly Gly Tyr Gly
                    565             570

TTA GGA CAA GAT CTA AGC TTT GGT GTT TGT AAG AAA GTG GTG    1764
Leu Gly Gln Asp Leu Ser Phe Gly Val Cys Lys Lys Val Val
575                 580             585

CAG TTG ATT CAT GGG AAT ATC TCG GTG GTC CCT GGC TCG GAT    1806
Gln Leu Ile His Gly Asn Ile Ser Val Val Pro Gly Ser Asp
        590             595                 600

GGT TCA CCG GAG ACC ATG TCG TTG CTC CTT CGG TTT CGA CGT    1848
Gly Ser Pro Glu Thr Met Ser Leu Leu Leu Arg Phe Arg Arg
            605             610                 615

AGA CCC TCC ATA TCT GTC CAT GGA TCC AGC GAG TCG CCA GCT    1890
Arg Pro Ser Ile Ser Val His Gly Ser Ser Glu Ser Pro Ala
                620             625                 630

CCT GAC CAC CAC GCT CAC CCA CAT TCG AAT TCT CTG TTA CGT    1932
Pro Asp His His Ala His Pro His Ser Asn Ser Leu Leu Arg
                    635             640

GGC TTA CAA GTT TTA TTG GTA GAC ACC AAC GAT TCG AAC CGG    1974
Gly Leu Gln Val Leu Leu Val Asp Thr Asn Asp Ser Asn Arg
645                 650             655

GCA GTT ACA CGT AAA CTC TTA GAG AAA CTC GGG TGC GAT GTA    2016
Ala Val Thr Arg Lys Leu Leu Glu Lys Leu Gly Cys Asp Val
        660             665                 670
```

*FIG. 15C*

| | |
|---|---|
| ACC GCG GTT TCC TCT GGA TTC GAT TGC CTT ACC GCC ATT GCT<br>Thr Ala Val Ser Ser Gly Phe Asp Cys Leu Thr Ala Ile Ala<br>          675                            680                      685 | 2058 |
| CCC GGC TCG TCC TCG CCT TCT ACT TCG TTT CAA GTG GTG GTG<br>Pro Gly Ser Ser Ser Pro Ser Thr Ser Phe Gln Val Val Val<br>          690                            695                      700 | 2100 |
| CTT GAT CTT CAA ATG GCA GAG ATG GAC GGT TAT GAA GTG GCC<br>Leu Asp Leu Gln Met Ala Glu Met Asp Gly Tyr Glu Val Ala<br>                            705                      710 | 2142 |
| ATG AGG ATC AGG AGT CGA TCT TGG CCG TTG ATT GTG GCG ACG<br>Met Arg Ile Arg Ser Arg Ser Trp Pro Leu Ile Val Ala Thr<br>715                      720                            725 | 2184 |
| ACA GTG AGC TTG GAT GAA GAA ATG TGG GAC AAG TGT GCA CAG<br>Thr Val Ser Leu Asp Glu Glu Met Trp Asp Lys Cys Ala Gln<br>          730                            735                      740 | 2226 |
| ATT GGA ATC AAT GGA GTT GTG AGA AAG CCA GTG GTG TTA AGA<br>Ile Gly Ile Asn Gly Val Val Arg Lys Pro Val Val Leu Arg<br>          745                            750                      755 | 2268 |
| GCT ATG GAG AGT GAG CTC CGA AGA GTA TTG TTG CAA GCT GAC<br>Ala Met Glu Ser Glu Leu Arg Arg Val Leu Leu Gln Ala Asp<br>              760                            765                      770 | 2310 |
| CAA CTT CTC TAAGTTGTTA TCTCAACTTC TCTTCTACAT TCAAAATTTT<br>Gln Leu Leu | 2259 |
| TACACCATAG ATTTATGTCA AATATATCAA AATGAAATTT CGAAA | 2404 |

FIG. 15D

```
TTTTTTTTTT GTCAAAAGCT CGATGTAAAA ATCCGATGGC CACAAGCAAA        50

ACGACAGGTT CCAACTTCAC GGAGATTGTG AAAATGGAGT AGTAGTTCAG       100

TGAAGTAGTA GATACTGAGA TCGCATTCTC CGGCGTCGTT TTTCACATCG       150

AAATAGTCGT GTAAAAAAT GAAAAATTG CTGCGAGACA GGTATGTGTC         200

GCAGCAGGAA ATAGCATCTT AAAGGAAGGA AGGAAGGAAA CTCGAAAGTT       250

ACTAAAAATT TTTGATTCTT TGGGACGAAA CGAGATA ATG GAA TCC         296
                                         Met Glu Ser
                                          1

TGT GAT TGC ATT GAG GCT TTA CTG CCA ACT GGT GAC CTG CTG      338
Cys Asp Cys Ile Glu Ala Leu Leu Pro Thr Gly Asp Leu Leu
    5              10                  15

GTT AAA TAC CAA TAC CTC TCA GAT TTC TTC ATT GCT GTA GCC      380
Val Lys Tyr Gln Tyr Leu Ser Asp Phe Phe Ile Ala Val Ala
        20              25              30

TAC TTT TCC ATT CCG TTG GAG CTT ATT TAT TTT GTC CAC AAA      422
Tyr Phe Ser Ile Pro Leu Glu Leu Ile Tyr Phe Val His Lys
            35              40              45

TCT GCA TGC TTC CCA TAC AGA TGG GTC CTC ATG CAA TTT GGT      464
Ser Ala Cys Phe Pro Tyr Arg Trp Val Leu Met Gln Phe Gly
                50              55

GCT TTT ATT GTG CTC TGT GGA GCA ACA CAC TTT ATT AGC TTG      506
Ala Phe Ile Val Leu Cys Gly Ala Thr His Phe Ile Ser Leu
60              65              70

TGG ACC TTC TTT ATG CAC TCT AAG ACG GTC GCT GTG GTT ATG      548
Trp Thr Phe Phe Met His Ser Lys Thr Val Ala Val Val Met
    75              80              85

ACC ATA TCA AAA ATG TTG ACA GCT GCC GTG TCC TGT ATC ACA      590
Thr Ile Ser Lys Met Leu Thr Ala Ala Val Ser Cys Ile Thr
        90              95              100

GCT TTG ATG CTT GTT CAC ATT ATT CCT GAT TTG CTA AGT GTT      632
Ala Leu Met Leu Val His Ile Ile Pro Asp Leu Leu Ser Val
            105             110             115

AAA ACG CGA GAG TTG TTC TTG AAA ACT CGA GCT GAA GAG CTT      674
Lys Thr Arg Glu Leu Phe Leu Lys Thr Arg Ala Glu Glu Leu
                120             125

GAC AAG GAA ATG GGC CTA ATA ATA AGA CAA GAA GAA ACT GGC      716
Asp Lys Glu Met Gly Leu Ile Ile Arg Gln Glu Glu Thr Gly
130             135             140

AGA CAT GTC AGG ATG CTG ACT CAT GAG ATA AGA AGC ACA CTC      758
Arg His Val Arg Met Leu Thr His Glu Ile Arg Ser Thr Leu
    145             150             155

GAC AGA CAC ACA ATC TTG AAG ACT ACT CTT GTG GAG CTA GGT      800
Asp Arg His Thr Ile Leu Lys Thr Thr Leu Val Glu Leu Gly
        160             165             170
```

*FIG. 16A*

```
AGG ACC TTA GAC CTG GCA GAA TGT GCT TTG TGG ATG CCA TGC      842
Arg Thr Leu Asp Leu Ala Glu Cys Ala Leu Trp Met Pro Cys
            175                 180                 185

CAA GGA GGC CTG ACT TTG CAA CTT TCC CAT AAT TTA AAC AAT      884
Gln Gly Gly Leu Thr Leu Gln Leu Ser His Asn Leu Asn Asn
                190                 195

CTA ATA CCT CTG GGA TCT ACT GTG CCA ATT AAT CTT CCT ATT      926
Leu Ile Pro Leu Gly Ser Thr Val Pro Ile Asn Leu Pro Ile
200                     205                 210

ATC AAT GAA ATT TTT AGT AGC CCT GAA GCA ATA CAA ATT CCA      968
Ile Asn Glu Ile Phe Ser Ser Pro Glu Ala Ile Gln Ile Pro
            215                 220                 225

CAT ACA AAT CCT TTG GCA AGG ATG AGG AAT ACT GTT GGT AGA     1010
His Thr Asn Pro Leu Ala Arg Met Arg Asn Thr Val Gly Arg
                230                 235                 240

TAT ATT CCA CCA GAA GTA GTT GCT GTT CGT GTA CCG CTT TTA     1052
Tyr Ile Pro Pro Glu Val Val Ala Val Arg Val Pro Leu Leu
                    245                 250                 255

CAC CTC TCA AAT TTT ACT AAT GAC TGG GCT GAA CTG TCT ACT     1094
His Leu Ser Asn Phe Thr Asn Asp Trp Ala Glu Leu Ser Thr
                260                 265

AGA AGT TAT GCG GTT ATG GTT CTG GTT CTC CCG ATG AAT GGC     1136
Arg Ser Tyr Ala Val Met Val Leu Val Leu Pro Met Asn Gly
270                     275                 280

TTA AGA AAG TGG CGT GAA CAT GAG TTA GAA CTT GTG CAA GTT     1178
Leu Arg Lys Trp Arg Glu His Glu Leu Glu Leu Val Gln Val
        285                 290                 295

GTC GCA GAT CAG GTT GCT GTC GCT CTT TCA CAT GCT GCA ATT     1220
Val Ala Asp Gln Val Ala Val Ala Leu Ser His Ala Ala Ile
                300                 305                 310

TTA GAA GAT TCC ATG CGA GCC CAT GAT CAG CTC ATG GAA CAG     1262
Leu Glu Asp Ser Met Arg Ala His Asp Gln Leu Met Glu Gln
                    315                 320                 325

AAT ATT GCT TTG GAT GTA GCT CGA CAA GAA GCA GAG ATG GCC     1304
Asn Ile Ala Leu Asp Val Ala Arg Gln Glu Ala Glu Met Ala
                    330                 335

ATC CGT GCA CGT AAC GAC TTC CTT GCT GTG ATG AAC CAT GAA     1346
Ile Arg Ala Arg Asn Asp Phe Leu Ala Val Met Asn His Glu
340                     345                 350

ATG AGA ACG CCC ATG CAT GCA GTT ATT GCT CTG TGC TCT CTG     1388
Met Arg Thr Pro Met His Ala Val Ile Ala Leu Cys Ser Leu
        355                 360                 365

CTT TTA GAA ACA GAC TTA ACT CCA GAG CAG AGA GTT ATG ATT     1430
Leu Leu Glu Thr Asp Leu Thr Pro Glu Gln Arg Val Met Ile
            370                 375                 380

GAG ACC ATA TTG AAG AGC AGC AAT CTT CTT GCA ACA CTG ATA     1472
Glu Thr Ile Leu Lys Ser Ser Asn Leu Leu Ala Thr Leu Ile
                385                 390                 395
```

FIG. 16B

```
AAT GAT GTT CTA GAT CTT TCT AGA CTT GAA GAT GGT ATT CTT    1514
Asn Asp Val Leu Asp Leu Ser Arg Leu Glu Asp Gly Ile Leu
            400                     405

GAA CTA GAA AAC GGA ACA TTC AAT CTT CAT GGC ATC TTA AGA    1556
Glu Leu Glu Asn Gly Thr Phe Asn Leu His Gly Ile Leu Arg
410                 415                 420

GAG GCC GTT AAT TTG ATA AAG CCA ATT GCA TCT TTG AAG AAA    1598
Glu Ala Val Asn Leu Ile Lys Pro Ile Ala Ser Leu Lys Lys
    425                 430                 435

TTA TCT ATA ACT CTT GCT TTG GCT CTG GAT TTA CCT ATT CTT    1640
Leu Ser Ile Thr Leu Ala Leu Ala Leu Asp Leu Pro Ile Leu
            440                 445                 450

GCT GTG GGT GAT GCA AAA CGT CTT ATC CAA ACT CTC TTA AAC    1682
Ala Val Gly Asp Ala Lys Arg Leu Ile Gln Thr Leu Leu Asn
                455                 460                 465

GTG GTG GGA AAT GCT GTG AAG TTC ACT AAA GAA GGA CAT ATT    1724
Val Val Gly Asn Ala Val Lys Phe Thr Lys Glu Gly His Ile
                470                 475

TCA ATT GAG GCT TCA GTT GCC AAA CCA GAG TAT GCG AGA GAT    1766
Ser Ile Glu Ala Ser Val Ala Lys Pro Glu Tyr Ala Arg Asp
480                 485                 490

TGT CAT CCT CCT GAA ATG TTC CCT ATG CCA AGT GAT GGC CAG    1808
Cys His Pro Pro Glu Met Phe Pro Met Pro Ser Asp Gly Gln
    495                 500                 505

TTT TAT TTG CGT GTC CAG GTT AGA GAT ACT GGG TGT GGA ATT    1850
Phe Tyr Leu Arg Val Gln Val Arg Asp Thr Gly Cys Gly Ile
            510                 515                 520

AGC CCA CAA GAT ATA CCA CTA GTA TTC ACC AAA TTT GCA GAG    1892
Ser Pro Gln Asp Ile Pro Leu Val Phe Thr Lys Phe Ala Glu
                525                 530                 535

TCA CGG CCT ACG TCA AAT CGA AGT ACT GGA GGG GAA GGT CTA    1934
Ser Arg Pro Thr Ser Asn Arg Ser Thr Gly Gly Glu Gly Leu
                540                 545

GGG CTT GCC ATT TGG AGA CGA TTT ATT CAA CTT ATG AAA GGT    1976
Gly Leu Ala Ile Trp Arg Arg Phe Ile Gln Leu Met Lys Gly
550                 555                 560

AAC ATT TGG ATT GAG AGT GAG GGC CCT GGA AAG GGA ACC ACT    2018
Asn Ile Trp Ile Glu Ser Glu Gly Pro Gly Lys Gly Thr Thr
    565                 570                 575

GTC ACG TTT GTA GTG AAA CTC GGA ATC TGT CAC CAT CCA AAT    2060
Val Thr Phe Val Val Lys Leu Gly Ile Cys His His Pro Asn
            580                 585                 590

GCA TTA CCT CTG CTA CCT ATG CCT CCC AGA GGC AGA TTG AAC    2102
Ala Leu Pro Leu Leu Pro Met Pro Pro Arg Gly Arg Leu Asn
                595                 600                 605

AAA GGT AGC GAT GAT CTC TTC AGG TAT AGA CAG TTC CGT GGA    2144
Lys Gly Ser Asp Asp Leu Phe Arg Tyr Arg Gln Phe Arg Gly
                610                 615
```

FIG. 16C

```
GAT GAT GGT GGG ATG TCT GTG AAT GCT CAA CGC TAT CAA AGA    2186
Asp Asp Gly Gly Met Ser Val Asn Ala Gln Arg Tyr Gln Arg
620             625                 630

AGT ATG TAA A TGACAAAGG ACATTGGTGT GACAAAGAAC              2226
Ser Met  *
    635

ATTAAATCAT GACTAGTGAA TTTGAGATTT CTTCACTGTT CTGTACACTC    2276

CAAATGGCAC AGTTTGTCTT GTAACTAACC TAATTCAATG CTCGTAAAGT    2326

GAGTACTGGA GTATCTTGAA AATGTAACTA TCGAATTTAT ACATCGAGCT    2376

TTTGACAAAA AAAAAAAAAA AAAAAAAA                             2405
```

FIG. 16D

```
Tetr    1  MESCDCIEALLPTGDLLVKYQYLSDFFIAVAYFSIPLELIYFVHKSACFP    50
           |||:|:.|||:..|:::.|:|||:|||||||||||||||||:.||:.||
Etr1    1  MEVCNCIEPQWPADELLMKYQYISDFFIAVAYFSIPLELIYFVKKSAVFP    50

51  YRWVLMQFGAFIVLCGATHFISLWTFFMHSKTVAVVMTISKMLTAAVSCI   100
           |||:|:||||||||||||||:.|||:..|:|||||:||.:.:|||.||:.
       51  YRWVLVQFGAFIVLCGATHLINLWTFTTHSRTVALVMTTAKVLTAVVSCA   100

101  TALMLVHIIPDLLSVKTRELFLKTRAEELDKEMGLIIRQEETGRHVRMLT   150
           |||||||||||||||||||||||||:.|||:|||||||:|||||||||||
      101  TALMLVHIIPDLLSVKTRELFLKNKAAELDREMGLIRTQEETGRHVRMLT   150

151  HEIRSTLDRHTILKTTLVELGRTLDLAECALWMPCQGGLTLQLSHNLNNL   200
           |||||||||||||||||||||||||:|||||.|:..:...|:||...:.:
      151  HEIRSTLDRHTILKTTLVELGRTLALEECALWMPTRTGLELQLSYTLRHQ   200

201  IPLGSTVPINLPIINEIFSSPEAIQIPHTNPLARMRNTVGRYIPPEVVAV   250
           .|:..:|||:||:|:|..|..:...:..|:|.||:...|...:|||||||
      201  HPVEYTVPIQLPVINQVFGTSRAVKISPNSPVARLRPVSGKYMLGEVVAV   250

251  RVPLLHLSNF.TNDWAELSTRSYAVMVLVLPMNGLRKWREHELELVQVVA   299
           ||||||||||| ||:||||||:|||||:|||||:|:||:|||||||:||||
      251  RVPLLHLSNFQINDWPELSTKRYALMVLMLPSDSARQWHVHELELVEVVA   300

300  DQVAVALSHAAILEDS   315
           ||||||||||||||||
      301  DQVAVALSHAAILEES   316
```

FIG. 17

```
AGATCTGGTA CTACCAAAAG GTATCCAATT AATCCATGCT TGGCCTCCCA        50
TTACAATGCC TGTAAGAAAT AATTGTTCTT TCCACCTCCA CAACTAATTG       100
TCGAACTATT ATATCTATCT TTATTCCCTT AAATGTGAAA CGAATTACAC       150
AGACTATTTG GCGCTACTTT TTTCCTAGAT ATATTGAAGA CCTAGTTTCT       200
TATATTTGTG GGAAGCATTT GGAAGTTCTA TAAGAACTAT ATCATGTTCG       250
AAAACATTCT TATAATTTTC GACAAGATTG CTGAAGGAGT GTCTTATCTT       300
TTATGTATTC TTGACTAGAG GAGTTTAATA AAAAGAAAAT AGAAAGGAAC       350
AAAGAAACGT ACAAGTGTAT AAAAGGAGTT GGGGCAAAGA CATCAGAAAC       400
ATTTAGACCT ACGATTTCAT CCTACATGTT ATGGTTTTAG TTCGTTAGAG       450
GTTTTAACAT ATTAAATCAG CAAAGTTGTG ACATACATAA AGTGCATAAC       500
ATAAAGATGA AATTCACAAT TTGCTGGATC TTTTGGTGCA AGGGAACTAT       550
TTTTTACACT ATAAGTTAGC TGTTAATTTC AATATTGGCT CTTCTACACC       600
TTGTTGTTCT TGAGTATAAT TCTATTTTGC ATCAAACATA TGTCAGAACT       650
TATGCTGCAA TTAAATATAT TCAGGTTGTT TAACTCTTGT ACAGCTTGTT       700
ATTCTTCTGA GGTCTATTTC CTTCTCCTTA TTTGCTAACT TGTGCTGCAG       750
TTATCTTCCA TC GTG GAG TCA TGT AAC TGC ATC ATT GAC CCA        792
              Val Glu Ser Cys Asn Cys Ile Ile Asp Pro
              1               5                   10

CAG TTG CCT GCT GAC GAC TTG CTA ATG AAG TAT CAG TAC ATT      834
Gln Leu Pro Ala Asp Asp Leu Leu Met Lys Tyr Gln Tyr Ile
            15                  20

TCT GAT TTT TTC ATA GCA CTT GCT TAT TTC TCC ATT CCA GTG      876
Ser Asp Phe Phe Ile Ala Leu Ala Tyr Phe Ser Ile Pro Val
25                  30                  35

GAG TTG ATA TAC TTC GTT AAG AAG TCT GCT GTC TTT CCA TAT      918
Glu Leu Ile Tyr Phe Val Lys Lys Ser Ala Val Phe Pro Tyr
        40                  45                  50

AGA TGG GTT CTT GTG CAG TTC GGT GCT TTC ATA GTT CTT TGT      960
Arg Trp Val Leu Val Gln Phe Gly Ala Phe Ile Val Leu Cys
            55                  60                  65

GGA GCA ACC CAT CTT ATC AAC TTA TGG ACA TTT AAT ATG CAT     1002
Gly Ala Thr His Leu Ile Asn Leu Trp Thr Phe Asn Met His
                70                  75                  80

ACA AGG AAT GTG GCA ATA GTA ATG ACT ACT GCA AAG GCC TTG     1044
Thr Arg Asn Val Ala Ile Val Met Thr Thr Ala Lys Ala Leu
            85                  90

ACT GCA CTG GTG TCA TGT ATA ACT GCT CTC ATG CTT GTC CAC     1086
Thr Ala Leu Val Ser Cys Ile Thr Ala Leu Met Leu Val His
95                  100                 105
```

*FIG. 18A*

| | |
|---|---|
| ATC ATT CCT GAT TTA TTA AGT GTC AAA ACT AGA GAA CTG TTC<br>Ile Ile Pro Asp Leu Leu Ser Val Lys Thr Arg Glu Leu Phe<br>110                       115                    120 | 1128 |
| TTG AAA AAG AAA GCT GCA CAG CTT GAC CGT GAA ATG GGT ATT<br>Leu Lys Lys Lys Ala Ala Gln Leu Asp Arg Glu Met Gly Ile<br>         125                    130                 135 | 1170 |
| ATT CGG ACT CAG GAG GAG ACA GGT AGA CAT GTT AGA ATG CTA<br>Ile Arg Thr Gln Glu Glu Thr Gly Arg His Val Arg Met Leu<br>            140                  145                150 | 1212 |
| ACT CAT GAA ATC CGA AGC ACT CTT GAT AGA CAT ACT ATT TTA<br>Thr His Glu Ile Arg Ser Thr Leu Asp Arg His Thr Ile Leu<br>                  155                     160 | 1254 |
| AAG ACT ACA CTT GTT GAG CTA GGA AGA ACA TTG GCA TTG GAA<br>Lys Thr Thr Leu Val Glu Leu Gly Arg Thr Leu Ala Leu Glu<br>165                        170                    175 | 1296 |
| GAG TGT GCA TTA TGG ATG CCA ACA CGT ACT GGA CTA GAG CTT<br>Glu Cys Ala Leu Trp Met Pro Thr Arg Thr Gly Leu Glu Leu<br>     180                    185                 190 | 1338 |
| CAG CTT TCT TAC ACT TTA CGA CAC CAA AAT CCA GTT GGA TTA<br>Gln Leu Ser Tyr Thr Leu Arg His Gln Asn Pro Val Gly Leu<br>         195                   200               205 | 1380 |
| ACT GTA CCC ATT CAA CTT CCT GTA ATC AAT CAA GTT TTC GGT<br>Thr Val Pro Ile Gln Leu Pro Val Ile Asn Gln Val Phe Gly<br>             210                    215            220 | 1422 |
| ACA AAT CAT GTC GTG AAA ATA TCA CCA AAT TCT CCT GTC GCA<br>Thr Asn His Val Val Lys Ile Ser Pro Asn Ser Pro Val Ala<br>                  225                   230 | 1464 |
| AGA CTT CGA CCT GCT GGG AAA TAC ATG CCT GGT GAG GTG GTT<br>Arg Leu Arg Pro Ala Gly Lys Tyr Met Pro Gly Glu Val Val<br>235                       240                   245 | 1506 |
| GCT GTC AGG GTT CCA CTT CTG CAT CTG TCG AAC TTT CAG ATT<br>Ala Val Arg Val Pro Leu Leu His Leu Ser Asn Phe Gln Ile<br>     250                    255                 260 | 1548 |
| AAT GAT TGG CCT GAA CTT TCA ACA AAG CGC TAT GCT TTA ATG<br>Asn Asp Trp Pro Glu Leu Ser Thr Lys Arg Tyr Ala Leu Met<br>         265                   270               275 | 1590 |
| GTT CTG ATG CTT CCT TCA GAC AGT GCA AGA CAA TGG CAT GTT<br>Val Leu Met Leu Pro Ser Asp Ser Ala Arg Gln Trp His Val<br>             280                    285            290 | 1632 |
| CAT GAG CTG GAG CTT GTT GAA GTG GTA GCT GAT CAG GTT<br>His Glu Leu Glu Leu Val Glu Val Val Ala Asp Gln Val<br>                  295                   300 | 1671 |
| TGATTTTGT TATTGAAAAT TCCTTAATAT AATGTTAAAA TTTCTCTTTT | 1721 |
| ATATATTTTT GGGTTGAACA CAACCACGTT GACATACTGA GTTCTGGGTG | 1771 |
| TAAAATTAGA CATGGAGAAG ACCAATTACA AAAATCTGAG AATCTGCTAG | 1821 |
| CAGAATCACA AGGCTTAGTT GTTCTTAGTA TTATGGTTTT ATCCATTGGA | 1871 |

FIG. 18B

| | |
|---|---|
| ATTGCACAGC AGAATTGTTA TTACTGTTAT TTTTTTTTAA AATTTTCAAA | 1921 |
| GATAAATCAA AAGCTGAACT ATATGACTTT TTGCATACTT CGTCTGCTGA | 1971 |
| TTGCTTTTTG GTGATGGAAT AGTTAGGCTG GGTTGTGGAT GAGTATATCA | 2021 |
| TAGTAGATTT TCTGATAGGA TCTTAACTCC TTGGCTTTTG TTTTCTATAG | 2071 |
| ATGATCCCTT GTATTAGAAG CACGGGAAAT AGGATCGATG GTATATAGAA | 2121 |
| ATATTAGGAA CAGCTTTCTG AATCATTTGA ATATTCCTTT TATGGAACAT | 2171 |
| AGAACTCTTG ACGTGTATGT AGTTTTCTTA GTACTTTTAT CATATGAAGT | 2221 |
| GAAAATAACG TTTTGCGATA ATGTATTTGA GTGTGTAAAA TTAAATACTA | 2271 |
| CTGAGTTTTA CAAAAATAAT TCTTCAACGG AAGCCATTTA TTTTTTTTAC | 2321 |
| ATATCTGGCA TCTTACTTCT CCATCAAAGA CTTTAGAGAA CTTTAACTTT | 2371 |
| TTCATTCTGT CTCTCGTAGT GTACTGTTCT CTGATGTATG TAATTAGCTC | 2421 |
| ACTGGCAAGT AGCACACCTA GTCTTTGTTT GACTTGTTTA AAAATCATGA | 2471 |
| TGTATCATCA GTTACGGTGA AGTGTCCAAG TTTTACTGCT TTTTGCTATT | 2521 |
| TGCATTGCAG AGTCTTAAAA CATTTCAGTT ATTCCTGGAT TTCTCCTGTT | 2571 |
| TATCAATGGA AAATTCAACT ATCAACTATG CCTCAATCAA TAAATGAAAC | 2621 |
| CTCTATATCT AACCACTCCA ACTCAGATCC AGAAATCAGA TTTCAAAGAA | 2671 |
| ATTCATCATA ACTCAACTAT AGGATTGCTG TTAACCAAGA GTAATCCTCA | 2721 |
| TTTGTCCAGA CAGGCGACCA GCTATTATGC TTTCATTATG GAAAAATTG | 2771 |
| ACAATTAATT AAAGGAAGGA ACAACTGAAG AAAAGACATC CTTGTCAGCT | 2821 |
| TCCTCTCCCA ACCCTTGCCT GAATAAGACA AAAAGTTTCT TGGAGAAAAC | 2871 |
| TCTGAATATT GGTATCCACC TCCTTTCTCC TAATTTAGGA TGCTCTATTT | 2921 |
| CTAGACATAT AGGGGAATAC TCTATTCTAG TGGTCGGTGT CTGGTTGCAA | 2971 |
| CTAGTTTTAG ATGTTTATAT GTCTTATTTG ATTTAATAAG AGCTATCCTT | 3021 |
| GAGTGCCCAA TGTGATTTAA TCTACGCTTC GGCATTTCAG GTT GCT GTT<br>                                                                                                                                                                                                       Val Ala Val<br>                                                                           305 | 3070 |
| GCT CTT TCA CAT GCT GCT ATA TTA GAA GAA TCA ATG AGG GCT<br>Ala Leu Ser His Ala Ala Ile Leu Glu Glu Ser Met Arg Ala<br>             310                      315                 320 | 3112 |
| AGG GAT CTT CTT ATG GAG CAG AAT GTG GCT CTT GAT CTG GCA<br>Arg Asp Leu Leu Met Glu Gln Asn Val Ala Leu Asp Leu Ala<br>                 325                     330 | 3154 |
| AGA AGA GAA GCA GAA ATG GCT GTT CGT GCA CGT AAT GAT TTC<br>Arg Arg Glu Ala Glu Met Ala Val Arg Ala Arg Asn Asp Phe<br>335                   340                     345 | 3196 |

*FIG. 18C*

| | | | | | | | | | | | | | |
|---|---|---|---|---|---|---|---|---|---|---|---|---|---|
| TTG | GCT | GTT | ATG | AAT | CAT | GAA | ATG | AGA | ACT | CCC | ATG | CAT | GCA | 3238
| Leu | Ala | Val | Met | Asn | His | Glu | Met | Arg | Thr | Pro | Met | His | Ala |
| | 350 | | | | | 355 | | | | | 360 | | |

```
TTG GCT GTT ATG AAT CAT GAA ATG AGA ACT CCC ATG CAT GCA    3238
Leu Ala Val Met Asn His Glu Met Arg Thr Pro Met His Ala
    350             355                 360

ATA ATT GCA CTT TCT TCC TTA CTA CAA GAA ATC GAT CTA ACT    3280
Ile Ile Ala Leu Ser Ser Leu Leu Gln Glu Ile Asp Leu Thr
        365             370                 375

CCA GAG CAA CGT CTG ATG GTT GAA ACA ATC CTC AAA AGC AGC    3322
Pro Glu Gln Arg Leu Met Val Glu Thr Ile Leu Lys Ser Ser
            380             385                 390

AAC CTT TTA GCA ACG CTC ATC AAC GAT GTC TTG GAT CTT TCA    3364
Asn Leu Leu Ala Thr Leu Ile Asn Asp Val Leu Asp Leu Ser
                395             400

AGG CTA GAG GAT GGA AGT CTT CAA CTT GAT ATT GGC ACT TTC    3406
Arg Leu Glu Asp Gly Ser Leu Gln Leu Asp Ile Gly Thr Phe
405             410                 415

AAT CTC CAT GCT TTA TTT AGA GAG GTG CCCTTCATCA CCCTCTTTTC  3453
Asn Leu His Ala Leu Phe Arg Glu Val
    420             425

TTTTTTACTT GCAAATTCTA GATTACCTGT CAGAAAAAAA GTGTCATTAC    3503

AGATATTTTG CACTTCAATA TGTTTGCTGG ACCTGCTGAC TGATATATGT    3553

GTCTGCTTAT TCCTGTAG GTC CAT AGC TTA ATC AAG CCT ATT GCA    3598
                    Val His Ser Leu Ile Lys Pro Ile Ala
                                430             435

TCT GTG AAA AAG TCT GTT GCT CAA CTT AGT TTG TCG TCA GAT    3640
Ser Val Lys Lys Ser Val Ala Gln Leu Ser Leu Ser Ser Asp
            440             445                 450

TTG CCG GAA TAT GTA ATT GGG GAT GAA AAA CGG TTA ATG CAA    3682
Leu Pro Glu Tyr Val Ile Gly Asp Glu Lys Arg Leu Met Gln
                455             460

ATT CTC TTA AAC GTT GTT GGC AAT GCT GTA AAG TTC TCA AAG    3724
Ile Leu Leu Asn Val Val Gly Asn Ala Val Lys Phe Ser Lys
465             470                 475

GAA GGC AAC GTA TCA ATC TCC GCT TTT GTT GCA AAA TCA GAC    3766
Glu Gly Asn Val Ser Ile Ser Ala Phe Val Ala Lys Ser Asp
    480             485                 490

TCT TTA AGA GAT CCT AGA GCC CCT GAA TTT TTT GCT GTG CCT    3808
Ser Leu Arg Asp Pro Arg Ala Pro Glu Phe Phe Ala Val Pro
        495             500                 505

AGT GAA AAT CAC TTC TAT TTA CGG GTG CAG                    3838
Ser Glu Asn His Phe Tyr Leu Arg Val Gln
            510             515

GTATATTTTT ACAAGCTTGA TATACTATCT TCGTAGGTTA AGGATAGTCA    3888

CAAATATGAT ATTTTAGACT TATAACTGTC AGATGTTCTG TTCTTGATAT    3938

TTGTAATATT CTAAGTAATA CTTTCTGTAG                          3968
```

FIG. 18D

```
ATA AAA GAT ACG GGG ATA GGA ATT ACA CCA CAG GAT ATT CCC    4010
Ile Lys Asp Thr Gly Ile Gly Ile Thr Pro Gln Asp Ile Pro
            520                 525                 530
AAC CTG TTT AGC AAG TTT ACA CAA AGC CAA GCG CTA GCA ACT    4052
Asn Leu Phe Ser Lys Phe Thr Gln Ser Gln Ala Leu Ala Thr
            535                 540
ACA AAT TCT GGT GGC ACT GGG CTT GGT CTT GCA ATT TGT AAG    4094
Thr Asn Ser Gly Gly Thr Gly Leu Gly Leu Ala Ile Cys Lys
545             550                 555
AG GTACGGGTAC CAGTTCCTTA GTGTTCTTTT TCCGACTCTG              4136
Arg
ATTTTCATTC TACGTGAACT TGGTAACTGC TTCATATTCA ATTTCTTTCT      4186
CTTACTGTAT TTACGTATTG ACACATCTCC TGATGGGACA CAAAAAG G       4234
TTT GTG AAT CTT ATG GAA GGA CAT ATT TGG ATT GAA AGT GAA    4276
Phe Val Asn Leu Met Glu Gly His Ile Trp Ile Glu Ser Glu
560                 565                 570
GGT CTT GGC AAG GGG TCT ACT GCT ATA TTT ATC ATT AAA CTT    4318
Gly Leu Gly Lys Gly Ser Thr Ala Ile Phe Ile Ile Lys Leu
    575                 580                 585
GGA CTT CCT GGA CGT GCA AAT GAA TCT AAG CTC CCC TTT GTG    4360
Gly Leu Pro Gly Arg Ala Asn Glu Ser Lys Leu Pro Phe Val
            590                 595                 600
ACC AAA TTG CCA GCA AAT CAC ACG CAG ATG AGT TTT AAG GAT    4402
Thr Lys Leu Pro Ala Asn His Thr Gln Met Ser Phe Lys Asp
            605                 610                 615
TAAAGGTTTT GGTGATGGAT GAGAATGGGT GAGTACTATC TGGACCCCTT     4452
TATCCTCGAC TCTTGTCTTG CCATGCTGTT TAATGATCCA TCTGATTGCG     4502
TGATTTCTCA TCTTATATGT ATTGAGCTGT CTTACTCACT TTACATGAGA     4552
CTACAGTAAT ACTT                                            4566
```

FIG. 18E

```
AAGATAAGAG TGATTCATTA AGGAGTTTGT TC ATC ATG GAT TGT AAC        47
                                      Ile Met Asp Cys Asn
                                       1                 5

TGC TTC GAT CCA CTG TTG CCT GCC GAT GAG TTG TTA ATG AAG        89
Cys Phe Asp Pro Leu Leu Pro Ala Asp Glu Leu Leu Met Lys
             10                  15

TAT CAG TAC ATT TCT GAT TTT TTC ATT GCA GTT GCT TAT TTT        131
Tyr Gln Tyr Ile Ser Asp Phe Phe Ile Ala Val Ala Tyr Phe
 20              25                  30

TCC ATC CCA ATC GAA CTG GTA TTC TTT GTC CAG AAA TCA GCT        173
Ser Ile Pro Ile Glu Leu Val Phe Phe Val Gln Lys Ser Ala
     35              40                  45

GTT TTT CCG TAT CGA TGG GTG CTT GTG CAG TTT GGT GCT TTC        215
Val Phe Pro Tyr Arg Trp Val Leu Val Gln Phe Gly Ala Phe
         50                  55                  60

ATA GTT CTT TGT GGA GCA ACA CAC CTT ATC AAT TTG TGG ACT        257
Ile Val Leu Cys Gly Ala Thr His Leu Ile Asn Leu Trp Thr
             65                  70                  75

TCT ACT CCT CAT ACA AGG ACT GTG GCA ATG GTG ATG ACT ACG        299
Ser Thr Pro His Thr Arg Thr Val Ala Met Val Met Thr Thr
                 80                  85

GCG AAG TTC TCC ACT GCT GCG GTA TCA TGT GCA ACT GCT GTC        341
Ala Lys Phe Ser Thr Ala Ala Val Ser Cys Ala Thr Ala Val
 90              95                 100

ATG CTT GTC GCA ATT ATT CCG GAT TTA TTA AGT GTC AAA ACT        383
Met Leu Val Ala Ile Ile Pro Asp Leu Leu Ser Val Lys Thr
    105                 110                 115

AGG GAG CTA TTC TTG AAA AAC AAA GCG GCG GAA CTT GAT CGT        425
Arg Glu Leu Phe Leu Lys Asn Lys Ala Ala Glu Leu Asp Arg
        120                 125                 130

GAA ATG GGT CTT ATT CGG ACA CAG GAG GAG ACG GGT AGA TAT        467
Glu Met Gly Leu Ile Arg Thr Gln Glu Glu Thr Gly Arg Tyr
            135                 140                 145

GTT AGA ATG CTA ACA CAT GAA ATC AGA AGT ACT CTG GAT AGA        509
Val Arg Met Leu Thr His Glu Ile Arg Ser Thr Leu Asp Arg
                150                 155

CAT ACT ATT TTG AAG ACT ACA CTT GTT GAA CTT GGA AGA GCA        551
His Thr Ile Leu Lys Thr Thr Leu Val Glu Leu Gly Arg Ala
160                 165                 170

TTG CAA CTG GAA GAG TGT GCT TTG TGG ATG CCG ACT CGA ACT        593
Leu Gln Leu Glu Glu Cys Ala Leu Trp Met Pro Thr Arg Thr
        175                 180                 185

GGA GTG GAG CTT CAA CTT TCT TAC ACT TTA CAT CAT CAA AAT        635
Gly Val Glu Leu Gln Leu Ser Tyr Thr Leu His His Gln Asn
            190                 195                 200

CCA GTT GGA TTT ACA GTA CCT ATA CAA CTC CCT GTA ATT AAT        677
Pro Val Gly Phe Thr Val Pro Ile Gln Leu Pro Val Ile Asn
                201                 210                 215
```

FIG. 19A

```
CAA GTT TTC AGT GCA AAT TGT GCT GTT AAA ATT TCA CCT      716
Gln Val Phe Ser Ala Asn Cys Ala Val Lys Ile Ser Pro
                220                 225
TAATCTGCCG TTGCAAGGCT T                                  737
```

FIG. 19B

```
Tgetr1   1 VESCNCIIDPQLPADDLLMKYQVISDFFIALAYFSIPVELIYFVKKSAVF       50
           :|||||||:|  ||:|||||||||||||||||||| ||:|||||||||||
Etr1     1 MEVCNCI.EPQWPADELLMKYQVISDFFIAIAYFSIPLELIYFVKKSAVF       49

51 PYRWVLVQFGAFIVLCGATHLINLWTFNMHTRNVAIVMTTAKALTALVSC      100
           |||||||||||||||||||||||||||:|:|:||:|:|||||:||| ||
        50 PYRWVLVQFGAFIVLCGATHLINLWTFTHSRTVALVMTTAKVLTAVVSC       99

101 ITALMLVHIIPDLLSVKTRELFLKKAAQLDREMGIIRTQEETGRHVRML      150
           ||||||||||||||||||||||||||:|:|||||||||||||||||||
       100 ATALMLVHIIPDLLSVKTRELFLKNKAAELDREMGLIRTQEETGRHVRML     149

151 THEIRSTLDRHTILKTTLVELGRTLALEECALWMPTRTGLELQLSYTLRH      200
           |||||||||||||||||||||||||||||||||||||||||||||||||
       150 THEIRSTLDRHTILKTTLVELGRTLALEECALWMPTRTGLELQLSYTLRH     199

201 QNPVGLTVPIQLPVINQVFGTNHVVKISPNSPVARLRP.AGKYMPGEVVA      249
           |:|:.|||||||||||||||||:...||||||||||||.|.||||||||
       200 QHPVEYTVPIQLPVINQVFGTSRAVKISPNSPVARLRPVSGKYMLGEVVA     249

250 VRVPLLHLSNFQINDWPELSTKRYALMVLMLPSDSARQWHVHELELVEVV      299
           |||||||||||||||||||||||||||||||||||||||||||||||||
       250 VRVPLLHLSNFQINDWPELSTKRYALMVLMLPSDSARQWHVHELELVEVV     299

300 ADQVAVALSHAAILEES  316
           |||||||||||||||||
       300 ADQVAVALSHAAILEES  316
```

*FIG. 20*

```
Tgetr2   11  IMDCNCFDPLLPADELLMKYQISDFFIAVAYFSIPIELVFFVQKSAVFP   60
             . ||:::| .:||::|||||||||||::||||||:|||:::||.|||||
Etr1      1  MEVCNCIEPQWPADELLMKYQISDFFIAIAYFSIPLELIYFVKKSAVFP   50

61  YRWVLVQFGAFIVLCGATHLINLWTSTPHTRTVAMVMTTAKFSTAAVSCA  110
             ||||||||||||||||||||||||| |.|||||.||||||. ||.||||
         51  YRWVLVQFGAFIVLCGATHLINLWTFTTHSRTVALVMTTAKVLTAVVSCA  100

111  TAVMLVAIIPDLLSVKTRELFLKNKAAELDREMGLIRTQEETGRYVRMLT  160
             ||:|||  |||||||||||||||||||||||||||||||||||:|||||
        101  TALMLVHIIPDLLSVKTRELFLKNKAAELDREMGLIRTQEETGRHVRMLT  150

161  HEIRSTLDRHTILKTTLVELGRALQLEECALWMPTRTGVELQLSYTLHHQ  210
             |||||||||||||||||||||||.||||||||||||||||:|||||:|:
        151  HEIRSTLDRHTILKTTLVELGRTLALEECALWMPTRTGLELQLSYTLRHQ  200

211  NPVGFTVPIQLPVINQVFSANCAVKISP*SAVARL  245
             :||:::| ||||||||||||| ::.. ||| ::||
        201  HPVEYTVPIQLPVINQVFGTSRAVKISPNSPVARL  235
```

FIG. 21

```
TTTTTTTTTT GTCAAAAGCT CGATGTAAAA ATCCGATGGC CACAAGCAAA        50

ACGACAGGTT CCAACTTCAC GGAGATTGTG AAAATGGAGT AGTAGTTCAG       100

TGAAGTAGTA GATACTGAGA TCGCATTCTC CGGCGTCGTT TTTCACATCG       150

AAATAGTCGT GTAAAAAAAT GAAAAAATTG CTGCGAGACA GGTATGTGTC       200

GCAGCAGGAA ATAGCATCTT AAAGGAAGGA AGGAAGGAAA CTCGAAAGTT       250

ACTAAAAATT TTTGATTCTT TGGGACGAAA CGAGATA ATG GAA TCC TGT     299
                                         Met Glu Ser Cys
                                          1

GAT TGC ATT GAG GCT TTA CTG CCA ACT GGT GAC CTG CTG GTT      341
Asp Cys Ile Glu Ala Leu Leu Pro Thr Gly Asp Leu Leu Val
 5              10                  15

AAA TAC CAA TAC CTC TCA GAT TTC TTC ATT GCT GTA GCC TAC      383
Lys Tyr Gln Tyr Leu Ser Asp Phe Phe Ile Ala Val Ala Tyr
     20              25                  30

TTT TCC ATT CTG TTG GAG CTT ATT TAT TTT GTC CAC AAA TCT      425
Phe Ser Ile Leu Leu Glu Leu Ile Tyr Phe Val His Lys Ser
         35              40                  45

GCA TGC TTC CCA TAC AGA TGG GTC CTC ATG CAA TTT GGT GCT      467
Ala Cys Phe Pro Tyr Arg Trp Val Leu Met Gln Phe Gly Ala
             50              55                  60

TTT ATT GTG CTC TGT GGA GCA ACA CAC TTT ATT AGC TTG TGG      509
Phe Ile Val Leu Cys Gly Ala Thr His Phe Ile Ser Leu Trp
                 65              70

ACC TTC TTT ATG CAC TCT AAG ACG GTC GCT GTG GTT ATG ACC      551
Thr Phe Phe Met His Ser Lys Thr Val Ala Val Val Met Thr
 75              80                  85

ATA TCA AAA ATG TTG ACA GCT GCC GTG TCC TGT ATC ACA GCT      593
Ile Ser Lys Met Leu Thr Ala Ala Val Ser Cys Ile Thr Ala
     90              95                 100

TTG ATG CTT GTT CAC ATT ATT CCT GAT TTG CTA AGT GTT AAA      635
Leu Met Leu Val His Ile Ile Pro Asp Leu Leu Ser Val Lys
        105             110                 115

ACG CGA GAG TTG TTC TTG AAA ACT CGA GCT GAA GAG CTT GAC      677
Thr Arg Glu Leu Phe Leu Lys Thr Arg Ala Glu Glu Leu Asp
            120             125                 130

AAG GAA ATG GGC CTA ATA ATA AGA CAA GAA GAA ACT GGC AGA      719
Lys Glu Met Gly Leu Ile Ile Arg Gln Glu Glu Thr Gly Arg
                135             140

CAT GTC AGG ATG CTG ACT CAT GAG ATA AGA AGC ACA CTC GAC      761
His Val Arg Met Leu Thr His Glu Ile Arg Ser Thr Leu Asp
145             150                 155

AGA CAC ACA ATC TTG AAG ACT ACT CTT GTG GAG CTA GGT AGG      803
Arg His Thr Ile Leu Lys Thr Thr Leu Val Glu Leu Gly Arg
    160             165                 170
```

FIG. 22A

```
ACC TTA GAC CTG GCA GAA TGT GCT TTG TGG ATG CCA TGC CAA      845
Thr Leu Asp Leu Ala Glu Cys Ala Leu Trp Met Pro Cys Gln
        175                 180                 185

GGA GGC CTG ACT TTG CAA CTT TCC CAT AAT TTA AAC AAT CTA      887
Gly Gly Leu Thr Leu Gln Leu Ser His Asn Leu Asn Asn Leu
            190                 195                 200

ATA CCT CTG GGA TCT ACT GTG CCA ATT AAT CTT CCT ATT ATC      929
Ile Pro Leu Gly Ser Thr Val Pro Ile Asn Leu Pro Ile Ile
                205                 210

AAT GAA ATT TTT AGT AGC CCT GAA GCA ATA CAA ATT CCA CAT      971
Asn Glu Ile Phe Ser Ser Pro Glu Ala Ile Gln Ile Pro His
215                 220                 225

ACA AAT CCT TTG GCA AGG ATG AGG AAT ACT GTT GGT AGA TAT     1013
Thr Asn Pro Leu Ala Arg Met Arg Asn Thr Val Gly Arg Tyr
        230                 235                 240

ATT CCA CCA GAA GTA GTT GCT GTT CGT GTA CCG CTT TTA CAC     1055
Ile Pro Pro Glu Val Val Ala Val Arg Val Pro Leu Leu His
            245                 250                 255

CTC TCA AAT TTT ACT AAT GAC TGG GCT GAA CTG TCT ACT AGA     1097
Leu Ser Asn Phe Thr Asn Asp Trp Ala Glu Leu Ser Thr Arg
                260                 265                 270

AGT TAT GCG GTT ATG GTT CTG GTT CTC CCG ATG AAT GGC TTA     1139
Ser Tyr Ala Val Met Val Leu Val Leu Pro Met Asn Gly Leu
                    275                 280

AGA AAG TGG CGT GAA CAT GAG TTA GAA CTT GTG CAA GTT GTC     1181
Arg Lys Trp Arg Glu His Glu Leu Glu Leu Val Gln Val Val
285                 290                 295

GCA GAT CAG GTT GCT GTC GCT CTT TCA CAT GCT GCA ATT TTA     1223
Ala Asp Gln Val Ala Val Ala Leu Ser His Ala Ala Ile Leu
        300                 305                 310

GAA GAT TCC ATG CGA GCC CAT GAT CAG CTC ATG GAA CAG AAT     1265
Glu Asp Ser Met Arg Ala His Asp Gln Leu Met Glu Gln Asn
            315                 320                 325

ATT GCT TTG GAT GTA GCT CGA CAA GAA GCA GAG ATG GCC ATC     1307
Ile Ala Leu Asp Val Ala Arg Gln Glu Ala Glu Met Ala Ile
                330                 335                 340

CGT GCA CGT AAC GAC TTC CTT GCT GTG ATG AAC CAT GAA ATG     1349
Arg Ala Arg Asn Asp Phe Leu Ala Val Met Asn His Glu Met
                    345                 350

AGA ACG CCC ATG CAT GCA GTT ATT GCT CTG TGC TCT CTG CTT     1391
Arg Thr Pro Met His Ala Val Ile Ala Leu Cys Ser Leu Leu
355                 360                 365

TTA GAA ACA GAC TTA ACT CCA GAG CAG AGA GTT ATG ATT GAG     1433
Leu Glu Thr Asp Leu Thr Pro Glu Gln Arg Val Met Ile Glu
        370                 375                 380
```

*FIG. 22B*

| | | | | | | | | | | | | | |
|---|---|---|---|---|---|---|---|---|---|---|---|---|---|
| ACC | ATA | TTG | AAG | AGC | AGC | AAT | CTT | CTT | GCA | ACA | CTG | ATA | AAT | 1475
| Thr | Ile | Leu 385 | Lys | Ser | Ser | Asn | Leu 390 | Leu | Ala | Thr | Leu | Ile 395 | Asn |
| GAT | GTT | CTA | GAT | CTT | TCT | AGA | CTT | GAA | GAT | GGT | ATT | CTT | GAA | 1517
| Asp | Val | Leu | Asp 400 | Leu | Ser | Arg | Leu | Glu 405 | Asp | Gly | Ile | Leu | Glu 410 |
| CTA | GAA | AAC | GGA | ACA | TTC | AAT | CTT | CAT | GGC | ATC | TTA | AGA | GAG | 1559
| Leu | Glu | Asn | Gly | Thr 415 | Phe | Asn | Leu | His | Gly 420 | Ile | Leu | Arg | Glu |
| GCC | GTT | AAT | TTG | ATA | AAG | CCA | ATT | GCA | TCT | TTG | AAG | AAA | TTA | 1601
| Ala 425 | Val | Asn | Leu | Ile | Lys 430 | Pro | Ile | Ala | Ser | Leu 435 | Lys | Lys | Leu |
| TCT | ATA | ACT | CTT | GCT | TTG | GCT | CTG | GAT | TTA | CCT | ATT | CTT | GCT | 1643
| Ser | Ile | Thr 440 | Leu | Ala | Leu | Ala 445 | Leu | Asp | Leu | Pro | Ile 450 | Leu | Ala |
| GTG | GGT | GAT | GCA | AAA | CGT | CTT | ATC | CAA | ACT | CTC | TTA | AAC | GTG | 1685
| Val | Gly | Asp 455 | Ala | Lys | Arg | Leu | Ile 460 | Gln | Thr | Leu | Leu | Asn 465 | Val |
| GTG | GGA | AAT | GCT | GTG | AAG | TTC | ACT | AAA | GAA | GGA | CAT | ATT | TCA | 1727
| Val | Gly | Asn | Ala 470 | Val | Lys | Phe | Thr | Lys 475 | Glu | Gly | His | Ile | Ser 480 |
| ATT | GAG | GCT | TCA | GTT | GCC | AAA | CCA | GAG | TAT | GCG | AGA | GAT | TGT | 1769
| Ile | Glu | Ala | Ser | Val 485 | Ala | Lys | Pro | Glu | Tyr 490 | Ala | Arg | Asp | Cys |
| CAT | CCT | CCT | GAA | ATG | TTC | CCT | ATG | CCA | AGT | GAT | GGC | CAG | TTT | 1811
| His 495 | Pro | Pro | Glu | Met | Phe 500 | Pro | Met | Pro | Ser | Asp 505 | Gly | Gln | Phe |
| TAT | TTG | CGT | GTC | CAG | GTT | AGA | GAT | ACT | GGG | TGT | GGA | ATT | AGC | 1853
| Tyr | Leu 510 | Arg | Val | Gln | Val | Arg 515 | Asp | Thr | Gly | Cys | Gly 520 | Ile | Ser |
| CCA | CAA | GAT | ATA | CCA | CTA | GTA | TTC | ACC | AAA | TTT | GCA | GAG | TCA | 1895
| Pro | Gln | Asp 525 | Ile | Pro | Leu | Val | Phe 530 | Thr | Lys | Phe | Ala | Glu 535 | Ser |
| CGG | CCT | ACG | TCA | AAT | CGA | AGT | ACT | GGA | GGG | GAA | GGT | CTA | GGG | 1937
| Arg | Pro | Thr | Ser 540 | Asn | Arg | Ser | Thr | Gly 545 | Gly | Glu | Gly | Leu | Gly 550 |
| CTT | GCC | ATT | TGG | AGA | CGA | TTT | ATT | CAA | CTT | ATG | AAA | GGT | AAC | 1979
| Leu | Ala | Ile | Trp | Arg 555 | Arg | Phe | Ile | Gln | Leu 560 | Met | Lys | Gly | Asn |
| ATT | TGG | ATT | GAG | AGT | GAG | GGC | CCT | GGA | AAG | GGA | ACC | ACT | GTC | 2021
| Ile Trp 565 | Ile | Glu | Ser | Glu 570 | Gly | Pro | Gly | Lys | Gly 575 | Thr | Thr | Val |
| ACG | TTT | GTA | GTG | AAA | CTC | GGA | ATC | TGT | CAC | CAT | CCA | AAT | GCA | 2063
| Thr | Phe 580 | Val | Val | Lys | Leu | Gly 585 | Ile | Cys | His | His | Pro 590 | Asn | Ala |

FIG. 22C

| | |
|---|---|
| TTA CCT CTG CTA CCT ATG CCT CCC AGA GGC AGA TTG AAC AAA<br>Leu Pro Leu Leu Pro Met Pro Pro Arg Gly Arg Leu Asn Lys<br>          595                          600                    605 | 2105 |
| GGT AGC GAT GAT CTC TTC AGG TAT AGA CAG TTC CGT GGA GAT<br>Gly Ser Asp Asp Leu Phe Arg Tyr Arg Gln Phe Arg Gly Asp<br>                610                         615                    620 | 2147 |
| GAT GGT GGG ATG TCT GTG AAT GCT CAA CGC TAT CAA AGA AGT<br>Asp Gly Gly Met Ser Val Asn Ala Gln Arg Tyr Gln Arg Ser<br>                     625                         630 | 2189 |
| ATG TAA A TGACAAAGG ACATTGGTGT GACAAAGAAC ATTAAATCAT<br>Met  *<br>635 | 2236 |
| GACTAGTGAA TTTGAGATTT CTTCACTGTT CTGTACACTC CAAATGGCAC | 2286 |
| AGTTTGTCTT GTAACTAACC TAATTCAATG CTCGTAAAGT GAGTACTGGA | 2336 |
| GTATCTTGAA AATGTAACTA TCGAATTTAT ACATCGAGCT TTTGACAAAA | 2386 |
| AAAAAAAAAA AAAAAAAA | 2405 |

PLANTS HAVING MODIFIED RESPONSE TO ETHYLENE

This a continuation-in-part of U.S. application Ser. No. 08/263,480 filed Jun. 28, 1994, now abandoned, which in turn is a continuation-in-part of U.S. application Ser. No. 08/086,555 filed Jul. 1, 1993, now abandoned.

The U.S. Government has certain rights in this invention pursuant to Department of Energy Contract No. DE-FG03-88ER13873.

TECHNICAL FIELD OF THE INVENTION

The invention generally relates to modified ETR nucleic acid and plants transformed with such nucleic acid which have a phenotype characterized by a modification in the normal response to ethylene.

BACKGROUND OF THE INVENTION

Ethylene has been recognized as a plant hormone since the turn of the century when its effect on pea seedling development was first described. Neljubow (1901), *Pflanzen Beih. Bot. Zentralb.* 10:128–139. Since then, numerous reports have appeared which demonstrate that ethylene is an endogenous regulator of growth and development in higher plants. For example, ethylene has been implicated in seed dormancy, seedling growth, flower initiation, leaf abscission, senescence and fruit ripening. Ethylene is a plant hormone whose biosynthesis is induced by environmental stress such as oxygen deficiency, wounding, pathogen invasion and flooding. Recently, genes encoding some of the enzymes involved in ethylene biosynthesis have been cloned. Sato, et al. (1989) *Proc. Natl. Acad. Sci. U.S.A.* 86:6621–6625; Nakajima, et al. (1990) *Plant Cell Phys. Physiol.* 29:989–996; Van Der Straeten, et al. (1990) *Proc. Natl. Acad. Sci U.S.A.* 87:4859–4963; Hamilton, et al. (1991) *Proc. Natl. Acad. Sci. U.S.A.* 88:7434–7437; and Spanu, et al. (1991) *EMBO J.* 10:2007–2013. The pathway for ethylene biosynthesis is shown in FIG. 1. As can be seen the amino acid methionine is converted to S-adenosyl-methionine (SAM) by SAM synthetase which in turn is converted to 1-aminocyclopropane-1-carboxylic acid (ACC) by ACC synthase. Adams, et al. (1979) *Proc. Natl. Acad. Sci. U.S.A.* 76:170–174. The ACC is then converted to ethylene by way of the enzyme ACC oxidase. Yang, et al. (1984) *Annu. Rev. Plant. Physiol.* 35:155189.

A number of approaches have been taken in an attempt to control ethylene biosynthesis to thereby control fruit ripening. Oeller, et al. (1991) *Science* 254:437–439 report that expression of an antisense RNA to ACC synthase inhibits fruit ripening in tomato plants. Hamilton, et al. (1990) *Nature* 346:284–287 report the use of an antisense TOM13 (ACC oxidase) gene in transgenic plants. Picton et al. (1993) *Plant Journal* 3:469–481, report altered fruit ripening and leaf senescence in tomatoes expressing an antisense ethylene-forming enzyme.

In a second approach, ethylene biosynthesis was reportedly modulated by expressing an ACC deaminase in plant tissue to lower the level of ACC available for conversion to ethylene. See PCT publication No. WO92/12249 published Jul. 23, 1992, and Klee et al. (1991) *Plant Cell* 3:1187–1193.

While a substantial amount of information has been gathered regarding the biosynthesis of ethylene, very little is known about how ethylene controls plant development. Although several reports indicate that a high affinity binding site for ethylene is present in plant tissues, such receptors have not been identified. Jerie, et al. (1979) *Planta* 144:503; Sisler (1979) *Plant Physiol.* 64:538; Sisler, et al. (1990) *Plant Growth Reg.* 9:157–164, and Sisler (1990) "Ethylene-Binding Component in Plants", *The Plant Hormone Ethylene*, A. K. Mattoo and J. C. Suttle, eds. (Boston) C.R.C. Press, Inc., pp. 81–90. In Arabidopsis, several categories of mutants have been reported. In the first two categories, mutants were reported which produce excess ethylene or reduced ethylene as compared to the wild-type. Guzman, et al. (1990) *The Plant Cell* 2:513–523. In a third category, mutants failed to respond to ethylene. Id.; Bleecker, et al. (1988) *Science* 241:1086–1089, Harpham, et al. (1991) *Ann. of Botany* 68:55–61. The observed insensitivity to ethylene was described as being either a dominant or recessive mutation. Id.

Based upon the foregoing, it is clear that the genetic basis and molecular mechanism of ethylene interaction with plants has not been clearly delineated. Given the wide range of functions regulated by ethylene and the previous attempts to control ethylene function by regulating its synthesis, it would be desirable to have an alternate approach to modulate growth and development in various plant tissues such as fruits, vegetables and flowers by altering the interaction of ethylene with plant tissue.

Accordingly, it is an object of the invention to provide isolated nucleic acids comprising an ethylene response (ETR) nucleic acid.

In addition, it is an object to provide modifications to such ETR nucleic acids to substitute, insert and/or delete one or more nucleotides so as to substitute, insert and/or delete one or more amino acid residues in the protein encoded by the ETR nucleic acid.

Still further, it is an object to provide plant cells transformed with one or more modified ETR nucleic acids. Such transformed plant cells can be used to produce transformed plants wherein the phenotype vis-a-vis the response of one or more tissues of the plant to ethylene is modulated.

SUMMARY OF THE INVENTION

In accordance with the foregoing objects, the invention includes transformed plants having at least one cell transformed with a modified ETR nucleic acid. Such plants have a phenotype characterized by a decrease in the response of at least one transformed plant cell to ethylene as compared to a plant not containing the transformed plant cell.

The invention also includes vectors capable of transforming a plant cell to alter the response to ethylene. In one embodiment, the vector comprises a modified ETR nucleic acid which causes a decrease in cellular response to ethylene. Tissue and/or temporal specificity for expression of the modified ETR nucleic acid is controlled by selecting appropriate expression regulation sequences to target the location and/or time of expression of the transformed nucleic acid.

The invention also includes methods for producing plants having a phenotype characterized by a decrease in the response of at least one transformed plant cell to ethylene as compared to a wild-type plant not containing such a transformed cell. The method comprises transforming at least one plant cell with a modified ETR nucleic acid, regenerating plants from one or more of the transformed plant cells and selecting at least one plant having the desired phenotype.

BRIEF DESCRIPTION OF THE DRAWINGS

FIGS. 2A–2C depict the genomic nucleic acid sequence (SEQ ID NO:1) for the ETR gene from *Arabidopsis thaliana*.

FIGS. 3A–3D depict the cDNA nucleic acid (SEQ ID NO:2) and deduced amino acid sequence (SEQ ID NO:3) for the ETR gene from *Arabidopsis thaliana*.

FIGS. 4A–4D, 5A–5D, 6A–6D and 7A–7D depict the cDNA and deduced amino acid sequence for four mutant ETR genes from *Arabidopsis thaliana* which confer ethylene insensitivity. Each sequence differs from the wild type sequence set forth in FIG. 3 by substitution of one amino acid residue. The etr1-3 (formerly ein1-1) mutation in FIG. 4 (SEQ ID NOs:8 and 9) comprises the substitution of alanine-31 with valine. The etr1-4 mutation in FIG. 5 (SEQ ID NOs:10 and 11) comprises the substitution of isoleucine-62 with phenylalanine. The etr1-1 (formerly etr) mutation in FIG. 6 (SEQ ID NOs:4 and 5) comprises the substitution of cysteine-65 with tyrosine. The etr1-2 mutation in FIG. 7 (SEQ ID NOs:6 and 7) comprises the substitution of alanine-102 with threonine.

FIGS. 9A–9B depict the amino acid sequence alignments of the predicted ETR1 protein and the conserved domains of several bacterial histidine kinases and response regulators. Amino acids are shown in boldface type at positions where there are at least two identities with ETR1. In FIG. 9A, the deduced ETR1 amino acid sequence (SEQ ID NOs:12 and 27) (residues 326 to 562) aligned with the histidine kinase domains of *E. coli* BarA (SEQ ID NOs:13 and 28), *P. syringae* LemA (SEQ ID NOs:14 and 29) and *X. campestris* RpfC (SEQ ID NOs:15 and 30). Boxes surround the five conserved motifs characteristic of the bacterial histidine kinase domain as compiled by Parkinson and Kofoid (Parkinson et al. (1992) *Annu. Rev. Genet.* 26:71). The conserved histidine residue that is the supposed site of autophosphorylation is indicated by an asterisk. Numbers and positions of amino acids not shown are given in parentheses. In FIG. 9B, the deduced ETR1 amino acid sequence (residues 610 to 729) (SEQ ID NOs:15 and 31) are aligned with the response regulator domains of *B. parapertussis* BvgS (SEQ ID NOs:17 and 32), *P. syringae* LemA (SEQ ID NOs:19 and 34) and *E. coli* RscC (SEQ ID NOs:18 and 33). Amino acids are shown in boldface type where there are at least two identities with ETR1. Boxes surround the four highly conserved residues in bacterial response regulators. The conserved aspartate residue that is the site of phosphorylation is indicated by an asterisk. Numbers and positions of amino acids not shown are given in parentheses. For alignment purposes, a gap (———) was introduced in the ETR1 sequence.

FIGS. 10A–10B depict specific DNA sequences for ETR nucleic acids from tomato and *Arabidopsis thaliana*. FIG. 10A compares the DNA sequence encoding amino acid residues 1 through 123 (SEQ ID NOs:20 and 21). FIG. 10B compares the ETR nucleic acid sequence encoding amino acids 306 through 403 (SEQ ID NOs:22 and 23). The vertical lines in each figure identify homologous nucleotides.

FIGS. 11A–11B compare partial amino acid sequences (using single letter designation) for an ETR protein from tomato and *Arabidopsis thaliana*. FIG. 11A compares the amino acid sequence for the ETR protein for amino acids 1 through 123 (SEQ ID NOs:24 and 25). FIG. 11B compares the amino acid sequence for the ETR protein for residues 306 through 403 (SEQ ID NOs:26 and 27). The vertical lines indicate exact sequence homology. Two vertical dots indicate that the amino acid residues are functionally conserved. One dot indicates weak functional conservation as between amino acid residues.

FIGS. 12A–12D depict the genomic nucleic acid sequence (SEQ ID NO:45) and deduced amino acid sequence (SEQ ID NO:46) for the QITR ETR gene from *Arabidopsis thaliana*.

FIGS. 13A–13C depict the cDNA nucleic acid sequence and deduced protein sequence for the QITR ETR gene from *Arabidopsis thaliana*.

FIGS. 14A–14F depict the genomic nucelic acid sequence (SEQ ID NO:41) and deduced amino acid sequence (SEQ ID NO:42) for the Q8 ETR gene from *Arabidopsis thaliana*.

FIGS. 15A–15D depict the cDNA nucleic acid sequence (SEQ ID NO:43) and deduced amino acid sequence (SEQ ID NO:44) for the Q8 ETR gene from *Arabidopsis thaliana*.

FIGS. 16A–16C depict the nucleic acid sequence (SEQ ID NO:35) and deduced amino acid sequence (SEQ ID NO:36) for the TETR nucleic acid from tomato.

FIG. 17 is a comparison of the amino terminal portions of the TETR and ETR1 proteins from tomato and Arabidopsis respectively. The top line is the TETR sequence and extends through amino acid residue 315. The lower line represents the ETR1 protein sequence and extends through amino acid residue 316. The vertical lines and single and double vertical dots have the same meaning as set forth in the description of FIGS. 11A and 11B. The percent identity between these sequence portions is 73.33%. The percent similarity is 84.76%.

FIGS. 18A–18E depict the nucleic acid (SEQ ID NO:37) and deduced amino acid sequence (SEQ ID NO:38) for the TGETR1 ETR nucleic acid from tomato.

FIG. 19 depicts the nucleic acid (SEQ ID NO:39) and deduced amino acid sequence (SEQ ID NO:40) for a partial sequence of the TGETR2 ETR nucleic acid from tomato.

FIG. 20 is a comparison of the amino terminal portions for the TGETR1 and ETR1 proteins from tomato and Arabidopsis respectively. The top line is the TGETR1 sequence through amino acid residue 316. The bottom line represents the ETR1 protein sequence through amino acid residue 316. The identity as between these two sequences is 91.75%. The percent similarity is 95.87%. The vertical lines and single and double dots have the same meaning as for FIGS. 11A and 11B.

FIG. 21 is a comparison of an amino terminal portion of the TGETR2 protein with the corresponding ETR1 sequence. The top line is the TGETR2 sequence from amino acid residue 11 through amino acid residue 245. The lower line is the ETR1 sequence from amino acid residue 1 through amino acid residue 235. The sequence identity is 85.11% as between these two sequences. The sequence similarity is 92.34%. The vertical lines and single and double dots have the same meaning as for FIGS. 11A and 11B.

FIGS. 22A–22C depict the nucleic acid (SEQ ID NO:50) and deduced amino acid sequence (SEQ ID NO:51) for the Nr (Never-ripe) ETR nucleic acid from Never-ripe tomato. The amino acid sequence in FIG. 22 differs from the TETR sequence in FIG. 16 in that the amino acid residue proline at residue 36 is replaced with leucine.

DETAILED DESCRIPTION OF THE INVENTION

Figure 1:
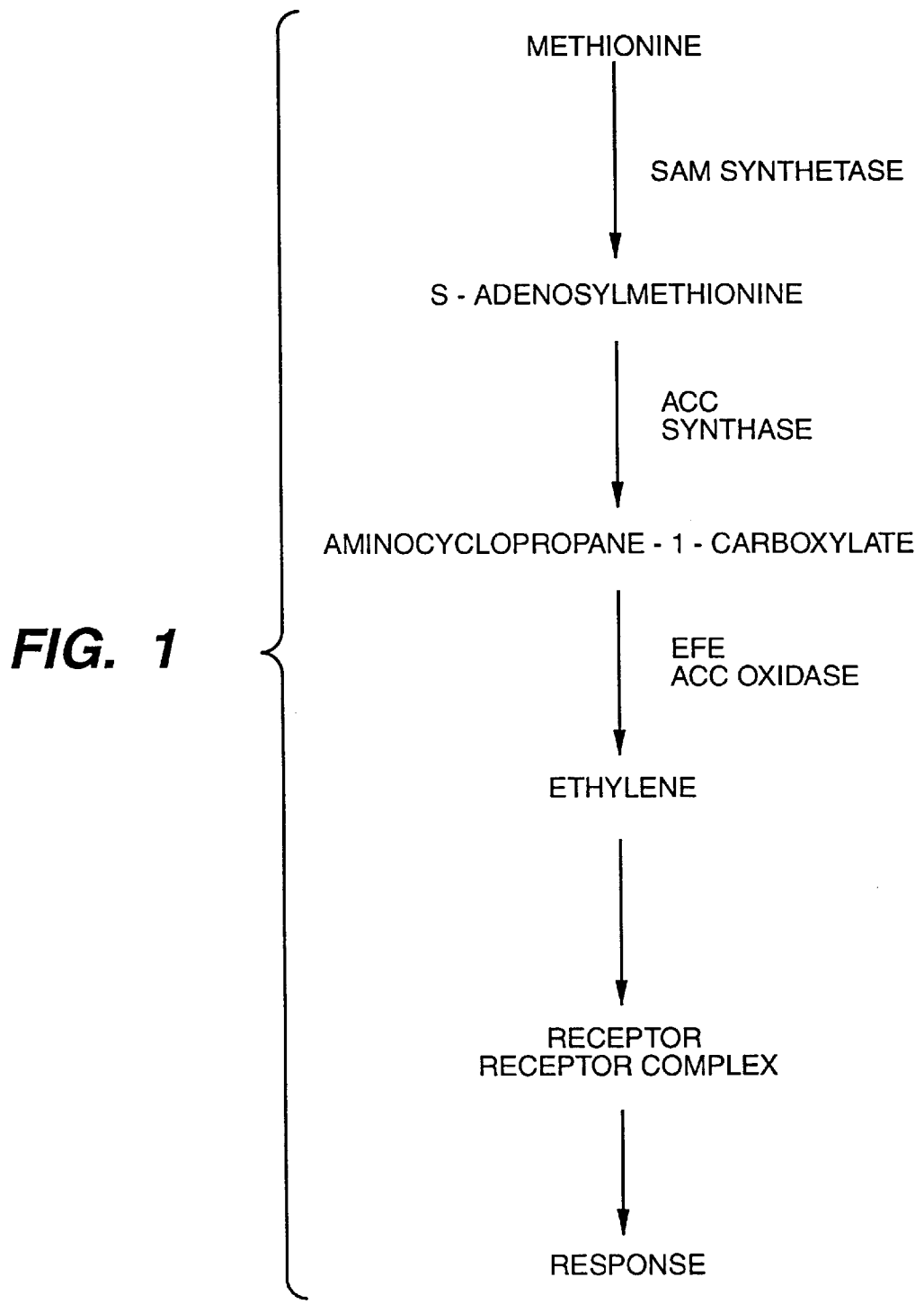
FIG. 1 depicts the biosynthetic pathway for ethylene.

The invention provides, in part, plants having cells transformed with a vector comprising an ETR nucleic acid or a modified ETR nucleic acid. Such transformed plant cells have a modulated response to ethylene. In a preferred embodiment, the expression of a modified ETR nucleic acid confers a phenotype on the plant characterized by a decrease in the response to ethylene for at least for those cells expressing the modified ETR nucleic acid as compared to a corresponding non-transformed plant. Thus, for example, when the modified ETR nucleic acid is expressed in fruit such as tomato, the fruit ripening process is retarded thereby reducing spoilage and extending the shelf life and/or harvesting season for the fruit. The invention is similarly useful to prevent spoilage of vegetative tissue and to enhance the longevity of cut flowers.

As used herein, a "plant ETR nucleic acid" refers to nucleic acid encoding all or part of a "plant ETR protein". ETR nucleic acids can initially be identified by homology to the ETR nucleic acid sequences disclosed herein but can also be identified by homology to any identified ETR nucleic acid or amino acid sequence. Examples of ETR nucleic acids include ETR1, QITR and Q8 from Arabidopsis and TETR, TGETR1 and TGETR2 from tomato. ETR nucleic acids, however, are also defined functionally by their ability to confer a modulated ethylene response upon transformation into plant tissue. In addition, antisense constructs of ETR nucleic acids or modified ETR nucleic acids, under certain conditions, are capable of modulating the ethylene response in plant tissue expressing the wild-type and/or modified antisense ETR nucleic acid. In addition, transformation with an ETR nucleic acid or modified ETR nucleic acid can result in co-suppression of the endogenous ETR alleles which in turn modifies the ethylene response. Furthermore, ETR nucleic acids can be modified as described herein to produce modified ETR nucleic acids which when used to transform plant tissue result in varying degrees of ethylene insensitivity in the tissue expressing such modified ETR nucleic acids. When evaluating a putative ETR nucleic acid for the ability of a modified form of the ETR nucleic acid to confer ethylene insensitivity, it is preferred that a codon or combination of codons encoding the amino acid residues equivalent to Ala-31, Ile-62, Cys-65 or Tyr-102 in the ETR1 protein of *Arabidopsis thaliana* or Pro-36 in the TETR protein in tomato be modified so as to substitute a different amino acid residue such as those disclosed herein for the specified residues.

Plant ETR nucleic acids include genomic DNA, cDNA and oligonucleotides including sense and anti-sense nucleic acids as well as RNA transcripts thereof. The genomic DNA sequence (SEQ ID NO:1) for the ETR1 gene from *Arabidopsis thaliana* is shown in FIG. 2. The corresponding cDNA sequence (SEQ ID NO:2) and deduced ETR amino acid sequence (SEQ ID NO:3) are shown in FIG. 3. An amino terminal domain (i.e., resides 1 through about 316) of the predicted ETR protein sequence has no homology to known protein sequences. Approximately midway in the ETR protein (i.e., residues 295 through 313) is a putative transmembrane domain followed by a putative intracellular domain (i.e., residues 314 through 738). A substantial portion of this putative intracellular domain unexpectedly has sequence homology to the two component environmental sensor-regulators known in bacteria. These two families in bacteria form a conserved sensor-regulator system that allows the bacteria to respond to a broad range of environmental fluctuations. It is believed that the amino terminal portion of the ETR protein interacts either directly with ethylene or indirectly (e.g., with an ethylene binding protein or another protein) and that upon such interaction, signal transduction through the intracellular domain occurs. An ETR nucleic acid or ETR protein can be identified by substantial nucleic acid and/or amino acid sequence homology to a known ETR sequence. Such homology can be based upon the overall nucleic acid or amino acid sequence in which case the overall homology of the protein sequence is preferably greater than about 50%, preferably greater than 60%, still more preferably greater than 75% and most preferably greater than 90% homologous. Notwithstanding overall sequence homology, it is preferred that the unique amino-terminal portion of an ETR protein sequence or the nucleic acid sequence encoding this portion of the molecule (i.e., the 5' terminal portion) be used to identify an ETR protein or ETR nucleic acid. When using this amino terminal sequence portion, it is preferred that the amino acid sequence homology with the known ETR sequence be greater than about 55%, more preferably about 60%, still more preferably about 70%, more preferably greater than 85% and most preferably greater than 95% homologous. Homology based on nucleic acid sequence is commensurate with amino acid homology but takes into account the degeneracy in the genetic code and codon bias in different plants. Accordingly, the nucleic acid sequence homology may be substantially lower than that based on protein sequence. Thus, an ETR protein is any protein which has an amino-terminal portion which is substantially homologous to the amino-terminal domain of a known ETR protein. One such known ETR protein is the ETR1 protein (see FIG. 3) from *Arabidopsis thaliana*. An ETR nucleic acid by analogy also encodes at least the amino-terminal domain of an ETR protein.

An ETR nucleic acid from a plant species other than *Arabidopsis thaliana* can be readily identified by standard methods utilizing known ETR nucleic acid. For example, labelled probes corresponding to a known ETR nucleic acid or encoding the unique amino-terminal domain can be used for in situ hybridization to detect the presence of an ETR gene in a particular plant species. In addition, such probes can be used to screen genomic or cDNA libraries of a different plant species or to identify one or more bands containing all or part of an ETR gene by hybridization to an electrophoretically separated preparation of genomic DNA digested with one or more restriction endonucleases.

The hybridization conditions will vary depending upon the probe used. When a unique nucleotide sequence of an ETR nucleic acid is used, e.g., an oligonucleotide encoding all or part of the amino terminal domain, relatively high stringency, e.g., about 0.1×SSPE at 65° C. is used. When the hybridization probe covers a region which has a potentially lower sequence homology to known ETR nucleic acids, e.g., a region covering a portion of the unique amino terminal domain and a portion covering a transmembrane domain, the hybridization is preferably carried out under moderate stringency conditions, e.g., about 5×SSPE at 50° C.

For example, using the above criteria, a ripening tomato cDNA library (Stratagene, LaJolla, Calif., Catalog No. 936004) was screened with a labeled probe comprising a nucleic acid sequence encoding an amino terminal portion of the Arabidopsis ETR protein sequence disclosed herein in FIG. 3A, B, C and D. Several clones were identified and sequenced by standard techniques. The DNA sequences for this ETR nucleic acid from tomato (TETR) and *Arabidopsis thaliana* (ETR1) encoding amino acid residues 1 through 123 (SEQ ID NOs:20 and 21) and amino acids 306 through 403 (SEQ ID NOs:22 and 23) are set forth in FIGS. 10A and 10B, respectively.

The amino acid sequences for the ETR1 protein from *Arabidopsis thaliana* and tomato (TETR) for residues 1 through 123 (SEQ ID NOs:25 and 24) and 306 through 403 (SEQ ID NOs:27 and 26) are set forth in FIGS. 11A and 11B, respectively.

The complete ETR nucleic acid (SEQ ID NO:35) and amino acid sequence (SEQ ID NO:36) for TETR is shown in FIG. 16. A direct comparison of the amino acid sequence between the TETR and ETR1 proteins for the amino terminal 316 amino acid residues is shown in FIG. 17.

As can be seen, there is substantial homology between these particular Arabidopsis and tomato ETR sequences both on the level of DNA sequence and amino acid sequence. In particular, the homology on the DNA level for the sequence encoding amino acids 1 through 45 is slightly greater than 72%. The homology on the amino acid level for amino acid residues 1 through 123 is approximately 79%. For the amino terminal portion (residues 1 through 316) the overall homology is approximately 73%. In the case of amino acid sequence homology, when the differences between the amino acids at equivalent residues are compared and such differences comprise the substitution of a conserved residue, i.e., amino acid residues which are functionally equivalent, the amino acid sequence similarity rises to about 90% for the first 123 residues. The sequence antibody for the amino terminal 316 amino acids rises to almost 85%. Such sequence similarity was determined using a Best Fit sequence program as described by Devereux et al. (1984) *Nucl. Acids Res.* 12:387–395. Functionally equivalent (i.e., conserved) residues are identified by double and single data in the comparative sequences. Similarly, the nucleic acid sequence homology between Arabidopsis and tomato for the sequence encoding amino acid residues 306 to 403 is approximately 75%. The sequence homology on the amino acid level for identical amino acids is almost 86% whereas the similarity is almost 96%.

In addition to ETR1 from Arabidopsis and TETR (sometimes referred to TXTR) from tomato, a number of other ETR nucleic acids have been identified in Arabidopsis and tomato. In Arabidopsis, the QITR and Q8 ETR nucleic acids and proteins have been identified. See FIGS. 12, 13, 14 and 15 and Seq. ID Nos. 41 through 48. For QITR, the overall nucleic acid homology with ETR1 is approximately 69%. With regard to the amino terminal portion between residues 1 and 316, the homology is approximately 71% identical for amino acid sequence and approximately 72% identical in terms of nucleic acid sequence. With reqard to Q8, the overall sequence homology to ETR1 from Arabidopsis is approximately 69% for the overall nucleic acid sequence as compared to approximately 81% homology for that portion of the Q8 encoding the amino terminal 316 amino acids. The homology on the amino acid level for the amino terminal portion is between Q8 and ETR1 is approximatley 72%.

The other ETR nucleic acids identified in tomato include TGETR1 (SEQ ID NO:37) and TGETR2 (SEQ ID NO:39). The deduced protein sequence for TGETR1 (SEQ ID NO:38) and TGETR2 (SEQ ID NO:40) are set forth in FIGS. 18 and 19 respectively. The sequence of TGETR2 is incomplete. A comparison of the sequence homology for the first 316 amino acid residues of the TGETR1 protein and the ETR1 protein is shown in FIG. 20. The sequence identity is just under 92%. The sequence similarity rises to almost 96% between this portion of these two proteins. With regard to TGETR2, FIG. 21 sets forth a comparison of the amino terminal portion of this molecule (through amino acid residue 245) with the corresponding portion of the ETR1 protein. The identity of sequences between these two sequence portions is approximately 85%. The sequence similarity rises to just above 92%.

The cloning and sequencing of the ETR nucleic acids from Arabidopsis is described in the examples herein. However, given the extensive disclosure of the sequences for these ETR nucleic acids, one skilled in the art can readily construct oligonucleotide probes, perform PCR amplification or utilize other standard protocols known to those skilled in the art to isolate the disclosed genes as well as other ETR nucleic acids having homology thereto from other species. When screening the same plant species, relatively moderate to high stringency conditions can be used for hybridization which would vary from between 55° C. to 65° C. in 5×SSPE. When it is desirable to probe for lower homology or in other plant species, lower stringency conditions such as 50° C. at 5×SSPE can be used. Washing conditions however required 0.2×SSPE.

The isolation of the TETR1 ETR nucleic acid from tomato is described in the examples. The isolation of this sequence utilized the amino terminal portion of the ETR1 gene from Arabidopsis. The other tomato ETR nucleic acids disclosed herein (TGETR1 and TGETR2) were identified by probing a tomato genomic library with an ETR1 probe. The genomic library was made from EMBL 3 to which was ligated a partially Sau3A digested genomic DNA extract of tomato. Conditions were 65° C. 5×SSC with washes at 2×SSC.

In reviewing the overall structure of the various ETR nucleic acids and proteins identified to date, it appears that at least one class of ETR protein contains a unique amino terminal portion followed by a histine-kinase domain followed by a response regulatory region. This is the ETR1 protein in Arabidopsis. A second class of ETR protein does not contain the response regulatory region. Examples of such ETR proteins include QITR in Arabidopsis and TETR in tomato. The significance of this is not understood at this time. However, as described hereinafter, mutations in the ETR nucleic acids encoding members from each class can confer a dominate ethylene insensitivity to transgenic plants containing such nucleic acids.

As described hereinafter, substitution of amino acid residues Ala-31, Ile-62, Cys-65 and Tyr-102 with a different amino acid results in modified Arabidopsis ETR nucleic acid which are capable of conferring ethylene insensitivity in a transformed plant. Each of these residues are identical as between the ETR protein of tomato (TETR) and Arabidopsis thaliana (ETR1).

Once the ETR nucleic acid is identified, it can be cloned and, if necessary, its constituent parts recombined to form the entire ETR nucleic acid. Once isolated from its natural source, e.g., contained within a plasmid or other vector or excised therefrom as a linear nucleic acid segment, the ETR nucleic acid can be further used as a probe to identify and isolate other ETR nucleic acids. It can also be used as a "precursor" nucleic acid to make modified ETR nucleic acids and proteins.

As used herein, the term "modified ETR nucleic acid" refers to an ETR nucleic acid containing the substitution, insertion or deletion of one or more nucleotides of a precursor ETR nucleic acid. The precursor ETR nucleic acids include naturally-occurring ETR nucleic acids as well as other modified ETR nucleic acids. The naturally-occurring ETR nucleic acid from *Arabidopsis thaliana* can be used as a precursor nucleic acid which can be modified by standard techniques, such as site-directed mutagenesis, cassette mutagenesis and the like, to substitute one or more nucleotides at a codon such as that which encodes alanine at residue 31 in the Arabidopsis ETR nucleic acid. Such in vitro codon modification can result in the generation of a codon at position 31 which encodes any one of the other naturally occurring amino acid residues. Such modification results in a modified ETR nucleic acid.

For example, the mutation responsible for the pheno-type observed in the Never-ripe mutant is disclosed in the examples. As described, a single point mutation changes the proline normally present at residue 36 in the TETR protein to leucine. This single mutation is sufficient to confer a dominant ethylene insensitivity phenotype on the wild-type plant. The transformation of tomato and other plants with this modified ETR nucleic acid is expected to confer the dominant ethylene insensitivity phenotype on such transformed plant cells.

Alternatively, the precursor nucleic acid can be one wherein one or more of the nucleotides of a wild-type ETR nucleic acid have already been modified. Thus, for example, the *Arabidopsis thaliana* ETR nucleic acid can be modified at codon 31 to form a modified nucleic acid containing the substitution of that codon with a codon encoding an amino acid other than alanine, e.g., valine. This modified ETR nucleic acid can also act as a precursor nucleic acid to introduce a second modification. For example, the codon encoding Ala-102 can be modified to encode the substitution of threonine in which case the thus formed modified nucleic acid encodes the substitution of two different amino acids at residues 31 and 102.

Deletions within the ETR nucleic acid are also contemplated. For example, an ETR nucleic acid can be modified to delete that portion encoding the putative transmembrane or intracellular domains. The thus formed modified ETR nucleic acid when expressed within a plant cell produces only an amino-terminal portion of the ETR protein which is potentially capable of binding ethylene, either directly or indirectly, to modulate the effective level of ethylene in plant tissue.

In addition, the modified ETR nucleic acid can be identified and isolated from a mutant plant having a dominant or recessive phenotype characterized by an altered response to ethylene. Such mutant plants can be spontaneously arising or can be induced by well known chemical or radiation mutagenesis techniques followed by the determination of the ethylene response in the progeny of such plants. Examples of such mutant plants which occur spontaneously include the Never ripe mutant of tomato and the ethylene insensitive mutant of carnation. Thus, modified ETR nucleic acids can be obtained by recombinant modification of wild-type ETR nucleic acids or by the identification and isolation of modified ETR alleles from mutant plant species.

It is preferred that the modified ETR nucleic acid encode the substitution, insertion and/or deletion of one or more amino acid residues in the precursor ETR protein. Upon expression of the modified nucleic acid in host plant cells, the modified ETR protein thus produced is capable of modulating at least the host cell's response to ethylene. In connection with the generation of such a phenotype, a number of codons have been identified in the ETR nucleic acid from *Arabidopsis thaliana* which when modified and reintroduced into a wild-type plant result in a decrease in the ethylene response by the transformed plant. These codons encode amino acid residues Ala-31, Ile-62, Cys-65 and Tyr-102 in the ETR protein of *Arabidopsis thaliana*. The ETR gene and each of these particular modified amino acid residues were identified by cloning the wild-type ETR gene from *Arabidopsis thaliana* and chemically modified alleles from four different varieties (etr1-1, etr1-2, etr1-3 and etr1-4) of *Arabidopsis thaliana* (each of which exhibited a dominant phenotype comprising insensitivity to ethylene) and comparing the nucleotide and deduced amino acid sequences. The invention, however, is not limited to modified ETR nucleic acids from *Arabidopsis thaliana* as described in the examples. Rather, the invention includes other readily identifiable modified ETR nucleic acids which modulate ethylene sensitivity.

The above four varieties exhibiting dominant ethylene insensitivity were generated by chemical modification of seedlings of *Arabidopsis thaliana* and identified by observing plant development from such modified seedlings with the addition of exogenous ethylene. Using a similar approach either with or without the addition of exogenous ethylene, the skilled artisan can readily generate other variants of any selected plant species which also have a modulated response to ethylene. Then, using ETR probes based upon the wild-type or modified ETR nucleic acid sequences disclosed herein, other modified ETR nucleic acids can be isolated by probing appropriate genomic or cDNA libraries of the modified selected plant species. The nucleotide and/or encoded amino acid sequence of such newly generated modified ETR nucleic acids is then preferably compared with the wild-type ETR nucleic acid from the selected plant species to determine which modifications, if any, in the ETR nucleic acid are responsible for the observed phenotype. If the wild-type sequence of the selected plant species is not available, the wild-type or modified ETR sequences disclosed herein for *Arabidopsis thaliana* or other ETR sequences which have been identified can be used for comparison. In this manner, other modifications to ETR proteins can be identified which can confer the ethylene insensitivity phenotype. Such modifications include the identification of amino acids other than those disclosed herein which can be substituted at residues equivalent to Ala-31, Ile-62, Cys-65 and Ala-102 in the Arabidopsis thaliana ETR protein and the identification of other amino acid residues which can be modified by substitution, insertion and/or deletion of one or more amino acid residues to produce the desired phenotype.

Other amino acid residues can be selected for modification to confer an ethylene insensitive phenotype. Suitable amino acid residues for modification are those residues that are conserved between various ETR proteins. However, conserved amino acid residues are preferably selected from domains containing amino acid residues that are equivalent to *Arabidopsis thaliana* ETR1 residues 1–313, and more preferably 10–200, and still more preferably to amino acid residues 15–120, and most preferably to amino acid residues 30–105.

Alternatively, a cloned precursor ETR nucleic acid can be systematically modified such that it encodes the substitution, insertion and/or deletion of one or more amino acid residues and tested to determine the effect of such modification on a plant's ethylene response.

Such modifications are preferably made within that portion of the ETR nucleic acid which encodes the amino-terminal portion of the ETR protein. However, modifications to the carboxy-terminal or putative transmembrane domains to modulate signal transduction are also contemplated (e.g., modifications of the conserved histidine of the histidine kinase domain which is the supposed site of autophosphorylation or the conserved aspartate of the response regulator domain which is the supposed site of phosphorylation). One method which may be used for identifying particular amino acid residues involved in the direct or indirect interaction with ethylene is the sequential substitution of the codons of an ETR nucleic acid with codons encoding a scanning amino acid such as glycine or alanine (See, e.g., PCT Publication WO90/04788 published May 3, 1990) followed by transformation of each of the thus formed modified nucleic acids into a plant to determine the effect of such sequential substitution on the ethylene response. Other approaches include random modifications or predetermined targeted modifications of the cloned ETR nucleic (See, e.g., PCT Publication No. WO92/07090 published Apr. 30, 1992) followed by transformation of plant cells and the identification of progeny having an altered ethylene response. The ETR nucleic acid from those plants having the desired phenotype is isolated and sequenced to confirm or identify the modification responsible for the observed phenotype.

Amino acid residues equivalent to those specifically identified in an ETR protein which can be modified to alter the ethylene response can also be readily identified in ETR proteins from other plant species. For example, equivalent amino acid residues to those identified in the ETR protein from *Arabidopsis thaliana* can be readily identified in other ETR proteins. An amino acid residue in a precursor ETR protein is equivalent to a particular residue in the ETR protein of *Arabidopsis* thaliana if it is homologous in position in either primary or tertiary structure to the specified residue of the Arabidopsis ETR protein.

In order to establish homology by way of primary structure, the primary amino acid sequence of a precursor ETR protein is directly compared by alignment with the primary sequence of the ETR protein from *Arabidopsis thaliana*. Such alignment is preferably of the amino-terminal domain and will take into account the potential insertion or deletion of one or more amino acid residues as between the two sequences so as to maximize the amino acid sequence homology. A comparison of a multiplicity of ETR protein sequences with that of *Arabidopsis thaliana* provides for the identification of conserved residues among such sequences which conservation is preferably maintained for further comparison of primary amino acid sequence. Based on the alignment of such sequences, the skilled artisan can readily identify amino acid residues in other ETR proteins which are equivalent to Ala-31, Ile-62, Cys-65, Ala-102 and other residues in *Arabidopsis thaliana* ETR protein. Such equivalent residues are selected for modifications analogous to those of other modified ETR proteins which confer the desired ethylene responsive phenotype. Such modified ETR proteins are preferably made by modifying a precursor ETR nucleic acid to encode the corresponding substitution, insertion and/or deletion at the equivalent amino acid residue.

In addition to homology at the primary sequence level, equivalent residues can be identified based upon homology at the level of tertiary structure. The determination of equivalency at this level will generally require three-dimensional crystal structures for an ETR protein or modified ETR protein from Arabidopsis (or crystal structure of another ETR protein having defined equivalent residues) and the crystal structure of a selected ETR protein. Equivalent residues at the level of tertiary structure are defined as those for which the atomic coordinates of two or more of the main chain atoms of a particular amino acid residue of the selected ETR protein, as compared to the ETR protein from Arabidopsis, are within 0.13 nm and preferably 0.10 nm after alignment. Alignment is achieved after the best model has been oriented and positioned to give the maximum overlap of atomic coordinates of non-hydrogen protein atoms of the ETR proteins in question.

ETR nucleic acids can be derived from any of the higher plants which are responsive to ethylene. Particularly suitable plants include tomato, banana, kiwi fruit, avocado, melon, mango, papaya, apple, peach and other climacteric fruit plants. Non-climacteric species from which ETR nucleic acids can be isolated include strawberry, raspberry, blackberry, blueberry, lettuce, cabbage, cauliflower, onion, broccoli, brussel sprout, cotton, canola, grape, soybean and oil seed rape. In addition, ETR nucleic acids can be isolated from flowering plants within the Division Magnoliophyta which comprise the angiosperms which include dicotyledons (Class Magnoliopsida and Dicotyledoneae) and monocotyledons (Class Liliopsida). Particularly preferred Orders of angiosperm according to "Taxonomy of Flowering Plants", by A. M. Johnson, The Century Co., NY, 1931 include Rosales, Cucurbitales, Rubiales, Campanulatae, Contortae, Tubiflorae, Plantaginales, Ericales, Primulales, Ebenales, Diapensiales, Primulales, Plumbaginales, Opuntiales, Parietales, Myritiflorae, Umbelliflorae, Geraniales, Sapindales, Rhamnales, Malvales, Pandales, Rhoendales, Sarraceniales, Ramales, Centrospermae, Santalales, Euphorbiales, Capparales, Aristolochiales, Julianiales, Juglandales, Fagales, Urticales, Myricales, Polygonales, Batidales, Balanopsidales, Proteales, Salicales, Leitneriales, Garryales, Verticillatae and Piperales. Particularly preferred plants include lily, carnation, chrysanthemum, petunia, rose, geranium, violet, gladioli, orchid, lilac, crabapple, sweetgum, maple, poinsettia, locust, ash and linden tree.

In addition to providing a source for ETR nucleic acids which can be modified or isolated according to the teachings herein, the foregoing plants can be used as recipients of the modified nucleic acid to produce chimeric or transgenic plants which exhibit an ethylene resistance phenotype in one or more tissue types of the transformed plant.

Once a modified ETR nucleic acid has been cloned, it is used to construct vectors for transforming plant cells. The construction of such vectors is facilitated by the use of a shuttle vector which is capable of manipulation and selection in both plant and a convenient cloning host such as a prokaryote. Such shuttle vectors thus can include an antibiotic resistance gene for selection in plant cells (e.g., kanamycin resistance) and an antibiotic resistance gene for selection in a bacterial host (e.g. actinomycin resistance). Such shuttle vectors also contain an origin of replication appropriate for the prokaryotic host used and preferably at least one unique restriction site or a polylinker containing unique restriction sites to facilitate vector construction. Examples of such shuttle vectors include pMON530 (Rogers et al. (1988) *Methods in Enzymology* 153:253–277) and pCGN1547 (McBride et al. (1990) *Plant Molecular Biology* 14:269-276).

In the preferred embodiments, which comprise the best mode for practicing the invention, a promoter is used to drive expression of an ETR or a modified ETR nucleic acid within at least a portion of the tissues of a transformed plant. Expression of a modified ETR nucleic acid results in the production of a modified ETR protein which is capable of conferring ethylene insensitivity. Such promoters may be obtained from plants, plant pathogenic bacteria or plant viruses. Constitutive promoters include the 35S and 19S promoters of cauliflower mosaic virus (CaMV35S and CaMV19S), the full-length transcript promoter from the Figwort mosaic virus (FMV35S) (See PCT Publication No. WO92/12249 published Jul. 23, 1992) and promoters associated with Agrobacterium genes such as nopaline, synthase (NOS), mannopine synthase (MOS) or octopine synthase (OCS). Other constitutive promoters include the α-1 and β-1 tubulin promoters (Silflow et al. (1987) *Devel. Genet.* 8:435–460), the histone promoters (Chaubet (1987) *Devl. Genet.* 8:461–473) and the promoters which regulate transcription of ETR nucleic acids.

In some embodiments, tissue and/or temporal-specific promoters can be used to control expression of ETR and modified ETR nucleic acids. Examples of fruit specific promoters include the E8, E4, E17 and J49 promoters from tomato (Lincoln et al. (1988) *Mol. Gen. Genet.* 212:71–75) and the 2A11, Z130 and Z70 promoters from tomato as described in U.S. Pat. Nos. 4,943,674, 5,175,095 and 5,177,307. In addition, preferential expression in rapidly dividing tissue can be obtained utilizing the plant EF-1α promoter as described in U.S. Pat. No. 5,177,011. Examples of floral specific promoters include the leafy promoter and promoters from the apetala, pistillata and agamous genes. A promoter system for targeting expression in the leaves of a transformed plant is a chimeric promoter comprising the CaMV35S promoter ligated to the portion of the ssRUBISCO gene which represses the expression of ssRUBISCO in the absence of light. In addition, pollen-specific promoters can also be used. Such promoters are well known to those skilled in the art and are readily available. A example of such a promoter is Zn13 (Hamilton et al. (1992) *Plant Mol. Biol.* 18:211–218). This promoter was cloned from corn (Monocot) but functions as a strong and pollen-specific promoter when used in tobacco (Dicot).

Examples of inducible promoters which can be used for conditional expression of ETR nucleic acids include those from heat-shock protein genes such as the PHS1 heat-shock protein gene (Takahashi et al. (1989) *Mol. Gen. Genet.* 219:365–372) and light-inducible promoters including the three chlorophyll a/b light harvesting protein promoters (Leutwiler et al. (1986) *Nucl. Acids. Res.* 14:4051–4064) and the pre-ferredoxin promoter (Vorst et al. (1990) *Plant Mol. Biol.* 14:491–499).

In a further embodiment of the invention, the vector used to transform plant cells is constructed to target the insertion of the ETR nucleic acid into an endogenous promoter within a plant cell. One type of vector which can be used to target the integration of a modified ETR nucleic acid to an endogenous promoter comprises a positive-negative selection vector analogous to that set forth by Monsour, et al. *Nature* 336:348–352 (1988) which describes the targeting of exogenous DNA to a predetermined endogenous locus in mammalian ES cells. Similar constructs utilizing positive and negative selection markers functional in plant cells can be readily designed based upon the identification of the endogenous plant promoter and the sequence surrounding it. When such an approach is used, it is preferred that a replacement-type vector be used to minimize the likelihood of reversion to the wild-type genotype.

In another embodiment, expression of an ETR nucleic acid in the antisense orientation is capable of modulating the ethylene response by reduction in expression of one or more endogenous wild-type or modified ETR alleles. For example, in some plants having more than one ETR gene, it is necessary to use more than one antisense construct such that the different constructs have one or more ETR nucleic acids in an antisense orientation. Alternatively, antisense constructs can be used in combination with targeted inactivation of one or more of the endogenous ETR genes in the genome of the plant. In this approach, the antisense constructs are used to modify expression of remaining functional ETR genes.

In addition, one or more antisense constructs can be used to modulate a dominant mutant ethylene insensitive phenotype to obtain partial ethylene insensitivity. See e.g., Example 5. Such constructs are especially useful with tissue or temporal, and/or conditional promoters as a way to control the ethylene insensitive phenotype in tissues of said plants.

The vectors of the invention are designed such that the promoter sequence contained in the vector or the promoter sequence targeted in the plant cell genome are operably linked to the nucleic acid encoding the ETR or modified ETR nucleic acid. When the positive strand of the ETR nucleic acid is used, the term "operably linked" means that the promoter sequence is positioned relative to the coding sequence of the ETR nucleic acid such that RNA polymerase is capable of initiating transcription of the ETR nucleic acid from the promoter sequence. In such embodiments it is also preferred to provide appropriate ribosome binding sites, transcription initiation and termination sequences, translation initiation and termination sequences and polyadenylation sequences to produce a functional RNA transcript which can be translated into ETR protein. When an antisense orientation of the ETR nucleic acid is used, all that is required is that the promoter be operably linked to transcribe the ETR antisense strand. Thus, in such embodiments, only transcription start and termination sequences are needed to provide an RNA transcript capable of hybridizing with the mRNA or other RNA transcript from an endogenous ETR gene or modified ETR nucleic acid contained within a transformed plant cell. In addition to promoters, other expression regulation sequences, such as enhancers, can be added to the vector to facilitate the expression of ETR nucleic acid in vivo.

Once a vector is constructed, the transformation of plants can be carried out in accordance with the invention by essentially any of the various transformation methods known to those skilled in the art of plant molecular biology. Such methods are generally described in *Methods and Enzymology*, Vol. 153 ("Recombinant DNA Part D") 1987, Wu and Grossman, Academic Press, eds. As used herein, the term "transformation" means the alteration of the genotype of a plant cell by the introduction of exogenous nucleic acid. Particular methods for transformation of plant cells include the direct microinjection of the nucleic acid into a plant cell by use of micropipettes. Alternatively, the nucleic acid can be transferred into a plant cell by using polyethylene glycol (Paszkowski et al. *EMBO J.* 3:2717–2722 (1984)). Other transformation methods include electroporation of protoplasts (Fromm, et al. *Proc. Natl. Acad. Sci. U.S.A.* 82:5824 (1985); infection with a plant specific virus, e.g., cauliflower mosaic virus (Hohn et al. "Molecular Biology of Plant Tumors", Academic Press, New York (1982), pp. 549–560) or use of transformation sequences from plant specific bacteria such as *Agrobacterium tumefaciens*, e.g., a Ti plasmid transmitted to a plant cell upon infection by *Agrobacterium tumefaciens* (Horsch et al. *Science* 233:496–498 (1984); Fraley et al. *Proc. Natl. Acad. Sci. U.S.A.* 80:4803 (1983)). Alternatively, plant cells can be transformed by introduction of nucleic acid contained within the matrix or on the surface of small beads or particles by way of high velocity ballistic penetration of the plant cell (Klein et al. *Nature* 327:70–73 (1987)).

After the vector is introduced into a plant cell, selection for successful transformation in typically carried out prior to regeneration of a plant. Such selection for transformation is not necessary, but facilitates the selection of regenerated plants having the desired phenotype by reducing wild-type background. Such selection is conveniently based upon the antibiotic resistance and/or herbicide resistance genes which may be incorporated into the transformation vector.

Practically all plants can be regenerated from cultured cells or tissues. As used herein, the term "regeneration" refers to growing a whole plant from a plant cell, a group of plant cells or a plant part. The methods for plant regeneration are well known to those skilled in the art. For example, regeneration from cultured protoplasts is described by Evans et al. "Protoplasts Isolation and Culture", *Handbook of Plant Cell Cultures* 1:124–176 (MacMillan Publishing Co., New York (1983); M. R. Davey, "Recent Developments in the Culture and Regeneration of Plant Protoplasts", *Protoplasts* (1983) *Lecture Proceedings*, pp. 12–29 (Birkhauser, Basil 1983); and H. Binding "Regeneration of Plants", *Plant Protoplasts*, pp. 21–73 (CRC Press, Bocaraton 1985). When transformation is of an organ part, regeneration can be from the plant callus, explants, organs or parts. Such methods for regeneration are also known to those skilled in the art. See, e.g., *Methods in Enzymology*, supra.; *Methods in Enzymology*, Vol. 118; and Klee et al. *Annual Review of Plant Physiology* 38:467–486.

A preferred method for transforming and regenerating petunia with the vectors of the invention is described by Horsch, R. B. et al. (1985) *Science* 227:1229–1231. A preferred method for transforming cotton with the vectors of the invention and regenerating plants therefrom is described by Trolinder et al. (1987) *Plant Cell Reports* 6:231–234.

Tomato plant cells are preferably transformed utilizing Agrobacterium strains by the method as described in McCormick et al., Plant Cell Reports 5:81–84 (1986). In particular, cotyledons are obtained from 7–8 day old seedlings. The seeds are surface sterilized for 20 minutes in 30% Clorox bleach and germinated in Plantcons boxes on Davis germination media. Davis germination media is comprised of 4.3 g/l MS salts, 20 g/l sucrose and 10 mls/l Nitsch vitamins, pH 5.8. The Nitsch vitamin solution is comprised of 100 mg/l myo-inositol, 5 mg/l nicotinic acid, 0.5 mg/l pyridoxine HCl, 0.5 mg/l thiamine HCl, 0.05 mg/l folic acid, 0.05 mg/l biotin, 2 mg/l glycine. The seeds are allowed to germinate for 7–8 days in the growth chamber at 25° C., 40% humidity under cool white lights with an intensity of 80 einsteins $m^2$–$s^{-1}$. The photoperiod is 16 hours of light and 8 hours of dark.

Once germination occurs, the cotyledons are explanted using a #15 feather blade by cutting away the apical meristem and the hypocotyl to create a rectangular explant. These cuts at the short ends of the germinating cotyledon increase the surface area for infection. The explants are bathed in sterile Davis regeneration liquid to prevent desiccation. Davis regeneration media is composed of 1× MS salts, 3% sucrose, 1× Nitsch vitamins, 2.0 mg/l zeatin, pH 5.8. This solution was autoclaved with 0.8% Noble Agar.

The cotyledons are pre-cultured on "feeder plates" composed of media containing no antibiotics. The media is composed of 4.3 g/l MS salts, 30 g/l sucrose, 0.1 g/l myo-inositol, 0.2 g/l $KH_2PO_4$, 1.45 mls/l of a 0.9 mg/ml solution of thiamine HCl, 0.2 mls of a 0.5 mg/ml solution of kinetin and 0.1 ml of a 0.2 mg/ml solution of 2,4 D. This solution is adjusted to pH 6.0 with KOH. These plates are overlaid with 1.5–2.0 mls of tobacco suspension cells (TXD's) and a sterile Whitman filter soaked in 2COO5K media. 2COO5K media is composed of 4.3 g/l Gibco MS salt mixture, 1 ml B5 vitamins (1000× stock), 30 g/l sucrose, 2 mls/l PCPA from 2 mg/ml stock, and 10 µl/l kinetin from 0.5 mg/ml stock. The cotyledons were cultured for 1 day in a growth chamber at 25° C. under cool white lights with a light intensity of 40–50 einsteins $m^2s^{-1}$ with a continuous light photoperiod.

Cotyledons are then inoculated with a log phase solution of Agrobacterium containing the modified or wild type ETR nucleic acid. The concentration of the Agrobacterium is approximately $5 \times 10^8$ cells/ml. The cotyledons are allowed to soak in the bacterial solution for six minutes and are then blotted to remove excess solution on sterile Whatman filter disks and subsequently replaced to the original feeder plate where they are allowed to co-culture for 2 days. After the two days, cotyledons are transferred to selection plates containing Davis regeneration media with 2 mg/l zeatin riboside, 500 µg/ml carbenicillin, and 100 µg/ml kanamycin. After 2–3 weeks, cotyledons with callus and/or shoot formation are transferred to fresh Davis regeneration plates containing carbenicillin and kanamycin at the same levels. The experiment is scored for transformants at this time. The callus tissue is subcultured at regular 3 week intervals and any abnormal structures are trimmed so that the developing shoot buds continue to regenerate. Shoots develop within 3–4 months. Once shoots develop, they are excised cleanly from callus tissue and planted on rooting selection plates. These plates contain 0.5× MSO containing 50 µg/ml kanamycin and 500 µg/ml carbenicillin. These shoots form roots on the selection media within two weeks. If no roots appear after 2 weeks, shoots are trimmed and replanted on the selection media. Shoot cultures are incubated in percivals at a temperature of 22° C. Shoots with roots are then potted when roots were about 2 cm in length. The plants are hardened off in a growth chamber at 21° C. with a photoperiod of 18 hours light and 6 hours dark for 2–3 weeks prior to transfer to a greenhouse. In the greenhouse, the plants are grown at a temperature of 26° C. during the day and 21° C. during the night. The photoperiod is 13 hours light and 11 hours dark and the plants are allowed to mature.

Once plants have been regenerated, one or more plants are selected based upon a change in the ethylene response phenotype. For example, when a modified ETR nucleic acid is used with its native promoter, selection can be based upon an alteration in any of one of the "triple responses" of seedlings from such plants. Guzman et al. (1990) *The Plant Cell* 2:523. Alternatively, or when constitutive promoters are used, various other ethylene responses can be assayed and compared to the wild type plant. Such other ethylene responses include epinasty (which is observed primarily in tomato), epsision, abscission, flower petal senescence and fruit ripening. In addition to overt changes in the ethylene response, the levels of various enzymes can be determined followed by exposure to ethylene to determine the response time for the typical increase or decrease in the level of a particular protein such as an enzyme. Examples of various ethylene responses which can be used to determine whether a particular plant has a decreased response to ethylene are set forth in Chapter 7, The Mechanisms of Ethylene Action in "Ethylene in Plant Biology" 2d Ed. F. B. Abels, P. W. Morgan and M. E. Salveit, Jr., eds., San Diego, Academic Press, Inc. (1992). When a tissue and/or temporal-specific promoter or inducible promoter is used, the determination of a modulation in the ethylene response is determined in the appropriate tissue at the appropriate time and if necessary under the appropriate conditions to activate/inactivate an inducible promoter. In each case, the ethylene response is preferably compared to the same ethylene response from a wild-type plant.

The following are particularly preferred embodiments for modulating the ethylene response in fruit. However, such embodiments can be readily modified to modulate the ethylene response in vegetative tissue and flowers.

In one approach, a modified ETR nucleic acid operably linked to a constitutive promoter of moderate strength is used to reduce the ethylene response. This results in a lengthening of the time for fruit ripening.

In an alternate embodiment, a modified ETR nucleic acid operably linked to a regulatable (inducible) promoter is used so that the condition that turns on the expression of the modified ETR nucleic acid can be maintained to prevent fruit ripening. The condition that turns off the expression of the modified ETR nucleic acid can then be maintained to obtain ripening. For example, a heat-inducible promoter can be used which is active in high (field) temperatures, but not in low temperatures such as during refrigeration. A further example utilizes an auxin or gibberellin-induced promoter such that transformed plants can be treated with commercial auxin analogs such as 2, 4-D or with commercial gibberellin analogs such as Pro-Gibb to prevent early ripening.

Alternatively, a strong constitutive promoter can be operably linked to a modified ETR nucleic acid to prevent fruit ripening. So as to allow eventual fruit ripening, the plant is also transformed with a wild-type ETR nucleic acid operably linked to an inducible promoter. Expression of the wild-type ETR nucleic acid is increased by exposing the plant to the appropriate condition to which the inducible promoter responds. When the wild-type ETR nucleic acid expression is increased, the effect of expression of the modified ETR nucleic acid is reduced such that fruit ripening occurs.

Particular constructs which are desirable for use in transforming plants to confer ethylene insensitivity include the CMV35S promoter operably linked to any other mutant Arabidopsis ETR genomic or cDNA clones including the corresponding modification at residue 36 to convert proline to leucine. Such constructs are expected to confer a dominant ethylene insensitivity phenotype tp cells and plants transformed with and expressing such constructs.

In addition, a preferred constructs include operably linking the FMV promoter to drive expression of the tomato TETR cDNA which has been engineered to contain a mutation analogous to any of those identified in the ETR genes from Arabidopsis as well as the Nr mutation found in the tomato ETR gene. Such constructs are expected to confer a dominant ethylene insensitivity phenotype to cells and plants. which are transformed with and express such constructs.

Other possible constructs include the operable linking the FMV promoter to ETR antisense cDNAs including TETR and ETR1. Such constructs are expected to reduce the the translation of ETR RNA and, under some conditions, modify the plants' ethylene sensitivity (or, if a plant has a dominant ethylene insensitive mutation, its insensitivity) to ethylene.

The invention can be practiced in a wide variety of plants to obtain useful phenotypes. For example, the invention can be used to delay or prevent floral senescence and abscission during growth or during transport or storage as occurs in flower beds or cotton crops (Hall, et al. (1957) *Physiol. Plant* 10:306–317) and in ornamental flowers (e.g., carnations, roses) that are either cut (Halevy, et al. (1981) *Hort. Rev.* 3:59–143) or not cut. In addition, the invention can be practiced to delay or prevent senescence and abscission of leaves and fruits in cucumber (Jackson, et al. (1972) *Can. J. Bot.* 50:1465–1471), legumes and other crops (Heck, et al. (1962) *Texas Agric. Expt. Sta. Misc. Publ.* MP 613:1–13) and ornamental plants (e.g., holly wreaths) (Curtis et al. (1952) *Proc. Am. Soc. Hort. Sci.* 560:104–108). Other uses include the reduction or prevention of bitter-tasting phenolic compounds (isocoumarins) which are induced by ethylene for example in sweet potatoes (Kitinoja (1978) "Manipulation of Ethylene Responses in Horticulture", Reid, ed., *Acta. Hort. Vol* 201, 377–42) carrots (Coxon et al. (1973) *Phyto. Chem. Istry.* 12:1881–1885), parsnip (Shattuck et al. (1988) *Hort. Sci.* 23:912) and Brassica. Other uses include the prevention of selective damage to reproductive tissues as occurs in oats and canola (Reid et al. (1985) in "Ethylene in Plant Development", Roberts, Tucker, eds. (London), Butterworths, pp. 277–286), the loss of flavor, firmness and/or texture as occurs in stored produce such as apples and watermelons (Risse et al. (1982) *Hort. Sci.* 17:946–948), russet spotting (a post-harvest disorder) which is ethylene induced in crisphead lettuce (Hyodo et al. (1978) *Plant Physiol.* 62:31–35), to promote male flower production (Jaiswal et al. (1985) *Proc. Indian Acad. Sci.* (Plantg Sci. 95:453–459) and to increase plant size, e.g., by delaying the formation of flowers in ornamental bromeliads (Mekers et al. (9183) *Acta Hortic* 137:217–223). Furthermore, a decrease in ethylene response can be used to delay disease developments such as the preventing of lesions and senescence in cucumbers infected with *Colletotrichum lagenarium* and to reduce diseases in plants in which ethylene causes an increase in disease development, e.g., in barley, citrus, Douglas fir seedlings, grapefruit, plum, rose, carnation, strawberry, tobacco, tomato, wheat, watermelon and ornamental plants. In addition, the invention can be used to reduce the effect of ethylene found in the environment and indirectly the effect of various environmental stresses which result in the biosynthesis of ethylene in plant tissue. For example, ethylene exists at biologically detrimental levels in localized atmospheres due to fires, automobile exhaust and industry. See, e.g., Chapter 8, Ethylene in the Environment in "Ethylene in Plant Biology", supra. In addition, the invention can be used to minimize the effect of ethylene synthesized in response to environmental stresses such as flooding, drought, oxygen deficiency, wounding (including pressure and bruising), chilling, pathogen invasion (by viruses, bacteria, fungi, insects, nematodes and the like), chemical exposure (e.g., ozone salt and heavy metal ions) and radiation.

The following is presented by way of example and is not to be construed as a limitation on the scope of the invention. Further, all references referred to herein are expressly incorporated by reference.

EXAMPLE 1

Cloning of the ETR1 Gene etr1-1 plants were crossed with two lines carrying the recessive visible markers ap1 and clv2 respectively. The $F_1$ progeny were allowed to self-pollinate. Phenotypes were scored in the $F_2$. The recombination percentages (using the Kosambi mapping function (D. D. Kosambi (1944) *Ann. Eugen.* 12:172)) were determined in centimorgans. The ETR1 locus mapped to the lower portion of chromosome 1 between the visible genetic markers ap1 and clv2 (6.5+/−1.0 cM from AP1 and 2.8+/−1.1 cM from CLV2). etr1-1 was crossed to tester line W100 (ecotype Landsberg (Koornneef et al. (1987) *Arabidopsis Inf. Serv.* 23:46) and the $F_1$ plants were allowed to self-pollinate. Linkage of RFLP markers to the ETR1 locus was analyzed in 56 $F_2$ plants as described in Chang, et al. (1988) *Proc. Natl. Acad. Sci. U.S.A.* 85:6856.

Figure 8:
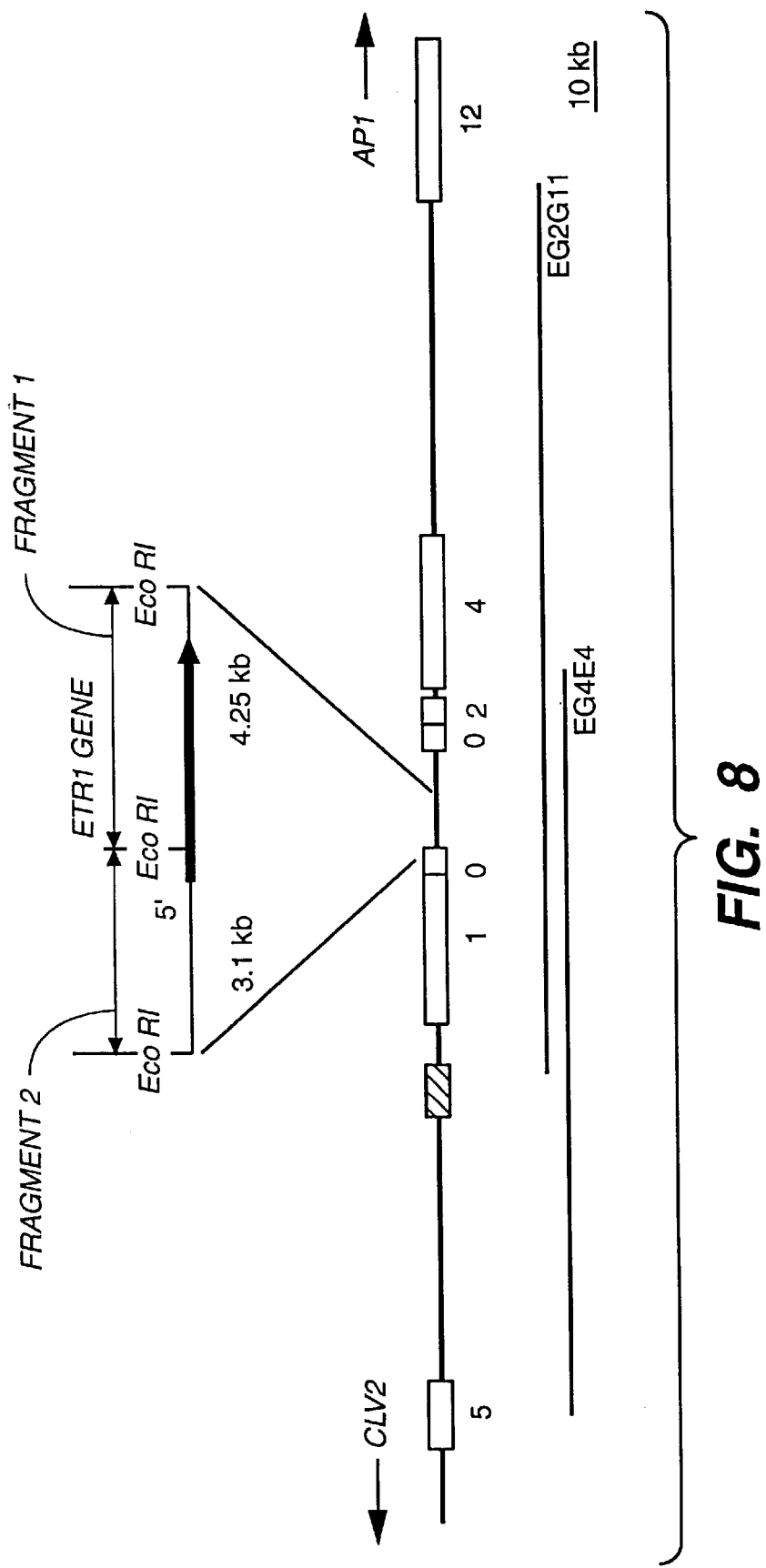
FIG. 8 depicts the structure of the cosmid insert used to localize the ETR1 gene from *Arabidopsis thaliana*. The starting position for the chromosome walk is indicated by a hatched bar. The open bars give the location and length of DNA segments used as probes to detect recombination break points. The maximum number of break points detected by each probe is shown. The numbers to the right of the ETR1 gene are out of 74 F2 recombinants between etr1-1 and ap-1, and those to the left of the ETR-1 gene are out of 25 F2 recombinants between etr1-1 and clv2. Overlapping YAC clones EG4E4 and EG2G11 are also shown.

Of the RFLP markers that reside in this region of chromosome 1, one marker, 1bAt315, completely cosegregated with the etr1-1 mutant phenotype out of 112 chromosomes. The 1bAt315 clone was therefore used as a probe to initiate a chromosome walk in the ETR1 gene region. Various genomic DNA cosmid libraries were utilized. One library contained subclones of two yeast artificial chromosomes (YACs EG4E4 and EG2G11 (Grill et al. (1991) *Mol. Gen. Genet.* 226:484)) that hybridized to 1bAt315. To subclone the YACs, total DNA from yeast cells harboring EG4E4 or EG2G11 was partially digested with Sau3AI, and cloned into the BglII site of cosmid vector pCIT30 (Ma et al. (1992) *Gene* 117:161). Standard cloning and screening methods were used (Sambrook et al, *Molecular Cloning: A Laboratory Manual* (Cold Spring Harbor Laboratory, Cold Spring Harbor, N.Y., 1989)). A library from the etr1-1 mutant was similarly constructed in pCIT30. The wild type library was constructed previously (Yanofsky et al. (1990) *Nature* 346:35). By restriction analysis and sequential hybridization to these libraries, overlapping cosmids (a contig) were obtained that spanned a distance of approximately 230 kb. See FIG. 8.

The ETR1 gene was localized to a subregion of approximately 47 kb using fine structure RFLP mapping. To create the fine structure map, meiotic recombinants were isolated based on phenotype from the F2 self-progeny of the above crosses between the etr1-1 mutant (ecotype Columbia) and two lines (both ecotype Landsberg) carrying ap1 and clv2. Recombinants were identified in the F2 progeny as plants that were either wild type at both loci or mutant at both loci. ETR1 was scored in dark grown seedlings (Bleecker et al. (1988) *Science* 241:1086). Seventy-four (74) recombinants between ETR1 and AP1 were obtained, and 25 recombinants between ETR1 and CLV2. The recombination break points were mapped using DNA fragments from the chromosome walk as RFLP probes. Given the number of recombinants isolated, the calculated average distance between break points was roughly 20 kb for each cross. Over the 230 kb contig, the actual density of break points found was consistent with the calculated density on the CLV2 side (with 5 break points in approximately 120 kb). The nearest break points flanking the ETR1 gene defined a DNA segment of approximately 47 kb.

To search for transcripts derived from this 47 kb region, cDNA libraries were screened using DNA fragments. One cDNA clone was designated λC4 and was detected with the 4.25 kb EcoRI fragment 1 shown in FIG. 8. Because λC4 potentially represented the ETR1 gene, this clone was further characterized.

EXAMPLE 2

ETR Gene Characterization

The nucleotide sequences of the λC4 cDNA and the corresponding genomic DNA (FIG. 2) (SEQ ID NO:1) was determined using sequenase version 2.0 (United States Biochemical Co., Cleveland, Ohio) and synthetic oligonucleotide primers having a length of 17 nucleotides. The primer sequences were chosen from existing ETR1 sequences in order to extend the sequence until the entire sequence was determined. The initial sequence was obtained using primers that annealed to the cloning vector. Templates were double-stranded plasmids. Both strands of the genomic DNA were sequenced, including 225 bp upstream of the presumed transcriptional start site, and 90 bp downstream of the polyadenylation site. λC4 was sequenced on a single strand.

λC4 was 1812 base pairs long, including a polyA tail of 18 bases. From the DNA sequences and RNA blots (described below), it was determined that λC4 lacked approximately 1000 base pairs of the 5' end.

To obtain longer cDNAs, first strand cDNA was synthesized (RiboClone cDNA Synthesis System, Promega, Madison Wis.) from seedling polyA+ RNA using sequence-specific primers internal to λC4. The cDNA was then amplified by PCR (Saiki, R. K. et al. (1985) *Science* 230:1350) using various pairs of primers: 3' PCR primers were chosen to anneal to different exons as deduced from the cDNA and genomic DNA sequences, and 5' PCR primers were chosen to anneal to various 5' portions of genomic DNA sequences. Six different primers at the 5' end were used. The farthest upstream primer which amplified the cDNA was primer Q (5'AGTAAGAACGAAGAAG AAGTG) (SEQ ID NO:26). An overlapping primer, which was shifted twelve bases downstream, also amplified the cDNA. The cDNA could not be amplified using a 5' end primer that was 98 base pairs farther upstream. Genomic DNA templates were used for PCR controls. The longest cDNA was considered to extend to the 5' end of primer Q. The amplified cDNAs were sequenced directly with Sequenase Version 2.0 as follows; after concentrating the PCR reactions by ethanol precipitation, the amplified products were separated by electrophoresis in 0.8% LMP agarose gels. The DNA fragments were excised, and a mixture of 10 ul excised gel (melted at 70° C.), 1 ml 10 mM primer and 1.2 ml 5% Nonidet P-40 was heated at 90° C. for two minutes to denature the DNA. The mixture was then cooled to 37° C. prior to proceeding with sequencing reactions.

The longest cDNA, which was 2786 bases (not including the polyA tail), was consistent with the estimated size of 2800 bases from RNA blots, and was presumed to be close to full length. A potential TATA box (5'ATAATAATAA) lies 33 bp upstream of the 5' end in the genomic sequence. Based on comparison of the cDNA and the genomic DNA sequences, the gene has six introns, one of which is in the 5' untranslated leader. The exons contain a single open reading frame of 738 amino acids. See FIG. 3.

The determination that this gene is, in fact, ETR1 was established by comparing the nucleotide sequences of the wild type allele and the four mutant alleles. For each mutant allele, an EcoRI size-selected library was constructed in the vector lambda ZAPII (Stratagene, LaJolla, Calif.). Clones of the 4.25 kb EcoRI fragment were isolated by hybridization with the wild type fragment. These clones were converted into plasmids (pBluescript vector) by in vivo excision according to the supplier (Stratagene) and sequenced. Two independent clones were sequenced on a single strand for each mutant allele. The 5' ends (535 bp not contained on the 4.25 kb EcoRI fragment) were amplified by PCR and directly sequenced as previously described. Codon differences were as follows: Codon 65 TGT to TAT in etr1-1 (FIGS. 6A, B, C and D), Codon 102 GCG to ACG in etr1-2 (FIGS. 7A, B, C and D), Codon 31 GCG to GTG in etr1-3 (FIGS. 4A, B, C and D), Codon 62 ATC to TTC in etr1-4 (FIGS. 5A, B, C and D). All four mutations are clustered in the amino-terminal region of the deduced protein sequence.

The ETR1 message was examined in standard RNA electrophoresis (formaldehyde) gel blots. The 2.8 kb ETR1 transcript was present in all plant parts examined—leaves, roots, stems, flowers and seedlings (data not shown). In addition, no differences were observed between ETR1 transcripts of the wild type and the mutant alleles (data not shown). Treatment with ethylene did not detectably alter the amount of ETR1 mRNA in dark-grown wild type seedlings (data not shown).

When the ETR1 gene was hybridized to Arabidopsis genomic DNA blots at normal stringency (i.e., overnight in 5×SSPE (0.9M NaCl, 50 mM NaH₂PO₄, 40 mM NaOH, 4.5 mM EDTA, pH 7.4 at 65° C., with the most stringent wash in 0.1×SSPE at 65° C. for 30 minutes), only the expected fragments of the ETR1 locus were observed (data not shown). At reduced stringency (i.e., hybridization in 5×SSPE at 50° C. and washs in 5×SSPE at 50° C.), however, numerous fragments were detected, which suggests that a family of similar genes exists in Arabidopsis.

The predicted amino terminal sequence of ETR1 (residues 1–316) has no similarity to sequences in the GenBank database (version 77.0). The carboxy-terminal portion, however, is highly similar to the conserved domains of both the sensor and the response regulator of the prokaryotic two-component system of signal transduction. In bacteria, the histidine protein kinase domain of the sensor is characterized by five sequence motifs arranged in a specific order with loosely conserved spacing (Parkinson (1992) *Annu. Rev. Genet.* 26:71). The deduced ETR1 sequence contains all five motifs with the same relative order and spacing found in the bacterial proteins (FIG. 9A). The deduced sequence is most similar to the sequences of *Escherichia coli* Bar A (Nagasawa et al. (1992) *Mol. Microbiol.* 6:3011) and *Pseudomonas syringae* LemA (Harbak et al. (1992) *J. Bact.* 174:3011); over the entire histidine kinase domain (the 241 amino acids from residues 336 through 566), there are 43% and 41% amino acid identities with BarA and LemA respectively, and 72% and 71% similarities respectively. The function of BarA is unknown, although it was cloned based on its ability to complement a deletion in the *E. coli* osmotic sensor protein, EnvZ (Nagasawa, supra.). LemA is required for pathogenicity of *P. syringae* on bean plants (Hrabak, supra.). Other bacterial proteins with sequences highly similar to this putative ETR1 domain are: *Xanthomonas campestris* RpfC (35% identity) which is possibly involved in host recognition for pathogenicity in cruciferous plants (Tang et al (1991) *Mol. Gen. Genet.* 226:409), *E. coli* RcsC (34% identity) which is involved in regulation of capsule synthesis (Stout et al. (1990) *J. Bacteriol.* 172:659) and *E. coli* ArcB (25% identity) which is responsible for repression of anaerobic enzymes (Luchi et al. (1990) *Mol. Microbiol.* 4:715).

Adjacent to the putative histidine kinase domain, the deduced ETR1 sequence exhibits structural characteristics and conserved residues of bacterial response regulators. Structural characteristics of response regulators are based on the known three-dimensional structure of CheY (the response regulator for chemotaxis) in *Salmonella typhimurium* and *E. coli*, which consists of five parallel β-strands surrounded by five α-helices (Stock et al. (1989) *Nature* 337:745; Volz et al. (1991) *J. Biol. Chem.* 266:15511). Sequences of bacterial response regulators have been aligned to this structure based on residues that are compatible with the hydrophobic core of the CheY (Stock et al. (1989) *Microbiological Rev.* 53:450). The deduced ETR1 sequence can be similarly aligned (data not shown). At four specific positions, response regulators contain highly conserved residues—three aspartates and a lysine (Parkinson et al. (1992) *Annu. Rev. Genet.* 26:71; Stock et al., supra.); the three aspartates form an acidic pocket into which protrudes the side chain of the conserved lysine (Stock et al. (1989) *Nature* 337:745; Volz et al. (1991) *J. Biol. Chem.* 266:15511) and the third aspartate is the receiver of the phosphate from phosphohistidine (Stock et al. (1989), supra.). Except for the conservative substitution of glutamate for the second aspartate, these conserved amino acids are found in the same positions in the deduced ETR1 sequence (FIG. 9B). The deduced sequence in this domain (a stretch of 121 amino acids from residues 609 through 729 in ETR1) is most similar to the sequences of *Bordetella parapertussis* BvgS (29% identity, 60% similarity) which controls virulence-associated genes for pathogenicity in humans (Arico et al. (1991) *Mol. Microbiol.* 5:2481), *E. coli* RcsC (29% identity, 64% similarity), *P. syringae* LemA (26% identity, 57% similarity), *X. campestris* RpfC (25% identity) and *E. coli* BarA (20% identity). All of the bacterial proteins that are similar to ETR1 in sequence are also structurally similar to ETR1 in that they contain both the histidine kinase domain and the response regulator domain. Although these features are shared, the sensing functions are clearly diverged.

A potential membrane spanning domain (residues 295–313) exists in the deduced ETR1 sequence based on hydropathy analysis (Kyte et al. (1982) *J. Mol. Biol.* 157:105), but it is unclear whether ETR1 is actually a transmembrane protein since there is no clear signal sequence. There are also no N-linked glycosylation sites. While all of the bacterial proteins to which the deduced ETR1 sequence is similar have two potential membrane spanning domains flanking the amino terminal domain, a few bacterial sensors (those which lack the response regulator) do not.

EXAMPLE 3

An etr1 Mutant Gene Confers Ethylene Insensitivity to Wild Type Plants

Dominant ethylene insensitivity was conferred to wild type Arabidopsis plants when the etr1-1 mutant gene was stably introduced using Agrobacterium-mediated transformation. The gene was carried on a 7.3 kb genomic DNA fragment (fragments 1 and 2 in FIG. 8 which included approximately 2.7 kb upstream of the transcription initiation site, and approximately 1 kb downstream of the polyadenylation site). It was cloned into binary transformation vector pCGN1547 obtained from Calgene, Inc., Davis, Calif. The vector also carried a selectable marker for kanamycin resistance in plants.

For the etr1-1 construct, the 4.25 kb EcoRI plasmid clone containing the etr1-1 mutation was linearized by partial EcoRI digestion and ligated with the 3.1 kb EcoRI fragment which was agarose gel-purified from cosmid clone theta8 (a subclone of YAC EG4E4 in the walk). The resulting plasmid, containing the two EcoRI fragments in the correct relative orientation, was linearized at polylinker site Asp718, the ends were filled in using Klenow enzyme, and BamHI linkers were ligated to the blunt ends. Finally, the 7.3 kb insert was removed from the plasmid at the polylinker site BamHI, and ligated into the BamHI site of binary transformation vector pCGN1547 (McBride, K. E. et al. (1990) *Plant Molecular Biology* 14:269). For the control construct, the wild type 7.3 kb fragment was agarose gel-purified from EcoRI partially digested cosmid theta8, and subcloned into the EcoRI site of pBluescript. The fragment was then removed using the BamHI and KpnI sites of the polylinker, and ligated into pCGN1547 that had been digested with BamHI and KpnI. The mutant and wild type constructs were transformed into Agrobacterium (Holsters et al. (1978) *Mol. Gen. Genet.* 163:181) strain ASE (Monsanto) (Rogers et al. (1988) *Meth. Enzymol.* 153:253). Arabidopsis ecotype Nossen was transformed (Valvekens, D. et al. (1988) *Natl. Proc. Acad. Sci. U.S.A.* 85:5536) using root-tissue cultured in liquid rather than on solid medium. Triploid plants having one mutant copy of the ETR1 gene were obtained as the progeny of crosses between the etr1-1 homozygote (diploid) and a tetraploid wild type in ecotype Bensheim which has the same triple response phenotype as ecotype Columbia. Triploid wild type plants were similarly obtained by crossing the diploid wild type to the tetraploid. Ethylene sensitivity was assayed in dark-grown seedlings treated with either ethylene (Bleecker et al., supra.) or 0.5 mM ACC. For ACC treatment, plants were germinated and grown on Murashige and Skoog basal salt mixture (MS, Sigma), pH 5.7, 0.5 mM ACC (Sigma), 1% Bacto-agar (Difco). Kanamycin resistance was measured by the extent of root elongation in one week old seedlings grown on MS pH 5.7 µg/ml Kanamycin, 1% Bacto-agar.

Ten kanamycin resistant plants were produced. Eight of the ten exhibited ethylene insensitive self-progeny as evaluated by the dark-grown seedling response to ethylene. In each line, ethylene insensitivity cosegregated with kanamycin resistance. As a control, transformations were performed using the corresponding 7.3 kb genomic DNA fragment of the wild type from which six kanamycin resistant plants were obtained. These lines gave rise to only ethylene sensitive self-progeny which did not appear to be different from the wild type.

The etr1-1 transformants displayed different levels of ethylene insensitivity. Thus, the wild type gene is capable of attenuating the mutant phenotype and the etr1-1 mutation is not fully dominant in the transformed plants. Of the ten kanamycin resistant lines, six gave completely dominant ethylene insensitivity, indicating the presence of multiple copies of the mutant gene. Two other lines displayed partial dominance, and two lines appeared to be wild type. Reduced ethylene insensitivity was presumably due to low expression levels which can be caused by position effects (e.g., DNA methylation) or possibly by truncation of the transferred DNA.

EXAMPLE 4

Vector Constructs Containing Heterologous Promoter

This example describes the construction of a plant transformation vector containing a heterologous promoter to control expression of wild type and mutant ETR1 nucleic acids.

The cauliflower mosaic virus 35S protein promoter (Guilley et al. (1982) Cell 30:763–773; Odell, et al. (1985) Nature 313:810–812 and Sanders et al. (1987) Nucl. Acids Res. 15:1543–1558) and the 3' end of the Nopaline synthase (NOS) gene were cloned into the pCGN1547 vector to create pCGN18. The 35S promoter, on a HindIII-BamHI fragment of approximately 1.6 kb, was cloned into the unique HindIII-BamHI site of pCGN1547.

The 1 kb BamHI-KpnI NOS fragment was cloned into the unique BamHI-KpnI site of pCGN1547.

The 4.25 kb EcoRI fragment of both the wild type and mutant ETR1-1 allele were independently cloned into the unique BamHI site of the above pCGN18 vector using BamHI linkers. This 4.25 kb EcoRI genomic fragment contains the entire coding sequence including five introns and approximately 1 kb genomic DNA downstream of the polyadenylation site. It does not contain the ETR1 promoter which is on the 3.1 EcoRI fragment 2 in FIG. 5.

These vectors were used to transform root explants as described in Example 3. Kanamycin resistant plants containing the mutant ETR1-1 gene were obtained and demonstrated an ethylene insensitivity phenotype similar to that found in Example 3. Control plants transformed with the wild type ETR1 gene produced only ethylene sensitive self-progeny.

EXAMPLE 5

Vector Construct Utilizing Antisense ETR1

An ETR1 antisense nucleic acid which was introduced into Arabidopsis using standard Agrobacterium root transformation procedure. Valvekens et al. (1988) Proc. Natl. Acad. Sci. U.S.A. 85:5536. The antisense nucleic acid consisted of a 1.9 kb ETR1 cDNA fragment. Expression of this fragment, which extended from the MscI restriction site at nucleotide 220 to the first SmaI site at nucleotide 2176 in FIGS. 3A, 3B, 3C and 3D was driven in the reverse orientation by the CaMV 35S promoter. To construct the antisense nucleic acid, BamHI linkers were ligated to the ends of the 1.9 kb MscI-SmaI DNA fragment and the thus formed fragment was ligated into the BamHI site of pCGN 18 transformation vector. Jack et al. (1994) Cell 76:703. The construct was transformed into Agrobacterium strain ASE as described above and then into Arabidopsis.

Seedlings derived from this transformation experiment were tested for sensitivity to ethylene as previously described. The seedlings containing the antisense construct had a wild-type ethylene response.

Plants carrying the antisense construct were crossed with Arabidopsis having ETR1 mutation and having a dominant ethylene insensitive phenotype. The progeny of the cross between the antisense plants and the ethylene insensitive plants exhibited a modulated, partially ethylene insensitive phenotype.

EXAMPLE 6

Identification of QITR, a Second ETR Nucleic Acid in Arabidopsis

Genomic DNA from *Arabidopsis thaliana* was partially digested with Sau3A and cloned into a λGEM11 (half-site arms) obtained from Promega, Madison, Wis. The genomic digest was partial end filled prior to cloning with λGEM11 and plated on media as suggested by the manufacturer.

The thus cloned library was screened with a $^{32}$P-labeled cDNA XbaI fragment extending from nucleotides 993–2308 as set forth in FIGS. 3B, 3C and 3D. Hybridization conditions were 50° C. and 5XSSPE. Washes were made at 50° C. 0.2xSSPE. Several positively hybridizing clones were identified, replated and rescreened. Positively hybridizing clones were digested with SacI (which cleaves within the arms of the cloning phage and within the insert). The multiple fragments obtained therefrom were subcloned into bacterial plasmids for sequencing. The genomic DNA sequence (SEQ ID NO.:45) together with the deduced amino acid sequence (SEQ ID NO.:46 and 48) is set forth in FIG. 12. This ETR nucleic acid and amino acid sequence is referred to as the QITR nucleic or amino acid sequence respectively. The QITR cDNA sequence (SEQ ID NO.:47) and the QITR amino acid sequence (SEQ ID NOs:46 and 48) are shown in FIG. 13.

By comparison to the ETR1 Arabidopsis nucleic acid and amino acid sequence (see FIGS. 2 and 3), the QITR protein appears to contain an amino terminal portion having a relatively high level of homology to the amino terminal portion of the ETR1 protein and a histidine kinase portion with a moderate level of homology to the same sequence in ETR1. The response regulatory region found in ETR1 is not present in the QITR protein. The overall nucleic acid homology is approximately 69%. With regard to the amino terminal portion (i.e., between residues 1 through 316) the homology is approximately 71% identical in terms of amino acid sequence and 72% identical in terms of nucleic acid sequence.

EXAMPLE 7

Modification of QITR Nucleic Acid to Confer Ethylene Insensitivity

An amino acid substitution was made in a 5 kb QITR genomic clone which was analogous to that for the ETR1-4 mutation, namely the substitution of the isoleucine at position 62 with phenylalanine. Compare FIG. 3A with FIG. 5A at residue 62. As further indicated at FIGS. 12 and 13, residue 62 in the QITR protein is also isoleucine as in the ETR1 protein.

The amino acid substitution was made to the QITR nucleic acid using oligonucleotide-directed in vitro mutagenesis. Kunkel et al. (1987) *Methods in Enzymology* 154:367–382. A Muta-gene kit from Bio-Rad Laboratories, Hercules, Calif., was used in connection with this particular mutation. The sequence of the oligonucleotide used was 5' GGA GCC TTT TTC ATT CTC. Replacement of nucleotide A with T in the codon ATC changed the amino acid Ile at residue 62 to Phe in the deduced protein sequence.

The QITR nucleic acid spanning approximately 5 kb from the first HindIII site to the second KpnI site contained approximately 2.4 kb of nucleotides upstream from the start codon. This 5 kb fragment was ligated into the pCGN1547 transformation vector (supra.). This construct was then transformed into Agrobacterium strain ASE as described supra and then into Arabidopsis.

Seedlings derived from this transformation experiment were tested for sensitivity to ethylene as previously described. Seedlings containing the QITR nucleic acid containing the modification at residue 62 were ethylene insensitive.

EXAMPLE 8

Identification of Arabidopsis ETR Nucleic Acid Q8

The ETR nucleic acid Q8 (SEQ ID NOS:41 and 43) was identified by direct sequence comparison with the ETR1 nucleic acid from Arabidopsis. The Arabidopsis Q8 nucleic acid was identified in connection with a chromosome walk on chromosome 3 of *Arabidopsis thaliana*.

Briefly, overlapping YAC clones were generated which were thereafter subcloned into plasmids. The genomic inserts in such plasmids were extricated by digesting with restriction endonuclease and hybridized to a cDNA library from Arabidopsis floral tissue.

Positively hybridizing inserts were sequenced to produce the overall genomic sequence (SEQ ID NO.:41) together with the deduced amino acid sequence (SEQ ID NOS:42 and 44) as set forth in FIG. 14. The cDNA sequence (SEQ ID NO:43) and deduced amino acid sequence (SEQ ID NOs:42 and 44) is set forth in FIG. 15.

The overall nucleic acid homology as between the Q8 nucleic acid and the ETR1 nucleic acid is approximately 69%. With regard to the amino terminal portion extending from residues 1 through 316, the overall amino sequence homology is approximately 72% whereas the nucleic acid encoding this sequence is approximately has a sequence homology of approximately 71% as between the Q8 and ETR1 nucleic acids.

EXAMPLE 9

Isolation of the TETR cDNA

A $^{32}$P-labeled hybridization probe was prepared by random-primer labeling of a 1.3 kb PCR fragment generated by PCR amplification of the Arabidopsis ETR1 gene with the PCR primers "5'BamHI" (CCCGGATCCATA GTGTAAAAAATTCATAATGG) and "3'BamHIB" (CCGGATCCGTTGAAGACTTCCATCTTCTAACC).

This probe was used to screen a cDNA library of red tomato fruit mRNA cloned in the EcoRI site of lambda ZAP II vector from Stratagene, LaJolla, Calif. Twenty (20) positive primary plaques were identified that hybridized to this probe (2× SSC at 65° C. wash conditions) and secondary screens were performed on these to obtain pure plaques. In vivo excision was then performed with resultant recombinant phage and 19 independent plasmid clones were obtained.

Complementary DNAs, from plasmid clones containing the largest fragments that hybridized to the ETR1 probe, were sequenced and the nucleotide sequence and predicted amino acid sequences of the longest tomato cDNA (TETR14, also referred to as TXTR) were compared to the ETR1 and QITR sequences. The nucleotide sequence of TETR14 predicted that the encoded peptide was more similar to the QITR peptide than the ETR1 peptide. This conclusion was based on the fact that the response regulatory domain (which is present in ETR1) is absent in both TETR14 and QITR. The sequence (or partial sequence) of several of the other cDNA clones was determined and they were found to correspond to the same gene.

EXAMPLE 10

Analysis of TETR14 Gene Expression

Northern analysis was performed with mRNA from developing fruits of normal, or mutant tomato (Ripening inhibitor (rin), Non-ripening (nor) or Never-ripe (Nr)) fruit. Stages of developing fruits used were mature green, breaker, breaker plus 7 days, and mature green fruit treated with ethylene. Messenger RNA that hybridized to the TETR14 gene probe was not present at the mature green stage, but was present in breaker, breaker plus 7 days, and ethylene treated mature green fruit. Thus, it was concluded that accumulation of the ETR14 mRNA was regulated by ethylene. Accumulation of the TETR14 mRNA was attenuated in all three ripening mutants, further supporting the finding that mRNA accumulation is ethylene regulated.

EXAMPLE 11

Analysis of the TETR14 Gene from Pearson and Never-ripe DNA

PCR primers were obtained that would specifically amplify the N-terminal region of the TETR14 gene. The amplified portion was between Met1 and Ile214 in FIGS. 16A and 16B. The primers were (CCGGATCCATGGAATCCTGTGATTGCATTG) and TETR4A (GATAATAGGAAGATTAATTGGC). PCR conditions (Perkin-Elmer Cetus): 1 ug of tomato genomic DNA, 40 picomole of each primer, 1 min 94° C., 2 min 45° C., 2 min 72° C., 35 cycles. PCR products, obtained with these primers, resulting from two independent amplification reactions of pearson and Nr DNA were agarose gel purified and subcloned into either the T/A vector (Invitrogen) or digested with BamHI and XhoI and subcloned into Bluescript KS- that had been linearized with BamHI and SalI. Single stranded template DNA was prepared from the resultant plasmids and sequenced. The sequence of the PCR products from the pearson DNA were identical to the sequence of the TETR14 clone. Sequence analysis revealed that the PCR fragments resulting from PCR of the Nr DNA (TETR14-Nr) were not identical to those obtained from the Pearson DNA. The cytosine nucleotide at position 395 of the TETR14 gene is a thymine in the gene amplified from the Nr DNA. This nucleotide substitution in TETR14-Nr changes the proline at amino acid position 36 of the predicted peptide to a leucine. See FIG. 22 and Seq. ID Nos. 49 and 50 for the overall nucleic acid and amino acid sequence respectively. This Pro-36 of the TETR14 corresponds to the Pro-36 of the ETR1 peptide and to the Pro-36 of the QITR peptide. This results indicates that a mutation in the tomato TETR14 gene confers dominant ethylene-insensitivity. And thus, it is possible to predict that other changes in the TETR14 gene and other tomato ETR1 homologues will result in ethylene insensitivity in tomato.

Having described the preferred embodiments of the invention, it will appear to those of ordinary skill in the art that various modifications may be made to the disclosed embodiments, and that such modifications are intended to be within the scope of the invention.

All references are expressly incorporated herein by reference.

What is claimed is:

1. An antisense expression construct comprising a promoter and an ETR nucleic acid in the antisense orientation, wherein said ETR nucleic acid encodes an ETR protein with at least 50% overall similarity to the ETR protein sequence of *Arabidopsis thaliana* as set forth in SEQ ID NO:3 and at least 60% similarity to the N-terminal 316 amino acids of SEQ ID NO:3, and wherein expression of said construct in a plant cell results in a decreased response to ethylene by said cell.

2. An antisense expression construct comprising a promoter and an ETR nucleic acid in the antisense orientation, wherein said ETR nucleic acid hybridizes to the nucleic acid sequence of SEQ ID NO:2 at hybridization conditions of 50° C. in 5× SSPE and wash conditions of 50° C. in 0.2× SSPE, and wherein expression of said construct in a plant cell results in a decreased response to ethylene by said cell.

3. The antisense construct of claim 1 or 2 further comprising a second different ETR nucleic acid in the antisense orientation.

4. The antisense expression construct according to claim 3 wherein said promoter is heterologous to said antisense ETR nucleic acid and causes expression of said antisense ETR nucleic acid in a plant cell.

5. The antisense expression construct according to claim 3 wherein said promoter is a tissue-specific or temporal-specific promoter.

6. The antisense expression construct according to claim 3 wherein said promoter is inducible.

7. The antisense expression construct according to claim 3 wherein expression of the two different antisense ETR nucleic acids inhibits expression of one or more ETR nucleic acids in a plant cell.

8. The antisense expression construct according to claim 7 wherein expression of the two different antisense ETR nucleic acids inhibits production of the ETR protein encoded by two or more ETR genes in a plant cell.

9. A plant cell transformed with said antisense expression construct according to claim 7.

10. A plant comprising the plant cell of claim 9.

11. A plant comprising at least one plant cell according to claim 10 and having a phenotype characterized by a decrease in the response of at least one transformed plant cell to ethylene as compared to a corresponding wild-type plant not containing said transformed plant cell.

12. A plant according to claim 11 wherein said promoter comprises a tissue-specific or temporal-specific promoter.

13. A method for producing a plant having at least one transformed plant cell and a phenotype characterized by a decrease in the response of said at least one transformed plant cell to ethylene as compared to a plant not containing said transformed plant cell, said method comprising the steps of:

a) transforming at least one plant cell with said antisense expression construct according to claim 3;

b) regenerating plants from one or more of the thus transformed plant cells; and c) selecting at least one plant having said phenotype.

14. The method according to claim 13 wherein said promoter is a tissue-specific or temporal-specific promoter.

* * * * *

UNITED STATES PATENT AND TRADEMARK OFFICE
CERTIFICATE OF CORRECTION

PATENT NO. : 5,824,868
DATED : October 20, 1998
INVENTOR(S) : MEYEROWITZ et al.

It is certified that error appears in the above-indentified patent and that said Letters Patent is hereby corrected as shown below:

Column 1, line 45, delete "35:155189" and insert therefore --35:155-189.--.

Column 5, line 10, after "ethylene", delete "for "

Column 7, line 56, after "portion", delete "is "

Column 15, line 19, delete "Bocaraton" and insert therefore --Boca Raton--.

Column 17, line 40, delete "tp" and insert therefore --to--.

Column 21, lines 31, delete "Hrabak" and insert therefore --Harbak--.

Column 25, line 59, after "this sequence", delete "is".

Signed and Sealed this

Ninth Day of May, 2000

Attest:

Q. TODD DICKINSON

*Attesting Officer*     *Director of Patents and Trademarks*

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
( A ) LENGTH: 3879 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| AAAGATAGTA | TTTGTTGATA | AATATGGGGA | TATTTATCCT | ATATTATCTG | TATTTTTCTT | 60 |
| ACCATTTTTA | CTCTATTCCT | TTATCTACAT | TACGTCATTA | CACTATCATA | AGATATTTGA | 120 |
| ATGAACAAAT | TCATGCACCC | ACCAGCTATA | TTACCCTTTT | TTATTAAAAA | AAAACATCTG | 180 |
| ATAATAATAA | CAAAAAAATT | AGAGAAATGA | CGTCGAAAAA | AAAAGTAAGA | ACGAAGAAGA | 240 |
| AGTGTTAAAC | CCAACCAATT | TTGACTTGAA | AAAAAGCTTC | AACGCTCCCC | TTTTCTCCTT | 300 |
| CTCCGTCGCT | CTCCGCCGCG | TCCCAAATCC | CCAATTCCTC | CTCTTCTCCG | ATCAATTCTT | 360 |
| CCCAAGTAAG | CTTCTTCTTC | CTCGATTCTC | TCCTCAGATT | GTTTCGTGAC | TTCTTTATAT | 420 |
| ATATTCTTCA | CTTCCACAGT | TTTCTTCTGT | TGTTGTCGTC | GATCTCAAAT | CATAGAGATT | 480 |
| GATTAACCTA | ATTGGTCTTT | ATCTAGTGTA | ATGCATCGTT | ATTAGGAACT | TTAAATTAAG | 540 |
| ATTTAATCGT | TAATTTCATG | ATTCGGATTC | GAATTTTACT | GTTCTCGAGA | CTGAAATATG | 600 |
| CAACCTATTT | TTTCGTAATC | GTTGTGATCG | AATTCGATTC | TTCAGAATTT | ATAGCAATTT | 660 |
| TGATGCTCAT | GATCTGTCTA | CGCTACGTTC | TCGTCGTAAA | TCGAAGTTGA | TAATGCTATG | 720 |
| TGTTTGTTAC | ACAGGTGTGT | GTATGTGTGA | GAGAGGAACT | ATAGTGTAAA | AAATTCATAA | 780 |
| TGGAAGTCTG | CAATTGTATT | GAACCGCAAT | GGCCAGCGGA | TGAATTGTTA | ATGAAATACC | 840 |
| AATACATCTC | CGATTTCTTC | ATTGCGATTG | CGTATTTTC | GATTCCTCTT | GAGTTGATTT | 900 |
| ACTTTGTGAA | GAAATCAGCC | GTGTTTCCGT | ATAGATGGGT | ACTTGTTCAG | TTTGGTGCTT | 960 |
| TTATCGTTCT | TTGTGGAGCA | ACTCATCTTA | TTAACTTATG | GACTTCACT | ACGCATTCGA | 1020 |
| GAACCGTGGC | GCTTGTGATG | ACTACCGCGA | AGGTGTTAAC | CGCTGTTGTC | TCGTGTGCTA | 1080 |
| CTGCGTTGAT | GCTTGTTCAT | ATTATTCCTG | ATCTTTTGAG | TGTTAAGACT | CGGGAGCTTT | 1140 |
| TCTTGAAAAA | TAAAGCTGCT | GAGCTCGATA | GAGAAATGGG | ATTGATTCGA | ACTCAGGAAG | 1200 |
| AAACCGGAAG | GCATGTGAGA | ATGTTGACTC | ATGAGATTAG | AAGCACTTTA | GATAGACATA | 1260 |
| CTATTTTAAA | GACTACACTT | GTTGAGCTTG | GTAGGACATT | AGCTTTGGAG | GAGTGTGCAT | 1320 |
| TGTGGATGCC | TACTAGAACT | GGGTTAGAGC | TACAGCTTTC | TTATACACTT | CGTCATCAAC | 1380 |

```
ATCCCGTGGA GTATACGGTT CCTATTCAAT TACCGGTGAT TAACCAAGTG TTTGGTACTA    1440
GTAGGGCTGT AAAAATATCT CCTAATTCTC CTGTGGCTAG GTTGAGACCT GTTTCTGGGA    1500
AATATATGCT AGGGGAGGTG GTCGCTGTGA GGGTTCCGCT TCTCCACCTT TCTAATTTTC    1560
AGATTAATGA CTGGCCTGAG CTTTCAACAA AGAGATATGC TTTGATGGTT TTGATGCTTC    1620
CTTCAGATAG TGCAAGGCAA TGGCATGTCC ATGAGTTGGA ACTCGTTGAA GTCGTCGCTG    1680
ATCAGGTTTT ACATTGCTGA GAATTTCTCT TCTTTGCTAT GTTCATGATC TTGTCTATAA    1740
CTTTTCTTCT CTTATTATAG GTGGCTGTAG CTCTCTCACA TGCTGCGATC CTAGAAGAGT    1800
CGATGCGAGC TAGGGACCTT CTCATGGAGC AGAATGTTGC TCTTGATCTA GCTAGACGAG    1860
AAGCAGAAAC AGCAATCCGT GCCCGCAATG ATTTCCTAGC GGTTATGAAC CATGAAATGC    1920
GAACACCGAT GCATGCGATT ATTGCACTCT CTTCCTTACT CCAAGAAACG AACTAACCC    1980
CTGAACAAAG ACTGATGGTG GAAACAATAC TTAAAGTAG TAACCTTTTG GCAACTTTGA     2040
TGAATGATGT CTTAGATCTT TCAAGGTTAG AAGATGGAAG TCTTCAACTT GAACTTGGGA    2100
CATTCAATCT TCATACATTA TTTAGAGAGG TAACTTTTGA ACAGCTCTAT GTTTCATAAG    2160
TTTATACTAT TTGTGTACTT GATTGTCATA TTGAATCTTG TTGCAGGTCC TCAATCTGAT    2220
AAAGCCTATA GCGGTTGTTA AGAAATTACC CATCACACTA AATCTTGCAC CAGATTTGCC    2280
AGAATTTGTT GTTGGGGATG AGAAACGGCT AATGCAGATA ATATTAAATA TAGTTGGTAA    2340
TGCTGTGAAA TTCTCCAAAC AAGGTAGTAT CTCCGTAACC GCTCTTGTCA CCAAGTCAGA    2400
CACACGAGCT GCTGACTTTT TTGTCGTGCC AACTGGGAGT CATTTCTACT TGAGAGTGAA    2460
GGTTATTATC TTGTATCTTG GGATCTTATA CCATAGCTGA AAGTATTTCT TAGGTCTTAA    2520
TTTTGATGAT TATTCAAATA TAGGTAAAAG ACTCTGGAGC AGGAATAAAT CCTCAAGACA    2580
TTCCAAAGAT TTTCACTAAA TTTGCTCAAA CACAATCTTT AGCGACGAGA AGCTCGGGTG    2640
GTAGTGGGCT TGGCCTCGCC ATCTCCAAGA GGTTTGAGCC TTATTAAAAG ACGTTTTTT     2700
CCAACTTTTT CTTGTCTTCT GTGTTGTTAA AAGTTTACTC ATAAGCGTTT AATATGACAA    2760
GGTTTGTGAA TCTGATGGAG GGTAACATTT GGATTGAGAG CGATGGTCTT GGAAAAGGAT    2820
GCACGGCTAT CTTTGATGTT AAACTTGGGA TCTCAGAACG TTCAAACGAA TCTAAACAGT    2880
CGGGCATACC GAAAGTTCCA GCCATTCCCC GACATTCAAA TTTCACTGGA CTTAAGGTTC    2940
TTGTCATGGA TGAGAACGGG TTAGTATAAG CTTCTCACCT TTCTCTTTGC AAAATCTCTC    3000
GCCTTACTTC TTGCAAATGC AGATATTGGC GTTAGAAAA AACGCAAATT TAATCTTATG     3060
AGAAACCGAT GATTATTTTG GTTGCAGGGT AAGTAGAATG GTGACGAAGG GACTTCTTGT    3120
ACACCTTGGG TGCGAAGTGA CCACGGTGAG TTCAAACGAG GAGTGTCTCC GAGTTGTGTC    3180
CCATGAGCAC AAAGTGGTCT TCATGGACGT GTGCATGCCC GGGGTCGAAA ACTACCAAAT    3240
CGCTCTCCGT ATTCACGAGA AATTCACAAA ACAACGCCAC CAACGGCCAC TACTTGTGGC    3300
ACTCAGTGGT AACACTGACA AATCCACAAA AGAGAAATGC ATGAGCTTTG GTCTAGACGG    3360
TGTGTTGCTC AAACCCGTAT CACTAGACAA CATAAGAGAT GTTCTGTCTG ATCTTCTCGA    3420
GCCCCGGGTA CTGTACGAGG GCATGTAAAG GCGATGGATG CCCCATGCCC CAGAGGAGTA    3480
ATTCCGCTCC CGCCTTCTTC TCCCGTAAAA CATCGGAAGC TGATGTTCTC TGGTTTAATT    3540
GTGTACATAT CAGAGATTGT CGGAGCGTTT TGGATGATAT CTTAAAACAG AAAGGGAATA    3600
ACAAAATAGA AACTCTAAAC CGGTATGTGT CCGTGGCGAT TCGGTTATA GAGGAACAAG     3660
ATGGTGGTGG TATAATCATA CCATTTCAGA TTACATGTTT GACTAATGTT GTATCCTTAT    3720
ATATGTAGTT ACATTCTTAT AAGAATTTGG ATCGAGTTAT GGATGCTTGT TGCGTGCATG    3780
```

```
TATGACATTG ATGCAGTATT ATGGCGTCAG CTTTGCGCCG CTTAGTAGAA CAACAACAAT      3840

GGCGTTACTT AGTTTCTCAA TCAACCCGAT CTCCAAAAC                             3879
```

( 2 ) INFORMATION FOR SEQ ID NO:2:

( i ) SEQUENCE CHARACTERISTICS:
        ( A ) LENGTH: 2787 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 188..2401

( x i ) SEQUENCE DESCRIPTION: SEQ ID NO:2:

```
AGTAAGAACG AAGAAGAAGT GTTAAACCCA ACCAATTTTG ACTTGAAAAA AAGCTTCAAC       60

GCTCCCCTTT TCTCCTTCTC CGTCGCTCTC CGCCGCGTCC CAAATCCCCA ATTCCTCCTC     120

TTCTCCGATC AATTCTTCCC AAGTGTGTGT ATGTGTGAGA GAGGAACTAT AGTGTAAAAA     180

ATTCATA ATG GAA GTC TGC AAT TGT ATT GAA CCG CAA TGG CCA GCG GAT       229
        Met Glu Val Cys Asn Cys Ile Glu Pro Gln Trp Pro Ala Asp
         1           5                  10

GAA TTG TTA ATG AAA TAC CAA TAC ATC TCC GAT TTC TTC ATT GCG ATT       277
Glu Leu Leu Met Lys Tyr Gln Tyr Ile Ser Asp Phe Phe Ile Ala Ile
 15              20                  25                      30

GCG TAT TTT TCG ATT CCT CTT GAG TTG ATT TAC TTT GTG AAG AAA TCA       325
Ala Tyr Phe Ser Ile Pro Leu Glu Leu Ile Tyr Phe Val Lys Lys Ser
                 35                  40                      45

GCC GTG TTT CCG TAT AGA TGG GTA CTT GTT CAG TTT GGT GCT TTT ATC       373
Ala Val Phe Pro Tyr Arg Trp Val Leu Val Gln Phe Gly Ala Phe Ile
             50                  55                  60

GTT CTT TGT GGA GCA ACT CAT CTT ATT AAC TTA TGG ACT TTC ACT ACG       421
Val Leu Cys Gly Ala Thr His Leu Ile Asn Leu Trp Thr Phe Thr Thr
         65                  70                  75

CAT TCG AGA ACC GTG GCG CTT GTG ATG ACT ACC GCG AAG GTG TTA ACC       469
His Ser Arg Thr Val Ala Leu Val Met Thr Thr Ala Lys Val Leu Thr
     80                  85                  90

GCT GTT GTC TCG TGT GCT ACT GCG TTG ATG CTT GTT CAT ATT ATT CCT       517
Ala Val Val Ser Cys Ala Thr Ala Leu Met Leu Val His Ile Ile Pro
 95                 100                 105                    110

GAT CTT TTG AGT GTT AAG ACT CGG GAG CTT TTC TTG AAA AAT AAA GCT       565
Asp Leu Leu Ser Val Lys Thr Arg Glu Leu Phe Leu Lys Asn Lys Ala
            115                 120                 125

GCT GAG CTC GAT AGA GAA ATG GGA TTG ATT CGA ACT CAG GAA GAA ACC       613
Ala Glu Leu Asp Arg Glu Met Gly Leu Ile Arg Thr Gln Glu Glu Thr
        130                 135                 140

GGA AGG CAT GTG AGA ATG TTG ACT CAT GAG ATT AGA AGC ACT TTA GAT       661
Gly Arg His Val Arg Met Leu Thr His Glu Ile Arg Ser Thr Leu Asp
        145                 150                 155

AGA CAT ACT ATT TTA AAG ACT ACA CTT GTT GAG CTT GGT AGG ACA TTA       709
Arg His Thr Ile Leu Lys Thr Thr Leu Val Glu Leu Gly Arg Thr Leu
        160                 165                 170

GCT TTG GAG GAG TGT GCA TTG TGG ATG CCT ACT AGA ACT GGG TTA GAG       757
Ala Leu Glu Glu Cys Ala Leu Trp Met Pro Thr Arg Thr Gly Leu Glu
175                 180                 185                 190

CTA CAG CTT TCT TAT ACA CTT CGT CAT CAA CAT CCC GTG GAG TAT ACG       805
Leu Gln Leu Ser Tyr Thr Leu Arg His Gln His Pro Val Glu Tyr Thr
                195                 200                 205
```

| | | | | | | | | | | | | | | | | |
|---|---|---|---|---|---|---|---|---|---|---|---|---|---|---|---|---|
| GTT | CCT | ATT | CAA | TTA | CCG | GTG | ATT | AAC | CAA | GTG | TTT | GGT | ACT | AGT | AGG | 853 |
| Val | Pro | Ile | Gln<br>210 | Leu | Pro | Val | Ile | Asn<br>215 | Gln | Val | Phe | Gly | Thr<br>220 | Ser | Arg | |
| GCT | GTA | AAA | ATA | TCT | CCT | AAT | TCT | CCT | GTG | GCT | AGG | TTG | AGA | CCT | GTT | 901 |
| Ala | Val | Lys<br>225 | Ile | Ser | Pro | Asn | Ser<br>230 | Pro | Val | Ala | Arg | Leu<br>235 | Arg | Pro | Val | |
| TCT | GGG | AAA | TAT | ATG | CTA | GGG | GAG | GTG | GTC | GCT | GTG | AGG | GTT | CCG | CTT | 949 |
| Ser | Gly | Lys<br>240 | Tyr | Met | Leu | Gly | Glu<br>245 | Val | Val | Ala | Val | Arg<br>250 | Val | Pro | Leu | |
| CTC | CAC | CTT | TCT | AAT | TTT | CAG | ATT | AAT | GAC | TGG | CCT | GAG | CTT | TCA | ACA | 997 |
| Leu<br>255 | His | Leu | Ser | Asn | Phe<br>260 | Gln | Ile | Asn | Asp | Trp<br>265 | Pro | Glu | Leu | Ser | Thr<br>270 | |
| AAG | AGA | TAT | GCT | TTG | ATG | GTT | TTG | ATG | CTT | CCT | TCA | GAT | AGT | GCA | AGG | 1045 |
| Lys | Arg | Tyr | Ala | Leu<br>275 | Met | Val | Leu | Met | Leu<br>280 | Pro | Ser | Asp | Ser | Ala<br>285 | Arg | |
| CAA | TGG | CAT | GTC | CAT | GAG | TTG | GAA | CTC | GTT | GAA | GTC | GTC | GCT | GAT | CAG | 1093 |
| Gln | Trp | His | Val<br>290 | His | Glu | Leu | Glu | Leu<br>295 | Val | Glu | Val | Val | Ala<br>300 | Asp | Gln | |
| GTG | GCT | GTA | GCT | CTC | TCA | CAT | GCT | GCG | ATC | CTA | GAA | GAG | TCG | ATG | CGA | 1141 |
| Val | Ala | Val<br>305 | Ala | Leu | Ser | His | Ala<br>310 | Ala | Ile | Leu | Glu | Glu<br>315 | Ser | Met | Arg | |
| GCT | AGG | GAC | CTT | CTC | ATG | GAG | CAG | AAT | GTT | GCT | CTT | GAT | CTA | GCT | AGA | 1189 |
| Ala | Arg<br>320 | Asp | Leu | Leu | Met | Glu<br>325 | Gln | Asn | Val | Ala | Leu<br>330 | Asp | Leu | Ala | Arg | |
| CGA | GAA | GCA | GAA | ACA | GCA | ATC | CGT | GCC | CGC | AAT | GAT | TTC | CTA | GCG | GTT | 1237 |
| Arg<br>335 | Glu | Ala | Glu | Thr | Ala<br>340 | Ile | Arg | Ala | Arg | Asn<br>345 | Asp | Phe | Leu | Ala | Val<br>350 | |
| ATG | AAC | CAT | GAA | ATG | CGA | ACA | CCG | ATG | CAT | GCG | ATT | ATT | GCA | CTC | TCT | 1285 |
| Met | Asn | His | Glu | Met<br>355 | Arg | Thr | Pro | Met | His<br>360 | Ala | Ile | Ile | Ala | Leu<br>365 | Ser | |
| TCC | TTA | CTC | CAA | GAA | ACG | GAA | CTA | ACC | CCT | GAA | CAA | AGA | CTG | ATG | GTG | 1333 |
| Ser | Leu | Leu | Gln<br>370 | Glu | Thr | Glu | Leu | Thr<br>375 | Pro | Glu | Gln | Arg | Leu<br>380 | Met | Val | |
| GAA | ACA | ATA | CTT | AAA | AGT | AGT | AAC | CTT | TTG | GCA | ACT | TTG | ATG | AAT | GAT | 1381 |
| Glu | Thr | Ile<br>385 | Leu | Lys | Ser | Ser | Asn<br>390 | Leu | Leu | Ala | Thr | Leu<br>395 | Met | Asn | Asp | |
| GTC | TTA | GAT | CTT | TCA | AGG | TTA | GAA | GAT | GGA | AGT | CTT | CAA | CTT | GAA | CTT | 1429 |
| Val | Leu<br>400 | Asp | Leu | Ser | Arg | Leu<br>405 | Glu | Asp | Gly | Ser | Leu<br>410 | Gln | Leu | Glu | Leu | |
| GGG | ACA | TTC | AAT | CTT | CAT | ACA | TTA | TTT | AGA | GAG | GTC | CTC | AAT | CTG | ATA | 1477 |
| Gly | Thr | Phe | Asn | Leu | His<br>420 | Thr | Leu | Phe | Arg | Glu<br>425 | Val | Leu | Asn | Leu | Ile<br>430 | |
| Gly<br>415 | | | | | | | | | | | | | | | | |
| AAG | CCT | ATA | GCG | GTT | GTT | AAG | AAA | TTA | CCC | ATC | ACA | CTA | AAT | CTT | GCA | 1525 |
| Lys | Pro | Ile | Ala | Val<br>435 | Val | Lys | Lys | Leu | Pro<br>440 | Ile | Thr | Leu | Asn | Leu<br>445 | Ala | |
| CCA | GAT | TTG | CCA | GAA | TTT | GTT | GTT | GGG | GAT | GAG | AAA | CGG | CTA | ATG | CAG | 1573 |
| Pro | Asp | Leu | Pro<br>450 | Glu | Phe | Val | Val | Gly<br>455 | Asp | Glu | Lys | Arg | Leu<br>460 | Met | Gln | |
| ATA | ATA | TTA | AAT | ATA | GTT | GGT | AAT | GCT | GTG | AAA | TTC | TCC | AAA | CAA | GGT | 1621 |
| Ile | Ile | Leu<br>465 | Asn | Ile | Val | Gly | Asn<br>470 | Ala | Val | Lys | Phe | Ser<br>475 | Lys | Gln | Gly | |
| AGT | ATC | TCC | GTA | ACC | GCT | CTT | GTC | ACC | AAG | TCA | GAC | ACA | CGA | GCT | GCT | 1669 |
| Ser | Ile<br>480 | Ser | Val | Thr | Ala | Leu<br>485 | Val | Thr | Lys | Ser | Asp<br>490 | Thr | Arg | Ala | Ala | |
| GAC | TTT | TTT | GTC | GTG | CCA | ACT | GGG | AGT | CAT | TTC | TAC | TTG | AGA | GTG | AAG | 1717 |
| Asp<br>495 | Phe | Phe | Val | Val | Pro<br>500 | Thr | Gly | Ser | His<br>505 | Phe | Tyr | Leu | Arg | Val<br>510 | Lys | |
| GTA | AAA | GAC | TCT | GGA | GCA | GGA | ATA | AAT | CCT | CAA | GAC | ATT | CCA | AAG | ATT | 1765 |
| Val | Lys | Asp | Ser | Gly<br>515 | Ala | Gly | Ile | Asn | Pro<br>520 | Gln | Asp | Ile | Pro | Lys<br>525 | Ile | |

| | | | | | | | | | | | | | | | | |
|---|---|---|---|---|---|---|---|---|---|---|---|---|---|---|---|---|
| TTC | ACT | AAA | TTT | GCT | CAA | ACA | CAA | TCT | TTA | GCG | ACG | AGA | AGC | TCG | GGT | 1813 |
| Phe | Thr | Lys | Phe | Ala | Gln | Thr | Gln | Ser | Leu | Ala | Thr | Arg | Ser | Ser | Gly | |
| | | 530 | | | | | 535 | | | | | | 540 | | | |
| GGT | AGT | GGG | CTT | GGC | CTC | GCC | ATC | TCC | AAG | AGG | TTT | GTG | AAT | CTG | ATG | 1861 |
| Gly | Ser | Gly | Leu | Gly | Leu | Ala | Ile | Ser | Lys | Arg | Phe | Val | Asn | Leu | Met | |
| | | 545 | | | | | 550 | | | | | | 555 | | | |
| GAG | GGT | AAC | ATT | TGG | ATT | GAG | AGC | GAT | GGT | CTT | GGA | AAA | GGA | TGC | ACG | 1909 |
| Glu | Gly | Asn | Ile | Trp | Ile | Glu | Ser | Asp | Gly | Leu | Gly | Lys | Gly | Cys | Thr | |
| | 560 | | | | | 565 | | | | | 570 | | | | | |
| GCT | ATC | TTT | GAT | GTT | AAA | CTT | GGG | ATC | TCA | GAA | CGT | TCA | AAC | GAA | TCT | 1957 |
| Ala | Ile | Phe | Asp | Val | Lys | Leu | Gly | Ile | Ser | Glu | Arg | Ser | Asn | Glu | Ser | |
| 575 | | | | 580 | | | | | 585 | | | | | 590 | | |
| AAA | CAG | TCG | GGC | ATA | CCG | AAA | GTT | CCA | GCC | ATT | CCC | CGA | CAT | TCA | AAT | 2005 |
| Lys | Gln | Ser | Gly | Ile | Pro | Lys | Val | Pro | Ala | Ile | Pro | Arg | His | Ser | Asn | |
| | | | | 595 | | | | | 600 | | | | | 605 | | |
| TTC | ACT | GGA | CTT | AAG | GTT | CTT | GTC | ATG | GAT | GAG | AAC | GGG | GTA | AGT | AGA | 2053 |
| Phe | Thr | Gly | Leu | Lys | Val | Leu | Val | Met | Asp | Glu | Asn | Gly | Val | Ser | Arg | |
| | | | 610 | | | | | 615 | | | | | 620 | | | |
| ATG | GTG | ACG | AAG | GGA | CTT | CTT | GTA | CAC | CTT | GGG | TGC | GAA | GTG | ACC | ACG | 2101 |
| Met | Val | Thr | Lys | Gly | Leu | Leu | Val | His | Leu | Gly | Cys | Glu | Val | Thr | Thr | |
| | | 625 | | | | | 630 | | | | | 635 | | | | |
| GTG | AGT | TCA | AAC | GAG | GAG | TGT | CTC | CGA | GTT | GTG | TCC | CAT | GAG | CAC | AAA | 2149 |
| Val | Ser | Ser | Asn | Glu | Glu | Cys | Leu | Arg | Val | Val | Ser | His | Glu | His | Lys | |
| | 640 | | | | | 645 | | | | | 650 | | | | | |
| GTG | GTC | TTC | ATG | GAC | GTG | TGC | ATG | CCC | GGG | GTC | GAA | AAC | TAC | CAA | ATC | 2197 |
| Val | Val | Phe | Met | Asp | Val | Cys | Met | Pro | Gly | Val | Glu | Asn | Tyr | Gln | Ile | |
| 655 | | | | | 660 | | | | | 665 | | | | | 670 | |
| GCT | CTC | CGT | ATT | CAC | GAG | AAA | TTC | ACA | AAA | CAA | CGC | CAC | CAA | CGG | CCA | 2245 |
| Ala | Leu | Arg | Ile | His | Glu | Lys | Phe | Thr | Lys | Gln | Arg | His | Gln | Arg | Pro | |
| | | | | 675 | | | | | 680 | | | | | 685 | | |
| CTA | CTT | GTG | GCA | CTC | AGT | GGT | AAC | ACT | GAC | AAA | TCC | ACA | AAA | GAG | AAA | 2293 |
| Leu | Leu | Val | Ala | Leu | Ser | Gly | Asn | Thr | Asp | Lys | Ser | Thr | Lys | Glu | Lys | |
| | | | 690 | | | | | 695 | | | | | 700 | | | |
| TGC | ATG | AGC | TTT | GGT | CTA | GAC | GGT | GTG | TTG | CTC | AAA | CCC | GTA | TCA | CTA | 2341 |
| Cys | Met | Ser | Phe | Gly | Leu | Asp | Gly | Val | Leu | Leu | Lys | Pro | Val | Ser | Leu | |
| | | 705 | | | | | 710 | | | | | 715 | | | | |
| GAC | AAC | ATA | AGA | GAT | GTT | CTG | TCT | GAT | CTT | CTC | GAG | CCC | CGG | GTA | CTG | 2389 |
| Asp | Asn | Ile | Arg | Asp | Val | Leu | Ser | Asp | Leu | Leu | Glu | Pro | Arg | Val | Leu | |
| | 720 | | | | | 725 | | | | | 730 | | | | | |
| TAC | GAG | GGC | ATG | TAAAGGCGAT | GGATGCCCCA | TGCCCCAGAG | GAGTAATTCC | | | | | | | | | 2441 |
| Tyr | Glu | Gly | Met | | | | | | | | | | | | | |
| 735 | | | | | | | | | | | | | | | | |

| | | | | | |
|---|---|---|---|---|---|
| GCTCCCGCCT | TCTTCTCCCG | TAAAACATCG | GAAGCTGATG | TTCTCTGGTT | TAATTGTGTA | 2501 |
| CATATCAGAG | ATTGTCGGAG | CGTTTTGGAT | GATATCTTAA | AACAGAAAGG | GAATAACAAA | 2561 |
| ATAGAAACTC | TAAACCGGTA | TGTGTCCGTG | GCGATTTCGG | TTATAGAGGA | ACAAGATGGT | 2621 |
| GGTGGTATAA | TCATACCATT | TCAGATTACA | TGTTTGACTA | ATGTTGTATC | CTTATATATG | 2681 |
| TAGTTACATT | CTTATAAGAA | TTTGGATCGA | GTTATGGATG | CTTGTTGCGT | GCATGTATGA | 2741 |
| CATTGATGCA | GTATTATGGC | GTCAGCTTTG | CGCCGCTTAG | TAGAAC | | 2787 |

( 2 ) INFORMATION FOR SEQ ID NO:3:

( i ) SEQUENCE CHARACTERISTICS:
        ( A ) LENGTH: 738 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Met<br>1 | Glu | Val | Cys | Asn<br>5 | Cys | Ile | Glu | Pro | Gln<br>10 | Trp | Pro | Ala | Asp | Glu<br>15 | Leu |
| Leu | Met | Lys | Tyr<br>20 | Gln | Tyr | Ile | Ser | Asp<br>25 | Phe | Phe | Ile | Ala | Ile<br>30 | Ala | Tyr |
| Phe | Ser | Ile<br>35 | Pro | Leu | Glu | Leu | Ile<br>40 | Tyr | Phe | Val | Lys | Lys<br>45 | Ser | Ala | Val |
| Phe | Pro<br>50 | Tyr | Arg | Trp | Val | Leu<br>55 | Val | Gln | Phe | Gly | Ala<br>60 | Phe | Ile | Val | Leu |
| Cys<br>65 | Gly | Ala | Thr | His | Leu<br>70 | Ile | Asn | Leu | Trp | Thr<br>75 | Phe | Thr | Thr | His | Ser<br>80 |
| Arg | Thr | Val | Ala | Leu<br>85 | Val | Met | Thr | Thr | Ala<br>90 | Lys | Val | Leu | Thr | Ala<br>95 | Val |
| Val | Ser | Cys | Ala<br>100 | Thr | Ala | Leu | Met | Leu<br>105 | Val | His | Ile | Ile | Pro<br>110 | Asp | Leu |
| Leu | Ser | Val<br>115 | Lys | Thr | Arg | Glu | Leu<br>120 | Phe | Leu | Lys | Asn | Lys<br>125 | Ala | Ala | Glu |
| Leu | Asp<br>130 | Arg | Glu | Met | Gly | Leu<br>135 | Ile | Arg | Thr | Gln | Glu<br>140 | Glu | Thr | Gly | Arg |
| His<br>145 | Val | Arg | Met | Leu | Thr<br>150 | His | Glu | Ile | Arg | Ser<br>155 | Thr | Leu | Asp | Arg | His<br>160 |
| Thr | Ile | Leu | Lys | Thr<br>165 | Thr | Leu | Val | Glu | Leu<br>170 | Gly | Arg | Thr | Leu | Ala<br>175 | Leu |
| Glu | Glu | Cys | Ala<br>180 | Leu | Trp | Met | Pro | Thr<br>185 | Arg | Thr | Gly | Leu | Glu<br>190 | Leu | Gln |
| Leu | Ser | Tyr<br>195 | Thr | Leu | Arg | His | Gln<br>200 | His | Pro | Val | Glu | Tyr<br>205 | Thr | Val | Pro |
| Ile | Gln<br>210 | Leu | Pro | Val | Ile | Asn<br>215 | Gln | Val | Phe | Gly | Thr<br>220 | Ser | Arg | Ala | Val |
| Lys<br>225 | Ile | Ser | Pro | Asn | Ser<br>230 | Pro | Val | Ala | Arg | Leu<br>235 | Arg | Pro | Val | Ser | Gly<br>240 |
| Lys | Tyr | Met | Leu | Gly<br>245 | Glu | Val | Val | Ala | Val<br>250 | Arg | Val | Pro | Leu | Leu<br>255 | His |
| Leu | Ser | Asn | Phe<br>260 | Gln | Ile | Asn | Asp | Trp<br>265 | Pro | Glu | Leu | Ser | Thr<br>270 | Lys | Arg |
| Tyr | Ala | Leu<br>275 | Met | Val | Leu | Met | Leu<br>280 | Pro | Ser | Asp | Ser | Ala<br>285 | Arg | Gln | Trp |
| His | Val<br>290 | His | Glu | Leu | Glu | Leu<br>295 | Val | Glu | Val | Val | Ala<br>300 | Asp | Gln | Val | Ala |
| Val<br>305 | Ala | Leu | Ser | His | Ala<br>310 | Ala | Ile | Leu | Glu | Glu<br>315 | Ser | Met | Arg | Ala | Arg<br>320 |
| Asp | Leu | Leu | Met | Glu<br>325 | Gln | Asn | Val | Ala | Leu<br>330 | Asp | Leu | Ala | Arg | Arg<br>335 | Glu |
| Ala | Glu | Thr | Ala<br>340 | Ile | Arg | Ala | Arg | Asn<br>345 | Asp | Phe | Leu | Ala | Val<br>350 | Met | Asn |
| His | Glu | Met<br>355 | Arg | Thr | Pro | Met | His<br>360 | Ala | Ile | Ile | Ala | Leu<br>365 | Ser | Ser | Leu |
| Leu | Gln<br>370 | Glu | Thr | Glu | Leu | Thr<br>375 | Pro | Glu | Gln | Arg | Leu<br>380 | Met | Val | Glu | Thr |
| Ile<br>385 | Leu | Lys | Ser | Ser | Asn<br>390 | Leu | Leu | Ala | Thr | Leu<br>395 | Met | Asn | Asp | Val | Leu<br>400 |
| Asp | Leu | Ser | Arg | Leu<br>405 | Glu | Asp | Gly | Ser | Leu<br>410 | Gln | Leu | Glu | Leu | Gly<br>415 | Thr |
| Phe | Asn | Leu | His<br>420 | Thr | Leu | Phe | Arg | Glu<br>425 | Val | Leu | Asn | Leu | Ile<br>430 | Lys | Pro |

Ile Ala Val Val Lys Lys Leu Pro Ile Thr Leu Asn Leu Ala Pro Asp
        435                 440                 445

Leu Pro Glu Phe Val Val Gly Asp Glu Lys Arg Leu Met Gln Ile Ile
    450                 455                 460

Leu Asn Ile Val Gly Asn Ala Val Lys Phe Ser Lys Gln Gly Ser Ile
465                 470                 475                 480

Ser Val Thr Ala Leu Val Thr Lys Ser Asp Thr Arg Ala Ala Asp Phe
                485                 490                 495

Phe Val Val Pro Thr Gly Ser His Phe Tyr Leu Arg Val Lys Val Lys
            500                 505                 510

Asp Ser Gly Ala Gly Ile Asn Pro Gln Asp Ile Pro Lys Ile Phe Thr
        515                 520                 525

Lys Phe Ala Gln Thr Gln Ser Leu Ala Thr Arg Ser Ser Gly Gly Ser
    530                 535                 540

Gly Leu Gly Leu Ala Ile Ser Lys Arg Phe Val Asn Leu Met Glu Gly
545                 550                 555                 560

Asn Ile Trp Ile Glu Ser Asp Gly Leu Gly Lys Gly Cys Thr Ala Ile
                565                 570                 575

Phe Asp Val Lys Leu Gly Ile Ser Glu Arg Ser Asn Glu Ser Lys Gln
            580                 585                 590

Ser Gly Ile Pro Lys Val Pro Ala Ile Pro Arg His Ser Asn Phe Thr
        595                 600                 605

Gly Leu Lys Val Leu Val Met Asp Glu Asn Gly Val Ser Arg Met Val
    610                 615                 620

Thr Lys Gly Leu Leu Val His Leu Gly Cys Glu Val Thr Thr Val Ser
625                 630                 635                 640

Ser Asn Glu Glu Cys Leu Arg Val Val Ser His Glu His Lys Val Val
                645                 650                 655

Phe Met Asp Val Cys Met Pro Gly Val Glu Asn Tyr Gln Ile Ala Leu
            660                 665                 670

Arg Ile His Glu Lys Phe Thr Lys Gln Arg His Gln Arg Pro Leu Leu
        675                 680                 685

Val Ala Leu Ser Gly Asn Thr Asp Lys Ser Thr Lys Glu Lys Cys Met
    690                 695                 700

Ser Phe Gly Leu Asp Gly Val Leu Leu Lys Pro Val Ser Leu Asp Asn
705                 710                 715                 720

Ile Arg Asp Val Leu Ser Asp Leu Leu Glu Pro Arg Val Leu Tyr Glu
                725                 730                 735

Gly Met ( 2 ) INFORMATION FOR SEQ ID NO:4:

( i ) SEQUENCE CHARACTERISTICS:
        ( A ) LENGTH: 2787 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 188..2401

( x i ) SEQUENCE DESCRIPTION: SEQ ID NO:4:

AGTAAGAACG AAGAAGAAGT GTTAAACCCA ACCAATTTTG ACTTGAAAAA AAGCTTCAAC 60

GCTCCCCTTT TCTCCTTCTC CGTCGCTCTC CGCCGCGTCC CAAATCCCCA ATTCCTCCTC 120

```
TTCTCCGATC AATTCTTCCC AAGTGTGTGT ATGTGTGAGA GAGGAACTAT AGTGTAAAAA      180

ATTCATA ATG GAA GTC TGC AAT TGT ATT GAA CCG CAA TGG CCA GCG GAT        229
        Met Glu Val Cys Asn Cys Ile Glu Pro Gln Trp Pro Ala Asp
        1           5                   10

GAA TTG TTA ATG AAA TAC CAA TAC ATC TCC GAT TTC TTC ATT GCG ATT        277
Glu Leu Leu Met Lys Tyr Gln Tyr Ile Ser Asp Phe Phe Ile Ala Ile
15              20                  25                          30

GCG TAT TTT TCG ATT CCT CTT GAG TTG ATT TAC TTT GTG AAG AAA TCA        325
Ala Tyr Phe Ser Ile Pro Leu Glu Leu Ile Tyr Phe Val Lys Lys Ser
                35                  40                  45

GCC GTG TTT CCG TAT AGA TGG GTA CTT GTT CAG TTT GGT GCT TTT ATC        373
Ala Val Phe Pro Tyr Arg Trp Val Leu Val Gln Phe Gly Ala Phe Ile
            50                  55                  60

GTT CTT TAT GGA GCA ACT CAT CTT ATT AAC TTA TGG ACT TTC ACT ACG        421
Val Leu Tyr Gly Ala Thr His Leu Ile Asn Leu Trp Thr Phe Thr Thr
        65                  70                  75

CAT TCG AGA ACC GTG GCG CTT GTG ATG ACT ACC GCG AAG GTG TTA ACC        469
His Ser Arg Thr Val Ala Leu Val Met Thr Thr Ala Lys Val Leu Thr
    80                  85                  90

GCT GTT GTC TCG TGT GCT ACT GCG TTG ATG CTT GTT CAT ATT ATT CCT        517
Ala Val Val Ser Cys Ala Thr Ala Leu Met Leu Val His Ile Ile Pro
95              100                 105                         110

GAT CTT TTG AGT GTT AAG ACT CGG GAG CTT TTC TTG AAA AAT AAA GCT        565
Asp Leu Leu Ser Val Lys Thr Arg Glu Leu Phe Leu Lys Asn Lys Ala
                115                 120                 125

GCT GAG CTC GAT AGA GAA ATG GGA TTG ATT CGA ACT CAG GAA GAA ACC        613
Ala Glu Leu Asp Arg Glu Met Gly Leu Ile Arg Thr Gln Glu Glu Thr
            130                 135                 140

GGA AGG CAT GTG AGA ATG TTG ACT CAT GAG ATT AGA AGC ACT TTA GAT        661
Gly Arg His Val Arg Met Leu Thr His Glu Ile Arg Ser Thr Leu Asp
        145                 150                 155

AGA CAT ACT ATT TTA AAG ACT ACA CTT GTT GAG CTT GGT AGG ACA TTA        709
Arg His Thr Ile Leu Lys Thr Thr Leu Val Glu Leu Gly Arg Thr Leu
    160                 165                 170

GCT TTG GAG GAG TGT GCA TTG TGG ATG CCT ACT AGA ACT GGG TTA GAG        757
Ala Leu Glu Glu Cys Ala Leu Trp Met Pro Thr Arg Thr Gly Leu Glu
175                 180                 185                     190

CTA CAG CTT TCT TAT ACA CTT CGT CAT CAA CAT CCC GTG GAG TAT ACG        805
Leu Gln Leu Ser Tyr Thr Leu Arg His Gln His Pro Val Glu Tyr Thr
                195                 200                 205

GTT CCT ATT CAA TTA CCG GTG ATT AAC CAA GTG TTT GGT ACT AGT AGG        853
Val Pro Ile Gln Leu Pro Val Ile Asn Gln Val Phe Gly Thr Ser Arg
            210                 215                 220

GCT GTA AAA ATA TCT CCT AAT TCT CCT GTG GCT AGG TTG AGA CCT GTT        901
Ala Val Lys Ile Ser Pro Asn Ser Pro Val Ala Arg Leu Arg Pro Val
        225                 230                 235

TCT GGG AAA TAT ATG CTA GGG GAG GTG GTC GCT GTG AGG GTT CCG CTT        949
Ser Gly Lys Tyr Met Leu Gly Glu Val Val Ala Val Arg Val Pro Leu
    240                 245                 250

CTC CAC CTT TCT AAT TTT CAG ATT AAT GAC TGG CCT GAG CTT TCA ACA        997
Leu His Leu Ser Asn Phe Gln Ile Asn Asp Trp Pro Glu Leu Ser Thr
255                 260                 265                     270

AAG AGA TAT GCT TTG ATG GTT TTG ATG CTT CCT TCA GAT AGT GCA AGG        1045
Lys Arg Tyr Ala Leu Met Val Leu Met Leu Pro Ser Asp Ser Ala Arg
                275                 280                 285

CAA TGG CAT GTC CAT GAG TTG GAA CTC GTT GAA GTC GTC GCT GAT CAG       1093
Gln Trp His Val His Glu Leu Glu Leu Val Glu Val Val Ala Asp Gln
            290                 295                 300

GTG GCT GTA GCT CTC TCA CAT GCT GCG ATC CTA GAA GAG TCG ATG CGA        1141
```

```
Val Ala Val Ala Leu Ser His Ala Ala Ile Leu Glu Glu Ser Met Arg
        305                 310                 315

GCT AGG GAC CTT CTC ATG GAG CAG AAT GTT GCT CTT GAT CTA GCT AGA           1189
Ala Arg Asp Leu Leu Met Glu Gln Asn Val Ala Leu Asp Leu Ala Arg
    320                 325                 330

CGA GAA GCA GAA ACA GCA ATC CGT GCC CGC AAT GAT TTC CTA GCG GTT           1237
Arg Glu Ala Glu Thr Ala Ile Arg Ala Arg Asn Asp Phe Leu Ala Val
335                 340                 345                 350

ATG AAC CAT GAA ATG CGA ACA CCG ATG CAT GCG ATT ATT GCA CTC TCT           1285
Met Asn His Glu Met Arg Thr Pro Met His Ala Ile Ile Ala Leu Ser
                355                 360                 365

TCC TTA CTC CAA GAA ACG GAA CTA ACC CCT GAA CAA AGA CTG ATG GTG           1333
Ser Leu Leu Gln Glu Thr Glu Leu Thr Pro Glu Gln Arg Leu Met Val
            370                 375                 380

GAA ACA ATA CTT AAA AGT AGT AAC CTT TTG GCA ACT TTG ATG AAT GAT           1381
Glu Thr Ile Leu Lys Ser Ser Asn Leu Leu Ala Thr Leu Met Asn Asp
        385                 390                 395

GTC TTA GAT CTT TCA AGG TTA GAA GAT GGA AGT CTT CAA CTT GAA CTT           1429
Val Leu Asp Leu Ser Arg Leu Glu Asp Gly Ser Leu Gln Leu Glu Leu
    400                 405                 410

GGG ACA TTC AAT CTT CAT ACA TTA TTT AGA GAG GTC CTC AAT CTG ATA           1477
Gly Thr Phe Asn Leu His Thr Leu Phe Arg Glu Val Leu Asn Leu Ile
415                 420                 425                 430

AAG CCT ATA GCG GTT GTT AAG AAA TTA CCC ATC ACA CTA AAT CTT GCA           1525
Lys Pro Ile Ala Val Val Lys Lys Leu Pro Ile Thr Leu Asn Leu Ala
                435                 440                 445

CCA GAT TTG CCA GAA TTT GTT GTT GGG GAT GAG AAA CGG CTA ATG CAG           1573
Pro Asp Leu Pro Glu Phe Val Val Gly Asp Glu Lys Arg Leu Met Gln
            450                 455                 460

ATA ATA TTA AAT ATA GTT GGT AAT GCT GTG AAA TTC TCC AAA CAA GGT           1621
Ile Ile Leu Asn Ile Val Gly Asn Ala Val Lys Phe Ser Lys Gln Gly
        465                 470                 475

AGT ATC TCC GTA ACC GCT CTT GTC ACC AAG TCA GAC ACA CGA GCT GCT           1669
Ser Ile Ser Val Thr Ala Leu Val Thr Lys Ser Asp Thr Arg Ala Ala
    480                 485                 490

GAC TTT TTT GTC GTG CCA ACT GGG AGT CAT TTC TAC TTG AGA GTG AAG           1717
Asp Phe Phe Val Val Pro Thr Gly Ser His Phe Tyr Leu Arg Val Lys
495                 500                 505                 510

GTA AAA GAC TCT GGA GCA GGA ATA AAT CCT CAA GAC ATT CCA AAG ATT           1765
Val Lys Asp Ser Gly Ala Gly Ile Asn Pro Gln Asp Ile Pro Lys Ile
                515                 520                 525

TTC ACT AAA TTT GCT CAA ACA CAA TCT TTA GCG ACG AGA AGC TCG GGT           1813
Phe Thr Lys Phe Ala Gln Thr Gln Ser Leu Ala Thr Arg Ser Ser Gly
            530                 535                 540

GGT AGT GGG CTT GGC CTC GCC ATC TCC AAG AGG TTT GTG AAT CTG ATG           1861
Gly Ser Gly Leu Gly Leu Ala Ile Ser Lys Arg Phe Val Asn Leu Met
        545                 550                 555

GAG GGT AAC ATT TGG ATT GAG AGC GAT GGT CTT GGA AAA GGA TGC ACG           1909
Glu Gly Asn Ile Trp Ile Glu Ser Asp Gly Leu Gly Lys Gly Cys Thr
    560                 565                 570

GCT ATC TTT GAT GTT AAA CTT GGG ATC TCA GAA CGT TCA AAC GAA TCT           1957
Ala Ile Phe Asp Val Lys Leu Gly Ile Ser Glu Arg Ser Asn Glu Ser
575                 580                 585                 590

AAA CAG TCG GGC ATA CCG AAA GTT CCA GCC ATT CCC CGA CAT TCA AAT           2005
Lys Gln Ser Gly Ile Pro Lys Val Pro Ala Ile Pro Arg His Ser Asn
                595                 600                 605

TTC ACT GGA CTT AAG GTT CTT GTC ATG GAT GAG AAC GGG GTA AGT AGA           2053
Phe Thr Gly Leu Lys Val Leu Val Met Asp Glu Asn Gly Val Ser Arg
            610                 615                 620

ATG GTG ACG AAG GGA CTT CTT GTA CAC CTT GGG TGC GAA GTG ACC ACG           2101
```

| | | | | | | | | | | | | | | |
|---|---|---|---|---|---|---|---|---|---|---|---|---|---|---|
| Met | Val | Thr | Lys | Gly | Leu | Leu | Val | His | Leu | Gly | Cys | Glu | Val | Thr | Thr |
| | | 625 | | | | 630 | | | | | 635 | | | | |

```
GTG  AGT  TCA  AAC  GAG  GAG  TGT  CTC  CGA  GTT  GTG  TCC  CAT  GAG  CAC  AAA        2149
Val  Ser  Ser  Asn  Glu  Glu  Cys  Leu  Arg  Val  Val  Ser  His  Glu  His  Lys
     640                      645                      650

GTG  GTC  TTC  ATG  GAC  GTG  TGC  ATG  CCC  GGG  GTC  GAA  AAC  TAC  CAA  ATC        2197
Val  Val  Phe  Met  Asp  Val  Cys  Met  Pro  Gly  Val  Glu  Asn  Tyr  Gln  Ile
655                 660                      665                      670

GCT  CTC  CGT  ATT  CAC  GAG  AAA  TTC  ACA  AAA  CAA  CGC  CAC  CAA  CGG  CCA        2245
Ala  Leu  Arg  Ile  His  Glu  Lys  Phe  Thr  Lys  Gln  Arg  His  Gln  Arg  Pro
               675                      680                      685

CTA  CTT  GTG  GCA  CTC  AGT  GGT  AAC  ACT  GAC  AAA  TCC  ACA  AAA  GAG  AAA        2293
Leu  Leu  Val  Ala  Leu  Ser  Gly  Asn  Thr  Asp  Lys  Ser  Thr  Lys  Glu  Lys
               690                      695                      700

TGC  ATG  AGC  TTT  GGT  CTA  GAC  GGT  GTG  TTG  CTC  AAA  CCC  GTA  TCA  CTA        2341
Cys  Met  Ser  Phe  Gly  Leu  Asp  Gly  Val  Leu  Leu  Lys  Pro  Val  Ser  Leu
          705                      710                      715

GAC  AAC  ATA  AGA  GAT  GTT  CTG  TCT  GAT  CTT  CTC  GAG  CCC  CGG  GTA  CTG        2389
Asp  Asn  Ile  Arg  Asp  Val  Leu  Ser  Asp  Leu  Leu  Glu  Pro  Arg  Val  Leu
     720                      725                      730

TAC  GAG  GGC  ATG  TAAAGGCGAT  GGATGCCCCA  TGCCCCAGAG  GAGTAATTCC                    2441
Tyr  Glu  Gly  Met
735

GCTCCCGCCT  TCTTCTCCCG  TAAAACATCG  GAAGCTGATG  TTCTCTGGTT  TAATTGTGTA                2501

CATATCAGAG  ATTGTCGGAG  CGTTTTGGAT  GATATCTTAA  AACAGAAAGG  GAATAACAAA                2561

ATAGAAACTC  TAAACCGGTA  TGTGTCCGTG  GCGATTTCGG  TTATAGAGGA  ACAAGATGGT                2621

GGTGGTATAA  TCATACCATT  TCAGATTACA  TGTTTGACTA  ATGTTGTATC  CTTATATATG                2681

TAGTTACATT  CTTATAAGAA  TTTGGATCGA  GTTATGGATG  CTTGTTGCGT  GCATGTATGA                2741

CATTGATGCA  GTATTATGGC  GTCAGCTTTG  CGCCGCTTAG  TAGAAC                                2787
```

( 2 ) INFORMATION FOR SEQ ID NO:5:

( i ) SEQUENCE CHARACTERISTICS:
        ( A ) LENGTH: 738 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Glu  Val  Cys  Asn  Cys  Ile  Glu  Pro  Gln  Trp  Pro  Ala  Asp  Glu  Leu
1                   5                        10                       15

Leu  Met  Lys  Tyr  Gln  Tyr  Ile  Ser  Asp  Phe  Phe  Ile  Ala  Ile  Ala  Tyr
               20                  25                       30

Phe  Ser  Ile  Pro  Leu  Glu  Leu  Ile  Tyr  Phe  Val  Lys  Lys  Ser  Ala  Val
          35                       40                       45

Phe  Pro  Tyr  Arg  Trp  Val  Leu  Val  Gln  Phe  Gly  Ala  Phe  Ile  Val  Leu
     50                       55                       60

Tyr  Gly  Ala  Thr  His  Leu  Ile  Asn  Leu  Trp  Thr  Phe  Thr  Thr  His  Ser
65                       70                       75                       80

Arg  Thr  Val  Ala  Leu  Val  Met  Thr  Thr  Ala  Lys  Val  Leu  Thr  Ala  Val
               85                       90                       95

Val  Ser  Cys  Ala  Thr  Ala  Leu  Met  Leu  Val  His  Ile  Ile  Pro  Asp  Leu
               100                      105                      110

Leu  Ser  Val  Lys  Thr  Arg  Glu  Leu  Phe  Leu  Lys  Asn  Lys  Ala  Ala  Glu
          115                      120                      125

Leu  Asp  Arg  Glu  Met  Gly  Leu  Ile  Arg  Thr  Gln  Glu  Glu  Thr  Gly  Arg
```

|     |     |     |     |     | 130 |     |     |     |     | 135 |     |     |     |     | 140 |     |     |     |     |
| --- | --- | --- | --- | --- | --- | --- | --- | --- | --- | --- | --- | --- | --- | --- | --- | --- | --- | --- | --- |

His Val Arg Met Leu Thr His Glu Ile Arg Ser Thr Leu Asp Arg His
145                     150                     155                     160

Thr Ile Leu Lys Thr Thr Leu Val Glu Leu Gly Arg Thr Leu Ala Leu
                    165                     170                     175

Glu Glu Cys Ala Leu Trp Met Pro Thr Arg Thr Gly Leu Glu Leu Gln
                180                     185                     190

Leu Ser Tyr Thr Leu Arg His Gln His Pro Val Glu Tyr Thr Val Pro
            195                     200                     205

Ile Gln Leu Pro Val Ile Asn Gln Val Phe Gly Thr Ser Arg Ala Val
        210                     215                     220

Lys Ile Ser Pro Asn Ser Pro Val Ala Arg Leu Arg Pro Val Ser Gly
225                     230                     235                     240

Lys Tyr Met Leu Gly Glu Val Val Ala Val Arg Val Pro Leu Leu His
                245                     250                     255

Leu Ser Asn Phe Gln Ile Asn Asp Trp Pro Glu Leu Ser Thr Lys Arg
            260                     265                     270

Tyr Ala Leu Met Val Leu Met Leu Pro Ser Asp Ser Ala Arg Gln Trp
        275                     280                     285

His Val His Glu Leu Glu Leu Val Glu Val Val Ala Asp Gln Val Ala
290                     295                     300

Val Ala Leu Ser His Ala Ala Ile Leu Glu Glu Ser Met Arg Ala Arg
305                     310                     315                     320

Asp Leu Leu Met Glu Gln Asn Val Ala Leu Asp Leu Ala Arg Arg Glu
                325                     330                     335

Ala Glu Thr Ala Ile Arg Ala Arg Asn Asp Phe Leu Ala Val Met Asn
            340                     345                     350

His Glu Met Arg Thr Pro Met His Ala Ile Ile Ala Leu Ser Ser Leu
        355                     360                     365

Leu Gln Glu Thr Glu Leu Thr Pro Glu Gln Arg Leu Met Val Glu Thr
        370                     375                     380

Ile Leu Lys Ser Ser Asn Leu Leu Ala Thr Leu Met Asn Asp Val Leu
385                     390                     395                     400

Asp Leu Ser Arg Leu Glu Asp Gly Ser Leu Gln Leu Glu Leu Gly Thr
                405                     410                     415

Phe Asn Leu His Thr Leu Phe Arg Glu Val Leu Asn Leu Ile Lys Pro
            420                     425                     430

Ile Ala Val Val Lys Lys Leu Pro Ile Thr Leu Asn Leu Ala Pro Asp
        435                     440                     445

Leu Pro Glu Phe Val Val Gly Asp Glu Lys Arg Leu Met Gln Ile Ile
450                     455                     460

Leu Asn Ile Val Gly Asn Ala Val Lys Phe Ser Lys Gln Gly Ser Ile
465                     470                     475                     480

Ser Val Thr Ala Leu Val Thr Lys Ser Asp Thr Arg Ala Ala Asp Phe
                485                     490                     495

Phe Val Val Pro Thr Gly Ser His Phe Tyr Leu Arg Val Lys Val Lys
            500                     505                     510

Asp Ser Gly Ala Gly Ile Asn Pro Gln Asp Ile Pro Lys Ile Phe Thr
        515                     520                     525

Lys Phe Ala Gln Thr Gln Ser Leu Ala Thr Arg Ser Ser Gly Gly Ser
        530                     535                     540

Gly Leu Gly Leu Ala Ile Ser Lys Arg Phe Val Asn Leu Met Glu Gly
545                     550                     555                     560

| | | | | | | | | | | | | | | |
|---|---|---|---|---|---|---|---|---|---|---|---|---|---|---|
| Asn | Ile | Trp | Ile | Glu | Ser | Asp | Gly | Leu | Gly | Lys | Gly | Cys | Thr | Ala | Ile |
| | | | | 565 | | | | 570 | | | | | 575 | |
| Phe | Asp | Val | Lys | Leu | Gly | Ile | Ser | Glu | Arg | Ser | Asn | Glu | Ser | Lys | Gln |
| | | | 580 | | | | 585 | | | | | 590 | | | |
| Ser | Gly | Ile | Pro | Lys | Val | Pro | Ala | Ile | Pro | Arg | His | Ser | Asn | Phe | Thr |
| | | 595 | | | | | 600 | | | | | 605 | | | |
| Gly | Leu | Lys | Val | Leu | Val | Met | Asp | Glu | Asn | Gly | Val | Ser | Arg | Met | Val |
| | 610 | | | | | 615 | | | | 620 | | | | | |
| Thr | Lys | Gly | Leu | Leu | Val | His | Leu | Gly | Cys | Glu | Val | Thr | Thr | Val | Ser |
| 625 | | | | | 630 | | | | 635 | | | | | 640 | |
| Ser | Asn | Glu | Glu | Cys | Leu | Arg | Val | Val | Ser | His | Glu | His | Lys | Val | Val |
| | | | | 645 | | | | | 650 | | | | | 655 | |
| Phe | Met | Asp | Val | Cys | Met | Pro | Gly | Val | Glu | Asn | Tyr | Gln | Ile | Ala | Leu |
| | | | 660 | | | | | 665 | | | | | 670 | | |
| Arg | Ile | His | Glu | Lys | Phe | Thr | Lys | Gln | Arg | His | Gln | Arg | Pro | Leu | Leu |
| | | 675 | | | | | 680 | | | | | 685 | | | |
| Val | Ala | Leu | Ser | Gly | Asn | Thr | Asp | Lys | Ser | Thr | Lys | Glu | Lys | Cys | Met |
| | 690 | | | | | 695 | | | | 700 | | | | | |
| Ser | Phe | Gly | Leu | Asp | Gly | Val | Leu | Leu | Lys | Pro | Val | Ser | Leu | Asp | Asn |
| 705 | | | | | 710 | | | | 715 | | | | | 720 | |
| Ile | Arg | Asp | Val | Leu | Ser | Asp | Leu | Leu | Glu | Pro | Arg | Val | Leu | Tyr | Glu |
| | | | | 725 | | | | | 730 | | | | | 735 | |
| Gly | Met | | | | | | | | | | | | | | |

( 2 ) INFORMATION FOR SEQ ID NO:6:

( i ) SEQUENCE CHARACTERISTICS:
        ( A ) LENGTH: 2787 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 188..2401

( x i ) SEQUENCE DESCRIPTION: SEQ ID NO:6:

```
AGTAAGAACG AAGAAGAAGT GTTAAACCCA ACCAATTTTG ACTTGAAAAA AAGCTTCAAC        60

GCTCCCCTTT TCTCCTTCTC CGTCGCTCTC CGCCGCGTCC CAAATCCCCA ATTCCTCCTC       120

TTCTCCGATC AATTCTTCCC AAGTGTGTGT ATGTGTGAGA GAGGAACTAT AGTGTAAAAA       180
```

| ATTCATA | ATG | GAA | GTC | TGC | AAT | TGT | ATT | GAA | CCG | CAA | TGG | CCA | GCG | GAT | 229 |
|---|---|---|---|---|---|---|---|---|---|---|---|---|---|---|---|
| | Met | Glu | Val | Cys | Asn | Cys | Ile | Glu | Pro | Gln | Trp | Pro | Ala | Asp | |
| | 1 | | | | 5 | | | | | 10 | | | | | |

| GAA | TTG | TTA | ATG | AAA | TAC | CAA | TAC | ATC | TCC | GAT | TTC | TTC | ATT | GCG | ATT | 277 |
|---|---|---|---|---|---|---|---|---|---|---|---|---|---|---|---|---|
| Glu | Leu | Leu | Met | Lys | Tyr | Gln | Tyr | Ile | Ser | Asp | Phe | Phe | Ile | Ala | Ile | |
| 15 | | | | 20 | | | | | 25 | | | | | 30 | | |

| GCG | TAT | TTT | TCG | ATT | CCT | CTT | GAG | TTG | ATT | TAC | TTT | GTG | AAG | AAA | TCA | 325 |
|---|---|---|---|---|---|---|---|---|---|---|---|---|---|---|---|---|
| Ala | Tyr | Phe | Ser | Ile | Pro | Leu | Glu | Leu | Ile | Tyr | Phe | Val | Lys | Lys | Ser | |
| | | | | 35 | | | | | 40 | | | | | 45 | | |

| GCC | GTG | TTT | CCG | TAT | AGA | TGG | GTA | CTT | GTT | CAG | TTT | GGT | GCT | TTT | ATC | 373 |
|---|---|---|---|---|---|---|---|---|---|---|---|---|---|---|---|---|
| Ala | Val | Phe | Pro | Tyr | Arg | Trp | Val | Leu | Val | Gln | Phe | Gly | Ala | Phe | Ile | |
| | | | 50 | | | | 55 | | | | | 60 | | | | |

| GTT | CTT | TGT | GGA | GCA | ACT | CAT | CTT | ATT | AAC | TTA | TGG | ACT | TTC | ACT | ACG | 421 |
|---|---|---|---|---|---|---|---|---|---|---|---|---|---|---|---|---|
| Val | Leu | Cys | Gly | Ala | Thr | His | Leu | Ile | Asn | Leu | Trp | Thr | Phe | Thr | Thr | |
| | | 65 | | | | | 70 | | | | | 75 | | | | |

| CAT | TCG | AGA | ACC | GTG | GCG | CTT | GTG | ATG | ACT | ACC | GCG | AAG | GTG | TTA | ACC | 469 |
|---|---|---|---|---|---|---|---|---|---|---|---|---|---|---|---|---|
| His | Ser | Arg | Thr | Val | Ala | Leu | Val | Met | Thr | Thr | Ala | Lys | Val | Leu | Thr | |

```
                80                              85                              90
GCT  GTT  GTC  TCG  TGT  GCT  ACT  ACG  TTG  ATG  CTT  GTT  CAT  ATT  ATT  CCT      517
Ala  Val  Val  Ser  Cys  Ala  Thr  Thr  Leu  Met  Leu  Val  His  Ile  Ile  Pro
 95            100                      105                           110

GAT  CTT  TTG  AGT  GTT  AAG  ACT  CGG  GAG  CTT  TTC  TTG  AAA  AAT  AAA  GCT      565
Asp  Leu  Leu  Ser  Val  Lys  Thr  Arg  Glu  Leu  Phe  Leu  Lys  Asn  Lys  Ala
               115                      120                      125

GCT  GAG  CTC  GAT  AGA  GAA  ATG  GGA  TTG  ATT  CGA  ACT  CAG  GAA  GAA  ACC      613
Ala  Glu  Leu  Asp  Arg  Glu  Met  Gly  Leu  Ile  Arg  Thr  Gln  Glu  Glu  Thr
                130                      135                      140

GGA  AGG  CAT  GTG  AGA  ATG  TTG  ACT  CAT  GAG  ATT  AGA  AGC  ACT  TTA  GAT      661
Gly  Arg  His  Val  Arg  Met  Leu  Thr  His  Glu  Ile  Arg  Ser  Thr  Leu  Asp
          145                      150                      155

AGA  CAT  ACT  ATT  TTA  AAG  ACT  ACA  CTT  GTT  GAG  CTT  GGT  AGG  ACA  TTA      709
Arg  His  Thr  Ile  Leu  Lys  Thr  Thr  Leu  Val  Glu  Leu  Gly  Arg  Thr  Leu
     160                      165                      170

GCT  TTG  GAG  GAG  TGT  GCA  TTG  TGG  ATG  CCT  ACT  AGA  ACT  GGG  TTA  GAG      757
Ala  Leu  Glu  Glu  Cys  Ala  Leu  Trp  Met  Pro  Thr  Arg  Thr  Gly  Leu  Glu
175                      180                      185                      190

CTA  CAG  CTT  TCT  TAT  ACA  CTT  CGT  CAT  CAA  CAT  CCC  GTG  GAG  TAT  ACG      805
Leu  Gln  Leu  Ser  Tyr  Thr  Leu  Arg  His  Gln  His  Pro  Val  Glu  Tyr  Thr
                    195                      200                      205

GTT  CCT  ATT  CAA  TTA  CCG  GTG  ATT  AAC  CAA  GTG  TTT  GGT  ACT  AGT  AGG      853
Val  Pro  Ile  Gln  Leu  Pro  Val  Ile  Asn  Gln  Val  Phe  Gly  Thr  Ser  Arg
               210                      215                      220

GCT  GTA  AAA  ATA  TCT  CCT  AAT  TCT  CCT  GTG  GCT  AGG  TTG  AGA  CCT  GTT      901
Ala  Val  Lys  Ile  Ser  Pro  Asn  Ser  Pro  Val  Ala  Arg  Leu  Arg  Pro  Val
          225                      230                      235

TCT  GGG  AAA  TAT  ATG  CTA  GGG  GAG  GTG  GTC  GCT  GTG  AGG  GTT  CCG  CTT      949
Ser  Gly  Lys  Tyr  Met  Leu  Gly  Glu  Val  Val  Ala  Val  Arg  Val  Pro  Leu
     240                      245                      250

CTC  CAC  CTT  TCT  AAT  TTT  CAG  ATT  AAT  GAC  TGG  CCT  GAG  CTT  TCA  ACA      997
Leu  His  Leu  Ser  Asn  Phe  Gln  Ile  Asn  Asp  Trp  Pro  Glu  Leu  Ser  Thr
255                      260                      265                      270

AAG  AGA  TAT  GCT  TTG  ATG  GTT  TTG  ATG  CTT  CCT  TCA  GAT  AGT  GCA  AGG     1045
Lys  Arg  Tyr  Ala  Leu  Met  Val  Leu  Met  Leu  Pro  Ser  Asp  Ser  Ala  Arg
                    275                      280                      285

CAA  TGG  CAT  GTC  CAT  GAG  TTG  GAA  CTC  GTT  GAA  GTC  GTC  GCT  GAT  CAG     1093
Gln  Trp  His  Val  His  Glu  Leu  Glu  Leu  Val  Glu  Val  Val  Ala  Asp  Gln
               290                      295                      300

GTG  GCT  GTA  GCT  CTC  TCA  CAT  GCT  GCG  ATC  CTA  GAA  GAG  TCG  ATG  CGA     1141
Val  Ala  Val  Ala  Leu  Ser  His  Ala  Ala  Ile  Leu  Glu  Glu  Ser  Met  Arg
          305                      310                      315

GCT  AGG  GAC  CTT  CTC  ATG  GAG  CAG  AAT  GTT  GCT  CTT  GAT  CTA  GCT  AGA     1189
Ala  Arg  Asp  Leu  Leu  Met  Glu  Gln  Asn  Val  Ala  Leu  Asp  Leu  Ala  Arg
     320                      325                      330

CGA  GAA  GCA  GAA  ACA  GCA  ATC  CGT  GCC  CGC  AAT  GAT  TTC  CTA  GCG  GTT     1237
Arg  Glu  Ala  Glu  Thr  Ala  Ile  Arg  Ala  Arg  Asn  Asp  Phe  Leu  Ala  Val
335                      340                      345                      350

ATG  AAC  CAT  GAA  ATG  CGA  ACA  CCG  ATG  CAT  GCG  ATT  ATT  GCA  CTC  TCT     1285
Met  Asn  His  Glu  Met  Arg  Thr  Pro  Met  His  Ala  Ile  Ile  Ala  Leu  Ser
                    355                      360                      365

TCC  TTA  CTC  CAA  GAA  ACG  GAA  CTA  ACC  CCT  GAA  CAA  AGA  CTG  ATG  GTG     1333
Ser  Leu  Leu  Gln  Glu  Thr  Glu  Leu  Thr  Pro  Glu  Gln  Arg  Leu  Met  Val
               370                      375                      380

GAA  ACA  ATA  CTT  AAA  AGT  AGT  AAC  CTT  TTG  GCA  ACT  TTG  ATG  AAT  GAT     1381
Glu  Thr  Ile  Leu  Lys  Ser  Ser  Asn  Leu  Leu  Ala  Thr  Leu  Met  Asn  Asp
          385                      390                      395

GTC  TTA  GAT  CTT  TCA  AGG  TTA  GAA  GAT  GGA  AGT  CTT  CAA  CTT  GAA  CTT     1429
Val  Leu  Asp  Leu  Ser  Arg  Leu  Glu  Asp  Gly  Ser  Leu  Gln  Leu  Glu  Leu
```

|              |              |              | 400          |              |              |              | 405          |              |              |              | 410          |              |              |              |      |
|--------------|--------------|--------------|--------------|--------------|--------------|--------------|--------------|--------------|--------------|--------------|--------------|--------------|--------------|--------------|------|
| GGG Gly 415  | ACA Thr      | TTC Phe      | AAT Asn      | CTT Leu      | CAT His 420  | ACA Thr      | TTA Leu      | TTT Phe      | AGA Arg      | GAG Glu 425  | GTC Val      | CTC Leu      | AAT Asn      | CTG Leu      | ATA Ile 430 | 1477 |
| AAG Lys      | CCT Pro      | ATA Ile      | GCG Ala      | GTT Val 435  | GTT Val      | AAG Lys      | AAA Lys      | TTA Leu      | CCC Pro 440  | ATC Ile      | ACA Thr      | CTA Leu      | AAT Asn      | CTT Leu 445  | GCA Ala | 1525 |
| CCA Pro      | GAT Asp      | TTG Leu      | CCA Pro 450  | GAA Glu      | TTT Phe      | GTT Val      | GTT Val      | GGG Gly 455  | GAT Asp      | GAG Glu      | AAA Lys      | CGG Arg      | CTA Leu 460  | ATG Met      | CAG Gln | 1573 |
| ATA Ile      | ATA Ile      | TTA Leu 465  | AAT Asn      | ATA Ile      | GTT Val      | GGT Gly      | AAT Asn 470  | GCT Ala      | GTG Val      | AAA Lys      | TTC Phe      | TCC Ser 475  | AAA Lys      | CAA Gln      | GGT Gly | 1621 |
| AGT Ser      | ATC Ile 480  | TCC Ser      | GTA Val      | ACC Thr      | GCT Ala      | CTT Leu 485  | GTC Val      | ACC Thr      | AAG Lys      | TCA Ser      | GAC Asp 490  | ACA Thr      | CGA Arg      | GCT Ala      | GCT Ala | 1669 |
| GAC Asp 495  | TTT Phe      | TTT Phe      | GTC Val      | GTG Val      | CCA Pro 500  | ACT Thr      | GGG Gly      | AGT Ser      | CAT His      | TTC Phe 505  | TAC Tyr      | TTG Leu      | AGA Arg      | GTG Val      | AAG Lys 510 | 1717 |
| GTA Val      | AAA Lys      | GAC Asp      | TCT Ser      | GGA Gly 515  | GCA Ala      | GGA Gly      | ATA Ile      | AAT Asn      | CCT Pro 520  | CAA Gln      | GAC Asp      | ATT Ile      | CCA Pro      | AAG Lys 525  | ATT Ile | 1765 |
| TTC Phe      | ACT Thr      | AAA Lys      | TTT Phe 530  | GCT Ala      | CAA Gln      | ACA Thr      | CAA Gln      | TCT Ser 535  | TTA Leu      | GCG Ala      | ACG Thr      | AGA Arg      | AGC Ser 540  | TCG Ser      | GGT Gly | 1813 |
| GGT Gly      | AGT Ser      | GGG Gly 545  | CTT Leu      | GGC Gly      | CTC Leu      | GCC Ala      | ATC Ile 550  | TCC Ser      | AAG Lys      | AGG Arg      | TTT Phe      | GTG Val 555  | AAT Asn      | CTG Leu      | ATG Met | 1861 |
| GAG Glu      | GGT Gly      | AAC Asn 560  | ATT Ile      | TGG Trp      | ATT Ile      | GAG Glu      | AGC Ser 565  | GAT Asp      | GGT Gly      | CTT Leu      | GGA Gly      | AAA Lys 570  | GGA Gly      | TGC Cys      | ACG Thr | 1909 |
| GCT Ala 575  | ATC Ile      | TTT Phe      | GAT Asp      | GTT Val      | AAA Lys 580  | CTT Leu      | GGG Gly      | ATC Ile      | TCA Ser      | GAA Glu 585  | CGT Arg      | TCA Ser      | AAC Asn      | GAA Glu      | TCT Ser 590 | 1957 |
| AAA Lys      | CAG Gln      | TCG Ser      | GGC Gly      | ATA Ile 595  | CCG Pro      | AAA Lys      | GTT Val      | CCA Pro      | GCC Ala 600  | ATT Ile      | CCC Pro      | CGA Arg      | CAT His      | TCA Ser 605  | AAT Asn | 2005 |
| TTC Phe      | ACT Thr      | GGA Gly      | CTT Leu 610  | AAG Lys      | GTT Val      | CTT Leu      | GTC Val      | ATG Met 615  | GAT Asp      | GAG Glu      | AAC Asn      | GGG Gly      | GTA Val 620  | AGT Ser      | AGA Arg | 2053 |
| ATG Met      | GTG Val      | ACG Thr 625  | AAG Lys      | GGA Gly      | CTT Leu      | CTT Leu      | GTA Val 630  | CAC His      | CTT Leu      | GGG Gly      | TGC Cys      | GAA Glu 635  | GTG Val      | ACC Thr      | ACG Thr | 2101 |
| GTG Val      | AGT Ser 640  | TCA Ser      | AAC Asn      | GAG Glu      | GAG Glu      | TGT Cys 645  | CTC Leu      | CGA Arg      | GTT Val      | GTG Val      | TCC Ser 650  | CAT His      | GAG Glu      | CAC His      | AAA Lys | 2149 |
| GTG Val 655  | GTC Val      | TTC Phe      | ATG Met      | GAC Asp      | GTG Val 660  | TGC Cys      | ATG Met      | CCC Pro      | GGG Gly      | GTC Val 665  | GAA Glu      | AAC Asn      | TAC Tyr      | CAA Gln      | ATC Ile 670 | 2197 |
| GCT Ala      | CTC Leu      | CGT Arg      | ATT Ile      | CAC His 675  | GAG Glu      | AAA Lys      | TTC Phe      | ACA Thr      | AAA Lys 680  | CAA Gln      | CGC Arg      | CAC His      | CAA Gln      | CGG Arg 685  | CCA Pro | 2245 |
| CTA Leu      | CTT Leu      | GTG Val      | GCA Ala      | CTC Leu 690  | AGT Ser      | GGT Gly      | AAC Asn      | ACT Thr      | GAC Asp 695  | AAA Lys      | TCC Ser      | ACA Thr      | AAA Lys      | GAG Glu 700  | AAA Lys | 2293 |
| TGC Cys      | ATG Met      | AGC Ser      | TTT Phe 705  | GGT Gly      | CTA Leu      | GAC Asp      | GGT Gly      | GTG Val 710  | TTG Leu      | CTC Leu      | AAA Lys      | CCC Pro      | GTA Val 715  | TCA Ser      | CTA Leu | 2341 |
| GAC Asp      | AAC Asn      | ATA Ile      | AGA Arg      | GAT Asp      | GTT Val      | CTG Leu      | TCT Ser      | GAT Asp      | CTT Leu      | CTC Leu      | GAG Glu      | CCC Pro      | CGG Arg      | GTA Val      | CTG Leu | 2389 |

-continued

```
                720                    725                    730
TAC GAG GGC ATG TAAAGGCGAT GGATGCCCCA TGCCCCAGAG GAGTAATTCC                2441
Tyr Glu Gly Met
735

GCTCCCGCCT TCTTCTCCCG TAAAACATCG GAAGCTGATG TTCTCTGGTT TAATTGTGTA          2501

CATATCAGAG ATTGTCGGAG CGTTTTGGAT GATATCTTAA AACAGAAAGG GAATAACAAA          2561

ATAGAAACTC TAAACCGGTA TGTGTCCGTG GCGATTTCGG TTATAGAGGA ACAAGATGGT          2621

GGTGGTATAA TCATACCATT TCAGATTACA TGTTTGACTA ATGTTGTATC CTTATATATG          2681

TAGTTACATT CTTATAAGAA TTTGGATCGA GTTATGGATG CTTGTTGCGT GCATGTATGA          2741

CATTGATGCA GTATTATGGC GTCAGCTTTG CGCCGCTTAG TAGAAC                        2787
```

( 2 ) INFORMATION FOR SEQ ID NO:7:

( i ) SEQUENCE CHARACTERISTICS:
        ( A ) LENGTH: 738 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Glu Val Cys Asn Cys Ile Glu Pro Gln Trp Pro Ala Asp Glu Leu
 1               5                  10                   15

Leu Met Lys Tyr Gln Tyr Ile Ser Asp Phe Phe Ile Ala Ile Ala Tyr
                20                  25                  30

Phe Ser Ile Pro Leu Glu Leu Ile Tyr Phe Val Lys Lys Ser Ala Val
            35                  40                  45

Phe Pro Tyr Arg Trp Val Leu Val Gln Phe Gly Ala Phe Ile Val Leu
        50                  55                  60

Cys Gly Ala Thr His Leu Ile Asn Leu Trp Thr Phe Thr Thr His Ser
 65                 70                  75                  80

Arg Thr Val Ala Leu Val Met Thr Thr Ala Lys Val Leu Thr Ala Val
                85                  90                  95

Val Ser Cys Ala Thr Thr Leu Met Leu Val His Ile Ile Pro Asp Leu
            100                 105                 110

Leu Ser Val Lys Thr Arg Glu Leu Phe Leu Lys Asn Lys Ala Ala Glu
        115                 120                 125

Leu Asp Arg Glu Met Gly Leu Ile Arg Thr Gln Glu Glu Thr Gly Arg
130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Ala Leu
                165                 170                 175

Glu Glu Cys Ala Leu Trp Met Pro Thr Arg Thr Gly Leu Glu Leu Gln
            180                 185                 190

Leu Ser Tyr Thr Leu Arg His Gln His Pro Val Glu Tyr Thr Val Pro
        195                 200                 205

Ile Gln Leu Pro Val Ile Asn Gln Val Phe Gly Thr Ser Arg Ala Val
210                 215                 220

Lys Ile Ser Pro Asn Ser Pro Val Ala Arg Leu Arg Pro Val Ser Gly
225                 230                 235                 240

Lys Tyr Met Leu Gly Glu Val Val Ala Val Arg Val Pro Leu Leu His
                245                 250                 255

Leu Ser Asn Phe Gln Ile Asn Asp Trp Pro Glu Leu Ser Thr Lys Arg
            260                 265                 270
```

```
Tyr Ala Leu Met Val Leu Met Leu Pro Ser Asp Ser Ala Arg Gln Trp
        275                 280                 285
His Val His Glu Leu Glu Leu Val Glu Val Val Ala Asp Gln Val Ala
    290                 295                 300
Val Ala Leu Ser His Ala Ala Ile Leu Glu Glu Ser Met Arg Ala Arg
305                 310                 315                 320
Asp Leu Leu Met Glu Gln Asn Val Ala Asp Leu Ala Arg Arg Glu
                325                 330                 335
Ala Glu Thr Ala Ile Arg Ala Arg Asn Asp Phe Leu Ala Val Met Asn
            340                 345                 350
His Glu Met Arg Thr Pro Met His Ala Ile Ile Ala Leu Ser Ser Leu
        355                 360                 365
Leu Gln Glu Thr Glu Leu Thr Pro Glu Gln Arg Leu Met Val Glu Thr
    370                 375                 380
Ile Leu Lys Ser Ser Asn Leu Leu Ala Thr Leu Met Asn Asp Val Leu
385                 390                 395                 400
Asp Leu Ser Arg Leu Glu Asp Gly Ser Leu Gln Leu Glu Leu Gly Thr
                405                 410                 415
Phe Asn Leu His Thr Leu Phe Arg Glu Val Leu Asn Leu Ile Lys Pro
            420                 425                 430
Ile Ala Val Val Lys Lys Leu Pro Ile Thr Leu Asn Leu Ala Pro Asp
        435                 440                 445
Leu Pro Glu Phe Val Val Gly Asp Glu Lys Arg Leu Met Gln Ile Ile
    450                 455                 460
Leu Asn Ile Val Gly Asn Ala Val Lys Phe Ser Lys Gln Gly Ser Ile
465                 470                 475                 480
Ser Val Thr Ala Leu Val Thr Lys Ser Asp Thr Arg Ala Ala Asp Phe
                485                 490                 495
Phe Val Val Pro Thr Gly Ser His Phe Tyr Leu Arg Val Lys Val Lys
            500                 505                 510
Asp Ser Gly Ala Gly Ile Asn Pro Gln Asp Ile Pro Lys Ile Phe Thr
        515                 520                 525
Lys Phe Ala Gln Thr Gln Ser Leu Ala Thr Arg Ser Ser Gly Gly Ser
    530                 535                 540
Gly Leu Gly Leu Ala Ile Ser Lys Arg Phe Val Asn Leu Met Glu Gly
545                 550                 555                 560
Asn Ile Trp Ile Glu Ser Asp Gly Leu Gly Lys Gly Cys Thr Ala Ile
                565                 570                 575
Phe Asp Val Lys Leu Gly Ile Ser Glu Arg Ser Asn Glu Ser Lys Gln
            580                 585                 590
Ser Gly Ile Pro Lys Val Pro Ala Ile Pro Arg His Ser Asn Phe Thr
        595                 600                 605
Gly Leu Lys Val Leu Val Met Asp Glu Asn Gly Val Ser Arg Met Val
    610                 615                 620
Thr Lys Gly Leu Leu Val His Leu Gly Cys Glu Val Thr Thr Val Ser
625                 630                 635                 640
Ser Asn Glu Glu Cys Leu Arg Val Val Ser His Glu His Lys Val Val
                645                 650                 655
Phe Met Asp Val Cys Met Pro Gly Val Glu Asn Tyr Gln Ile Ala Leu
            660                 665                 670
Arg Ile His Glu Lys Phe Thr Lys Gln Arg His Gln Arg Pro Leu Leu
        675                 680                 685
Val Ala Leu Ser Gly Asn Thr Asp Lys Ser Thr Lys Glu Lys Cys Met
```

```
                         690                              695                       700
Ser    Phe    Gly    Leu    Asp    Gly    Val    Leu    Leu    Lys    Pro    Val    Ser    Leu    Asp    Asn
705                                710                            715                                  720

Ile    Arg    Asp    Val    Leu    Ser    Asp    Leu    Leu    Glu    Pro    Arg    Val    Leu    Tyr    Glu
                            725                            730                            735

Gly    Met
```

( 2 ) INFORMATION FOR SEQ ID NO:8:

( i ) SEQUENCE CHARACTERISTICS:
        ( A ) LENGTH: 2787 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 188..2401

( x i ) SEQUENCE DESCRIPTION: SEQ ID NO:8:

```
AGTAAGAACG    AAGAAGAAGT    GTTAAACCCA    ACCAATTTTG    ACTTGAAAAA    AAGCTTCAAC              60

GCTCCCCTTT    TCTCCTTCTC    CGTCGCTCTC    CGCCGCGTCC    CAAATCCCCA    ATTCCTCCTC             120

TTCTCCGATC    AATTCTTCCC    AAGTGTGTGT    ATGTGTGAGA    GAGGAACTAT    AGTGTAAAAA             180

ATTCATA    ATG    GAA    GTC    TGC    AAT    TGT    ATT    GAA    CCG    CAA    TGG    CCA    GCG    GAT       229
           Met    Glu    Val    Cys    Asn    Cys    Ile    Glu    Pro    Gln    Trp    Pro    Ala    Asp
            1                    5                                   10

GAA    TTG    TTA    ATG    AAA    TAC    CAA    TAC    ATC    TCC    GAT    TTC    TTC    ATT    GCG    ATT   277
Glu    Leu    Leu    Met    Lys    Tyr    Gln    Tyr    Ile    Ser    Asp    Phe    Phe    Ile    Ala    Ile
15                           20                                    25                                    30

GTG    TAT    TTT    TCG    ATT    CCT    CTT    GAG    TTG    ATT    TAC    TTT    GTG    AAG    AAA    TCA   325
Val    Tyr    Phe    Ser    Ile    Pro    Leu    Glu    Leu    Ile    Tyr    Phe    Val    Lys    Lys    Ser
                           35                                    40                                    45

GCC    GTG    TTT    CCG    TAT    AGA    TGG    GTA    CTT    GTT    CAG    TTT    GGT    GCT    TTT    ATC   373
Ala    Val    Phe    Pro    Tyr    Arg    Trp    Val    Leu    Val    Gln    Phe    Gly    Ala    Phe    Ile
                    50                                    55                                    60

GTT    CTT    TGT    GGA    GCA    ACT    CAT    CTT    ATT    AAC    TTA    TGG    ACT    TTC    ACT    ACG   421
Val    Leu    Cys    Gly    Ala    Thr    His    Leu    Ile    Asn    Leu    Trp    Thr    Phe    Thr    Thr
            65                                    70                                    75

CAT    TCG    AGA    ACC    GTG    GCG    CTT    GTG    ATG    ACT    ACC    GCG    AAG    GTG    TTA    ACC   469
His    Ser    Arg    Thr    Val    Ala    Leu    Val    Met    Thr    Thr    Ala    Lys    Val    Leu    Thr
       80                                    85                                    90

GCT    GTT    GTC    TCG    TGT    GCT    ACT    GCG    TTG    ATG    CTT    GTT    CAT    ATT    ATT    CCT   517
Ala    Val    Val    Ser    Cys    Ala    Thr    Ala    Leu    Met    Leu    Val    His    Ile    Ile    Pro
95                           100                                  105                                  110

GAT    CTT    TTG    AGT    GTT    AAG    ACT    CGG    GAG    CTT    TTC    TTG    AAA    AAT    AAA    GCT   565
Asp    Leu    Leu    Ser    Val    Lys    Thr    Arg    Glu    Leu    Phe    Leu    Lys    Asn    Lys    Ala
                           115                                  120                                  125

GCT    GAG    CTC    GAT    AGA    GAA    ATG    GGA    TTG    ATT    CGA    ACT    CAG    GAA    GAA    ACC   613
Ala    Glu    Leu    Asp    Arg    Glu    Met    Gly    Leu    Ile    Arg    Thr    Gln    Glu    Glu    Thr
                    130                                  135                                  140

GGA    AGG    CAT    GTG    AGA    ATG    TTG    ACT    CAT    GAG    ATT    AGA    AGC    ACT    TTA    GAT   661
Gly    Arg    His    Val    Arg    Met    Leu    Thr    His    Glu    Ile    Arg    Ser    Thr    Leu    Asp
            145                                  150                                  155

AGA    CAT    ACT    ATT    TTA    AAG    ACT    ACA    CTT    GTT    GAG    CTT    GGT    AGG    ACA    TTA   709
Arg    His    Thr    Ile    Leu    Lys    Thr    Thr    Leu    Val    Glu    Leu    Gly    Arg    Thr    Leu
       160                                  165                                  170

GCT    TTG    GAG    GAG    TGT    GCA    TTG    TGG    ATG    CCT    ACT    AGA    ACT    GGG    TTA    GAG   757
Ala    Leu    Glu    Glu    Cys    Ala    Leu    Trp    Met    Pro    Thr    Arg    Thr    Gly    Leu    Glu
175                          180                                  185                                  190
```

| | | | | | | | | | | | | | | | | |
|---|---|---|---|---|---|---|---|---|---|---|---|---|---|---|---|---|
| CTA | CAG | CTT | TCT | TAT | ACA | CTT | CGT | CAT | CAA | CAT | CCC | GTG | GAG | TAT | ACG | 805 |
| Leu | Gln | Leu | Ser | Tyr | Thr | Leu | Arg | His | Gln | His | Pro | Val | Glu | Tyr | Thr | |
| | | | 195 | | | | | 200 | | | | | 205 | | | |
| GTT | CCT | ATT | CAA | TTA | CCG | GTG | ATT | AAC | CAA | GTG | TTT | GGT | ACT | AGT | AGG | 853 |
| Val | Pro | Ile | Gln | Leu | Pro | Val | Ile | Asn | Gln | Val | Phe | Gly | Thr | Ser | Arg | |
| | | | 210 | | | | 215 | | | | | 220 | | | | |
| GCT | GTA | AAA | ATA | TCT | CCT | AAT | TCT | CCT | GTG | GCT | AGG | TTG | AGA | CCT | GTT | 901 |
| Ala | Val | Lys | Ile | Ser | Pro | Asn | Ser | Pro | Val | Ala | Arg | Leu | Arg | Pro | Val | |
| | | 225 | | | | | 230 | | | | | 235 | | | | |
| TCT | GGG | AAA | TAT | ATG | CTA | GGG | GAG | GTG | GTC | GCT | GTG | AGG | GTT | CCG | CTT | 949 |
| Ser | Gly | Lys | Tyr | Met | Leu | Gly | Glu | Val | Val | Ala | Val | Arg | Val | Pro | Leu | |
| | 240 | | | | | 245 | | | | | 250 | | | | | |
| CTC | CAC | CTT | TCT | AAT | TTT | CAG | ATT | AAT | GAC | TGG | CCT | GAG | CTT | TCA | ACA | 997 |
| Leu | His | Leu | Ser | Asn | Phe | Gln | Ile | Asn | Asp | Trp | Pro | Glu | Leu | Ser | Thr | |
| 255 | | | | | 260 | | | | | 265 | | | | | 270 | |
| AAG | AGA | TAT | GCT | TTG | ATG | GTT | TTG | ATG | CTT | CCT | TCA | GAT | AGT | GCA | AGG | 1045 |
| Lys | Arg | Tyr | Ala | Leu | Met | Val | Leu | Met | Leu | Pro | Ser | Asp | Ser | Ala | Arg | |
| | | | | 275 | | | | | 280 | | | | | 285 | | |
| CAA | TGG | CAT | GTC | CAT | GAG | TTG | GAA | CTC | GTT | GAA | GTC | GTC | GCT | GAT | CAG | 1093 |
| Gln | Trp | His | Val | His | Glu | Leu | Glu | Leu | Val | Glu | Val | Val | Ala | Asp | Gln | |
| | | | 290 | | | | | 295 | | | | | 300 | | | |
| GTG | GCT | GTA | GCT | CTC | TCA | CAT | GCT | GCG | ATC | CTA | GAA | GAG | TCG | ATG | CGA | 1141 |
| Val | Ala | Val | Ala | Leu | Ser | His | Ala | Ala | Ile | Leu | Glu | Glu | Ser | Met | Arg | |
| | | 305 | | | | | 310 | | | | | 315 | | | | |
| GCT | AGG | GAC | CTT | CTC | ATG | GAG | CAG | AAT | GTT | GCT | CTT | GAT | CTA | GCT | AGA | 1189 |
| Ala | Arg | Asp | Leu | Leu | Met | Glu | Gln | Asn | Val | Ala | Leu | Asp | Leu | Ala | Arg | |
| | 320 | | | | | 325 | | | | | 330 | | | | | |
| CGA | GAA | GCA | GAA | ACA | GCA | ATC | CGT | GCC | CGC | AAT | GAT | TTC | CTA | GCG | GTT | 1237 |
| Arg | Glu | Ala | Glu | Thr | Ala | Ile | Arg | Ala | Arg | Asn | Asp | Phe | Leu | Ala | Val | |
| 335 | | | | | 340 | | | | | 345 | | | | | 350 | |
| ATG | AAC | CAT | GAA | ATG | CGA | ACA | CCG | ATG | CAT | GCG | ATT | ATT | GCA | CTC | TCT | 1285 |
| Met | Asn | His | Glu | Met | Arg | Thr | Pro | Met | His | Ala | Ile | Ile | Ala | Leu | Ser | |
| | | | | 355 | | | | | 360 | | | | | 365 | | |
| TCC | TTA | CTC | CAA | GAA | ACG | GAA | CTA | ACC | CCT | GAA | CAA | AGA | CTG | ATG | GTG | 1333 |
| Ser | Leu | Leu | Gln | Glu | Thr | Glu | Leu | Thr | Pro | Glu | Gln | Arg | Leu | Met | Val | |
| | | | 370 | | | | | 375 | | | | | 380 | | | |
| GAA | ACA | ATA | CTT | AAA | AGT | AGT | AAC | CTT | TTG | GCA | ACT | TTG | ATG | AAT | GAT | 1381 |
| Glu | Thr | Ile | Leu | Lys | Ser | Ser | Asn | Leu | Leu | Ala | Thr | Leu | Met | Asn | Asp | |
| | | 385 | | | | | 390 | | | | | 395 | | | | |
| GTC | TTA | GAT | CTT | TCA | AGG | TTA | GAA | GAT | GGA | AGT | CTT | CAA | CTT | GAA | CTT | 1429 |
| Val | Leu | Asp | Leu | Ser | Arg | Leu | Glu | Asp | Gly | Ser | Leu | Gln | Leu | Glu | Leu | |
| | 400 | | | | | 405 | | | | | 410 | | | | | |
| GGG | ACA | TTC | AAT | CTT | CAT | ACA | TTA | TTT | AGA | GAG | GTC | CTC | AAT | CTG | ATA | 1477 |
| Gly | Thr | Phe | Asn | Leu | His | Thr | Leu | Phe | Arg | Glu | Val | Leu | Asn | Leu | Ile | |
| 415 | | | | | 420 | | | | | 425 | | | | | 430 | |
| AAG | CCT | ATA | GCG | GTT | GTT | AAG | AAA | TTA | CCC | ATC | ACA | CTA | AAT | CTT | GCA | 1525 |
| Lys | Pro | Ile | Ala | Val | Val | Lys | Lys | Leu | Pro | Ile | Thr | Leu | Asn | Leu | Ala | |
| | | | | 435 | | | | | 440 | | | | | 445 | | |
| CCA | GAT | TTG | CCA | GAA | TTT | GTT | GTT | GGG | GAT | GAG | AAA | CGG | CTA | ATG | CAG | 1573 |
| Pro | Asp | Leu | Pro | Glu | Phe | Val | Val | Gly | Asp | Glu | Lys | Arg | Leu | Met | Gln | |
| | | | 450 | | | | | 455 | | | | | 460 | | | |
| ATA | ATA | TTA | AAT | ATA | GTT | GGT | AAT | GCT | GTG | AAA | TTC | TCC | AAA | CAA | GGT | 1621 |
| Ile | Ile | Leu | Asn | Ile | Val | Gly | Asn | Ala | Val | Lys | Phe | Ser | Lys | Gln | Gly | |
| | | 465 | | | | | 470 | | | | | 475 | | | | |
| AGT | ATC | TCC | GTA | ACC | GCT | CTT | GTC | ACC | AAG | TCA | GAC | ACA | CGA | GCT | GCT | 1669 |
| Ser | Ile | Ser | Val | Thr | Ala | Leu | Val | Thr | Lys | Ser | Asp | Thr | Arg | Ala | Ala | |
| | 480 | | | | | 485 | | | | | 490 | | | | | |
| GAC | TTT | TTT | GTC | GTG | CCA | ACT | GGG | AGT | CAT | TTC | TAC | TTG | AGA | GTG | AAG | 1717 |
| Asp | Phe | Phe | Val | Val | Pro | Thr | Gly | Ser | His | Phe | Tyr | Leu | Arg | Val | Lys | |
| 495 | | | | | 500 | | | | | 505 | | | | | 510 | |

-continued

```
GTA AAA GAC TCT GGA GCA GGA ATA AAT CCT CAA GAC ATT CCA AAG ATT        1765
Val Lys Asp Ser Gly Ala Gly Ile Asn Pro Gln Asp Ile Pro Lys Ile
            515                 520                 525

TTC ACT AAA TTT GCT CAA ACA CAA TCT TTA GCG ACG AGA AGC TCG GGT        1813
Phe Thr Lys Phe Ala Gln Thr Gln Ser Leu Ala Thr Arg Ser Ser Gly
        530                 535                 540

GGT AGT GGG CTT GGC CTC GCC ATC TCC AAG AGG TTT GTG AAT CTG ATG        1861
Gly Ser Gly Leu Gly Leu Ala Ile Ser Lys Arg Phe Val Asn Leu Met
        545                 550                 555

GAG GGT AAC ATT TGG ATT GAG AGC GAT GGT CTT GGA AAA GGA TGC ACG        1909
Glu Gly Asn Ile Trp Ile Glu Ser Asp Gly Leu Gly Lys Gly Cys Thr
        560                 565                 570

GCT ATC TTT GAT GTT AAA CTT GGG ATC TCA GAA CGT TCA AAC GAA TCT        1957
Ala Ile Phe Asp Val Lys Leu Gly Ile Ser Glu Arg Ser Asn Glu Ser
575                 580                 585                 590

AAA CAG TCG GGC ATA CCG AAA GTT CCA GCC ATT CCC CGA CAT TCA AAT        2005
Lys Gln Ser Gly Ile Pro Lys Val Pro Ala Ile Pro Arg His Ser Asn
                595                 600                 605

TTC ACT GGA CTT AAG GTT CTT GTC ATG GAT GAG AAC GGG GTA AGT AGA        2053
Phe Thr Gly Leu Lys Val Leu Val Met Asp Glu Asn Gly Val Ser Arg
            610                 615                 620

ATG GTG ACG AAG GGA CTT CTT GTA CAC CTT GGG TGC GAA GTG ACC ACG        2101
Met Val Thr Lys Gly Leu Leu Val His Leu Gly Cys Glu Val Thr Thr
        625                 630                 635

GTG AGT TCA AAC GAG GAG TGT CTC CGA GTT GTG TCC CAT GAG CAC AAA        2149
Val Ser Ser Asn Glu Glu Cys Leu Arg Val Val Ser His Glu His Lys
        640                 645                 650

GTG GTC TTC ATG GAC GTG TGC ATG CCC GGG GTC GAA AAC TAC CAA ATC        2197
Val Val Phe Met Asp Val Cys Met Pro Gly Val Glu Asn Tyr Gln Ile
655                 660                 665                 670

GCT CTC CGT ATT CAC GAG AAA TTC ACA AAA CAA CGC CAC CAA CGG CCA        2245
Ala Leu Arg Ile His Glu Lys Phe Thr Lys Gln Arg His Gln Arg Pro
                675                 680                 685

CTA CTT GTG GCA CTC AGT GGT AAC ACT GAC AAA TCC ACA AAA GAG AAA        2293
Leu Leu Val Ala Leu Ser Gly Asn Thr Asp Lys Ser Thr Lys Glu Lys
            690                 695                 700

TGC ATG AGC TTT GGT CTA GAC GGT GTG TTG CTC AAA CCC GTA TCA CTA        2341
Cys Met Ser Phe Gly Leu Asp Gly Val Leu Leu Lys Pro Val Ser Leu
        705                 710                 715

GAC AAC ATA AGA GAT GTT CTG TCT GAT CTT CTC GAG CCC CGG GTA CTG        2389
Asp Asn Ile Arg Asp Val Leu Ser Asp Leu Leu Glu Pro Arg Val Leu
        720                 725                 730

TAC GAG GGC ATG TAAAGGCGAT GGATGCCCCA TGCCCCAGAG GAGTAATTCC           2441
Tyr Glu Gly Met
735

GCTCCCGCCT TCTTCTCCCG TAAAACATCG GAAGCTGATG TTCTCTGGTT TAATTGTGTA     2501

CATATCAGAG ATTGTCGGAG CGTTTTGGAT GATATCTTAA AACAGAAAGG GAATAACAAA     2561

ATAGAAACTC TAAACCGGTA TGTGTCCGTG GCGATTTCGG TTATAGAGGA ACAAGATGGT     2621

GGTGGTATAA TCATACCATT TCAGATTACA TGTTTGACTA ATGTTGTATC CTTATATATG     2681

TAGTTACATT CTTATAAGAA TTTGGATCGA GTTATGGATG CTTGTTGCGT GCATGTATGA     2741

CATTGATGCA GTATTATGGC GTCAGCTTTG CGCCGCTTAG TAGAAC                    2787
```

( 2 ) INFORMATION FOR SEQ ID NO:9:

( i ) SEQUENCE CHARACTERISTICS:
        ( A ) LENGTH: 738 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Met | Glu | Val | Cys | Asn | Cys | Ile | Glu | Pro | Gln | Trp | Pro | Ala | Asp | Glu | Leu |
|---|---|---|---|---|---|---|---|---|---|---|---|---|---|---|---|
| 1 | | | | 5 | | | | | 10 | | | | | | 15 |
| Leu | Met | Lys | Tyr | Gln | Tyr | Ile | Ser | Asp | Phe | Phe | Ile | Ala | Ile | Val | Tyr |
| | | | 20 | | | | | 25 | | | | | 30 | | |
| Phe | Ser | Ile | Pro | Leu | Glu | Leu | Ile | Tyr | Phe | Val | Lys | Lys | Ser | Ala | Val |
| | | | 35 | | | | 40 | | | | | 45 | | | |
| Phe | Pro | Tyr | Arg | Trp | Val | Leu | Val | Gln | Phe | Gly | Ala | Phe | Ile | Val | Leu |
| | 50 | | | | | 55 | | | | | | 60 | | | |
| Cys | Gly | Ala | Thr | His | Leu | Ile | Asn | Leu | Trp | Thr | Phe | Thr | Thr | His | Ser |
| 65 | | | | | 70 | | | | | 75 | | | | | 80 |
| Arg | Thr | Val | Ala | Leu | Val | Met | Thr | Thr | Ala | Lys | Val | Leu | Thr | Ala | Val |
| | | | | 85 | | | | | 90 | | | | | 95 | |
| Val | Ser | Cys | Ala | Thr | Ala | Leu | Met | Leu | Val | His | Ile | Ile | Pro | Asp | Leu |
| | | | 100 | | | | | 105 | | | | | 110 | | |
| Leu | Ser | Val | Lys | Thr | Arg | Glu | Leu | Phe | Leu | Lys | Asn | Lys | Ala | Ala | Glu |
| | | | 115 | | | | | 120 | | | | | 125 | | |
| Leu | Asp | Arg | Glu | Met | Gly | Leu | Ile | Arg | Thr | Gln | Glu | Glu | Thr | Gly | Arg |
| | 130 | | | | | 135 | | | | | 140 | | | | |
| His | Val | Arg | Met | Leu | Thr | His | Glu | Ile | Arg | Ser | Thr | Leu | Asp | Arg | His |
| 145 | | | | | 150 | | | | | 155 | | | | | 160 |
| Thr | Ile | Leu | Lys | Thr | Thr | Leu | Val | Glu | Leu | Gly | Arg | Thr | Leu | Ala | Leu |
| | | | | 165 | | | | | 170 | | | | | 175 | |
| Glu | Glu | Cys | Ala | Leu | Trp | Met | Pro | Thr | Arg | Thr | Gly | Leu | Glu | Leu | Gln |
| | | | 180 | | | | | 185 | | | | | 190 | | |
| Leu | Ser | Tyr | Thr | Leu | Arg | His | Gln | His | Pro | Val | Glu | Tyr | Thr | Val | Pro |
| | | | 195 | | | | | 200 | | | | | 205 | | |
| Ile | Gln | Leu | Pro | Val | Ile | Asn | Gln | Val | Phe | Gly | Thr | Ser | Arg | Ala | Val |
| | | | 210 | | | | | 215 | | | | | 220 | | |
| Lys | Ile | Ser | Pro | Asn | Ser | Pro | Val | Ala | Arg | Leu | Arg | Pro | Val | Ser | Gly |
| 225 | | | | | 230 | | | | | 235 | | | | | 240 |
| Lys | Tyr | Met | Leu | Gly | Glu | Val | Val | Ala | Val | Arg | Val | Pro | Leu | Leu | His |
| | | | | 245 | | | | | 250 | | | | | 255 | |
| Leu | Ser | Asn | Phe | Gln | Ile | Asn | Asp | Trp | Pro | Glu | Leu | Ser | Thr | Lys | Arg |
| | | | 260 | | | | | 265 | | | | | 270 | | |
| Tyr | Ala | Leu | Met | Val | Leu | Met | Leu | Pro | Ser | Asp | Ser | Arg | Gln | Trp | |
| | | | 275 | | | | | 280 | | | | | 285 | | |
| His | Val | His | Glu | Leu | Glu | Leu | Val | Glu | Val | Val | Ala | Asp | Gln | Val | Ala |
| | 290 | | | | | 295 | | | | | | 300 | | | |
| Val | Ala | Leu | Ser | His | Ala | Ala | Ile | Leu | Glu | Glu | Ser | Met | Arg | Ala | Arg |
| 305 | | | | | 310 | | | | | 315 | | | | | 320 |
| Asp | Leu | Leu | Met | Glu | Gln | Asn | Val | Ala | Leu | Asp | Leu | Ala | Arg | Arg | Glu |
| | | | | 325 | | | | | 330 | | | | | 335 | |
| Ala | Glu | Thr | Ala | Ile | Arg | Ala | Arg | Asn | Asp | Phe | Leu | Ala | Val | Met | Asn |
| | | | 340 | | | | 345 | | | | | 350 | | | |
| His | Glu | Met | Arg | Thr | Pro | Met | His | Ala | Ile | Ile | Ala | Leu | Ser | Ser | Leu |
| | | | 355 | | | | | 360 | | | | | 365 | | |
| Leu | Gln | Glu | Thr | Glu | Leu | Thr | Pro | Glu | Gln | Arg | Leu | Met | Val | Glu | Thr |
| | | 370 | | | | | 375 | | | | | 380 | | | |
| Ile | Leu | Lys | Ser | Ser | Asn | Leu | Leu | Ala | Thr | Leu | Met | Asn | Asp | Val | Leu |
| 385 | | | | | 390 | | | | | 395 | | | | | 400 |

| | | | | | | | | | | | | | |
|---|---|---|---|---|---|---|---|---|---|---|---|---|---|
|Asp|Leu|Ser|Arg|Leu|Glu|Asp|Gly|Ser|Leu|Gln|Leu|Glu|Leu|Gly|Thr|
| | | | |405| | | |410| | | | |415| | |
|Phe|Asn|Leu|His|Thr|Leu|Phe|Arg|Glu|Val|Leu|Asn|Leu|Ile|Lys|Pro|
| | | | |420| | | |425| | | | |430| | |
|Ile|Ala|Val|Val|Lys|Lys|Leu|Pro|Ile|Thr|Leu|Asn|Leu|Ala|Pro|Asp|
| | | |435| | | |440| | | | |445| | | |
|Leu|Pro|Glu|Phe|Val|Val|Gly|Asp|Glu|Lys|Arg|Leu|Met|Gln|Ile|Ile|
| |450| | | | |455| | | | |460| | | | |
|Leu|Asn|Ile|Val|Gly|Asn|Ala|Val|Lys|Phe|Ser|Lys|Gln|Gly|Ser|Ile|
|465| | | | |470| | | | |475| | | | |480|
|Ser|Val|Thr|Ala|Leu|Val|Thr|Lys|Ser|Asp|Thr|Arg|Ala|Ala|Asp|Phe|
| | | | |485| | | |490| | | | |495| | |
|Phe|Val|Val|Pro|Thr|Gly|Ser|His|Phe|Tyr|Leu|Arg|Val|Lys|Val|Lys|
| | | |500| | | |505| | | | |510| | | |
|Asp|Ser|Gly|Ala|Gly|Ile|Asn|Pro|Gln|Asp|Ile|Pro|Lys|Ile|Phe|Thr|
| | |515| | | |520| | | | |525| | | | |
|Lys|Phe|Ala|Gln|Thr|Gln|Ser|Leu|Ala|Thr|Arg|Ser|Ser|Gly|Gly|Ser|
| |530| | | |535| | | | |540| | | | | |
|Gly|Leu|Gly|Leu|Ala|Ile|Ser|Lys|Arg|Phe|Val|Asn|Leu|Met|Glu|Gly|
|545| | | | |550| | | | |555| | | | |560|
|Asn|Ile|Trp|Ile|Glu|Ser|Asp|Gly|Leu|Gly|Lys|Gly|Cys|Thr|Ala|Ile|
| | | | |565| | | |570| | | | |575| | |
|Phe|Asp|Val|Lys|Leu|Gly|Ile|Ser|Glu|Arg|Ser|Asn|Glu|Ser|Lys|Gln|
| | | |580| | | |585| | | | |590| | | |
|Ser|Gly|Ile|Pro|Lys|Val|Pro|Ala|Ile|Pro|Arg|His|Ser|Asn|Phe|Thr|
| | |595| | | |600| | | | |605| | | | |
|Gly|Leu|Lys|Val|Leu|Val|Met|Asp|Glu|Asn|Gly|Val|Ser|Arg|Met|Val|
| |610| | | | |615| | | | |620| | | | |
|Thr|Lys|Gly|Leu|Leu|Val|His|Leu|Gly|Cys|Glu|Val|Thr|Thr|Val|Ser|
|625| | | | |630| | | | |635| | | | |640|
|Ser|Asn|Glu|Glu|Cys|Leu|Arg|Val|Val|Ser|His|Glu|His|Lys|Val|Val|
| | | | |645| | | |650| | | | |655| | |
|Phe|Met|Asp|Val|Cys|Met|Pro|Gly|Val|Glu|Asn|Tyr|Gln|Ile|Ala|Leu|
| | | |660| | | |665| | | | |670| | | |
|Arg|Ile|His|Glu|Lys|Phe|Thr|Lys|Gln|Arg|His|Gln|Arg|Pro|Leu|Leu|
| | |675| | | |680| | | | |685| | | | |
|Val|Ala|Leu|Ser|Gly|Asn|Thr|Asp|Lys|Ser|Thr|Lys|Glu|Lys|Cys|Met|
| |690| | | | |695| | | | |700| | | | |
|Ser|Phe|Gly|Leu|Asp|Gly|Val|Leu|Leu|Lys|Pro|Val|Ser|Leu|Asp|Asn|
|705| | | | |710| | | | |715| | | | |720|
|Ile|Arg|Asp|Val|Leu|Ser|Asp|Leu|Leu|Glu|Pro|Arg|Val|Leu|Tyr|Glu|
| | | | |725| | | |730| | | | |735| | |
|Gly|Met| | | | | | | | | | | | | | |

( 2 ) INFORMATION FOR SEQ ID NO:10:

( i ) SEQUENCE CHARACTERISTICS:
        ( A ) LENGTH: 2787 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 188..2401

( x i ) SEQUENCE DESCRIPTION: SEQ ID NO:10:

```
AGTAAGAACG AAGAAGAAGT GTTAAACCCA ACCAATTTTG ACTTGAAAAA AAGCTTCAAC       60

GCTCCCCTTT TCTCCTTCTC CGTCGCTCTC CGCCGCGTCC CAAATCCCCA ATTCCTCCTC      120

TTCTCCGATC AATTCTTCCC AAGTGTGTGT ATGTGTGAGA GAGGAACTAT AGTGTAAAAA      180
```

| ATTCATA | ATG | GAA | GTC | TGC | AAT | TGT | ATT | GAA | CCG | CAA | TGG | CCA | GCG | GAT | 229 |
|---|---|---|---|---|---|---|---|---|---|---|---|---|---|---|---|
| | Met | Glu | Val | Cys | Asn | Cys | Ile | Glu | Pro | Gln | Trp | Pro | Ala | Asp | |
| | 1 | | | | 5 | | | | | 10 | | | | | |

| GAA | TTG | TTA | ATG | AAA | TAC | CAA | TAC | ATC | TCC | GAT | TTC | TTC | ATT | GCG | ATT | 277 |
|---|---|---|---|---|---|---|---|---|---|---|---|---|---|---|---|---|
| Glu | Leu | Leu | Met | Lys | Tyr | Gln | Tyr | Ile | Ser | Asp | Phe | Phe | Ile | Ala | Ile | |
| 15 | | | | 20 | | | | | 25 | | | | | | 30 | |

| GCG | TAT | TTT | TCG | ATT | CCT | CTT | GAG | TTG | ATT | TAC | TTT | GTG | AAG | AAA | TCA | 325 |
|---|---|---|---|---|---|---|---|---|---|---|---|---|---|---|---|---|
| Ala | Tyr | Phe | Ser | Ile | Pro | Leu | Glu | Leu | Ile | Tyr | Phe | Val | Lys | Lys | Ser | |
| | | | | 35 | | | | | 40 | | | | | 45 | | |

| GCC | GTG | TTT | CCG | TAT | AGA | TGG | GTA | CTT | GTT | CAG | TTT | GGT | GCT | TTT | TTC | 373 |
|---|---|---|---|---|---|---|---|---|---|---|---|---|---|---|---|---|
| Ala | Val | Phe | Pro | Tyr | Arg | Trp | Val | Leu | Val | Gln | Phe | Gly | Ala | Phe | Phe | |
| | | | 50 | | | | | 55 | | | | | 60 | | | |

| GTT | CTT | TGT | GGA | GCA | ACT | CAT | CTT | ATT | AAC | TTA | TGG | ACT | TTC | ACT | ACG | 421 |
|---|---|---|---|---|---|---|---|---|---|---|---|---|---|---|---|---|
| Val | Leu | Cys | Gly | Ala | Thr | His | Leu | Ile | Asn | Leu | Trp | Thr | Phe | Thr | Thr | |
| 65 | | | | | 70 | | | | | 75 | | | | | | |

| CAT | TCG | AGA | ACC | GTG | GCG | CTT | GTG | ATG | ACT | ACC | GCG | AAG | GTG | TTA | ACC | 469 |
|---|---|---|---|---|---|---|---|---|---|---|---|---|---|---|---|---|
| His | Ser | Arg | Thr | Val | Ala | Leu | Val | Met | Thr | Thr | Ala | Lys | Val | Leu | Thr | |
| | 80 | | | | | 85 | | | | | 90 | | | | | |

| GCT | GTT | GTC | TCG | TGT | GCT | ACT | GCG | TTG | ATG | CTT | GTT | CAT | ATT | ATT | CCT | 517 |
|---|---|---|---|---|---|---|---|---|---|---|---|---|---|---|---|---|
| Ala | Val | Val | Ser | Cys | Ala | Thr | Ala | Leu | Met | Leu | Val | His | Ile | Ile | Pro | |
| 95 | | | | | 100 | | | | | 105 | | | | | 110 | |

| GAT | CTT | TTG | AGT | GTT | AAG | ACT | CGG | GAG | CTT | TTC | TTG | AAA | AAT | AAA | GCT | 565 |
|---|---|---|---|---|---|---|---|---|---|---|---|---|---|---|---|---|
| Asp | Leu | Leu | Ser | Val | Lys | Thr | Arg | Glu | Leu | Phe | Leu | Lys | Asn | Lys | Ala | |
| | | | | 115 | | | | | 120 | | | | | 125 | | |

| GCT | GAG | CTC | GAT | AGA | GAA | ATG | GGA | TTG | ATT | CGA | ACT | CAG | GAA | GAA | ACC | 613 |
|---|---|---|---|---|---|---|---|---|---|---|---|---|---|---|---|---|
| Ala | Glu | Leu | Asp | Arg | Glu | Met | Gly | Leu | Ile | Arg | Thr | Gln | Glu | Glu | Thr | |
| | | | 130 | | | | | 135 | | | | | 140 | | | |

| GGA | AGG | CAT | GTG | AGA | ATG | TTG | ACT | CAT | GAG | ATT | AGA | AGC | ACT | TTA | GAT | 661 |
|---|---|---|---|---|---|---|---|---|---|---|---|---|---|---|---|---|
| Gly | Arg | His | Val | Arg | Met | Leu | Thr | His | Glu | Ile | Arg | Ser | Thr | Leu | Asp | |
| | | 145 | | | | | 150 | | | | | 155 | | | | |

| AGA | CAT | ACT | ATT | TTA | AAG | ACT | ACA | CTT | GTT | GAG | CTT | GGT | AGG | ACA | TTA | 709 |
|---|---|---|---|---|---|---|---|---|---|---|---|---|---|---|---|---|
| Arg | His | Thr | Ile | Leu | Lys | Thr | Thr | Leu | Val | Glu | Leu | Gly | Arg | Thr | Leu | |
| | 160 | | | | | 165 | | | | | 170 | | | | | |

| GCT | TTG | GAG | GAG | TGT | GCA | TTG | TGG | ATG | CCT | ACT | AGA | ACT | GGG | TTA | GAG | 757 |
|---|---|---|---|---|---|---|---|---|---|---|---|---|---|---|---|---|
| Ala | Leu | Glu | Glu | Cys | Ala | Leu | Trp | Met | Pro | Thr | Arg | Thr | Gly | Leu | Glu | |
| 175 | | | | | 180 | | | | | 185 | | | | | 190 | |

| CTA | CAG | CTT | TCT | TAT | ACA | CTT | CGT | CAT | CAA | CAT | CCC | GTG | GAG | TAT | ACG | 805 |
|---|---|---|---|---|---|---|---|---|---|---|---|---|---|---|---|---|
| Leu | Gln | Leu | Ser | Tyr | Thr | Leu | Arg | His | Gln | His | Pro | Val | Glu | Tyr | Thr | |
| | | | | 195 | | | | | 200 | | | | | 205 | | |

| GTT | CCT | ATT | CAA | TTA | CCG | GTG | ATT | AAC | CAA | GTG | TTT | GGT | ACT | AGT | AGG | 853 |
|---|---|---|---|---|---|---|---|---|---|---|---|---|---|---|---|---|
| Val | Pro | Ile | Gln | Leu | Pro | Val | Ile | Asn | Gln | Val | Phe | Gly | Thr | Ser | Arg | |
| | | | | 210 | | | | | 215 | | | | | 220 | | |

| GCT | GTA | AAA | ATA | TCT | CCT | AAT | TCT | CCT | GTG | GCT | AGG | TTG | AGA | CCT | GTT | 901 |
|---|---|---|---|---|---|---|---|---|---|---|---|---|---|---|---|---|
| Ala | Val | Lys | Ile | Ser | Pro | Asn | Ser | Pro | Val | Ala | Arg | Leu | Arg | Pro | Val | |
| | | 225 | | | | | 230 | | | | | 235 | | | | |

| TCT | GGG | AAA | TAT | ATG | CTA | GGG | GAG | GTG | GTC | GCT | GTG | AGG | GTT | CCG | CTT | 949 |
|---|---|---|---|---|---|---|---|---|---|---|---|---|---|---|---|---|
| Ser | Gly | Lys | Tyr | Met | Leu | Gly | Glu | Val | Val | Ala | Val | Arg | Val | Pro | Leu | |
| | 240 | | | | | 245 | | | | | 250 | | | | | |

| CTC | CAC | CTT | TCT | AAT | TTT | CAG | ATT | AAT | GAC | TGG | CCT | GAG | CTT | TCA | ACA | 997 |
|---|---|---|---|---|---|---|---|---|---|---|---|---|---|---|---|---|
| Leu | His | Leu | Ser | Asn | Phe | Gln | Ile | Asn | Asp | Trp | Pro | Glu | Leu | Ser | Thr | |
| 255 | | | | | 260 | | | | | 265 | | | | | 270 | |

| AAG | AGA | TAT | GCT | TTG | ATG | GTT | TTG | ATG | CTT | CCT | TCA | GAT | AGT | GCA | AGG | 1045 |
|---|---|---|---|---|---|---|---|---|---|---|---|---|---|---|---|---|
| Lys | Arg | Tyr | Ala | Leu | Met | Val | Leu | Met | Leu | Pro | Ser | Asp | Ser | Ala | Arg | |
| | | | | 275 | | | | | 280 | | | | | 285 | | |

| | | | | | | | | | | | | | | | | |
|---|---|---|---|---|---|---|---|---|---|---|---|---|---|---|---|---|
| CAA | TGG | CAT | GTC | CAT | GAG | TTG | GAA | CTC | GTT | GAA | GTC | GTC | GCT | GAT | CAG | 1093 |
| Gln | Trp | His | Val | His | Glu | Leu | Glu | Leu | Val | Glu | Val | Val | Ala | Asp | Gln | |
| | | | 290 | | | | 295 | | | | | 300 | | | | |
| GTG | GCT | GTA | GCT | CTC | TCA | CAT | GCT | GCG | ATC | CTA | GAA | GAG | TCG | ATG | CGA | 1141 |
| Val | Ala | Val | Ala | Leu | Ser | His | Ala | Ala | Ile | Leu | Glu | Glu | Ser | Met | Arg | |
| | | 305 | | | | | 310 | | | | | 315 | | | | |
| GCT | AGG | GAC | CTT | CTC | ATG | GAG | CAG | AAT | GTT | GCT | CTT | GAT | CTA | GCT | AGA | 1189 |
| Ala | Arg | Asp | Leu | Leu | Met | Glu | Gln | Asn | Val | Ala | Leu | Asp | Leu | Ala | Arg | |
| | 320 | | | | | 325 | | | | | 330 | | | | | |
| CGA | GAA | GCA | GAA | ACA | GCA | ATC | CGT | GCC | CGC | AAT | GAT | TTC | CTA | GCG | GTT | 1237 |
| Arg | Glu | Ala | Glu | Thr | Ala | Ile | Arg | Ala | Arg | Asn | Asp | Phe | Leu | Ala | Val | |
| 335 | | | | | 340 | | | | | 345 | | | | | 350 | |
| ATG | AAC | CAT | GAA | ATG | CGA | ACA | CCG | ATG | CAT | GCG | ATT | ATT | GCA | CTC | TCT | 1285 |
| Met | Asn | His | Glu | Met | Arg | Thr | Pro | Met | His | Ala | Ile | Ile | Ala | Leu | Ser | |
| | | | | 355 | | | | | 360 | | | | | 365 | | |
| TCC | TTA | CTC | CAA | GAA | ACG | GAA | CTA | ACC | CCT | GAA | CAA | AGA | CTG | ATG | GTG | 1333 |
| Ser | Leu | Leu | Gln | Glu | Thr | Glu | Leu | Thr | Pro | Glu | Gln | Arg | Leu | Met | Val | |
| | | | 370 | | | | 375 | | | | | 380 | | | | |
| GAA | ACA | ATA | CTT | AAA | AGT | AGT | AAC | CTT | TTG | GCA | ACT | TTG | ATG | AAT | GAT | 1381 |
| Glu | Thr | Ile | Leu | Lys | Ser | Ser | Asn | Leu | Leu | Ala | Thr | Leu | Met | Asn | Asp | |
| | | 385 | | | | | 390 | | | | | 395 | | | | |
| GTC | TTA | GAT | CTT | TCA | AGG | TTA | GAA | GAT | GGA | AGT | CTT | CAA | CTT | GAA | CTT | 1429 |
| Val | Leu | Asp | Leu | Ser | Arg | Leu | Glu | Asp | Gly | Ser | Leu | Gln | Leu | Glu | Leu | |
| | 400 | | | | | 405 | | | | | 410 | | | | | |
| GGG | ACA | TTC | AAT | CTT | CAT | ACA | TTA | TTT | AGA | GAG | GTC | CTC | AAT | CTG | ATA | 1477 |
| Gly | Thr | Phe | Asn | Leu | His | Thr | Leu | Phe | Arg | Glu | Val | Leu | Asn | Leu | Ile | |
| 415 | | | | | 420 | | | | | 425 | | | | | 430 | |
| AAG | CCT | ATA | GCG | GTT | GTT | AAG | AAA | TTA | CCC | ATC | ACA | CTA | AAT | CTT | GCA | 1525 |
| Lys | Pro | Ile | Ala | Val | Val | Lys | Lys | Leu | Pro | Ile | Thr | Leu | Asn | Leu | Ala | |
| | | | | 435 | | | | 440 | | | | | 445 | | | |
| CCA | GAT | TTG | CCA | GAA | TTT | GTT | GTT | GGG | GAT | GAG | AAA | CGG | CTA | ATG | CAG | 1573 |
| Pro | Asp | Leu | Pro | Glu | Phe | Val | Val | Gly | Asp | Glu | Lys | Arg | Leu | Met | Gln | |
| | | | 450 | | | | | 455 | | | | | 460 | | | |
| ATA | ATA | TTA | AAT | ATA | GTT | GGT | AAT | GCT | GTG | AAA | TTC | TCC | AAA | CAA | GGT | 1621 |
| Ile | Ile | Leu | Asn | Ile | Val | Gly | Asn | Ala | Val | Lys | Phe | Ser | Lys | Gln | Gly | |
| | | | 465 | | | | 470 | | | | | 475 | | | | |
| AGT | ATC | TCC | GTA | ACC | GCT | CTT | GTC | ACC | AAG | TCA | GAC | ACA | CGA | GCT | GCT | 1669 |
| Ser | Ile | Ser | Val | Thr | Ala | Leu | Val | Thr | Lys | Ser | Asp | Thr | Arg | Ala | Ala | |
| | | 480 | | | | | 485 | | | | | 490 | | | | |
| GAC | TTT | TTT | GTC | GTG | CCA | ACT | GGG | AGT | CAT | TTC | TAC | TTG | AGA | GTG | AAG | 1717 |
| Asp | Phe | Phe | Val | Val | Pro | Thr | Gly | Ser | His | Phe | Tyr | Leu | Arg | Val | Lys | |
| 495 | | | | | 500 | | | | | 505 | | | | | 510 | |
| GTA | AAA | GAC | TCT | GGA | GCA | GGA | ATA | AAT | CCT | CAA | GAC | ATT | CCA | AAG | ATT | 1765 |
| Val | Lys | Asp | Ser | Gly | Ala | Gly | Ile | Asn | Pro | Gln | Asp | Ile | Pro | Lys | Ile | |
| | | | | 515 | | | | | 520 | | | | | 525 | | |
| TTC | ACT | AAA | TTT | GCT | CAA | ACA | CAA | TCT | TTA | GCG | ACG | AGA | AGC | TCG | GGT | 1813 |
| Phe | Thr | Lys | Phe | Ala | Gln | Thr | Gln | Ser | Leu | Ala | Thr | Arg | Ser | Ser | Gly | |
| | | | 530 | | | | | 535 | | | | | 540 | | | |
| GGT | AGT | GGG | CTT | GGC | CTC | GCC | ATC | TCC | AAG | AGG | TTT | GTG | AAT | CTG | ATG | 1861 |
| Gly | Ser | Gly | Leu | Gly | Leu | Ala | Ile | Ser | Lys | Arg | Phe | Val | Asn | Leu | Met | |
| | | 545 | | | | | 550 | | | | | 555 | | | | |
| GAG | GGT | AAC | ATT | TGG | ATT | GAG | AGC | GAT | GGT | CTT | GGA | AAA | GGA | TGC | ACG | 1909 |
| Glu | Gly | Asn | Ile | Trp | Ile | Glu | Ser | Asp | Gly | Leu | Gly | Lys | Gly | Cys | Thr | |
| | | 560 | | | | | 565 | | | | | 570 | | | | |
| GCT | ATC | TTT | GAT | GTT | AAA | CTT | GGG | ATC | TCA | GAA | CGT | TCA | AAC | GAA | TCT | 1957 |
| Ala | Ile | Phe | Asp | Val | Lys | Leu | Gly | Ile | Ser | Glu | Arg | Ser | Asn | Glu | Ser | |
| 575 | | | | | 580 | | | | | 585 | | | | | 590 | |
| AAA | CAG | TCG | GGC | ATA | CCG | AAA | GTT | CCA | GCC | ATT | CCC | CGA | CAT | TCA | AAT | 2005 |
| Lys | Gln | Ser | Gly | Ile | Pro | Lys | Val | Pro | Ala | Ile | Pro | Arg | His | Ser | Asn | |
| | | | | 595 | | | | | 600 | | | | | 605 | | |

| | | | | | | | | | | | | | | | | |
|---|---|---|---|---|---|---|---|---|---|---|---|---|---|---|---|---|
| TTC | ACT | GGA | CTT | AAG | GTT | CTT | GTC | ATG | GAT | GAG | AAC | GGG | GTA | AGT | AGA | 2053 |
| Phe | Thr | Gly | Leu | Lys | Val | Leu | Val | Met | Asp | Glu | Asn | Gly | Val | Ser | Arg | |
| | | | 610 | | | | | 615 | | | | | 620 | | | |
| ATG | GTG | ACG | AAG | GGA | CTT | CTT | GTA | CAC | CTT | GGG | TGC | GAA | GTG | ACC | ACG | 2101 |
| Met | Val | Thr | Lys | Gly | Leu | Leu | Val | His | Leu | Gly | Cys | Glu | Val | Thr | Thr | |
| | | 625 | | | | | 630 | | | | | 635 | | | | |
| GTG | AGT | TCA | AAC | GAG | GAG | TGT | CTC | CGA | GTT | GTG | TCC | CAT | GAG | CAC | AAA | 2149 |
| Val | Ser | Ser | Asn | Glu | Glu | Cys | Leu | Arg | Val | Val | Ser | His | Glu | His | Lys | |
| | | 640 | | | | | 645 | | | | | 650 | | | | |
| GTG | GTC | TTC | ATG | GAC | GTG | TGC | ATG | CCC | GGG | GTC | GAA | AAC | TAC | CAA | ATC | 2197 |
| Val | Val | Phe | Met | Asp | Val | Cys | Met | Pro | Gly | Val | Glu | Asn | Tyr | Gln | Ile | |
| 655 | | | | | 660 | | | | | 665 | | | | | 670 | |
| GCT | CTC | CGT | ATT | CAC | GAG | AAA | TTC | ACA | AAA | CAA | CGC | CAC | CAA | CGG | CCA | 2245 |
| Ala | Leu | Arg | Ile | His | Glu | Lys | Phe | Thr | Lys | Gln | Arg | His | Gln | Arg | Pro | |
| | | | | 675 | | | | | 680 | | | | | 685 | | |
| CTA | CTT | GTG | GCA | CTC | AGT | GGT | AAC | ACT | GAC | AAA | TCC | ACA | AAA | GAG | AAA | 2293 |
| Leu | Leu | Val | Ala | Leu | Ser | Gly | Asn | Thr | Asp | Lys | Ser | Thr | Lys | Glu | Lys | |
| | | | 690 | | | | | 695 | | | | | 700 | | | |
| TGC | ATG | AGC | TTT | GGT | CTA | GAC | GGT | GTG | TTG | CTC | AAA | CCC | GTA | TCA | CTA | 2341 |
| Cys | Met | Ser | Phe | Gly | Leu | Asp | Gly | Val | Leu | Leu | Lys | Pro | Val | Ser | Leu | |
| | | 705 | | | | | 710 | | | | | 715 | | | | |
| GAC | AAC | ATA | AGA | GAT | GTT | CTG | TCT | GAT | CTT | CTC | GAG | CCC | CGG | GTA | CTG | 2389 |
| Asp | Asn | Ile | Arg | Asp | Val | Leu | Ser | Asp | Leu | Leu | Glu | Pro | Arg | Val | Leu | |
| | 720 | | | | | 725 | | | | | 730 | | | | | |
| TAC | GAG | GGC | ATG | TAAAGGCGAT | | GGATGCCCCA | | TGCCCCAGAG | | GAGTAATTCC | | | | | | 2441 |
| Tyr | Glu | Gly | Met | | | | | | | | | | | | | |
| 735 | | | | | | | | | | | | | | | | |

| | | |
|---|---|---|
| GCTCCCGCCT TCTTCTCCCG TAAAACATCG GAAGCTGATG TTCTCTGGTT TAATTGTGTA | 2501 |
| CATATCAGAG ATTGTCGGAG CGTTTTGGAT GATATCTTAA AACAGAAAGG GAATAACAAA | 2561 |
| ATAGAAACTC TAAACCGGTA TGTGTCCGTG GCGATTTCGG TTATAGAGGA ACAAGATGGT | 2621 |
| GGTGGTATAA TCATACCATT TCAGATTACA TGTTTGACTA ATGTTGTATC CTTATATATG | 2681 |
| TAGTTACATT CTTATAAGAA TTTGGATCGA GTTATGGATG CTTGTTGCGT GCATGTATGA | 2741 |
| CATTGATGCA GTATTATGGC GTCAGCTTTG CGCCGCTTAG TAGAAC | 2787 |

( 2 ) INFORMATION FOR SEQ ID NO:11:

( i ) SEQUENCE CHARACTERISTICS:
        ( A ) LENGTH: 738 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| | | | | | | | | | | | | | | |
|---|---|---|---|---|---|---|---|---|---|---|---|---|---|---|
| Met | Glu | Val | Cys | Asn | Cys | Ile | Glu | Pro | Gln | Trp | Pro | Ala | Asp | Glu | Leu |
| 1 | | | | 5 | | | | | 10 | | | | | 15 | |
| Leu | Met | Lys | Tyr | Gln | Tyr | Ile | Ser | Asp | Phe | Phe | Ile | Ala | Ile | Ala | Tyr |
| | | | 20 | | | | 25 | | | | | 30 | | | |
| Phe | Ser | Ile | Pro | Leu | Glu | Leu | Ile | Tyr | Phe | Val | Lys | Lys | Ser | Ala | Val |
| | | 35 | | | | | 40 | | | | | 45 | | | |
| Phe | Pro | Tyr | Arg | Trp | Val | Leu | Val | Gln | Phe | Gly | Ala | Phe | Phe | Val | Leu |
| | 50 | | | | | 55 | | | | | 60 | | | | |
| Cys | Gly | Ala | Thr | His | Leu | Ile | Asn | Leu | Trp | Thr | Phe | Thr | Thr | His | Ser |
| 65 | | | | | 70 | | | | | 75 | | | | | 80 |
| Arg | Thr | Val | Ala | Leu | Val | Met | Thr | Thr | Ala | Lys | Val | Leu | Thr | Ala | Val |
| | | | | 85 | | | | | 90 | | | | | 95 | |
| Val | Ser | Cys | Ala | Thr | Ala | Leu | Met | Leu | Val | His | Ile | Ile | Pro | Asp | Leu |
| | | | 100 | | | | | 105 | | | | | 110 | | |

| | | | | | | | | | | | | | |
|---|---|---|---|---|---|---|---|---|---|---|---|---|---|
|Leu|Ser|Val|Lys|Thr|Arg|Glu|Leu|Phe|Leu|Lys|Asn|Lys|Ala|Ala|Glu|
| | | |115| | |120| | | |125| | | |
|Leu|Asp|Arg|Glu|Met|Gly|Leu|Ile|Arg|Thr|Gln|Glu|Thr|Gly|Arg|
| |130| | | |135| | | |140| | | | |
|His|Val|Arg|Met|Leu|Thr|His|Glu|Ile|Arg|Ser|Thr|Leu|Asp|Arg|His|
|145| | | | |150| | | |155| | | | |160|
|Thr|Ile|Leu|Lys|Thr|Thr|Leu|Val|Glu|Leu|Gly|Arg|Thr|Leu|Ala|Leu|
| | | | |165| | | |170| | | | |175|
|Glu|Glu|Cys|Ala|Leu|Trp|Met|Pro|Thr|Arg|Thr|Gly|Leu|Glu|Leu|Gln|
| | | |180| | | |185| | | | |190| |
|Leu|Ser|Tyr|Thr|Leu|Arg|His|Gln|His|Pro|Val|Glu|Tyr|Thr|Val|Pro|
| | |195| | | |200| | | |205| | | |
|Ile|Gln|Leu|Pro|Val|Ile|Asn|Gln|Val|Phe|Gly|Thr|Ser|Arg|Ala|Val|
| |210| | | |215| | | |220| | | | |
|Lys|Ile|Ser|Pro|Asn|Ser|Pro|Val|Ala|Arg|Leu|Arg|Pro|Val|Ser|Gly|
|225| | | |230| | | |235| | | | |240|
|Lys|Tyr|Met|Leu|Gly|Glu|Val|Val|Ala|Val|Arg|Val|Pro|Leu|Leu|His|
| | | |245| | | |250| | | |255| |
|Leu|Ser|Asn|Phe|Gln|Ile|Asn|Asp|Trp|Pro|Glu|Leu|Ser|Thr|Lys|Arg|
| | |260| | | |265| | | |270| | |
|Tyr|Ala|Leu|Met|Val|Leu|Met|Leu|Pro|Ser|Asp|Ser|Ala|Arg|Gln|Trp|
| |275| | | |280| | | |285| | | |
|His|Val|His|Glu|Leu|Glu|Leu|Val|Glu|Val|Val|Ala|Asp|Gln|Val|Ala|
|290| | | |295| | | |300| | | | | |
|Val|Ala|Leu|Ser|His|Ala|Ala|Ile|Leu|Glu|Glu|Ser|Met|Arg|Ala|Arg|
|305| | | |310| | | |315| | | |320|
|Asp|Leu|Leu|Met|Glu|Gln|Asn|Val|Ala|Leu|Asp|Leu|Ala|Arg|Arg|Glu|
| | | |325| | | |330| | | |335| |
|Ala|Glu|Thr|Ala|Ile|Arg|Ala|Arg|Asn|Asp|Phe|Leu|Ala|Val|Met|Asn|
| | |340| | | |345| | | |350| |
|His|Glu|Met|Arg|Thr|Pro|Met|His|Ala|Ile|Ile|Ala|Leu|Ser|Ser|Leu|
| | |355| | | |360| | | |365| |
|Leu|Gln|Glu|Thr|Glu|Leu|Thr|Pro|Glu|Gln|Arg|Leu|Met|Val|Glu|Thr|
| |370| | | |375| | | |380| | | |
|Ile|Leu|Lys|Ser|Ser|Asn|Leu|Leu|Ala|Thr|Leu|Met|Asn|Asp|Val|Leu|
|385| | | |390| | | |395| | | |400|
|Asp|Leu|Ser|Arg|Leu|Glu|Asp|Gly|Ser|Leu|Gln|Leu|Glu|Leu|Gly|Thr|
| | | |405| | | |410| | | |415| |
|Phe|Asn|Leu|His|Thr|Leu|Phe|Arg|Glu|Val|Leu|Asn|Leu|Ile|Lys|Pro|
| | |420| | | |425| | | |430| |
|Ile|Ala|Val|Val|Lys|Lys|Leu|Pro|Ile|Thr|Leu|Asn|Leu|Ala|Pro|Asp|
| |435| | | |440| | | |445| | |
|Leu|Pro|Glu|Phe|Val|Val|Gly|Asp|Glu|Lys|Arg|Leu|Met|Gln|Ile|Ile|
|450| | | |455| | | |460| | | | |
|Leu|Asn|Ile|Val|Gly|Asn|Ala|Val|Lys|Phe|Ser|Lys|Gln|Gly|Ser|Ile|
|465| | | |470| | | |475| | | |480|
|Ser|Val|Thr|Ala|Leu|Val|Thr|Lys|Ser|Asp|Thr|Arg|Ala|Ala|Asp|Phe|
| | |485| | | |490| | | |495| |
|Phe|Val|Val|Pro|Thr|Gly|Ser|His|Phe|Tyr|Leu|Arg|Val|Lys|Val|Lys|
| | |500| | | |505| | | |510| |
|Asp|Ser|Gly|Ala|Gly|Ile|Asn|Pro|Gln|Asp|Ile|Pro|Lys|Ile|Phe|Thr|
| |515| | | |520| | | |525| | |
|Lys|Phe|Ala|Gln|Thr|Gln|Ser|Leu|Ala|Thr|Arg|Ser|Ser|Gly|Gly|Ser|

-continued

```
              530                     535                     540
Gly  Leu  Gly  Leu  Ala  Ile  Ser  Lys  Arg  Phe  Val  Asn  Leu  Met  Glu  Gly
545                      550                     555                     560

Asn  Ile  Trp  Ile  Glu  Ser  Asp  Gly  Leu  Gly  Lys  Gly  Cys  Thr  Ala  Ile
                         565                     570                     575

Phe  Asp  Val  Lys  Leu  Gly  Ile  Ser  Glu  Arg  Ser  Asn  Glu  Ser  Lys  Gln
                         580                     585                     590

Ser  Gly  Ile  Pro  Lys  Val  Pro  Ala  Ile  Pro  Arg  His  Ser  Asn  Phe  Thr
                595                     600                     605

Gly  Leu  Lys  Val  Leu  Val  Met  Asp  Glu  Asn  Gly  Val  Ser  Arg  Met  Val
                610                     615                     620

Thr  Lys  Gly  Leu  Leu  Val  His  Leu  Gly  Cys  Glu  Val  Thr  Thr  Val  Ser
625                      630                     635                     640

Ser  Asn  Glu  Glu  Cys  Leu  Arg  Val  Val  Ser  His  Glu  His  Lys  Val  Val
                645                     650                     655

Phe  Met  Asp  Val  Cys  Met  Pro  Gly  Val  Glu  Asn  Tyr  Gln  Ile  Ala  Leu
                660                     665                     670

Arg  Ile  His  Glu  Lys  Phe  Thr  Lys  Gln  Arg  His  Gln  Arg  Pro  Leu  Leu
                675                     680                     685

Val  Ala  Leu  Ser  Gly  Asn  Thr  Asp  Lys  Ser  Thr  Lys  Glu  Lys  Cys  Met
690                      695                     700

Ser  Phe  Gly  Leu  Asp  Gly  Val  Leu  Leu  Lys  Pro  Val  Ser  Leu  Asp  Asn
705                      710                     715                     720

Ile  Arg  Asp  Val  Leu  Ser  Asp  Leu  Leu  Glu  Pro  Arg  Val  Leu  Tyr  Glu
                         725                     730                     735

Gly  Met
```

( 2 ) INFORMATION FOR SEQ ID NO:12:

( i ) SEQUENCE CHARACTERISTICS:
( A ) LENGTH: 155 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

```
Gln  Asn  Val  Ala  Leu  Asp  Leu  Ala  Arg  Arg  Glu  Ala  Glu  Thr  Ala  Ile
1                    5                       10                      15

Arg  Ala  Arg  Asn  Asp  Phe  Leu  Ala  Val  Met  Asn  His  Glu  Met  Arg  Thr
                20                      25                      30

Pro  Met  His  Ala  Ile  Ile  Ala  Leu  Ser  Ser  Leu  Leu  Gln  Glu  Thr  Glu
                35                      40                      45

Leu  Thr  Pro  Glu  Gln  Arg  Leu  Met  Val  Glu  Thr  Ile  Leu  Lys  Ser  Ser
         50                      55                      60

Asn  Leu  Leu  Ala  Thr  Leu  Met  Asn  Asp  Val  Leu  Asp  Leu  Ser  Arg  Leu
65                       70                      75                       80

Glu  Asp  Gly  Ser  Leu  Gln  Leu  Glu  Leu  Gly  Thr  Phe  Asn  Leu  His  Thr
                    85                      90                       95

Leu  Phe  Arg  Glu  Val  Leu  Asn  Leu  Ile  Lys  Pro  Ile  Ala  Val  Val  Lys
                100                     105                     110

Lys  Leu  Pro  Ile  Thr  Leu  Asn  Leu  Ala  Pro  Asp  Leu  Pro  Glu  Phe  Val
                115                     120                     125

Val  Gly  Asp  Glu  Lys  Arg  Leu  Met  Gln  Ile  Ile  Leu  Asn  Ile  Val  Gly
                130                     135                     140
```

|     |     |     |     |     |     |     |     |     |     |
|-----|-----|-----|-----|-----|-----|-----|-----|-----|-----|
| Asn | Ala | Val | Lys | Phe | Ser | Lys | Gln | Gly | Ser | Ile |
| 145 |     |     |     | 150 |     |     |     |     | 155 |

(2) INFORMATION FOR SEQ ID NO:13:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

| Gln | Asn | Val | Glu | Leu | Asp | Leu | Ala | Lys | Lys | Arg | Ala | Gln | Glu | Ala | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Arg | Ile | Lys | Ser | Glu | Phe | Leu | Ala | Asn | Met | Ser | His | Glu | Leu | Arg | Thr |
|     |     |     | 20  |     |     |     |     | 25  |     |     |     |     | 30  |     |     |
| Pro | Leu | Asn | Gly | Val | Ile | Gly | Phe | Thr | Arg | Leu | Thr | Leu | Lys | Thr | Glu |
|     |     |     | 35  |     |     |     |     | 40  |     |     |     |     | 45  |     |     |
| Leu | Thr | Pro | Thr | Gln | Arg | Asp | His | Leu | Asn | Thr | Ile | Glu | Arg | Ser | Ala |
|     |     |     | 50  |     |     |     |     | 55  |     |     |     |     | 60  |     |     |
| Asn | Asn | Leu | Leu | Ala | Ile | Ile | Asn | Asp | Val | Leu | Asp | Phe | Ser | Lys | Leu |
| 65  |     |     |     |     | 70  |     |     |     |     | 75  |     |     |     |     | 80  |
| Glu | Ala | Gly | Lys | Leu | Ile | Leu | Glu | Ser | Ile | Pro | Phe | Pro | Leu | Arg | Ser |
|     |     |     |     | 85  |     |     |     |     | 90  |     |     |     |     | 95  |     |
| Thr | Leu | Asp | Glu | Val | Val | Thr | Leu | Leu | Ala | His | Ser | Ser | His | Asp | Lys |
|     |     |     | 100 |     |     |     |     | 105 |     |     |     |     | 110 |     |     |
| Gly | Leu | Glu | Leu | Thr | Leu | Asn | Ile | Lys | Ser | Asp | Val | Pro | Asp | Asn | Val |
|     |     |     | 115 |     |     |     |     | 120 |     |     |     |     | 125 |     |     |
| Ile | Gly | Asp | Pro | Leu | Arg | Leu | Gln | Gln | Ile | Ile | Thr | Asn | Leu | Val | Gly |
|     |     | 130 |     |     |     |     | 135 |     |     |     |     | 140 |     |     |     |
| Asn | Ala | Ile | Lys | Phe | Thr | Glu | Asn | Gly | Asn | Ile |
| 145 |     |     |     |     | 150 |     |     |     |     | 155 |

(2) INFORMATION FOR SEQ ID NO:14:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

| Gln | Asn | Ile | Glu | Leu | Asp | Leu | Ala | Arg | Lys | Glu | Ala | Leu | Glu | Ala | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Arg | Ile | Lys | Ser | Glu | Phe | Leu | Ala | Asn | Met | Ser | His | Glu | Ile | Arg | Thr |
|     |     |     | 20  |     |     |     |     | 25  |     |     |     |     | 30  |     |     |
| Pro | Leu | Asn | Gly | Ile | Leu | Gly | Phe | Thr | His | Leu | Leu | Gln | Lys | Ser | Glu |
|     |     |     | 35  |     |     |     |     | 40  |     |     |     |     | 45  |     |     |
| Leu | Thr | Pro | Arg | Gln | Phe | Asp | Tyr | Leu | Gly | Thr | Ile | Glu | Lys | Ser | Ala |
|     |     |     | 50  |     |     |     |     | 55  |     |     |     |     | 60  |     |     |
| Asp | Asn | Leu | Leu | Ser | Ile | Ile | Asn | Glu | Ile | Leu | Asp | Phe | Ser | Lys | Ile |
| 65  |     |     |     |     | 70  |     |     |     |     | 75  |     |     |     |     | 80  |
| Glu | Ala | Gly | Lys | Leu | Val | Leu | Asp | Asn | Ile | Pro | Phe | Asn | Leu | Arg | Asp |
|     |     |     |     | 85  |     |     |     |     | 90  |     |     |     |     | 95  |     |
| Leu | Leu | Gln | Asp | Thr | Leu | Thr | Ile | Leu | Ala | Pro | Ala | Ala | His | Ala | Lys |
|     |     |     | 100 |     |     |     |     | 105 |     |     |     |     | 110 |     |     |

```
Gln Leu Glu Leu Val Ser Leu Val Tyr Arg Asp Thr Pro Leu Ala Leu
        115             120             125

Ser Gly Asp Pro Leu Arg Leu Arg Gln Ile Leu Thr Asn Leu Val Ser
        130             135             140

Asn Ala Ile Lys Phe Thr Arg Glu Gly Thr Ile
145             150             155
```

( 2 ) INFORMATION FOR SEQ ID NO:15:

( i ) SEQUENCE CHARACTERISTICS:
        ( A ) LENGTH: 149 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Arg Ala Val Arg Glu Ala Arg His Ala Asn Gln Ala Lys Ser Arg Phe
1               5               10              15

Leu Ala Asn Met Ser His Glu Phe Arg Thr Pro Leu Asn Gly Leu Ser
        20              25              30

Gly Met Thr Glu Val Leu Ala Thr Thr Arg Leu Asp Ala Glu Gln Lys
        35              40              45

Glu Cys Leu Asn Thr Ile Gln Ala Ser Ala Arg Ser Leu Leu Ser Leu
        50              55              60

Val Glu Glu Val Leu Asp Ile Ser Ala Ile Glu Ala Gly Lys Ile Arg
65              70              75              80

Ile Asp Arg Arg Asp Phe Ser Leu Arg Glu Met Ile Gly Ser Val Asn
                85              90              95

Leu Ile Leu Gln Pro Gln Ala Arg Gly Arg Arg Leu Glu Tyr Gly Thr
            100             105             110

Gln Val Ala Asp Asp Val Pro Asp Leu Leu Lys Gly Asp Thr Ala His
        115             120             125

Leu Arg Gln Val Leu Leu Asn Leu Val Gly Asn Ala Val Lys Phe Thr
        130             135             140

Glu His Gly His Val
145
```

( 2 ) INFORMATION FOR SEQ ID NO:16:

( i ) SEQUENCE CHARACTERISTICS:
        ( A ) LENGTH: 66 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Leu Lys Val Leu Val Met Asp Glu Asn Gly Val Ser Arg Met Val Thr
1               5               10              15

Lys Gly Leu Leu Val His Leu Gly Cys Glu Val Thr Thr Val Ser Ser
        20              25              30

Asn Glu Glu Cys Leu Arg Val Val Ser His Glu His Lys Val Val Phe
        35              40              45

Met Asp Val Cys Met Pro Gly Val Glu Asn Tyr Gln Ile Ala Leu Arg
        50              55              60

Ile His
65
```

( 2 ) INFORMATION FOR SEQ ID NO:17:

( i ) SEQUENCE CHARACTERISTICS:
        ( A ) LENGTH: 67 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Leu Arg Val Leu Val Val Asp Asp His Lys Pro Asn Leu Met Leu Leu
 1               5                  10                  15
Arg Gln Gln Leu Asp Tyr Leu Gly Gln Arg Val Val Ala Ala Asp Ser
            20                  25                  30
Gly Glu Ala Ala Leu Ala Leu Trp His Glu His Ala Phe Asp Val Val
        35                  40                  45
Ile Thr Asp Cys Asn Met Pro Gly Ile Asn Gly Tyr Glu Leu Ala Arg
    50                  55                  60
Arg Ile Arg
65
```

( 2 ) INFORMATION FOR SEQ ID NO:18:

( i ) SEQUENCE CHARACTERISTICS:
        ( A ) LENGTH: 67 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Met Met Ile Leu Val Val Asp Asp His Pro Ile Asn Arg Arg Leu Leu
 1               5                  10                  15
Ala Asp Gln Leu Gly Ser Leu Gly Tyr Gln Cys Lys Thr Ala Asn Asp
            20                  25                  30
Gly Val Asp Ala Leu Asn Val Leu Ser Lys Asn His Ile Asp Ile Val
        35                  40                  45
Leu Ser Asp Val Asn Met Pro Asn Met Asp Gly Tyr Arg Leu Thr Gln
    50                  55                  60
Arg Ile Arg
65
```

( 2 ) INFORMATION FOR SEQ ID NO:19:

( i ) SEQUENCE CHARACTERISTICS:
        ( A ) LENGTH: 67 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Pro Arg Val Leu Cys Val Asp Asp Asn Pro Ala Asn Leu Leu Leu Val
 1               5                  10                  15
Gln Thr Leu Leu Glu Asp Met Gly Ala Glu Val Val Ala Val Glu Gly
            20                  25                  30
Gly Tyr Ala Ala Val Asn Ala Val Gln Gln Glu Ala Phe Asp Leu Val
        35                  40                  45
Leu Met Asp Val Gln Met Pro Gly Met Asp Gly Arg Gln Ala Thr Glu
    50                  55                  60
```

```
        Ala  Ile  Arg
         65
```

( 2 ) INFORMATION FOR SEQ ID NO:20:

( i ) SEQUENCE CHARACTERISTICS:
        ( A ) LENGTH: 369 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

```
ATGGAATCCT  GTGATTGCAT  TGAGGCTTTA  CTGCCAACTG  GTGACCTGCT  GGTTAAATAC      60
CAATACCTCT  CAGATTTCTT  CATTGCTGTA  GCCTACTTTT  CCATTCCGTT  GGAGCTTATT     120
TATTTTGTCC  ACAAATCTGC  ATGCTTCCCA  TACAGATGGG  TCCTCATGCA  ATTTGGTGCT     180
TTTATTGTGC  TCTGCGGAGC  AACACACTTT  ATTAGCTTGT  GGACCTTCTT  TATGCACTCT     240
AAGACGGTCG  CTGTGGTTAT  GACCATATCA  AAAATGTTGA  CAGCTGCCGT  GTCCTGTATC     300
ACAGCTTTGA  TGCTTGTTCA  CATTATTCCT  GATTTGCTAA  GTGTTAAAAC  GCGAGAGTTG     360
TTCTTGAAA                                                                  369
```

( 2 ) INFORMATION FOR SEQ ID NO:21:

( i ) SEQUENCE CHARACTERISTICS:
        ( A ) LENGTH: 369 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

```
ATGGAAGTCT  GCAATTGTAT  TGAACCGCAA  TGGCCAGCGG  ATGAATTGTT  AATGAAATAC      60
CAATACATCT  CCGATTTCTT  CATTGCGATT  GCGTATTTTT  CGATTCCTCT  TGAGTTGATT     120
TACTTTGTGA  AGAAATCAGC  CGTGTTTCCG  TATAGATGGG  TACTTGTTCA  GTTTGGTGCT     180
TTTATCGTTC  TTTGTGGAGC  AACTCATCTT  ATTAACTTAT  GGACTTTCAC  TACGCATTCG     240
AGAACCGTGG  CGCTTGTGAT  GACTACCGCG  AAGGTGTTAA  CCGCTGTTGT  CTCGTGTGCT     300
ACTGCGTTGA  TGCTTGTTCA  TATTATTCCT  GATCTTTTGA  GTGTTAAGAC  TCGGGAGCTT     360
TTCTTGAAA                                                                  369
```

( 2 ) INFORMATION FOR SEQ ID NO:22:

( i ) SEQUENCE CHARACTERISTICS:
        ( A ) LENGTH: 296 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

```
GCTCTTTCAC  ATGCTGCAAT  TTTAGAAGAT  TCCATGCGAG  CCCATGATCA  GCTCATGAA       60
CAGAATATTG  CTTTGGATGT  AGCTCGACAA  GAAGCAGAGA  TGGCCATCCG  TGCACGTAAC     120
GACTTCCTTG  CTGTGATGAA  CCATGAAATG  AGAACGCCCA  TGCATGCAGT  TATTGCTCTG     180
TGCTCTCTGC  TTTTAGAAAC  AGACTTAACT  CCAGAGCAGA  GAGTTATGAT  TGAGACCATA     240
TTGAAGAGCA  GCAATCTTCT  TGCAACACTG  ATAAATGATG  TTCTAGATCT  TTCTAG         296
```

( 2 ) INFORMATION FOR SEQ ID NO:23:

( i ) SEQUENCE CHARACTERISTICS:
        ( A ) LENGTH: 296 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

```
GCTCTCTCAC ATGCTGCGAT CCTAGAAGAG TCGATGCGAG CTAGGGACCT TCTCATGGAG      60
CAGAATGTTG CTCTTGATCT AGCTAGACGA GAAGCAGAAA CAGCAATCCG TGCCCGCAAT     120
GATTTCCTAG CGGTTATGAA CCATGAAATG CGAACACCGA TGCATGCGAT TATTGCACTC     180
TCTTCCTTAC TCCAAGAAAC GGAACTAACC CCTGAACAAA GACTGATGGT GGAAACAATA     240
CTTAAAAGTA GTAACCTTTT GGCAACTTTG ATGAATGATG TCTTAGATCT TTCAAG         296
```

( 2 ) INFORMATION FOR SEQ ID NO:24:

( i ) SEQUENCE CHARACTERISTICS:
        ( A ) LENGTH: 123 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

```
Met Glu Ser Cys Asp Cys Ile Glu Ala Leu Leu Pro Thr Gly Asp Leu
 1               5                  10                  15
Leu Val Lys Tyr Gln Tyr Leu Ser Asp Phe Phe Ile Ala Val Ala Tyr
             20                  25                  30
Phe Ser Ile Pro Leu Glu Leu Ile Tyr Phe Val His Lys Ser Ala Cys
         35                  40                  45
Phe Pro Tyr Arg Trp Val Leu Met Gln Phe Gly Ala Phe Ile Val Leu
     50                  55                  60
Cys Gly Ala Thr His Phe Ile Ser Leu Trp Thr Phe Phe Met His Ser
65                  70                  75                  80
Lys Thr Val Ala Val Val Met Thr Ile Ser Lys Met Leu Thr Ala Ala
                 85                  90                  95
Val Ser Cys Ile Thr Ala Leu Met Leu Val His Ile Ile Pro Asp Leu
                100                 105                 110
Leu Ser Val Lys Thr Arg Glu Leu Phe Leu Lys
             115                 120
```

( 2 ) INFORMATION FOR SEQ ID NO:25:

( i ) SEQUENCE CHARACTERISTICS:
        ( A ) LENGTH: 123 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
Met Glu Val Cys Asn Cys Ile Glu Pro Gln Trp Pro Ala Asp Glu Leu
 1               5                  10                  15
Leu Met Lys Tyr Gln Tyr Ile Ser Asp Phe Phe Ile Ala Ile Ala Tyr
             20                  25                  30
```

|     |     |     |     |     |     |     |     |     |     |     |     |     |     |     |
| --- | --- | --- | --- | --- | --- | --- | --- | --- | --- | --- | --- | --- | --- | --- |
| Phe | Ser | Ile | Pro | Leu | Glu | Leu | Ile | Tyr | Phe | Val | Lys | Lys | Ser | Ala | Val |
|     |     | 35  |     |     |     |     | 40  |     |     |     |     | 45  |     |     |     |
| Phe | Pro | Tyr | Arg | Trp | Val | Leu | Val | Gln | Phe | Gly | Ala | Phe | Ile | Val | Leu |
|     | 50  |     |     |     |     | 55  |     |     |     |     | 60  |     |     |     |     |
| Cys | Gly | Ala | Thr | His | Leu | Ile | Asn | Leu | Trp | Thr | Phe | Thr | Thr | His | Ser |
| 65  |     |     |     |     | 70  |     |     |     |     | 75  |     |     |     |     | 80  |
| Arg | Thr | Val | Ala | Leu | Val | Met | Thr | Thr | Ala | Lys | Val | Leu | Thr | Ala | Val |
|     |     |     |     | 85  |     |     |     |     | 90  |     |     |     |     | 95  |     |
| Val | Ser | Cys | Ala | Thr | Ala | Leu | Met | Leu | Val | His | Ile | Ile | Pro | Asp | Leu |
|     |     |     | 100 |     |     |     |     | 105 |     |     |     |     | 110 |     |     |
| Leu | Ser | Val | Lys | Thr | Arg | Glu | Leu | Phe | Leu | Lys |     |     |     |     |     |
|     |     | 115 |     |     |     |     | 120 |     |     |     |     |     |     |     |     |

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

AGTAAGAACG AAGAAGAAGT G      21

(2) INFORMATION FOR SEQ ID NO:27:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

|     |     |     |     |     |     |     |     |     |     |     |     |     |     |     |     |
| --- | --- | --- | --- | --- | --- | --- | --- | --- | --- | --- | --- | --- | --- | --- | --- |
| Leu | Arg | Val | Lys | Val | Lys | Asp | Ser | Gly | Ala | Gly | Ile | Asn | Pro | Gln | Asp |
| 1   |     |     |     | 5   |     |     |     |     | 10  |     |     |     |     | 15  |     |
| Ile | Pro | Lys | Ile | Phe | Thr | Lys | Phe | Ala | Gln | Thr | Gln | Ser | Leu | Ala | Thr |
|     |     |     | 20  |     |     |     |     | 25  |     |     |     |     | 30  |     |     |
| Arg | Ser | Ser | Gly | Gly | Ser | Gly | Leu | Gly | Leu | Ala | Ile | Ser | Lys | Arg | Phe |
|     |     | 35  |     |     |     |     | 40  |     |     |     |     | 45  |     |     |     |
| Val | Asn | Leu | Met | Glu | Gly | Asn | Ile |     |     |     |     |     |     |     |     |
|     | 50  |     |     |     |     | 55  |     |     |     |     |     |     |     |     |     |

(2) INFORMATION FOR SEQ ID NO:28:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

|     |     |     |     |     |     |     |     |     |     |     |     |     |     |     |     |
| --- | --- | --- | --- | --- | --- | --- | --- | --- | --- | --- | --- | --- | --- | --- | --- |
| Ile | Glu | Val | Gln | Ile | Arg | Asp | Thr | Gly | Ile | Gly | Ile | Pro | Glu | Arg | Asp |
| 1   |     |     |     | 5   |     |     |     |     | 10  |     |     |     |     | 15  |     |
| Gln | Ser | Arg | Leu | Phe | Gln | Ala | Phe | Arg | Gln | Ala | Asp | Ala | Ser | Ile | Ser |
|     |     |     | 20  |     |     |     |     | 25  |     |     |     |     | 30  |     |     |
| Arg | Arg | His | Gly | Gly | Thr | Gly | Leu | Gly | Leu | Val | Ile | Thr | Gln | Lys | Leu |
|     |     | 35  |     |     |     |     | 40  |     |     |     |     | 45  |     |     |     |

Val Asn Glu Met Gly Gly Asp Ile
        50                  55

( 2 ) INFORMATION FOR SEQ ID NO:29:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

Leu Arg Ile Ser Val Gln Asp Thr Gly Ile Gly Leu Ser Ser Gln Asp
        1               5                   10                  15

Val Arg Ala Leu Phe Gln Ala Phe Ser Gln Ala Asp Asn Ser Leu Ser
                        20                  25                  30

Arg Gln Pro Gly Gly Thr Gly Leu Gly Leu Val Ile Ser Lys Arg Leu
                    35                  40                  45

Ile Glu Gln Met Gly Gly Glu Ile
        50                  55

( 2 ) INFORMATION FOR SEQ ID NO:30:

( i ) SEQUENCE CHARACTERISTICS:
        ( A ) LENGTH: 56 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

Leu Arg Phe Asp Val Glu Asp Thr Gly Ile Gly Val Pro Met Asp Met
        1               5                   10                  15

Arg Pro Arg Leu Phe Glu Ala Phe Glu Gln Ala Asp Val Gly Leu Ser
                        20                  25                  30

Arg Arg Tyr Glu Gly Thr Gly Leu Gly Thr Thr Ile Ala Lys Gly Leu
                    35                  40                  45

Val Glu Ala Met Gly Gly Ser Ile
        50                  55

( 2 ) INFORMATION FOR SEQ ID NO:31:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

Pro Leu Leu Val Ala Leu Ser Gly Asn Thr Asp Lys Ser Thr Lys Glu
        1               5                   10                  15

Lys Cys Met Ser Phe Gly Leu Asp Gly Val Leu Leu Lys Pro Val Ser
                        20                  25                  30

Leu Asp Asn Ile Arg Asp Val Leu Ser Asp Leu Leu
                    35                  40

( 2 ) INFORMATION FOR SEQ ID NO:32:

( i ) SEQUENCE CHARACTERISTICS:
        ( A ) LENGTH: 44 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:32:

Cys Ile Leu Phe Gly Phe Thr Ala Ser Ala Gln Met Asp Glu Ala His
1               5                   10                  15

Ala Cys Arg Ala Ala Gly Met Asp Asp Cys Leu Phe Lys Pro Ile Gly
                20                  25                  30

Val Asp Ala Leu Arg Gln Arg Leu Asn Glu Ala Ala
            35                  40

(2) INFORMATION FOR SEQ ID NO:33:

(i) SEQUENCE CHARACTERISTICS:
    (A) LENGTH: 44 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:33:

Leu Pro Val Ile Gly Val Thr Ala Asn Ala Leu Ala Glu Glu Lys Gln
1               5                   10                  15

Arg Cys Leu Glu Ser Gly Met Asp Ser Cys Leu Ser Lys Pro Val Thr
                20                  25                  30

Leu Asp Val Ile Lys Gln Ser Leu Thr Leu Tyr Ala
            35                  40

(2) INFORMATION FOR SEQ ID NO:34:

(i) SEQUENCE CHARACTERISTICS:
    (A) LENGTH: 44 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:34:

Leu Pro Ile Val Ala Leu Thr Ala His Ala Met Ala Asn Glu Lys Arg
1               5                   10                  15

Ser Leu Leu Gln Ser Gly Met Asp Asp Tyr Leu Thr Lys Pro Ile Ser
                20                  25                  30

Glu Arg Gln Leu Ala Gln Val Val Leu Lys Trp Thr
            35                  40

(2) INFORMATION FOR SEQ ID NO:35:

(i) SEQUENCE CHARACTERISTICS:
    (A) LENGTH: 2405 base pairs
    (B) TYPE: nucleic acid
    (C) STRANDEDNESS: double
    (D) TOPOLOGY: linear (ix) FEATURE:
    (A) NAME/KEY: CDS
    (B) LOCATION: 288..2196

(xi) SEQUENCE DESCRIPTION: SEQ ID NO:35:

TTTTTTTTTT GTCAAAAGCT CGATGTAAAA ATCCGATGGC CACAAGCAAA ACGACAGGTT        60

CCAACTTCAC GGAGATTGTG AAAATGGAGT AGTAGTTCAG TGAAGTAGTA GATACTGAGA       120

-continued

```
TCGCATTCTC CGGCGTCGTT TTTCACATCG AAATAGTCGT GTAAAAAAAT GAAAAATTG          180

CTGCGAGACA GGTATGTGTC GCAGCAGGAA ATAGCATCTT AAAGGAAGGA AGGAAGGAAA          240

CTCGAAAGTT ACTAAAAATT TTTGATTCTT TGGGACGAAA CGAGATA ATG GAA TCC           296
                                                        Met Glu Ser
                                                         1

TGT GAT TGC ATT GAG GCT TTA CTG CCA ACT GGT GAC CTG CTG GTT AAA          344
Cys Asp Cys Ile Glu Ala Leu Leu Pro Thr Gly Asp Leu Leu Val Lys
     5              10                  15

TAC CAA TAC CTC TCA GAT TTC TTC ATT GCT GTA GCC TAC TTT TCC ATT          392
Tyr Gln Tyr Leu Ser Asp Phe Phe Ile Ala Val Ala Tyr Phe Ser Ile
 20              25                  30                       35

CCG TTG GAG CTT ATT TAT TTT GTC CAC AAA TCT GCA TGC TTC CCA TAC          440
Pro Leu Glu Leu Ile Tyr Phe Val His Lys Ser Ala Cys Phe Pro Tyr
             40                  45                       50

AGA TGG GTC CTC ATG CAA TTT GGT GCT TTT ATT GTG CTC TGT GGA GCA          488
Arg Trp Val Leu Met Gln Phe Gly Ala Phe Ile Val Leu Cys Gly Ala
              55                  60                  65

ACA CAC TTT ATT AGC TTG TGG ACC TTC TTT ATG CAC TCT AAG ACG GTC          536
Thr His Phe Ile Ser Leu Trp Thr Phe Phe Met His Ser Lys Thr Val
          70                  75                  80

GCT GTG GTT ATG ACC ATA TCA AAA ATG TTG ACA GCT GCC GTG TCC TGT          584
Ala Val Val Met Thr Ile Ser Lys Met Leu Thr Ala Ala Val Ser Cys
     85                  90                  95

ATC ACA GCT TTG ATG CTT GTT CAC ATT ATT CCT GAT TTG CTA AGT GTT          632
Ile Thr Ala Leu Met Leu Val His Ile Ile Pro Asp Leu Leu Ser Val
100                 105                 110                     115

AAA ACG CGA GAG TTG TTC TTG AAA ACT CGA GCT GAA GAG CTT GAC AAG          680
Lys Thr Arg Glu Leu Phe Leu Lys Thr Arg Ala Glu Glu Leu Asp Lys
                    120                 125                 130

GAA ATG GGC CTA ATA ATA AGA CAA GAA GAA ACT GGC AGA CAT GTC AGG          728
Glu Met Gly Leu Ile Ile Arg Gln Glu Glu Thr Gly Arg His Val Arg
                135                 140                 145

ATG CTG ACT CAT GAG ATA AGA AGC ACA CTC GAC AGA CAC ACA ATC TTG          776
Met Leu Thr His Glu Ile Arg Ser Thr Leu Asp Arg His Thr Ile Leu
            150                 155                 160

AAG ACT ACT CTT GTG GAG CTA GGT AGG ACC TTA GAC CTG GCA GAA TGT          824
Lys Thr Thr Leu Val Glu Leu Gly Arg Thr Leu Asp Leu Ala Glu Cys
    165                 170                 175

GCT TTG TGG ATG CCA TGC CAA GGA GGC CTG ACT TTG CAA CTT TCC CAT          872
Ala Leu Trp Met Pro Cys Gln Gly Gly Leu Thr Leu Gln Leu Ser His
180                 185                 190                 195

AAT TTA AAC AAT CTA ATA CCT CTG GGA TCT ACT GTG CCA ATT AAT CTT          920
Asn Leu Asn Asn Leu Ile Pro Leu Gly Ser Thr Val Pro Ile Asn Leu
                200                 205                 210

CCT ATT ATC AAT GAA ATT TTT AGT AGC CCT GAA GCA ATA CAA ATT CCA          968
Pro Ile Ile Asn Glu Ile Phe Ser Ser Pro Glu Ala Ile Gln Ile Pro
            215                 220                 225

CAT ACA AAT CCT TTG GCA AGG ATG AGG AAT ACT GTT GGT AGA TAT ATT          1016
His Thr Asn Pro Leu Ala Arg Met Arg Asn Thr Val Gly Arg Tyr Ile
        230                 235                 240

CCA CCA GAA GTA GTT GCT GTT CGT GTA CCG CTT TTA CAC CTC TCA AAT          1064
Pro Pro Glu Val Val Ala Val Arg Val Pro Leu Leu His Leu Ser Asn
    245                 250                 255

TTT ACT AAT GAC TGG GCT GAA CTG TCT ACT AGA AGT TAT GCG GTT ATG          1112
Phe Thr Asn Asp Trp Ala Glu Leu Ser Thr Arg Ser Tyr Ala Val Met
260                 265                 270                 275

GTT CTG GTT CTC CCG ATG AAT GGC TTA AGA AAG TGG CGT GAA CAT GAG          1160
Val Leu Val Leu Pro Met Asn Gly Leu Arg Lys Trp Arg Glu His Glu
                280                 285                 290
```

| | | | | | | | | | | | | | | | | |
|---|---|---|---|---|---|---|---|---|---|---|---|---|---|---|---|---|
| TTA | GAA | CTT | GTG | CAA | GTT | GTC | GCA | GAT | CAG | GTT | GCT | GTC | GCT | CTT | TCA | 1208 |
| Leu | Glu | Leu | Val | Gln | Val | Val | Ala | Asp | Gln | Val | Ala | Val | Ala | Leu | Ser | |
| | | | 295 | | | | | 300 | | | | | 305 | | | |
| CAT | GCT | GCA | ATT | TTA | GAA | GAT | TCC | ATG | CGA | GCC | CAT | GAT | CAG | CTC | ATG | 1256 |
| His | Ala | Ala | Ile | Leu | Glu | Asp | Ser | Met | Arg | Ala | His | Asp | Gln | Leu | Met | |
| | | 310 | | | | | 315 | | | | | 320 | | | | |
| GAA | CAG | AAT | ATT | GCT | TTG | GAT | GTA | GCT | CGA | CAA | GAA | GCA | GAG | ATG | GCC | 1304 |
| Glu | Gln | Asn | Ile | Ala | Leu | Asp | Val | Ala | Arg | Gln | Glu | Ala | Glu | Met | Ala | |
| 325 | | | | | 330 | | | | | 335 | | | | | | |
| ATC | CGT | GCA | CGT | AAC | GAC | TTC | CTT | GCT | GTG | ATG | AAC | CAT | GAA | ATG | AGA | 1352 |
| Ile | Arg | Ala | Arg | Asn | Asp | Phe | Leu | Ala | Val | Met | Asn | His | Glu | Met | Arg | |
| 340 | | | | | 345 | | | | | 350 | | | | | 355 | |
| ACG | CCC | ATG | CAT | GCA | GTT | ATT | GCT | CTG | TGC | TCT | CTG | CTT | TTA | GAA | ACA | 1400 |
| Thr | Pro | Met | His | Ala | Val | Ile | Ala | Leu | Cys | Ser | Leu | Leu | Leu | Glu | Thr | |
| | | | | 360 | | | | | 365 | | | | | 370 | | |
| GAC | TTA | ACT | CCA | GAG | CAG | AGA | GTT | ATG | ATT | GAG | ACC | ATA | TTG | AAG | AGC | 1448 |
| Asp | Leu | Thr | Pro | Glu | Gln | Arg | Val | Met | Ile | Glu | Thr | Ile | Leu | Lys | Ser | |
| | | | 375 | | | | | 380 | | | | | 385 | | | |
| AGC | AAT | CTT | CTT | GCA | ACA | CTG | ATA | AAT | GAT | GTT | CTA | GAT | CTT | TCT | AGA | 1496 |
| Ser | Asn | Leu | Leu | Ala | Thr | Leu | Ile | Asn | Asp | Val | Leu | Asp | Leu | Ser | Arg | |
| | | 390 | | | | | 395 | | | | | 400 | | | | |
| CTT | GAA | GAT | GGT | ATT | CTT | GAA | CTA | GAA | AAC | GGA | ACA | TTC | AAT | CTT | CAT | 1544 |
| Leu | Glu | Asp | Gly | Ile | Leu | Glu | Leu | Glu | Asn | Gly | Thr | Phe | Asn | Leu | His | |
| 405 | | | | | 410 | | | | | 415 | | | | | | |
| GGC | ATC | TTA | AGA | GAG | GCC | GTT | AAT | TTG | ATA | AAG | CCA | ATT | GCA | TCT | TTG | 1592 |
| Gly | Ile | Leu | Arg | Glu | Ala | Val | Asn | Leu | Ile | Lys | Pro | Ile | Ala | Ser | Leu | |
| 420 | | | | | 425 | | | | | 430 | | | | | 435 | |
| AAG | AAA | TTA | TCT | ATA | ACT | CTT | GCT | TTG | GCT | CTG | GAT | TTA | CCT | ATT | CTT | 1640 |
| Lys | Lys | Leu | Ser | Ile | Thr | Leu | Ala | Leu | Ala | Leu | Asp | Leu | Pro | Ile | Leu | |
| | | | | 440 | | | | | 445 | | | | | 450 | | |
| GCT | GTG | GGT | GAT | GCA | AAA | CGT | CTT | ATC | CAA | ACT | CTC | TTA | AAC | GTG | GTG | 1688 |
| Ala | Val | Gly | Asp | Ala | Lys | Arg | Leu | Ile | Gln | Thr | Leu | Leu | Asn | Val | Val | |
| | | | 455 | | | | | 460 | | | | | 465 | | | |
| GGA | AAT | GCT | GTG | AAG | TTC | ACT | AAA | GAA | GGA | CAT | ATT | TCA | ATT | GAG | GCT | 1736 |
| Gly | Asn | Ala | Val | Lys | Phe | Thr | Lys | Glu | Gly | His | Ile | Ser | Ile | Glu | Ala | |
| | | 470 | | | | | 475 | | | | | 480 | | | | |
| TCA | GTT | GCC | AAA | CCA | GAG | TAT | GCG | AGA | GAT | TGT | CAT | CCT | CCT | GAA | ATG | 1784 |
| Ser | Val | Ala | Lys | Pro | Glu | Tyr | Ala | Arg | Asp | Cys | His | Pro | Pro | Glu | Met | |
| | 485 | | | | | 490 | | | | | 495 | | | | | |
| TTC | CCT | ATG | CCA | AGT | GAT | GGC | CAG | TTT | TAT | TTG | CGT | GTC | CAG | GTT | AGA | 1832 |
| Phe | Pro | Met | Pro | Ser | Asp | Gly | Gln | Phe | Tyr | Leu | Arg | Val | Gln | Val | Arg | |
| 500 | | | | | 505 | | | | | 510 | | | | | 515 | |
| GAT | ACT | GGG | TGT | GGA | ATT | AGC | CCA | CAA | GAT | ATA | CCA | CTA | GTA | TTC | ACC | 1880 |
| Asp | Thr | Gly | Cys | Gly | Ile | Ser | Pro | Gln | Asp | Ile | Pro | Leu | Val | Phe | Thr | |
| | | | | 520 | | | | | 525 | | | | | 530 | | |
| AAA | TTT | GCA | GAG | TCA | CGG | CCT | ACG | TCA | AAT | CGA | AGT | ACT | GGA | GGG | GAA | 1928 |
| Lys | Phe | Ala | Glu | Ser | Arg | Pro | Thr | Ser | Asn | Arg | Ser | Thr | Gly | Gly | Glu | |
| | | | 535 | | | | | 540 | | | | | 545 | | | |
| GGT | CTA | GGG | CTT | GCC | ATT | TGG | AGA | CGA | TTT | ATT | CAA | CTT | ATG | AAA | GGT | 1976 |
| Gly | Leu | Gly | Leu | Ala | Ile | Trp | Arg | Arg | Phe | Ile | Gln | Leu | Met | Lys | Gly | |
| | | 550 | | | | | 555 | | | | | 560 | | | | |
| AAC | ATT | TGG | ATT | GAG | AGT | GAG | GGC | CCT | GGA | AAG | GGA | ACC | ACT | GTC | ACG | 2024 |
| Asn | Ile | Trp | Ile | Glu | Ser | Glu | Gly | Pro | Gly | Lys | Gly | Thr | Thr | Val | Thr | |
| | 565 | | | | | 570 | | | | | 575 | | | | | |
| TTT | GTA | GTG | AAA | CTC | GGA | ATC | TGT | CAC | CAT | CCA | AAT | GCA | TTA | CCT | CTG | 2072 |
| Phe | Val | Val | Lys | Leu | Gly | Ile | Cys | His | His | Pro | Asn | Ala | Leu | Pro | Leu | |
| 580 | | | | | 585 | | | | | 590 | | | | | 595 | |
| CTA | CCT | ATG | CCT | CCC | AGA | GGC | AGA | TTG | AAC | AAA | GGT | AGC | GAT | GAT | CTC | 2120 |
| Leu | Pro | Met | Pro | Pro | Arg | Gly | Arg | Leu | Asn | Lys | Gly | Ser | Asp | Asp | Leu | |
| | | | | 600 | | | | | 605 | | | | | 610 | | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| TTC | AGG | TAT | AGA | CAG | TTC | CGT | GGA | GAT | GAT | GGT | GGG | ATG | TCT | GTG | AAT | 2168 |
| Phe | Arg | Tyr | Arg | Gln | Phe | Arg | Gly | Asp | Asp | Gly | Gly | Met | Ser | Val | Asn |      |
|     |     | 615 |     |     |     |     | 620 |     |     |     |     | 625 |     |     |     |      |

|     |     |     |     |     |     |     |     |            |          |      |
| --- | --- | --- | --- | --- | --- | --- | --- | ---------- | -------- | ---- |
| GCT | CAA | CGC | TAT | CAA | AGA | AGT | ATG | TAA A      | TGACAAAGG ACATTGGTGT | 2216 |
| Ala | Gln | Arg | Tyr | Gln | Arg | Ser | Met | *          |          |      |
|     |     | 630 |     |     |     |     | 635 |            |          |      |

| | | | | |
|---|---|---|---|---|
| GACAAAGAAC | ATTAAATCAT | GACTAGTGAA | TTTGAGATTT | CTTCACTGTT CTGTACACTC | 2276 |
| CAAATGGCAC | AGTTTGTCTT | GTAACTAACC | TAATTCAATG | CTCGTAAAGT GAGTACTGGA | 2336 |
| GTATCTTGAA | AATGTAACTA | TCGAATTTAT | ACATCGAGCT | TTTGACAAAA AAAAAAAAA | 2396 |
| AAAAAAAA | | | | | 2405 |

( 2 ) INFORMATION FOR SEQ ID NO:36:

( i ) SEQUENCE CHARACTERISTICS:
        ( A ) LENGTH: 635 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

| | | | | | | | | | | | | | | |
|---|---|---|---|---|---|---|---|---|---|---|---|---|---|---|
| Met | Glu | Ser | Cys | Asp | Cys | Ile | Glu | Ala | Leu | Leu | Pro | Thr | Gly | Asp | Leu |
| 1 | | | | 5 | | | | | 10 | | | | | 15 | |
| Leu | Val | Lys | Tyr | Gln | Tyr | Leu | Ser | Asp | Phe | Phe | Ile | Ala | Val | Ala | Tyr |
| | | | 20 | | | | | 25 | | | | | 30 | | |
| Phe | Ser | Ile | Pro | Leu | Glu | Leu | Ile | Tyr | Phe | Val | His | Lys | Ser | Ala | Cys |
| | | 35 | | | | | 40 | | | | | 45 | | | |
| Phe | Pro | Tyr | Arg | Trp | Val | Leu | Met | Gln | Phe | Gly | Ala | Phe | Ile | Val | Leu |
| | 50 | | | | | 55 | | | | | 60 | | | | |
| Cys | Gly | Ala | Thr | His | Phe | Ile | Ser | Leu | Trp | Thr | Phe | Phe | Met | His | Ser |
| 65 | | | | | 70 | | | | | 75 | | | | | 80 |
| Lys | Thr | Val | Ala | Val | Val | Met | Thr | Ile | Ser | Lys | Met | Leu | Thr | Ala | Ala |
| | | | | 85 | | | | | 90 | | | | | 95 | |
| Val | Ser | Cys | Ile | Thr | Ala | Leu | Met | Leu | Val | His | Ile | Ile | Pro | Asp | Leu |
| | | | | 100 | | | | | 105 | | | | | 110 | |
| Leu | Ser | Val | Lys | Thr | Arg | Glu | Leu | Phe | Leu | Lys | Thr | Arg | Ala | Glu | Glu |
| | | | 115 | | | | | 120 | | | | | 125 | | |
| Leu | Asp | Lys | Glu | Met | Gly | Leu | Ile | Ile | Arg | Gln | Glu | Thr | Gly | Arg | |
| | 130 | | | | | 135 | | | | | 140 | | | | |
| His | Val | Arg | Met | Leu | Thr | His | Glu | Ile | Arg | Ser | Thr | Leu | Asp | Arg | His |
| 145 | | | | | 150 | | | | | 155 | | | | | 160 |
| Thr | Ile | Leu | Lys | Thr | Thr | Leu | Val | Glu | Leu | Gly | Arg | Thr | Leu | Asp | Leu |
| | | | | 165 | | | | | 170 | | | | | 175 | |
| Ala | Glu | Cys | Ala | Leu | Trp | Met | Pro | Cys | Gln | Gly | Gly | Leu | Thr | Leu | Gln |
| | | | 180 | | | | | 185 | | | | | 190 | | |
| Leu | Ser | His | Asn | Leu | Asn | Asn | Leu | Ile | Pro | Leu | Gly | Ser | Thr | Val | Pro |
| | | 195 | | | | | 200 | | | | | 205 | | | |
| Ile | Asn | Leu | Pro | Ile | Ile | Asn | Glu | Ile | Phe | Ser | Ser | Pro | Glu | Ala | Ile |
| | 210 | | | | | 215 | | | | | 220 | | | | |
| Gln | Ile | Pro | His | Thr | Asn | Pro | Leu | Ala | Arg | Met | Arg | Asn | Thr | Val | Gly |
| 225 | | | | | 230 | | | | | 235 | | | | | 240 |
| Arg | Tyr | Ile | Pro | Pro | Glu | Val | Val | Ala | Val | Arg | Val | Pro | Leu | Leu | His |
| | | | | 245 | | | | | 250 | | | | | 255 | |
| Leu | Ser | Asn | Phe | Thr | Asn | Asp | Trp | Ala | Glu | Leu | Ser | Thr | Arg | Ser | Tyr |
| | | | 260 | | | | | 265 | | | | | 270 | | |
| Ala | Val | Met | Val | Leu | Val | Leu | Pro | Met | Asn | Gly | Leu | Arg | Lys | Trp | Arg |

|     |     |     |     | 275 |     |     |     | 280 |     |     |     | 285 |     |     |
| --- | --- | --- | --- | --- | --- | --- | --- | --- | --- | --- | --- | --- | --- | --- |
| Glu | His | Glu | Leu | Glu | Leu | Val | Gln | Val | Val | Ala | Asp | Gln | Val | Ala | Val |
|     | 290 |     |     |     | 295 |     |     |     |     | 300 |     |     |     |     |
| Ala | Leu | Ser | His | Ala | Ala | Ile | Leu | Glu | Asp | Ser | Met | Arg | Ala | His | Asp |
| 305 |     |     |     | 310 |     |     |     |     | 315 |     |     |     |     |     | 320 |
| Gln | Leu | Met | Glu | Gln | Asn | Ile | Ala | Leu | Asp | Val | Ala | Arg | Gln | Glu | Ala |
|     |     |     |     | 325 |     |     |     |     | 330 |     |     |     |     | 335 |     |
| Glu | Met | Ala | Ile | Arg | Ala | Arg | Asn | Asp | Phe | Leu | Ala | Val | Met | Asn | His |
|     |     |     | 340 |     |     |     |     | 345 |     |     |     |     | 350 |     |     |
| Glu | Met | Arg | Thr | Pro | Met | His | Ala | Val | Ile | Ala | Leu | Cys | Ser | Leu | Leu |
|     |     | 355 |     |     |     |     | 360 |     |     |     |     | 365 |     |     |     |
| Leu | Glu | Thr | Asp | Leu | Thr | Pro | Glu | Gln | Arg | Val | Met | Ile | Glu | Thr | Ile |
|     | 370 |     |     |     |     | 375 |     |     |     |     | 380 |     |     |     |     |
| Leu | Lys | Ser | Ser | Asn | Leu | Leu | Ala | Thr | Leu | Ile | Asn | Asp | Val | Leu | Asp |
| 385 |     |     |     |     | 390 |     |     |     |     | 395 |     |     |     |     | 400 |
| Leu | Ser | Arg | Leu | Glu | Asp | Gly | Ile | Leu | Glu | Leu | Glu | Asn | Gly | Thr | Phe |
|     |     |     |     | 405 |     |     |     |     | 410 |     |     |     |     | 415 |     |
| Asn | Leu | His | Gly | Ile | Leu | Arg | Glu | Ala | Val | Asn | Leu | Ile | Lys | Pro | Ile |
|     |     |     | 420 |     |     |     |     | 425 |     |     |     |     | 430 |     |     |
| Ala | Ser | Leu | Lys | Lys | Leu | Ser | Ile | Thr | Leu | Ala | Leu | Ala | Leu | Asp | Leu |
|     |     | 435 |     |     |     |     | 440 |     |     |     |     | 445 |     |     |     |
| Pro | Ile | Leu | Ala | Val | Gly | Asp | Ala | Lys | Arg | Leu | Ile | Gln | Thr | Leu | Leu |
|     | 450 |     |     |     |     | 455 |     |     |     |     | 460 |     |     |     |     |
| Asn | Val | Val | Gly | Asn | Ala | Val | Lys | Phe | Thr | Lys | Glu | Gly | His | Ile | Ser |
| 465 |     |     |     |     | 470 |     |     |     |     | 475 |     |     |     |     | 480 |
| Ile | Glu | Ala | Ser | Val | Ala | Lys | Pro | Glu | Tyr | Ala | Arg | Asp | Cys | His | Pro |
|     |     |     |     | 485 |     |     |     |     | 490 |     |     |     |     | 495 |     |
| Pro | Glu | Met | Phe | Pro | Met | Pro | Ser | Asp | Gly | Gln | Phe | Tyr | Leu | Arg | Val |
|     |     |     | 500 |     |     |     |     | 505 |     |     |     |     | 510 |     |     |
| Gln | Val | Arg | Asp | Thr | Gly | Cys | Gly | Ile | Ser | Pro | Gln | Asp | Ile | Pro | Leu |
|     |     | 515 |     |     |     |     | 520 |     |     |     |     | 525 |     |     |     |
| Val | Phe | Thr | Lys | Phe | Ala | Glu | Ser | Arg | Pro | Thr | Ser | Asn | Arg | Ser | Thr |
|     | 530 |     |     |     |     | 535 |     |     |     |     | 540 |     |     |     |     |
| Gly | Gly | Glu | Gly | Leu | Gly | Leu | Ala | Ile | Trp | Arg | Arg | Phe | Ile | Gln | Leu |
| 545 |     |     |     |     | 550 |     |     |     |     | 555 |     |     |     |     | 560 |
| Met | Lys | Gly | Asn | Ile | Trp | Ile | Glu | Ser | Glu | Gly | Pro | Gly | Lys | Gly | Thr |
|     |     |     |     | 565 |     |     |     |     | 570 |     |     |     |     | 575 |     |
| Thr | Val | Thr | Phe | Val | Val | Lys | Leu | Gly | Ile | Cys | His | His | Pro | Asn | Ala |
|     |     |     | 580 |     |     |     |     | 585 |     |     |     |     | 590 |     |     |
| Leu | Pro | Leu | Leu | Pro | Met | Pro | Pro | Arg | Gly | Arg | Leu | Asn | Lys | Gly | Ser |
|     |     | 595 |     |     |     |     | 600 |     |     |     |     | 605 |     |     |     |
| Asp | Asp | Leu | Phe | Arg | Tyr | Arg | Gln | Phe | Arg | Gly | Asp | Asp | Gly | Gly | Met |
|     | 610 |     |     |     |     | 615 |     |     |     |     | 620 |     |     |     |     |
| Ser | Val | Asn | Ala | Gln | Arg | Tyr | Gln | Arg | Ser | Met |     |     |     |     |     |
| 625 |     |     |     |     | 630 |     |     |     | 635 |     |     |     |     |     |     |

( 2 ) INFORMATION FOR SEQ ID NO:37:

( i ) SEQUENCE CHARACTERISTICS:
        ( A ) LENGTH: 4566 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: join(763..1671, 3062..3433, 3572..3838, 3969

. . 4096, 4234..4402)

( x i ) SEQUENCE DESCRIPTION: SEQ ID NO:37:

| | | | | | |
|---|---|---|---|---|---|
| AGATCTGGTA | CTACCAAAAG | GTATCCAATT | AATCCATGCT | TGGCCTCCCA | TTACAATGCC | 60 |
| TGTAAGAAAT | AATTGTTCTT | TCCACCTCCA | CAACTAATTG | TCGAACTATT | ATATCTATCT | 120 |
| TTATTCCCTT | AAATGTGAAA | CGAATTACAC | AGACTATTTG | GCGCTACTTT | TTTCCTAGAT | 180 |
| ATATTGAAGA | CCTAGTTTCT | TATATTTGTG | GGAAGCATTT | GGAAGTTCTA | TAAGAACTAT | 240 |
| ATCATGTTCG | AAAACATTCT | TATAATTTTC | GACAAGATTG | CTGAAGGAGT | GTCTTATCTT | 300 |
| TTATGTATTC | TTGACTAGAG | GAGTTTAATA | AAAAGAAAAT | AGAAGGAAC | AAAGAAACGT | 360 |
| ACAAGTGTAT | AAAAGGAGTT | GGGGCAAAGA | CATCAGAAAC | ATTTAGACCT | ACGATTTCAT | 420 |
| CCTACATGTT | ATGGTTTTAG | TTCGTTAGAG | GTTTTAACAT | ATTAAATCAG | CAAAGTTGTG | 480 |
| ACATACATAA | AGTGCATAAC | ATAAAGATGA | AATTCACAAT | TGCTGGATC | TTTTGGTGCA | 540 |
| AGGGAACTAT | TTTTTACACT | ATAAGTTAGC | TGTTAATTTC | AATATTGGCT | CTTCTACACC | 600 |
| TTGTTGTTCT | TGAGTATAAT | TCTATTTTGC | ATCAAACATA | TGTCAGAACT | TATGCTGCAA | 660 |
| TTAAATATAT | TCAGGTTGTT | TAACTCTTGT | ACAGCTTGTT | ATTCTTCTGA | GGTCTATTTC | 720 |
| CTTCTCCTTA | TTTGCTAACT | TGTGCTGCAG | TTATCTTCCA | TC GTG GAG | TCA TGT | 774 |
| | | | | Val Glu | Ser Cys | |
| | | | | 1 | | |

```
AAC TGC ATC ATT GAC CCA CAG TTG CCT GCT GAC GAC TTG CTA ATG AAG    822
Asn Cys Ile Ile Asp Pro Gln Leu Pro Ala Asp Asp Leu Leu Met Lys
  5              10                  15                      20

TAT CAG TAC ATT TCT GAT TTT TTC ATA GCA CTT GCT TAT TTC TCC ATT    870
Tyr Gln Tyr Ile Ser Asp Phe Phe Ile Ala Leu Ala Tyr Phe Ser Ile
                25                  30                  35

CCA GTG GAG TTG ATA TAC TTC GTT AAG AAG TCT GCT GTC TTT CCA TAT    918
Pro Val Glu Leu Ile Tyr Phe Val Lys Lys Ser Ala Val Phe Pro Tyr
          40                  45                  50

AGA TGG GTT CTT GTG CAG TTC GGT GCT TTC ATA GTT CTT TGT GGA GCA    966
Arg Trp Val Leu Val Gln Phe Gly Ala Phe Ile Val Leu Cys Gly Ala
              55                  60                  65

ACC CAT CTT ATC AAC TTA TGG ACA TTT AAT ATG CAT ACA AGG AAT GTG    1014
Thr His Leu Ile Asn Leu Trp Thr Phe Asn Met His Thr Arg Asn Val
        70                  75                  80

GCA ATA GTA ATG ACT ACT GCA AAG GCC TTG ACT GCA CTG GTG TCA TGT    1062
Ala Ile Val Met Thr Thr Ala Lys Ala Leu Thr Ala Leu Val Ser Cys
 85                  90                  95                 100

ATA ACT GCT CTC ATG CTT GTC CAC ATC ATT CCT GAT TTA TTA AGT GTC    1110
Ile Thr Ala Leu Met Leu Val His Ile Ile Pro Asp Leu Leu Ser Val
                105                 110                 115

AAA ACT AGA GAA CTG TTC TTG AAA AAG AAA GCT GCA CAG CTT GAC CGT    1158
Lys Thr Arg Glu Leu Phe Leu Lys Lys Lys Ala Ala Gln Leu Asp Arg
                    120                 125                 130

GAA ATG GGT ATT ATT CGG ACT CAG GAG GAG ACA GGT AGA CAT GTT AGA    1206
Glu Met Gly Ile Ile Arg Thr Gln Glu Glu Thr Gly Arg His Val Arg
            135                 140                 145

ATG CTA ACT CAT GAA ATC CGA AGC ACT CTT GAT AGA CAT ACT ATT TTA    1254
Met Leu Thr His Glu Ile Arg Ser Thr Leu Asp Arg His Thr Ile Leu
        150                 155                 160

AAG ACT ACA CTT GTT GAG CTA GGA AGA ACA TTG GCA TTG GAA GAG TGT    1302
Lys Thr Thr Leu Val Glu Leu Gly Arg Thr Leu Ala Leu Glu Glu Cys
165                 170                 175                 180

GCA TTA TGG ATG CCA ACA CGT ACT GGA CTA GAG CTT CAG CTT TCT TAC    1350
Ala Leu Trp Met Pro Thr Arg Thr Gly Leu Glu Leu Gln Leu Ser Tyr
                185                 190                 195
```

| | | | | | | | | | | | | | | | | |
|---|---|---|---|---|---|---|---|---|---|---|---|---|---|---|---|---|
|ACT|TTA|CGA|CAC|CAA|AAT|CCA|GTT|GGA|TTA|ACT|GTA|CCC|ATT|CAA|CTT|1398|
|Thr|Leu|Arg|His 200|Gln|Asn|Pro|Val 205|Gly|Leu|Thr|Val|Pro 210|Ile|Gln|Leu| |
|CCT|GTA|ATC|AAT|CAA|GTT|TTC|GGT|ACA|AAT|CAT|GTC|GTG|AAA|ATA|TCA|1446|
|Pro|Val|Ile 215|Asn|Gln|Val|Phe|Gly 220|Thr|Asn|His|Val|Val 225|Lys|Ile|Ser| |
|CCA|AAT|TCT|CCT|GTC|GCA|AGA|CTT|CGA|CCT|GCT|GGG|AAA|TAC|ATG|CCT|1494|
|Pro|Asn 230|Ser|Pro|Val|Ala|Arg 235|Leu|Arg|Pro|Ala|Gly 240|Lys|Tyr|Met|Pro| |
|GGT|GAG|GTG|GTT|GCT|GTC|AGG|GTT|CCA|CTT|CTG|CAT|CTG|TCG|AAC|TTT|1542|
|Gly 245|Glu|Val|Val|Ala|Val 250|Arg|Val|Pro|Leu|Leu 255|His|Leu|Ser|Asn|Phe 260| |
|CAG|ATT|AAT|GAT|TGG|CCT|GAA|CTT|TCA|ACA|AAG|CGC|TAT|GCT|TTA|ATG|1590|
|Gln|Ile|Asn|Asp|Trp 265|Pro|Glu|Leu|Ser|Thr 270|Lys|Arg|Tyr|Ala|Leu 275|Met| |
|GTT|CTG|ATG|CTT|CCT|TCA|GAC|AGT|GCA|AGA|CAA|TGG|CAT|GTT|CAT|GAG|1638|
|Val|Leu|Met|Leu 280|Pro|Ser|Asp|Ser|Ala 285|Arg|Gln|Trp|His|Val 290|His|Glu| |
|CTG|GAG|CTT|GTT|GAA|GTG|GTA|GCT|GAT|CAG|GTT|TGATTTTGT|TATTGAAAAT| | | |1691|
|Leu|Glu|Leu 295|Val|Glu|Val|Val|Ala 300|Asp|Gln|Val| | | | | | |

TCCTTAATAT AATGTTAAAA TTTCTCTTTT ATATATTTTT GGGTTGAACA CAACCACGTT 1751

GACATACTGA GTTCTGGGTG TAAAATTAGA CATGGAGAAG ACCAATTACA AAAATCTGAG 1811

AATCTGCTAG CAGAATCACA AGGCTTAGTT GTTCTTAGTA TTATGGTTTT ATCCATTGGA 1871

ATTGCACAGC AGAATTGTTA TTACTGTTAT TTTTTTTTAA AATTTTCAAA GATAAATCAA 1931

AAGCTGAACT ATATGACTTT TTGCATACTT CGTCTGCTGA TTGCTTTTTG GTGATGGAAT 1991

AGTTAGGCTG GGTTGTGGAT GAGTATATCA TAGTAGATTT TCTGATAGGA TCTTAACTCC 2051

TTGGCTTTTG TTTTCTATAG ATGATCCCTT GTATTAGAAG CACGGGAAAT AGGATCGATG 2111

GTATATAGAA ATATTAGGAA CAGCTTTCTG AATCATTTGA ATATTCCTTT TATGGAACAT 2171

AGAACTCTTG ACGTGTATGT AGTTTTCTTA GTACTTTTAT CATATGAAGT GAAAATAACG 2231

TTTTGCGATA ATGTATTTGA GTGTGTAAAA TTAAATACTA CTGAGTTTTA CAAAAATAAT 2291

TCTTCAACGG AAGCCATTTA TTTTTTTTAC ATATCTGGCA TCTTACTTCT CCATCAAAGA 2351

CTTTAGAGAA CTTTAACTTT TTCATTCTGT CTCTCGTAGT GTACTGTTCT CTGATGTATG 2411

TAATTAGCTC ACTGGCAAGT AGCACACCTA GTCTTTGTTT GACTTGTTTA AAAATCATGA 2471

TGTATCATCA GTTACGGTGA AGTGTCCAAG TTTTACTGCT TTTTGCTATT TGCATTGCAG 2531

AGTCTTAAAA CATTTCAGTT ATTCCTGGAT TTCTCCTGTT TATCAATGGA AAATTCAACT 2591

ATCAACTATG CCTCAATCAA TAAATGAAAC CTCTATATCT AACCACTCCA ACTCAGATCC 2651

AGAAATCAGA TTTCAAAGAA ATTCATCATA ACTCAACTAT AGGATTGCTG TTAACCAAGA 2711

GTAATCCTCA TTTGTCCAGA CAGGCGACCA GCTATTATGC TTTCATTATG GGAAAAATTG 2771

ACAATTAATT AAAGGAAGGA ACAACTGAAG AAAAGACATC CTTGTCAGCT TCCTCTCCCA 2831

ACCCTTGCCT GAATAAGACA AAAAGTTTCT TGGAGAAAAC TCTGAATATT GGTATCCACC 2891

TCCTTTCTCC TAATTTAGGA TGCTCTATTT CTAGACATAT AGGGGAATAC TCTATTCTAG 2951

TGGTCGGTGT CTGGTTGCAA CTAGTTTTAG ATGTTTATAT GTCTTATTTG ATTTAATAAG 3011

| | | | | | | | | | | |
|---|---|---|---|---|---|---|---|---|---|---|
|AGCTATCCTT|GAGTGCCCAA|TGTGATTTAA|TCTACGCTTC|GGCATTTCAG|GTT|GCT| | | |3067|
| | | | | |Val|Ala 305| | | | |
|GTT|GCT|CTT|TCA|CAT|GCT|GCT|ATA|TTA|GAA|GAA|TCA|ATG|AGG|GCT|AGG|3115|
|Val|Ala|Leu|Ser|His 310|Ala|Ala|Ile|Leu|Glu 315|Glu|Ser|Met|Arg|Ala 320|Arg| |

| | | | | | | | | | | | | | | | | |
|---|---|---|---|---|---|---|---|---|---|---|---|---|---|---|---|---|
| GAT | CTT | CTT | ATG | GAG | CAG | AAT | GTG | GCT | CTT | GAT | CTG | GCA | AGA | AGA | GAA | 3163 |
| Asp | Leu | Leu | Met | Glu | Gln | Asn | Val | Ala | Leu | Asp | Leu | Ala | Arg | Arg | Glu | |
| | | | | 325 | | | | 330 | | | | | 335 | | | |
| GCA | GAA | ATG | GCT | GTT | CGT | GCA | CGT | AAT | GAT | TTC | TTG | GCT | GTT | ATG | AAT | 3211 |
| Ala | Glu | Met | Ala | Val | Arg | Ala | Arg | Asn | Asp | Phe | Leu | Ala | Val | Met | Asn | |
| | | | 340 | | | | 345 | | | | | 350 | | | | |
| CAT | GAA | ATG | AGA | ACT | CCC | ATG | CAT | GCA | ATA | ATT | GCA | CTT | TCT | TCC | TTA | 3259 |
| His | Glu | Met | Arg | Thr | Pro | Met | His | Ala | Ile | Ile | Ala | Leu | Ser | Ser | Leu | |
| | 355 | | | | | 360 | | | | | 365 | | | | | |
| CTA | CAA | GAA | ATC | GAT | CTA | ACT | CCA | GAG | CAA | CGT | CTG | ATG | GTT | GAA | ACA | 3307 |
| Leu | Gln | Glu | Ile | Asp | Leu | Thr | Pro | Glu | Gln | Arg | Leu | Met | Val | Glu | Thr | |
| 370 | | | | | 375 | | | | | 380 | | | | | 385 | |
| ATC | CTC | AAA | AGC | AGC | AAC | CTT | TTA | GCA | ACG | CTC | ATC | AAC | GAT | GTC | TTG | 3355 |
| Ile | Leu | Lys | Ser | Ser | Asn | Leu | Leu | Ala | Thr | Leu | Ile | Asn | Asp | Val | Leu | |
| | | | | 390 | | | | | 395 | | | | | 400 | | |
| GAT | CTT | TCA | AGG | CTA | GAG | GAT | GGA | AGT | CTT | CAA | CTT | GAT | ATT | GGC | ACT | 3403 |
| Asp | Leu | Ser | Arg | Leu | Glu | Asp | Gly | Ser | Leu | Gln | Leu | Asp | Ile | Gly | Thr | |
| | | | 405 | | | | | 410 | | | | | 415 | | | |
| TTC | AAT | CTC | CAT | GCT | TTA | TTT | AGA | GAG | GTG | CCCTTCATCA | | | CCCTCTTTTC | | | 3453 |
| Phe | Asn | Leu | His | Ala | Leu | Phe | Arg | Glu | Val | | | | | | | |
| | | 420 | | | | | 425 | | | | | | | | | |
| TTTTTTACTT | GCAAATTCTA | GATTACCTGT | CAGAAAAAAA | GTGTCATTAC | AGATATTTTG | 3513 |
| CACTTCAATA | TGTTTGCTGG | ACCTGCTGAC | TGATATATGT | GTCTGCTTAT | TCCTGTAG | 3571 |

| | | | | | | | | | | | | | | | | |
|---|---|---|---|---|---|---|---|---|---|---|---|---|---|---|---|---|
| GTC | CAT | AGC | TTA | ATC | AAG | CCT | ATT | GCA | TCT | GTG | AAA | AAG | TCT | GTT | GCT | 3619 |
| Val | His | Ser | Leu | Ile | Lys | Pro | Ile | Ala | Ser | Val | Lys | Lys | Ser | Val | Ala | |
| | | 430 | | | | | 435 | | | | | 440 | | | | |
| CAA | CTT | AGT | TTG | TCG | TCA | GAT | TTG | CCG | GAA | TAT | GTA | ATT | GGG | GAT | GAA | 3667 |
| Gln | Leu | Ser | Leu | Ser | Ser | Asp | Leu | Pro | Glu | Tyr | Val | Ile | Gly | Asp | Glu | |
| | | | 445 | | | | | 450 | | | | | 455 | | | |
| AAA | CGG | TTA | ATG | CAA | ATT | CTC | TTA | AAC | GTT | GTT | GGC | AAT | GCT | GTA | AAG | 3715 |
| Lys | Arg | Leu | Met | Gln | Ile | Leu | Leu | Asn | Val | Val | Gly | Asn | Ala | Val | Lys | |
| 460 | | | | | 465 | | | | | 470 | | | | | 475 | |
| TTC | TCA | AAG | GAA | GGC | AAC | GTA | TCA | ATC | TCC | GCT | TTT | GTT | GCA | AAA | TCA | 3763 |
| Phe | Ser | Lys | Glu | Gly | Asn | Val | Ser | Ile | Ser | Ala | Phe | Val | Ala | Lys | Ser | |
| | | | | 480 | | | | | 485 | | | | | 490 | | |
| GAC | TCT | TTA | AGA | GAT | CCT | AGA | GCC | CCT | GAA | TTT | TTT | GCT | GTG | CCT | AGT | 3811 |
| Asp | Ser | Leu | Arg | Asp | Pro | Arg | Ala | Pro | Glu | Phe | Phe | Ala | Val | Pro | Ser | |
| | | | 495 | | | | | 500 | | | | | 505 | | | |
| GAA | AAT | CAC | TTC | TAT | TTA | CGG | GTG | CAG | GTATATTTTT | | | ACAAGCTTGA | | | | 3858 |
| Glu | Asn | His | Phe | Tyr | Leu | Arg | Val | Gln | | | | | | | | |
| | | 510 | | | | | 515 | | | | | | | | | |

| | | | | | |
|---|---|---|---|---|---|
| TATACTATCT | TCGTAGGTTA | AGGATAGTCA | CAAATATGAT | ATTTTAGACT | TATAACTGTC | 3918 |
| AGATGTTCTG | TTCTTGATAT | TTGTAATATT | CTAAGTAATA | CTTTCTGTAG | ATA AAA | 3974 |
| | | | | | Ile Lys |

| | | | | | | | | | | | | | | | | |
|---|---|---|---|---|---|---|---|---|---|---|---|---|---|---|---|---|
| GAT | ACG | GGG | ATA | GGA | ATT | ACA | CCA | CAG | GAT | ATT | CCC | AAC | CTG | TTT | AGC | 4022 |
| Asp | Thr | Gly | Ile | Gly | Ile | Thr | Pro | Gln | Asp | Ile | Pro | Asn | Leu | Phe | Ser | |
| | 520 | | | | | 525 | | | | | 530 | | | | | |
| AAG | TTT | ACA | CAA | AGC | CAA | GCG | CTA | GCA | ACT | ACA | AAT | TCT | GGT | GGC | ACT | 4070 |
| Lys | Phe | Thr | Gln | Ser | Gln | Ala | Leu | Ala | Thr | Thr | Asn | Ser | Gly | Gly | Thr | |
| 535 | | | | | 540 | | | | | 545 | | | | | 550 | |
| GGG | CTT | GGT | CTT | GCA | ATT | TGT | AAG | AG | | GTACGGGTAC | | CAGTTCCTTA | | | | 4116 |
| Gly | Leu | Gly | Leu | Ala | Ile | Cys | Lys | Arg | | | | | | | | |
| | | | | 555 | | | | | | | | | | | | |

| | | | | | |
|---|---|---|---|---|---|
| GTGTTCTTTT | TCCGACTCTG | ATTTTCATTC | TACGTGAACT | TGGTAACTGC | TTCATATTCA | 4176 |
| ATTTCTTTCT | CTTACTGTAT | TTACGTATTG | ACACATCTCC | TGATGGACA | CAAAAAG G | 4234 |

| | | | | | | | | | | | | | | | | |
|---|---|---|---|---|---|---|---|---|---|---|---|---|---|---|---|---|
| TTT | GTG | AAT | CTT | ATG | GAA | GGA | CAT | ATT | TGG | ATT | GAA | AGT | GAA | GGT | CTT | 4282 |
| Phe | Val | Asn | Leu | Met | Glu | Gly | His | Ile | Trp | Ile | Glu | Ser | Glu | Gly | Leu | |
| 560 | | | | | 565 | | | | | 570 | | | | | 575 | |

|   |   |   |   |   |   |   |   |   |   |   |   |   |   |   |   |
|---|---|---|---|---|---|---|---|---|---|---|---|---|---|---|---|
| GGC | AAG | GGG | TCT | ACT | GCT | ATA | TTT | ATC | ATT | AAA | CTT | GGA | CTT | CCT | GGA | 4330
| Gly | Lys | Gly | Ser | Thr | Ala | Ile | Phe | Ile | Ile | Lys | Leu | Gly | Leu | Pro | Gly |
|     |     |     |     | 580 |     |     |     | 585 |     |     |     |     |     | 590 |     |

```
GGC AAG GGG TCT ACT GCT ATA TTT ATC ATT AAA CTT GGA CTT CCT GGA      4330
Gly Lys Gly Ser Thr Ala Ile Phe Ile Ile Lys Leu Gly Leu Pro Gly
            580                 585                     590

CGT GCA AAT GAA TCT AAG CTC CCC TTT GTG ACC AAA TTG CCA GCA AAT      4378
Arg Ala Asn Glu Ser Lys Leu Pro Phe Val Thr Lys Leu Pro Ala Asn
            595                 600                     605

CAC ACG CAG ATG AGT TTT AAG GAT TAAAGGTTTT GGTGATGGAT GAGAATGGGT     4432
His Thr Gln Met Ser Phe Lys Asp
            610                 615

GAGTACTATC TGGACCCCTT TATCCTCGAC TCTTGTCTTG CCATGCTGTT TAATGATCCA    4492

TCTGATTGCG TGATTTCTCA TCTTATATGT ATTGAGCTGT CTTACTCACT TTACATGAGA    4552

CTACAGTAAT ACTT                                                      4566
```

( 2 ) INFORMATION FOR SEQ ID NO:38:

( i ) SEQUENCE CHARACTERISTICS:
        ( A ) LENGTH: 615 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

```
Val Glu Ser Cys Asn Cys Ile Ile Asp Pro Gln Leu Pro Ala Asp Asp
 1               5                  10                      15

Leu Leu Met Lys Tyr Gln Tyr Ile Ser Asp Phe Phe Ile Ala Leu Ala
            20                  25                  30

Tyr Phe Ser Ile Pro Val Glu Leu Ile Tyr Phe Val Lys Lys Ser Ala
            35                  40                  45

Val Phe Pro Tyr Arg Trp Val Leu Val Gln Phe Gly Ala Phe Ile Val
        50                  55                  60

Leu Cys Gly Ala Thr His Leu Ile Asn Leu Trp Thr Phe Asn Met His
 65                 70                  75                  80

Thr Arg Asn Val Ala Ile Val Met Thr Thr Ala Lys Ala Leu Thr Ala
                85                  90                  95

Leu Val Ser Cys Ile Thr Ala Leu Met Leu Val His Ile Ile Pro Asp
                100                 105                 110

Leu Leu Ser Val Lys Thr Arg Glu Leu Phe Leu Lys Lys Lys Ala Ala
            115                 120                 125

Gln Leu Asp Arg Glu Met Gly Ile Ile Arg Thr Gln Glu Glu Thr Gly
    130                 135                 140

Arg His Val Arg Met Leu Thr His Glu Ile Arg Ser Thr Leu Asp Arg
145                 150                 155                 160

His Thr Ile Leu Lys Thr Thr Leu Val Glu Leu Gly Arg Thr Leu Ala
            165                 170                 175

Leu Glu Glu Cys Ala Leu Trp Met Pro Thr Arg Thr Gly Leu Glu Leu
            180                 185                 190

Gln Leu Ser Tyr Thr Leu Arg His Gln Asn Pro Val Gly Leu Thr Val
    195                 200                 205

Pro Ile Gln Leu Pro Val Ile Asn Gln Val Phe Gly Thr Asn His Val
    210                 215                 220

Val Lys Ile Ser Pro Asn Ser Pro Val Ala Arg Leu Arg Pro Ala Gly
225                 230                 235                 240

Lys Tyr Met Pro Gly Glu Val Val Ala Val Arg Val Pro Leu Leu His
            245                 250                 255

Leu Ser Asn Phe Gln Ile Asn Asp Trp Pro Glu Leu Ser Thr Lys Arg
```

|     |     |     |     | 260 |     |     |     |     | 265 |     |     |     |     | 270 |     |
|-----|-----|-----|-----|-----|-----|-----|-----|-----|-----|-----|-----|-----|-----|-----|-----|

Tyr Ala Leu Met Val Leu Met Leu Pro Ser Asp Ser Ala Arg Gln Trp
            275                 280                 285

His Val His Glu Leu Glu Leu Val Glu Val Val Ala Asp Gln Val Val
    290                 295                 300

Ala Val Ala Leu Ser His Ala Ala Ile Leu Glu Glu Ser Met Arg Ala
305                 310                 315                 320

Arg Asp Leu Leu Met Glu Gln Asn Val Ala Leu Asp Leu Ala Arg Arg
                325                 330                 335

Glu Ala Glu Met Ala Val Arg Ala Arg Asn Asp Phe Leu Ala Val Met
            340                 345                 350

Asn His Glu Met Arg Thr Pro Met His Ala Ile Ile Ala Leu Ser Ser
        355                 360                 365

Leu Leu Gln Glu Ile Asp Leu Thr Pro Glu Gln Arg Leu Met Val Glu
    370                 375                 380

Thr Ile Leu Lys Ser Ser Asn Leu Leu Ala Thr Leu Ile Asn Asp Val
385                 390                 395                 400

Leu Asp Leu Ser Arg Leu Glu Asp Gly Ser Leu Gln Leu Asp Ile Gly
            405                 410                 415

Thr Phe Asn Leu His Ala Leu Phe Arg Glu Val Val His Ser Leu Ile
        420                 425                 430

Lys Pro Ile Ala Ser Val Lys Lys Ser Val Ala Gln Leu Ser Leu Ser
        435                 440                 445

Ser Asp Leu Pro Glu Tyr Val Ile Gly Asp Glu Lys Arg Leu Met Gln
    450                 455                 460

Ile Leu Leu Asn Val Val Gly Asn Ala Val Lys Phe Ser Lys Glu Gly
465                 470                 475                 480

Asn Val Ser Ile Ser Ala Phe Val Ala Lys Ser Asp Ser Leu Arg Asp
            485                 490                 495

Pro Arg Ala Pro Glu Phe Phe Ala Val Pro Ser Glu Asn His Phe Tyr
            500                 505                 510

Leu Arg Val Gln Ile Lys Asp Thr Gly Ile Gly Ile Thr Pro Gln Asp
        515                 520                 525

Ile Pro Asn Leu Phe Ser Lys Phe Thr Gln Ser Gln Ala Leu Ala Thr
    530                 535                 540

Thr Asn Ser Gly Gly Thr Gly Leu Gly Leu Ala Ile Cys Lys Arg Phe
545                 550                 555                 560

Val Asn Leu Met Glu Gly His Ile Trp Ile Glu Ser Glu Gly Leu Gly
            565                 570                 575

Lys Gly Ser Thr Ala Ile Phe Ile Ile Lys Leu Gly Leu Pro Gly Arg
            580                 585                 590

Ala Asn Glu Ser Lys Leu Pro Phe Val Thr Lys Leu Pro Ala Asn His
        595                 600                 605

Thr Gln Met Ser Phe Lys Asp
    610                 615

( 2 ) INFORMATION FOR SEQ ID NO:39:

( i ) SEQUENCE CHARACTERISTICS:
        ( A ) LENGTH: 737 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 33..719

( x i ) SEQUENCE DESCRIPTION: SEQ ID NO:39:

```
AAGATAAGAG TGATTCATTA AGGAGTTTGT TC ATC ATG GAT TGT AAC TGC TTC          53
                                       Ile Met Asp Cys Asn Cys Phe
                                        1               5

GAT CCA CTG TTG CCT GCC GAT GAG TTG TTA ATG AAG TAT CAG TAC ATT         101
Asp Pro Leu Leu Pro Ala Asp Glu Leu Leu Met Lys Tyr Gln Tyr Ile
         10              15                  20

TCT GAT TTT TTC ATT GCA GTT GCT TAT TTC TCC ATC CCA ATC GAA CTG         149
Ser Asp Phe Phe Ile Ala Val Ala Tyr Phe Ser Ile Pro Ile Glu Leu
     25              30                  35

GTA TTC TTT GTC CAG AAA TCA GCT GTT TTT CCG TAT CGA TGG GTG CTT         197
Val Phe Phe Val Gln Lys Ser Ala Val Phe Pro Tyr Arg Trp Val Leu
 40              45                  50                      55

GTG CAG TTT GGT GCT TTC ATA GTT CTT TGT GGA GCA ACA CAC CTT ATC         245
Val Gln Phe Gly Ala Phe Ile Val Leu Cys Gly Ala Thr His Leu Ile
                 60              65                      70

AAT TTG TGG ACT TCT ACT CCT CAT ACA AGG ACT GTG GCA ATG GTG ATG         293
Asn Leu Trp Thr Ser Thr Pro His Thr Arg Thr Val Ala Met Val Met
             75              80                  85

ACT ACG GCG AAG TTC TCC ACT GCT GCG GTA TCA TGT GCA ACT GCT GTC         341
Thr Thr Ala Lys Phe Ser Thr Ala Ala Val Ser Cys Ala Thr Ala Val
         90              95                 100

ATG CTT GTC GCA ATT ATT CCG GAT TTA TTA AGT GTC AAA ACT AGG GAG         389
Met Leu Val Ala Ile Ile Pro Asp Leu Leu Ser Val Lys Thr Arg Glu
105             110                 115

CTA TTC TTG AAA AAC AAA GCG GCG GAA CTT GAT CGT GAA ATG GGT CTT         437
Leu Phe Leu Lys Asn Lys Ala Ala Glu Leu Asp Arg Glu Met Gly Leu
120             125                 130                     135

ATT CGG ACA CAG GAG GAG ACG GGT AGA TAT GTT AGA ATG CTA ACA CAT         485
Ile Arg Thr Gln Glu Glu Thr Gly Arg Tyr Val Arg Met Leu Thr His
             140                 145                 150

GAA ATC AGA AGT ACT CTG GAT AGA CAT ACT ATT TTG AAG ACT ACA CTT         533
Glu Ile Arg Ser Thr Leu Asp Arg His Thr Ile Leu Lys Thr Thr Leu
             155                 160                 165

GTT GAA CTT GGA AGA GCA TTG CAA CTG GAA GAG TGT GCT TTG TGG ATG         581
Val Glu Leu Gly Arg Ala Leu Gln Leu Glu Glu Cys Ala Leu Trp Met
        170                 175                 180

CCG ACT CGA ACT GGA GTG GAG CTT CAA CTT TCT TAC ACT TTA CAT CAT         629
Pro Thr Arg Thr Gly Val Glu Leu Gln Leu Ser Tyr Thr Leu His His
185                 190                 195

CAA AAT CCA GTT GGA TTT ACA GTA CCT ATA CAA CTC CCT GTA ATT AAT         677
Gln Asn Pro Val Gly Phe Thr Val Pro Ile Gln Leu Pro Val Ile Asn
200                 205                 210                 215

CAA GTT TTC AGT GCA AAT TGT GCT GTT AAA ATT TCA CCT TAATCTGCCG          726
Gln Val Phe Ser Ala Asn Cys Ala Val Lys Ile Ser Pro
             220                 225

TTGCAAGGCT T                                                            737
```

( 2 ) INFORMATION FOR SEQ ID NO:40:

( i ) SEQUENCE CHARACTERISTICS:
        ( A ) LENGTH: 228 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

```
Ile Met Asp Cys Asn Cys Phe Asp Pro Leu Leu Pro Ala Asp Glu Leu
 1               5                  10                  15
```

| Leu | Met | Lys | Tyr | Gln | Tyr | Ile | Ser | Asp | Phe | Phe | Ile | Ala | Val | Ala | Tyr |
|---|---|---|---|---|---|---|---|---|---|---|---|---|---|---|---|
| | | | 20 | | | | 25 | | | | | 30 | | | |

| Phe | Ser | Ile | Pro | Ile | Glu | Leu | Val | Phe | Phe | Val | Gln | Lys | Ser | Ala | Val |
|---|---|---|---|---|---|---|---|---|---|---|---|---|---|---|---|
| | | 35 | | | | | 40 | | | | | 45 | | | |

| Phe | Pro | Tyr | Arg | Trp | Val | Leu | Val | Gln | Phe | Gly | Ala | Phe | Ile | Val | Leu |
|---|---|---|---|---|---|---|---|---|---|---|---|---|---|---|---|
| | 50 | | | | | 55 | | | | | 60 | | | | |

| Cys | Gly | Ala | Thr | His | Leu | Ile | Asn | Leu | Trp | Thr | Ser | Thr | Pro | His | Thr |
|---|---|---|---|---|---|---|---|---|---|---|---|---|---|---|---|
| 65 | | | | | 70 | | | | | 75 | | | | | 80 |

| Arg | Thr | Val | Ala | Met | Val | Met | Thr | Thr | Ala | Lys | Phe | Ser | Thr | Ala | Ala |
|---|---|---|---|---|---|---|---|---|---|---|---|---|---|---|---|
| | | | | 85 | | | | | 90 | | | | | 95 | |

| Val | Ser | Cys | Ala | Thr | Ala | Val | Met | Leu | Val | Ala | Ile | Ile | Pro | Asp | Leu |
|---|---|---|---|---|---|---|---|---|---|---|---|---|---|---|---|
| | | | 100 | | | | | 105 | | | | | 110 | | |

| Leu | Ser | Val | Lys | Thr | Arg | Glu | Leu | Phe | Leu | Lys | Asn | Lys | Ala | Ala | Glu |
|---|---|---|---|---|---|---|---|---|---|---|---|---|---|---|---|
| | | 115 | | | | | 120 | | | | | 125 | | | |

| Leu | Asp | Arg | Glu | Met | Gly | Leu | Ile | Arg | Thr | Gln | Glu | Glu | Thr | Gly | Arg |
|---|---|---|---|---|---|---|---|---|---|---|---|---|---|---|---|
| | 130 | | | | | 135 | | | | | 140 | | | | |

| Tyr | Val | Arg | Met | Leu | Thr | His | Glu | Ile | Arg | Ser | Thr | Leu | Asp | Arg | His |
|---|---|---|---|---|---|---|---|---|---|---|---|---|---|---|---|
| 145 | | | | | 150 | | | | | 155 | | | | | 160 |

| Thr | Ile | Leu | Lys | Thr | Leu | Val | Glu | Leu | Gly | Arg | Ala | Leu | Gln | Leu |
|---|---|---|---|---|---|---|---|---|---|---|---|---|---|---|
| | | | | 165 | | | | | 170 | | | | | 175 |

| Glu | Glu | Cys | Ala | Leu | Trp | Met | Pro | Thr | Arg | Thr | Gly | Val | Glu | Leu | Gln |
|---|---|---|---|---|---|---|---|---|---|---|---|---|---|---|---|
| | | | 180 | | | | | 185 | | | | | 190 | | |

| Leu | Ser | Tyr | Thr | Leu | His | His | Gln | Asn | Pro | Val | Gly | Phe | Thr | Val | Pro |
|---|---|---|---|---|---|---|---|---|---|---|---|---|---|---|---|
| | | 195 | | | | | 200 | | | | | 205 | | | |

| Ile | Gln | Leu | Pro | Val | Ile | Asn | Gln | Val | Phe | Ser | Ala | Asn | Cys | Ala | Val |
|---|---|---|---|---|---|---|---|---|---|---|---|---|---|---|---|
| | 210 | | | | | 215 | | | | | 220 | | | | |

| Lys | Ile | Ser | Pro |
|---|---|---|---|
| 225 | | | |

( 2 ) INFORMATION FOR SEQ ID NO:41:

( i ) SEQUENCE CHARACTERISTICS:
        ( A ) LENGTH: 6202 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: join(3522..5288, 5372..5926)

( x i ) SEQUENCE DESCRIPTION: SEQ ID NO:41:

```
GAATTCGAAC  TGCAATGGGA  TAAACATTAT  ATGCGTTTTA  ATAATAGGTT  GGTGAAGTTT      60
ATAATTTACA  CCATTTGAAA  AGCCTTCCAA  ATTAGAAAC   TACATTTTTG  CAGACCCATG     120
TGAGCTCATA  TGAATCAATC  ATAGCCTTGA  TGTTGTAAAA  CAAATTATGA  TTATAAAAAT    180
GTGATAGTAT  ATTACATGCA  TAAAAATAA   AGGAGAGTAA  ATGAAAGTCA  AATCTGGGTT    240
TTATGAACTG  AAAGTTGAAG  TTTAGAAGTA  GAAGTAGCGA  TCAAAGTATG  ACCAGTTAAA    300
AGGCCCAATA  TCATTTGGAG  GTTTGATTTT  TGGGTTCGTA  AATTTCAAGA  GCCAGATTAT    360
GATTTGCTGG  GCTTAAAAAT  CATGGAAAAA  TTGAAATGAC  GGTGTTAAAA  TATATAACTC    420
AAATTAAAGA  TTTTAATTGG  GTGTAGTAGG  CTGATTTTTT  TATAAGAATC  TTGTCTATAG    480
ATGCTTCAAG  GTTATGCCTT  ATAGTACTGG  TTGTAAAACA  CCACTATCTA  ATTTTGAAGC    540
TGGTCAGAAC  TATAAGGTAT  GTTGTTGTTC  GCCTTGTTGC  TAATGAAGAT  TATAACATTC    600
TGTTGTTGCA  TTTTTTTTTT  TTTTTTGTG   TTAAATATAT  ATATTTTTT   TGCATATTTA    660
TTGTTGCATA  TTGTGTTGCA  TATTTAGTAA  TGGTTACATT  CCCTGTTATC  GGAGACCAAG    720
```

```
ATAATACGGC TCTGTGGCAT GGACTACTAC TCCATGGATT CTTCCAAGTA ATCTTGCTTT    780
GTGTGTCAAT GCAAAGTTTG TTTATCTTAA GGTTCGTCAA CAACACTGGA AAAGTCTACA    840
TTGTTGCTGA ATCTCGGTTG TCATCGCTTC CTAGTGATAA GCCTAAGGCC GGCTTAACTA    900
ATGGAACTTA CTAGTGATAC CATAATGCGA AAGGTGCTAA TTAAGCTTGA CAGTGAAGAG    960
GATTCTTATC AAGTTTTGGA AAATTTTAAT GGAGATTCCT TGGTTGGGAA GAAGTATGAA   1020
CCTTTGTTTG ATTACTTTTA GCGATTTCTC AAGTGTGACT TTTCGACTAG TAGCAGATGA   1080
TTATGTCATG AATGATAGTG GTACTGGTAT TGTCCATTGT GCTCCTGTCT TGGTGCAGA    1140
TGACTATCGT GTTTGTCTTG AGAACGAGAT AATTAAGAAG GTTAGATTTG ACAACATCTT   1200
CCTTATATCA CCACCTTTAA CATTAAGTTT ATTTTCTTTC TTGTTTAAGT TTACAGTATC   1260
TTCAAGAACC CATGTTCATG ACACATTTTG TTCATGTGTT GTTTAGATTG TCAGAGATTT   1320
CAAACGTCCA GATGGTTTGA AAGATACAGA GATTGATGCA GCTGTAGATA GTACATATCT   1380
TAATTAAAAA TACCACTTCT CTATGCTCTA TTGTTGAGGA AACATATAAT ATTTGCATTC   1440
GTTCATGGTT CAGATATGAT GTTATGGTAA TTCTTGATCT ACGAGAAGAT GAATCTTTGA   1500
AAAACGAAGG TGTTGCCCGT GAGGTAAATA AATGTAACCG AAGCGATTAA TGGTCATATA   1560
TAAGTTGTAT ATTTGATATA TGGGTTTCCT TCTCATTGTG CTCATGCATT GAAAAGCACC   1620
CTGTTATGAC TGTGGTTCTA GGAGAACATT TGCATTTGAC AGTCGGTGAC TAATTGTTAA   1680
GCAAGAAGAA CGCATGAGAG CCTTTTAAAG TGTTTTCTTC TAGATCGTTG CAAAAAGTTA   1740
AATGTCTCTT GAGACTTTGT ACTCATTCTA TAGATAAAGA TGGGATTTAT TACAAAAACA   1800
ACAAGAAACT TTGTTACTTG TGGAAATTCA AAATTATCCG AACTAGCTTC ACAAAATATG   1860
CTCAAGAGTT TCAATGTATT TTTTTTTGTT CTGTAATTGT ATGACTCCGT TGAAGCATC    1920
AAGATTATGG TTATAGGTAG TGATGCTAAA ACTCTCTGTT GTTACAGTGA CCACTAAAAA   1980
CACCAACAAA AAAAACTTAG GTAACGTGTC GTCTAAAAAC TTCTAGGTTC AATTTCTTTA   2040
GATAGTACTA TCAATAAATA AAATAAATAT GTACAAAGGC TTTAAACAAT GATGTTTTC    2100
AAAGATGATT GGTAGATACT AATTAGAGCT TCAATATAAA AGAACACATG CGATTCTGAC   2160
ATTCTGTGGT CTAACATGGT TTCTTCTAGA GTCAAAACCA TACAATTAAA AGTTAGGAAA   2220
GTAATAGCAA TGTGGTTTCA AATATATACT CATTACTCTT TAGATTCATG TATGGTGAAG   2280
GAAACATTAT AATAAAATCA AAGATCACAG TTTTGTAGGT CCCTCATATT AATCAACATC   2340
TTAAGGCGTT ATACATATCT TCTTTTTGTA AATATTTGAC TAATTAAAAT ATCTAATTAG   2400
AGTATTAGAC TAATCTCATC AAATATCCGA CTACTTGTGT CAGTTCAAAA CACAGTGATT   2460
ACGTTAGATT TTGTGCTCTT TTGTTTATAA ACAAAGCTAA TTTAAGAAAT ATATGATCTA   2520
TTTGCCTCCT TGGTCTTAAT TTTATACTTT CTTGGAATAA AACACATTTA TTAAAATAAT   2580
TTTTAGGGTC CTAGATTCAT GTCATGTGGC TTGATAGTTT CCAACAATTA TACCAATATT   2640
TTACTCATTC ATATACAAAT AAACAAGCTT TATTCTATTC TTCAGTCTCA TGATATACGG   2700
GATTTTGATA AAATTCAGAG TACCCATTAA TTATTCTATG TTACAGCTTG TAATAAGTTA   2760
AATTTATAAA ACGTACAAGT TGAGGAAATA ACAAATGTTT TCAATATTAA ATGATTTATT   2820
AATACATTAG TGACCAAAAA ATTATTAAGT GTAAGAAAAA AAACACAACT CAGAAAAAAT   2880
TCAAAGACC  GTCTAAGTTC GGTTCATGTA AGAACAAGTG GGACCTCTTT AAGTTTCTAA   2940
ATCAGAGAAT AAAGAAGAAG AAAAAATCTC AAAACCTTCC TCTAAAACCA ACGGCTCCTA   3000
CCTTTACTTA CACCCTATAC ATACACTTCT CTTTTTATCC TCCATCGGCG GCTTATGGCG   3060
GTTTTCCGGC ACTAATCATC TCCGGCATAT ATAAATAAAC GTACTTCACG TTTTTTTATA   3120
```

-continued

```
TAACTTCAAA GTAGTTTCAG ATTTGTCTCT ATCTCTTCAC TTTTAAGTCT TCTGGTTTTG        3180

TCATCACCAG CTTTTTTTGT TCTCTCTCTG TCTCTGTCTC TGTCTTTCTC TTTGTGTATT        3240

TTTATTCTCG TCATCGTTGT TCTTCTATGA GAGGAAGATC GGAATGTCGA AGAGAATTAG        3300

AAGATTCTCG TACATCACTT CGTTGGAATT TCACAGGTCG ATGAGAGATC TGAGAACTGT        3360

TTCATTTTGA TCCAAACTCA TCTCTTTCAG GTATTCCAAA TTTGTCTTTC TCTGTTCTTT        3420

CTACTATTAC CCAAATTAAA GTTTTGATTT TTATTTCTCA CTCTGTTTCT TGTTTTTCTA        3480

ATTGCAGAGT ATAATGGACT AAGCATTTTT TTTCTCCGAA G ATG GTT AAA GAA            3533
                                              Met Val Lys Glu
                                                1
```

| | | | | | | | | | | | | | | | | |
|---|---|---|---|---|---|---|---|---|---|---|---|---|---|---|---|---|
| ATA | GCT | TCT | TGG | TTA | TTG | ATA | CTA | TCA | ATG | GTG | GTG | TTT | GTT | TCT | CCG | 3581 |
| Ile | Ala | Ser | Trp | Leu | Leu | Ile | Leu | Ser | Met | Val | Val | Phe | Val | Ser | Pro | |
| 5 | | | | 10 | | | | | 15 | | | | | | 20 | |
| GTT | TTA | GCT | ATA | AAC | GGC | GGT | GGT | TAT | CCA | CGA | TGT | AAC | TGC | GAA | GAC | 3629 |
| Val | Leu | Ala | Ile | Asn | Gly | Gly | Gly | Tyr | Pro | Arg | Cys | Asn | Cys | Glu | Asp | |
| | | | | 25 | | | | | 30 | | | | | 35 | | |
| GAA | GGA | AAC | AGT | TTC | TGG | AGT | ACA | GAG | AAC | ATT | CTA | GAA | ACT | CAA | AGA | 3677 |
| Glu | Gly | Asn | Ser | Phe | Trp | Ser | Thr | Glu | Asn | Ile | Leu | Glu | Thr | Gln | Arg | |
| | | | 40 | | | | | 45 | | | | | 50 | | | |
| GTA | AGC | GAT | TTC | TTA | ATC | GCA | GTA | GCT | TAT | TTC | TCA | ATC | CCT | ATT | GAG | 3725 |
| Val | Ser | Asp | Phe | Leu | Ile | Ala | Val | Ala | Tyr | Phe | Ser | Ile | Pro | Ile | Glu | |
| | | 55 | | | | | 60 | | | | | 65 | | | | |
| TTA | CTT | TAC | TTC | GTG | AGT | TGT | TCC | AAT | GTT | CCA | TTC | AAA | TGG | GTT | CTC | 3773 |
| Leu | Leu | Tyr | Phe | Val | Ser | Cys | Ser | Asn | Val | Pro | Phe | Lys | Trp | Val | Leu | |
| | 70 | | | | | 75 | | | | | 80 | | | | | |
| TTT | GAG | TTT | ATC | GCC | TTC | ATT | GTT | CTT | TGT | GGT | ATG | ACT | CAT | CTT | CTT | 3821 |
| Phe | Glu | Phe | Ile | Ala | Phe | Ile | Val | Leu | Cys | Gly | Met | Thr | His | Leu | Leu | |
| 85 | | | | | 90 | | | | | 95 | | | | | 100 | |
| CAT | GGT | TGG | ACT | TAC | TCT | GCT | CAT | CCA | TTT | AGA | TTA | ATG | ATG | GCG | TTT | 3869 |
| His | Gly | Trp | Thr | Tyr | Ser | Ala | His | Pro | Phe | Arg | Leu | Met | Met | Ala | Phe | |
| | | | | 105 | | | | | 110 | | | | | 115 | | |
| ACT | GTT | TTC | AAG | ATG | TTG | ACT | GCT | TTA | GTC | TCT | TGT | GCT | ACT | GCG | ATT | 3917 |
| Thr | Val | Phe | Lys | Met | Leu | Thr | Ala | Leu | Val | Ser | Cys | Ala | Thr | Ala | Ile | |
| | | | 120 | | | | | 125 | | | | | 130 | | | |
| ACG | CTT | ATT | ACT | TTG | ATT | CCT | CTG | CTT | TTG | AAA | GTT | AAA | GTT | AGA | GAG | 3965 |
| Thr | Leu | Ile | Thr | Leu | Ile | Pro | Leu | Leu | Leu | Lys | Val | Lys | Val | Arg | Glu | |
| | | 135 | | | | | 140 | | | | | 145 | | | | |
| TTT | ATG | CTT | AAG | AAG | AAA | GCT | CAT | GAG | CTT | GGT | CGT | GAA | GTT | GGT | TTG | 4013 |
| Phe | Met | Leu | Lys | Lys | Lys | Ala | His | Glu | Leu | Gly | Arg | Glu | Val | Gly | Leu | |
| | 150 | | | | | 155 | | | | | 160 | | | | | |
| ATT | TTG | ATT | AAG | AAA | GAG | ACT | GGC | TTT | CAT | GTT | CGT | ATG | CTT | ACT | CAA | 4061 |
| Ile | Leu | Ile | Lys | Lys | Glu | Thr | Gly | Phe | His | Val | Arg | Met | Leu | Thr | Gln | |
| 165 | | | | | 170 | | | | | 175 | | | | | 180 | |
| GAG | ATT | CGT | AAG | TCT | TTG | GAT | CGT | CAT | ACG | ATT | CTT | TAT | ACT | ACT | TTG | 4109 |
| Glu | Ile | Arg | Lys | Ser | Leu | Asp | Arg | His | Thr | Ile | Leu | Tyr | Thr | Thr | Leu | |
| | | | | 185 | | | | | 190 | | | | | 195 | | |
| GTT | GAG | CTT | TCG | AAG | ACT | TTA | GGG | TTG | CAG | AAT | TGT | GCG | GTT | TGG | ATG | 4157 |
| Val | Glu | Leu | Ser | Lys | Thr | Leu | Gly | Leu | Gln | Asn | Cys | Ala | Val | Trp | Met | |
| | | | 200 | | | | | 205 | | | | | 210 | | | |
| CCG | AAT | GAC | GGT | GGA | ACG | GAG | ATG | GAT | TTG | ACT | CAT | GAG | TTG | AGA | GGG | 4205 |
| Pro | Asn | Asp | Gly | Gly | Thr | Glu | Met | Asp | Leu | Thr | His | Glu | Leu | Arg | Gly | |
| | | 215 | | | | | 220 | | | | | 225 | | | | |
| AGA | GGT | GGT | TAT | GGT | GGT | TGT | TCT | GTT | TCT | ATG | GAG | GAT | TTG | GAT | GTT | 4253 |
| Arg | Gly | Gly | Tyr | Gly | Gly | Cys | Ser | Val | Ser | Met | Glu | Asp | Leu | Asp | Val | |
| | 230 | | | | | 235 | | | | | 240 | | | | | |
| GTT | AGG | ATT | AGG | GAG | AGT | GAT | GAA | GTG | AAT | GTG | TTG | AGT | GTT | GAC | TCG | 4301 |
| Val | Arg | Ile | Arg | Glu | Ser | Asp | Glu | Val | Asn | Val | Leu | Ser | Val | Asp | Ser | |
| 245 | | | | | 250 | | | | | 255 | | | | | 260 | |

| | | | | | | | | | | | | | | | | |
|---|---|---|---|---|---|---|---|---|---|---|---|---|---|---|---|---|
| TCC | ATT | GCT | CGA | GCT | AGT | GGT | GGT | GGT | GGG | GAT | GTT | AGT | GAG | ATT | GGT | 4349 |
| Ser | Ile | Ala | Arg | Ala | Ser | Gly | Gly | Gly | Gly | Asp | Val | Ser | Glu | Ile | Gly | |
| | 265 | | | | | 270 | | | | | | 275 | | | | |
| GCC | GTG | GCT | GCT | ATT | AGA | ATG | CCG | ATG | CTT | CGT | GTT | TCG | GAT | TTT | AAT | 4397 |
| Ala | Val | Ala | Ala | Ile | Arg | Met | Pro | Met | Leu | Arg | Val | Ser | Asp | Phe | Asn | |
| | | | 280 | | | | | 285 | | | | | | 290 | | |
| GGA | GAG | CTA | AGT | TAT | GCG | ATA | CTT | GTT | TGT | GTT | TTA | CCG | GGC | GGG | ACC | 4445 |
| Gly | Glu | Leu | Ser | Tyr | Ala | Ile | Leu | Val | Cys | Val | Leu | Pro | Gly | Gly | Thr | |
| | | 295 | | | | | 300 | | | | | 305 | | | | |
| CGT | CGG | GAT | TGG | ACT | TAT | CAG | GAG | ATT | GAG | ATT | GTT | AAA | GTT | GTG | GCG | 4493 |
| Arg | Arg | Asp | Trp | Thr | Tyr | Gln | Glu | Ile | Glu | Ile | Val | Lys | Val | Val | Ala | |
| | 310 | | | | | 315 | | | | | 320 | | | | | |
| GAT | CAA | GTA | ACC | GTT | GCG | TTA | GAT | CAT | GCA | GCG | GTT | CTT | GAA | GAG | TCT | 4541 |
| Asp | Gln | Val | Thr | Val | Ala | Leu | Asp | His | Ala | Ala | Val | Leu | Glu | Glu | Ser | |
| 325 | | | | | 330 | | | | | 335 | | | | | 340 | |
| CAG | CTT | ATG | AGG | GAG | AAG | CTG | GCG | GAA | CAG | AAC | AGG | GCG | TTG | CAG | ATG | 4589 |
| Gln | Leu | Met | Arg | Glu | Lys | Leu | Ala | Glu | Gln | Asn | Arg | Ala | Leu | Gln | Met | |
| | | | | 345 | | | | | 350 | | | | | 355 | | |
| GCG | AAG | AGA | GAC | GCG | TTG | AGA | GCG | AGC | CAA | GCG | AGG | AAT | GCG | TTT | CAG | 4637 |
| Ala | Lys | Arg | Asp | Ala | Leu | Arg | Ala | Ser | Gln | Ala | Arg | Asn | Ala | Phe | Gln | |
| | | | 360 | | | | | 365 | | | | | 370 | | | |
| AAA | ACG | ATG | AGC | GAA | GGG | ATG | AGG | CGT | CCT | ATG | CAT | TCG | ATA | CTC | GGT | 4685 |
| Lys | Thr | Met | Ser | Glu | Gly | Met | Arg | Arg | Pro | Met | His | Ser | Ile | Leu | Gly | |
| | | 375 | | | | | 380 | | | | | 385 | | | | |
| CTT | TTG | TCG | ATG | ATT | CAG | GAC | GAG | AAG | TTG | AGT | GAC | GAG | CAG | AAA | ATG | 4733 |
| Leu | Leu | Ser | Met | Ile | Gln | Asp | Glu | Lys | Leu | Ser | Asp | Glu | Gln | Lys | Met | |
| | 390 | | | | | 395 | | | | | 400 | | | | | |
| ATT | GTT | GAT | ACG | ATG | GTT | AAA | ACA | GGG | AAT | GTT | ATG | TCG | AAT | TTG | GTG | 4781 |
| Ile | Val | Asp | Thr | Met | Val | Lys | Thr | Gly | Asn | Val | Met | Ser | Asn | Leu | Val | |
| 405 | | | | | 410 | | | | | 415 | | | | | 420 | |
| GGG | GAC | TCT | ATG | GAT | GTG | CCT | GAC | GGT | AGA | TTT | GGT | ACG | GAG | ATG | AAA | 4829 |
| Gly | Asp | Ser | Met | Asp | Val | Pro | Asp | Gly | Arg | Phe | Gly | Thr | Glu | Met | Lys | |
| | | | | 425 | | | | | 430 | | | | | 435 | | |
| CCG | TTT | AGT | CTG | CAT | CGT | ACG | ATC | CAT | GAA | GCA | GCT | TGT | ATG | GCG | AGA | 4877 |
| Pro | Phe | Ser | Leu | His | Arg | Thr | Ile | His | Glu | Ala | Ala | Cys | Met | Ala | Arg | |
| | | | 440 | | | | | 445 | | | | | 450 | | | |
| TGT | TTG | TGT | CTA | TGC | AAT | GGA | ATT | AGG | TTC | TTG | GTT | GAC | GCG | GAG | AAG | 4925 |
| Cys | Leu | Cys | Leu | Cys | Asn | Gly | Ile | Arg | Phe | Leu | Val | Asp | Ala | Glu | Lys | |
| | | 455 | | | | | 460 | | | | | 465 | | | | |
| TCT | CTA | CCT | GAT | AAT | GTA | GTA | GGT | GAT | GAA | AGA | AGG | GTC | TTT | CAA | GTG | 4973 |
| Ser | Leu | Pro | Asp | Asn | Val | Val | Gly | Asp | Glu | Arg | Arg | Val | Phe | Gln | Val | |
| | 470 | | | | | 475 | | | | | 480 | | | | | |
| ATA | CTT | CAT | ATG | GTT | GGT | AGT | TTA | GTA | AAG | CCT | AGA | AAA | CGT | CAA | GAA | 5021 |
| Ile | Leu | His | Met | Val | Gly | Ser | Leu | Val | Lys | Pro | Arg | Lys | Arg | Gln | Glu | |
| 485 | | | | | 490 | | | | | 495 | | | | | 500 | |
| GGA | TCT | TCA | TTG | ATG | TTT | AAG | GTT | TTG | AAA | GAA | AGA | GGA | AGC | TTG | GAT | 5069 |
| Gly | Ser | Ser | Leu | Met | Phe | Lys | Val | Leu | Lys | Glu | Arg | Gly | Ser | Leu | Asp | |
| | | | | 505 | | | | | 510 | | | | | 515 | | |
| AGG | AGT | GAT | CAT | AGA | TGG | GCT | GCT | TGG | AGA | TCA | CCG | GCT | TCT | TCA | GCA | 5117 |
| Arg | Ser | Asp | His | Arg | Trp | Ala | Ala | Trp | Arg | Ser | Pro | Ala | Ser | Ser | Ala | |
| | | | 520 | | | | | 525 | | | | | 530 | | | |
| GAT | GGA | GAT | GTG | TAT | ATA | AGA | TTT | GAA | ATG | AAT | GTA | GAG | AAT | GAT | GAT | 5165 |
| Asp | Gly | Asp | Val | Tyr | Ile | Arg | Phe | Glu | Met | Asn | Val | Glu | Asn | Asp | Asp | |
| | | 535 | | | | | 540 | | | | | 545 | | | | |
| TCA | AGT | TCT | CAA | TCA | TTT | GCT | TCT | GTT | TCC | TCC | AGA | GAT | CAA | GAA | GTT | 5213 |
| Ser | Ser | Ser | Gln | Ser | Phe | Ala | Ser | Val | Ser | Ser | Arg | Asp | Gln | Glu | Val | |
| | 550 | | | | | 555 | | | | | 560 | | | | | |
| GGT | GAT | GTT | AGA | TTC | TCC | GGC | GGC | TAT | GGG | TTA | GGA | CAA | GAT | CTA | AGC | 5261 |
| Gly | Asp | Val | Arg | Phe | Ser | Gly | Gly | Tyr | Gly | Leu | Gly | Gln | Asp | Leu | Ser | |
| 565 | | | | | 570 | | | | | 575 | | | | | 580 | |

```
TTT  GGT  GTT  TGT  AAG  AAA  GTG  GTG  CAG  GTGAGTTTCC  TTACATATCT                           5308
Phe  Gly  Val  Cys  Lys  Lys  Val  Val  Gln
                    585

CTTTCTAAAG  TTCCTGTCAT  TAGTCTGAGT  TTCTGTTTAG  GAGTTCTTTG  ATAATGTGTG                        5368

CAG  TTG  ATT  CAT  GGG  AAT  ATC  TCG  GTG  GTC  CCT  GGC  TCG  GAT  GGT  TCA               5416
     Leu  Ile  His  Gly  Asn  Ile  Ser  Val  Val  Pro  Gly  Ser  Asp  Gly  Ser
     590                 595                           600

CCG  GAG  ACC  ATG  TCG  TTG  CTC  CTT  CGG  TTT  CGA  CGT  AGA  CCC  TCC  ATA               5464
Pro  Glu  Thr  Met  Ser  Leu  Leu  Leu  Arg  Phe  Arg  Arg  Arg  Pro  Ser  Ile
605                      610                      615                      620

TCT  GTC  CAT  GGA  TCC  AGC  GAG  TCG  CCA  GCT  CCT  GAC  CAC  CAC  GCT  CAC               5512
Ser  Val  His  Gly  Ser  Ser  Glu  Ser  Pro  Ala  Pro  Asp  His  His  Ala  His
                    625                      630                      635

CCA  CAT  TCG  AAT  TCT  CTG  TTA  CGT  GGC  TTA  CAA  GTT  TTA  TTG  GTA  GAC               5560
Pro  His  Ser  Asn  Ser  Leu  Leu  Arg  Gly  Leu  Gln  Val  Leu  Leu  Val  Asp
               640                      645                      650

ACC  AAC  GAT  TCG  AAC  CGG  GCA  GTT  ACA  CGT  AAA  CTC  TTA  GAG  AAA  CTC               5608
Thr  Asn  Asp  Ser  Asn  Arg  Ala  Val  Thr  Arg  Lys  Leu  Leu  Glu  Lys  Leu
               655                      660                      665

GGG  TGC  GAT  GTA  ACC  GCG  GTT  TCC  TCT  GGA  TTC  GAT  TGC  CTT  ACC  GCC               5656
Gly  Cys  Asp  Val  Thr  Ala  Val  Ser  Ser  Gly  Phe  Asp  Cys  Leu  Thr  Ala
     670                      675                      680

ATT  GCT  CCC  GGC  TCG  TCC  TCG  CCT  TCT  ACT  TCG  TTT  CAA  GTG  GTG  GTG               5704
Ile  Ala  Pro  Gly  Ser  Ser  Ser  Pro  Ser  Thr  Ser  Phe  Gln  Val  Val  Val
685                      690                      695                      700

CTT  GAT  CTT  CAA  ATG  GCA  GAG  ATG  GAC  GGT  TAT  GAA  GTG  GCC  ATG  AGG               5752
Leu  Asp  Leu  Gln  Met  Ala  Glu  Met  Asp  Gly  Tyr  Glu  Val  Ala  Met  Arg
                    705                      710                      715

ATC  AGG  AGT  CGA  TCT  TGG  CCG  TTG  ATT  GTG  GCG  ACG  ACA  GTG  AGC  TTG               5800
Ile  Arg  Ser  Arg  Ser  Trp  Pro  Leu  Ile  Val  Ala  Thr  Thr  Val  Ser  Leu
               720                      725                      730

GAT  GAA  GAA  ATG  TGG  GAC  AAG  TGT  GCA  CAG  ATT  GGA  ATC  AAT  GGA  GTT               5848
Asp  Glu  Glu  Met  Trp  Asp  Lys  Cys  Ala  Gln  Ile  Gly  Ile  Asn  Gly  Val
          735                      740                      745

GTG  AGA  AAG  CCA  GTG  GTG  TTA  AGA  GCT  ATG  GAG  AGT  GAG  CTC  CGA  AGA               5896
Val  Arg  Lys  Pro  Val  Val  Leu  Arg  Ala  Met  Glu  Ser  Glu  Leu  Arg  Arg
     750                      755                      760

GTA  TTG  TTG  CAA  GCT  GAC  CAA  CTT  CTC  TAAGTTGTTA  TCTCAACTTC                           5943
Val  Leu  Leu  Gln  Ala  Asp  Gln  Leu  Leu
765                      770

TCTTCTACAT  TCAAAATTTT  TACACCATAG  ATTTATGTCA  AATATATCAA  AATGAAATTT                        6003

CGAAATTGTT  ATTATATATA  CCACCCATAT  CTCTATGATT  TGTACATCCT  GTTTTTTTTT                        6063

GTTCTTTTTC  TCATTTGAA   CCCCACGAAA  TTGCATTGAA  TCTTAGTATT  TCGTAGGGTC                        6123

AAGAAGGAGT  CAGTTTCGTA  GTTTTTTGTT  TTCTTTATGT  TACGAACTTA  CGAAACTGAA                        6183

TATGGCATTA  TAGAGTTTT                                                                         6202
```

( 2 ) INFORMATION FOR SEQ ID NO:42:

( i ) SEQUENCE CHARACTERISTICS:
        ( A ) LENGTH: 773 amino acids
        ( B ) TYPE: amino acid
        ( D ) TOPOLOGY: linear ( i i ) MOLECULE TYPE: protein ( x i ) SEQUENCE DESCRIPTION: SEQ ID NO:42:

```
Met  Val  Lys  Glu  Ile  Ala  Ser  Trp  Leu  Leu  Ile  Leu  Ser  Met  Val  Val
1              5                        10                       15
```

-continued

| Phe | Val | Ser | Pro | Val | Leu | Ala | Ile | Asn | Gly | Gly | Tyr | Pro | Arg | Cys |
|---|---|---|---|---|---|---|---|---|---|---|---|---|---|---|
| | | | 20 | | | | 25 | | | | | 30 | | |

| Asn | Cys | Glu | Asp | Glu | Gly | Asn | Ser | Phe | Trp | Ser | Thr | Glu | Asn | Ile | Leu |
|---|---|---|---|---|---|---|---|---|---|---|---|---|---|---|---|
| | | | 35 | | | | 40 | | | | 45 | | | | |

| Glu | Thr | Gln | Arg | Val | Ser | Asp | Phe | Leu | Ile | Ala | Val | Ala | Tyr | Phe | Ser |
| | 50 | | | | | 55 | | | | | 60 | | | | |

| Ile | Pro | Ile | Glu | Leu | Leu | Tyr | Phe | Val | Ser | Cys | Ser | Asn | Val | Pro | Phe |
| 65 | | | | | 70 | | | | | 75 | | | | | 80 |

| Lys | Trp | Val | Leu | Phe | Glu | Phe | Ile | Ala | Phe | Ile | Val | Leu | Cys | Gly | Met |
| | | | | 85 | | | | 90 | | | | | | 95 | |

| Thr | His | Leu | Leu | His | Gly | Trp | Thr | Tyr | Ser | Ala | His | Pro | Phe | Arg | Leu |
| | | | 100 | | | | | 105 | | | | | 110 | | |

| Met | Met | Ala | Phe | Thr | Val | Phe | Lys | Met | Leu | Thr | Ala | Leu | Val | Ser | Cys |
| | | 115 | | | | | 120 | | | | | 125 | | | |

| Ala | Thr | Ala | Ile | Thr | Leu | Ile | Thr | Leu | Ile | Pro | Leu | Leu | Leu | Lys | Val |
| | | 130 | | | | 135 | | | | | 140 | | | | |

| Lys | Val | Arg | Glu | Phe | Met | Leu | Lys | Lys | Ala | His | Glu | Leu | Gly | Arg |
| 145 | | | | | 150 | | | | 155 | | | | | 160 |

| Glu | Val | Gly | Leu | Ile | Leu | Ile | Lys | Lys | Thr | Gly | Phe | His | Val | Arg |
| | | | | 165 | | | | | 170 | | | | 175 | |

| Met | Leu | Thr | Gln | Glu | Ile | Arg | Lys | Ser | Leu | Asp | Arg | His | Thr | Ile | Leu |
| | | | 180 | | | | | 185 | | | | | 190 | | |

| Tyr | Thr | Thr | Leu | Val | Glu | Leu | Ser | Lys | Thr | Leu | Gly | Leu | Gln | Asn | Cys |
| | | 195 | | | | | 200 | | | | | 205 | | | |

| Ala | Val | Trp | Met | Pro | Asn | Asp | Gly | Gly | Thr | Glu | Met | Asp | Leu | Thr | His |
| | 210 | | | | | 215 | | | | | 220 | | | | |

| Glu | Leu | Arg | Gly | Arg | Gly | Gly | Tyr | Gly | Gly | Cys | Ser | Val | Ser | Met | Glu |
| 225 | | | | | 230 | | | | | 235 | | | | | 240 |

| Asp | Leu | Asp | Val | Val | Arg | Ile | Arg | Glu | Ser | Asp | Glu | Val | Asn | Val | Leu |
| | | | | 245 | | | | 250 | | | | | 255 | | |

| Ser | Val | Asp | Ser | Ser | Ile | Ala | Arg | Ala | Ser | Gly | Gly | Gly | Gly | Asp | Val |
| | | | 260 | | | | | 265 | | | | | 270 | | |

| Ser | Glu | Ile | Gly | Ala | Val | Ala | Ala | Ile | Arg | Met | Pro | Met | Leu | Arg | Val |
| | | 275 | | | | | 280 | | | | | 285 | | | |

| Ser | Asp | Phe | Asn | Gly | Glu | Leu | Ser | Tyr | Ala | Ile | Leu | Val | Cys | Val | Leu |
| | 290 | | | | | 295 | | | | | 300 | | | | |

| Pro | Gly | Gly | Thr | Arg | Arg | Asp | Trp | Thr | Tyr | Gln | Glu | Ile | Glu | Ile | Val |
| 305 | | | | | 310 | | | | | 315 | | | | | 320 |

| Lys | Val | Val | Ala | Asp | Gln | Val | Thr | Val | Ala | Leu | Asp | His | Ala | Ala | Val |
| | | | | 325 | | | | 330 | | | | | 335 | | |

| Leu | Glu | Glu | Ser | Gln | Leu | Met | Arg | Glu | Lys | Leu | Ala | Glu | Gln | Asn | Arg |
| | | | 340 | | | | | 345 | | | | | 350 | | |

| Ala | Leu | Gln | Met | Ala | Lys | Arg | Asp | Ala | Leu | Arg | Ala | Ser | Gln | Ala | Arg |
| | | | 355 | | | | | 360 | | | | | 365 | | |

| Asn | Ala | Phe | Gln | Lys | Thr | Met | Ser | Glu | Gly | Met | Arg | Arg | Pro | Met | His |
| | 370 | | | | | 375 | | | | | 380 | | | | |

| Ser | Ile | Leu | Gly | Leu | Leu | Ser | Met | Ile | Gln | Asp | Glu | Lys | Leu | Ser | Asp |
| 385 | | | | | 390 | | | | | 395 | | | | | 400 |

| Glu | Gln | Lys | Met | Ile | Val | Asp | Thr | Met | Val | Lys | Thr | Gly | Asn | Val | Met |
| | | | | 405 | | | | 410 | | | | | 415 | | |

| Ser | Asn | Leu | Val | Gly | Asp | Ser | Met | Asp | Val | Pro | Asp | Gly | Arg | Phe | Gly |
| | | | 420 | | | | | 425 | | | | | 430 | | |

| Thr | Glu | Met | Lys | Pro | Phe | Ser | Leu | His | Arg | Thr | Ile | His | Glu | Ala | Ala |
| | | 435 | | | | | 440 | | | | | 445 | | | |

| | | | | | | | | | | | | | | |
|---|---|---|---|---|---|---|---|---|---|---|---|---|---|---|
| Cys | Met<br>450 | Ala | Arg | Cys | Leu<br>455 | Cys | Leu | Cys | Asn | Gly<br>460 | Ile | Arg | Phe | Leu | Val |
| Asp<br>465 | Ala | Glu | Lys | Ser | Leu<br>470 | Pro | Asp | Asn | Val<br>475 | Val | Gly | Asp | Glu | Arg | Arg<br>480 |
| Val | Phe | Gln | Val | Ile<br>485 | Leu | His | Met | Val | Gly<br>490 | Ser | Leu | Val | Lys | Pro<br>495 | Arg |
| Lys | Arg | Gln | Glu<br>500 | Gly | Ser | Ser | Leu | Met<br>505 | Phe | Lys | Val | Leu | Lys<br>510 | Glu | Arg |
| Gly | Ser | Leu<br>515 | Asp | Arg | Ser | Asp | His<br>520 | Arg | Trp | Ala | Ala | Trp<br>525 | Arg | Ser | Pro |
| Ala | Ser<br>530 | Ser | Ala | Asp | Gly<br>535 | Asp | Val | Tyr | Ile | Arg<br>540 | Phe | Glu | Met | Asn | Val |
| Glu<br>545 | Asn | Asp | Asp | Ser | Ser<br>550 | Ser | Gln | Ser | Phe<br>555 | Ala | Ser | Val | Ser | Ser | Arg<br>560 |
| Asp | Gln | Glu | Val | Gly<br>565 | Asp | Val | Arg | Phe | Ser<br>570 | Gly | Gly | Tyr | Gly | Leu<br>575 | Gly |
| Gln | Asp | Leu | Ser<br>580 | Phe | Gly | Val | Cys | Lys<br>585 | Lys | Val | Val | Gln | Leu<br>590 | Ile | His |
| Gly | Asn | Ile<br>595 | Ser | Val | Val | Pro | Gly<br>600 | Ser | Asp | Gly | Ser | Pro<br>605 | Glu | Thr | Met |
| Ser | Leu<br>610 | Leu | Leu | Arg | Phe | Arg<br>615 | Arg | Arg | Pro | Ser | Ile<br>620 | Ser | Val | His | Gly |
| Ser<br>625 | Ser | Glu | Ser | Pro | Ala<br>630 | Pro | Asp | His | His | Ala<br>635 | His | Pro | His | Ser | Asn<br>640 |
| Ser | Leu | Leu | Arg | Gly<br>645 | Leu | Gln | Val | Leu | Leu<br>650 | Val | Asp | Thr | Asn | Asp<br>655 | Ser |
| Asn | Arg | Ala | Val<br>660 | Thr | Arg | Lys | Leu | Leu<br>665 | Glu | Lys | Leu | Gly | Cys<br>670 | Asp | Val |
| Thr | Ala | Val<br>675 | Ser | Ser | Gly | Phe | Asp<br>680 | Cys | Leu | Thr | Ala | Ile<br>685 | Ala | Pro | Gly |
| Ser | Ser<br>690 | Ser | Pro | Ser | Thr | Ser<br>695 | Phe | Gln | Val | Val | Val<br>700 | Leu | Asp | Leu | Gln |
| Met<br>705 | Ala | Glu | Met | Asp | Gly<br>710 | Tyr | Glu | Val | Ala | Met<br>715 | Arg | Ile | Arg | Ser | Arg<br>720 |
| Ser | Trp | Pro | Leu | Ile<br>725 | Val | Ala | Thr | Thr | Val<br>730 | Ser | Leu | Asp | Glu | Glu<br>735 | Met |
| Trp | Asp | Lys | Cys<br>740 | Ala | Gln | Ile | Gly | Ile<br>745 | Asn | Gly | Val | Val | Arg<br>750 | Lys | Pro |
| Val | Val | Leu<br>755 | Arg | Ala | Met | Glu | Ser<br>760 | Glu | Leu | Arg | Arg | Val<br>765 | Leu | Leu | Gln |
| Ala | Asp<br>770 | Gln | Leu | Leu | | | | | | | | | | | |

( 2 ) INFORMATION FOR SEQ ID NO:43:

( i ) SEQUENCE CHARACTERISTICS:
        ( A ) LENGTH: 2404 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..2322

( x i ) SEQUENCE DESCRIPTION: SEQ ID NO:43:

ATG GTT AAA GAA ATA GCT TCT TGG TTA TTG ATA CTA TCA ATG GTG GTG    48

```
Met Val Lys Glu Ile Ala Ser Trp Leu Leu Ile Leu Ser Met Val Val
 1               5                  10                  15

TTT GTT TCT CCG GTT TTA GCT ATA AAC GGC GGT GGT TAT CCA CGA TGT         96
Phe Val Ser Pro Val Leu Ala Ile Asn Gly Gly Gly Tyr Pro Arg Cys
             20                  25                  30

AAC TGC GAA GAC GAA GGA AAC AGT TTC TGG AGT ACA GAG AAC ATT CTA        144
Asn Cys Glu Asp Glu Gly Asn Ser Phe Trp Ser Thr Glu Asn Ile Leu
         35                  40                  45

GAA ACT CAA AGA GTA AGC GAT TTC TTA ATC GCA GTA GCT TAT TTC TCA        192
Glu Thr Gln Arg Val Ser Asp Phe Leu Ile Ala Val Ala Tyr Phe Ser
     50                  55                  60

ATC CCT ATT GAG TTA CTT TAC TTC GTG AGT TGT TCC AAT GTT CCA TTC        240
Ile Pro Ile Glu Leu Leu Tyr Phe Val Ser Cys Ser Asn Val Pro Phe
 65                  70                  75                  80

AAA TGG GTT CTC TTT GAG TTT ATC GCC TTC ATT GTT CTT TGT GGT ATG        288
Lys Trp Val Leu Phe Glu Phe Ile Ala Phe Ile Val Leu Cys Gly Met
                 85                  90                  95

ACT CAT CTT CTT CAT GGT TGG ACT TAC TCT GCT CAT CCA TTT AGA TTA        336
Thr His Leu Leu His Gly Trp Thr Tyr Ser Ala His Pro Phe Arg Leu
             100                 105                 110

ATG ATG GCG TTT ACT GTT TTC AAG ATG TTG ACT GCT TTA GTC TCT TGT        384
Met Met Ala Phe Thr Val Phe Lys Met Leu Thr Ala Leu Val Ser Cys
         115                 120                 125

GCT ACT GCG ATT ACG CTT ATT ACT TTG ATT CCT CTG CTT TTG AAA GTT        432
Ala Thr Ala Ile Thr Leu Ile Thr Leu Ile Pro Leu Leu Leu Lys Val
     130                 135                 140

AAA GTT AGA GAG TTT ATG CTT AAG AAG AAA GCT CAT GAG CTT GGT CGT        480
Lys Val Arg Glu Phe Met Leu Lys Lys Lys Ala His Glu Leu Gly Arg
145                 150                 155                 160

GAA GTT GGT TTG ATT TTG ATT AAG AAA GAG ACT GGC TTT CAT GTT CGT        528
Glu Val Gly Leu Ile Leu Ile Lys Lys Glu Thr Gly Phe His Val Arg
                 165                 170                 175

ATG CTT ACT CAA GAG ATT CGT AAG TCT TTG GAT CGT CAT ACG ATT CTT        576
Met Leu Thr Gln Glu Ile Arg Lys Ser Leu Asp Arg His Thr Ile Leu
             180                 185                 190

TAT ACT ACT TTG GTT GAG CTT TCG AAG ACT TTA GGG TTG CAG AAT TGT        624
Tyr Thr Thr Leu Val Glu Leu Ser Lys Thr Leu Gly Leu Gln Asn Cys
         195                 200                 205

GCG GTT TGG ATG CCG AAT GAC GGT GGA ACG GAG ATG GAT TTG ACT CAT        672
Ala Val Trp Met Pro Asn Asp Gly Gly Thr Glu Met Asp Leu Thr His
     210                 215                 220

GAG TTG AGA GGG AGA GGT GGT TAT GGT GGT TGT TCT GTT TCT ATG GAG        720
Glu Leu Arg Gly Arg Gly Gly Tyr Gly Gly Cys Ser Val Ser Met Glu
225                 230                 235                 240

GAT TTG GAT GTT GTT AGG ATT AGG GAG AGT GAT GAA GTG AAT GTG TTG        768
Asp Leu Asp Val Val Arg Ile Arg Glu Ser Asp Glu Val Asn Val Leu
                 245                 250                 255

AGT GTT GAC TCG TCC ATT GCT CGA GCT AGT GGT GGT GGG GAT GTT        816
Ser Val Asp Ser Ser Ile Ala Arg Ala Ser Gly Gly Gly Asp Val
             260                 265                 270

AGT GAG ATT GGT GCC GTG GCT GCT ATT AGA ATG CCG ATG CTT CGT GTT        864
Ser Glu Ile Gly Ala Val Ala Ala Ile Arg Met Pro Met Leu Arg Val
         275                 280                 285

TCG GAT TTT AAT GGA GAG CTA AGT TAT GCG ATA CTT GTT TGT GTT TTA        912
Ser Asp Phe Asn Gly Glu Leu Ser Tyr Ala Ile Leu Val Cys Val Leu
     290                 295                 300

CCG GGC GGG ACC CGT CGG GAT TGG ACT TAT CAG GAG ATT GAG ATT GTT        960
Pro Gly Gly Thr Arg Arg Asp Trp Thr Tyr Gln Glu Ile Glu Ile Val
305                 310                 315                 320

AAA GTT GTG GCG GAT CAA GTA ACC GTT GCG TTA GAT CAT GCA GCG GTT       1008
```

```
Lys Val Val Ala Asp Gln Val Thr Val Ala Leu Asp His Ala Ala Val
            325                 330                 335

CTT GAA GAG TCT CAG CTT ATG AGG GAG AAG CTG GCG GAA CAG AAC AGG   1056
Leu Glu Glu Ser Gln Leu Met Arg Glu Lys Leu Ala Glu Gln Asn Arg
            340                 345                 350

GCG TTG CAG ATG GCG AAG AGA GAC GCG TTG AGA GCG AGC CAA GCG AGG   1104
Ala Leu Gln Met Ala Lys Arg Asp Ala Leu Arg Ala Ser Gln Ala Arg
            355                 360                 365

AAT GCG TTT CAG AAA ACG ATG AGC GAA GGG ATG AGG CGT CCT ATG CAT   1152
Asn Ala Phe Gln Lys Thr Met Ser Glu Gly Met Arg Arg Pro Met His
    370                 375                 380

TCG ATA CTC GGT CTT TTG TCG ATG ATT CAG GAC GAG AAG TTG AGT GAC   1200
Ser Ile Leu Gly Leu Leu Ser Met Ile Gln Asp Glu Lys Leu Ser Asp
385                 390                 395                 400

GAG CAG AAA ATG ATT GTT GAT ACG ATG GTT AAA ACA GGG AAT GTT ATG   1248
Glu Gln Lys Met Ile Val Asp Thr Met Val Lys Thr Gly Asn Val Met
            405                 410                 415

TCG AAT TTG GTG GGG GAC TCT ATG GAT GTG CCT GAC GGT AGA TTT GGT   1296
Ser Asn Leu Val Gly Asp Ser Met Asp Val Pro Asp Gly Arg Phe Gly
            420                 425                 430

ACG GAG ATG AAA CCG TTT AGT CTG CAT CGT ACG ATC CAT GAA GCA GCT   1344
Thr Glu Met Lys Pro Phe Ser Leu His Arg Thr Ile His Glu Ala Ala
            435                 440                 445

TGT ATG GCG AGA TGT TTG TGT CTA TGC AAT GGA ATT AGG TTC TTG GTT   1392
Cys Met Ala Arg Cys Leu Cys Leu Cys Asn Gly Ile Arg Phe Leu Val
    450                 455                 460

GAC GCG GAG AAG TCT CTA CCT GAT AAT GTA GTA GGT GAT GAA AGA AGG   1440
Asp Ala Glu Lys Ser Leu Pro Asp Asn Val Val Gly Asp Glu Arg Arg
465                 470                 475                 480

GTC TTT CAA GTG ATA CTT CAT ATG GTT GGT AGT TTA GTA AAG CCT AGA   1488
Val Phe Gln Val Ile Leu His Met Val Gly Ser Leu Val Lys Pro Arg
                    485                 490                 495

AAA CGT CAA GAA GGA TCT TCA TTG ATG TTT AAG GTT TTG AAA GAA AGA   1536
Lys Arg Gln Glu Gly Ser Ser Leu Met Phe Lys Val Leu Lys Glu Arg
            500                 505                 510

GGA AGC TTG GAT AGG AGT GAT CAT AGA TGG GCT GCT TGG AGA TCA CCG   1584
Gly Ser Leu Asp Arg Ser Asp His Arg Trp Ala Ala Trp Arg Ser Pro
            515                 520                 525

GCT TCT TCA GCA GAT GGA GAT GTG TAT ATA AGA TTT GAA ATG AAT GTA   1632
Ala Ser Ser Ala Asp Gly Asp Val Tyr Ile Arg Phe Glu Met Asn Val
    530                 535                 540

GAG AAT GAT GAT TCA AGT TCT CAA TCA TTT GCT TCT GTT TCC TCC AGA   1680
Glu Asn Asp Asp Ser Ser Ser Gln Ser Phe Ala Ser Val Ser Ser Arg
545                 550                 555                 560

GAT CAA GAA GTT GGT GAT GTT AGA TTC TCC GGC GGC TAT GGG TTA GGA   1728
Asp Gln Glu Val Gly Asp Val Arg Phe Ser Gly Gly Tyr Gly Leu Gly
            565                 570                 575

CAA GAT CTA AGC TTT GGT GTT TGT AAG AAA GTG GTG CAG TTG ATT CAT   1776
Gln Asp Leu Ser Phe Gly Val Cys Lys Lys Val Val Gln Leu Ile His
            580                 585                 590

GGG AAT ATC TCG GTG GTC CCT GGC TCG GAT GGT TCA CCG GAG ACC ATG   1824
Gly Asn Ile Ser Val Val Pro Gly Ser Asp Gly Ser Pro Glu Thr Met
            595                 600                 605

TCG TTG CTC CTT CGG TTT CGA CGT AGA CCC TCC ATA TCT GTC CAT GGA   1872
Ser Leu Leu Leu Arg Phe Arg Arg Arg Pro Ser Ile Ser Val His Gly
            610                 615                 620

TCC AGC GAG TCG CCA GCT CCT GAC CAC CAC GCT CAC CCA CAT TCG AAT   1920
Ser Ser Glu Ser Pro Ala Pro Asp His His Ala His Pro His Ser Asn
625                 630                 635                 640

TCT CTG TTA CGT GGC TTA CAA GTT TTA TTG GTA GAC ACC AAC GAT TCG   1968
```

| | | | | | | | | | | | | | | | |
|---|---|---|---|---|---|---|---|---|---|---|---|---|---|---|---|
| Ser | Leu | Leu | Arg | Gly | Leu | Gln | Val | Leu | Leu | Val | Asp | Thr | Asn | Asp | Ser |
| | | | | 645 | | | | 650 | | | | | 655 | | |

| AAC | CGG | GCA | GTT | ACA | CGT | AAA | CTC | TTA | GAG | AAA | CTC | GGG | TGC | GAT | GTA | 2016 |
|---|---|---|---|---|---|---|---|---|---|---|---|---|---|---|---|---|
| Asn | Arg | Ala | Val | Thr | Arg | Lys | Leu | Leu | Glu | Lys | Leu | Gly | Cys | Asp | Val | |
| | | | 660 | | | | | 665 | | | | 670 | | | | |

| ACC | GCG | GTT | TCC | TCT | GGA | TTC | GAT | TGC | CTT | ACC | GCC | ATT | GCT | CCC | GGC | 2064 |
|---|---|---|---|---|---|---|---|---|---|---|---|---|---|---|---|---|
| Thr | Ala | Val | Ser | Ser | Gly | Phe | Asp | Cys | Leu | Thr | Ala | Ile | Ala | Pro | Gly | |
| | | 675 | | | | | 680 | | | | | 685 | | | | |

| TCG | TCC | TCG | CCT | TCT | ACT | TCG | TTT | CAA | GTG | GTG | GTG | CTT | GAT | CTT | CAA | 2112 |
|---|---|---|---|---|---|---|---|---|---|---|---|---|---|---|---|---|
| Ser | Ser | Ser | Pro | Ser | Thr | Ser | Phe | Gln | Val | Val | Val | Leu | Asp | Leu | Gln | |
| | | 690 | | | | | 695 | | | | | 700 | | | | |

| ATG | GCA | GAG | ATG | GAC | GGT | TAT | GAA | GTG | GCC | ATG | AGG | ATC | AGG | AGT | CGA | 2160 |
|---|---|---|---|---|---|---|---|---|---|---|---|---|---|---|---|---|
| Met | Ala | Glu | Met | Asp | Gly | Tyr | Glu | Val | Ala | Met | Arg | Ile | Arg | Ser | Arg | |
| 705 | | | | | 710 | | | | | 715 | | | | | 720 | |

| TCT | TGG | CCG | TTG | ATT | GTG | GCG | ACG | ACA | GTG | AGC | TTG | GAT | GAA | GAA | ATG | 2208 |
|---|---|---|---|---|---|---|---|---|---|---|---|---|---|---|---|---|
| Ser | Trp | Pro | Leu | Ile | Val | Ala | Thr | Thr | Val | Ser | Leu | Asp | Glu | Glu | Met | |
| | | | | 725 | | | | | 730 | | | | | 735 | | |

| TGG | GAC | AAG | TGT | GCA | CAG | ATT | GGA | ATC | AAT | GGA | GTT | GTG | AGA | AAG | CCA | 2256 |
|---|---|---|---|---|---|---|---|---|---|---|---|---|---|---|---|---|
| Trp | Asp | Lys | Cys | Ala | Gln | Ile | Gly | Ile | Asn | Gly | Val | Val | Arg | Lys | Pro | |
| | | | 740 | | | | | 745 | | | | | 750 | | | |

| GTG | GTG | TTA | AGA | GCT | ATG | GAG | AGT | GAG | CTC | CGA | AGA | GTA | TTG | TTG | CAA | 2304 |
|---|---|---|---|---|---|---|---|---|---|---|---|---|---|---|---|---|
| Val | Val | Leu | Arg | Ala | Met | Glu | Ser | Glu | Leu | Arg | Arg | Val | Leu | Leu | Gln | |
| | | 755 | | | | | 760 | | | | | 765 | | | | |

| GCT | GAC | CAA | CTT | CTC | TAAGTTGTTA | TCTCAACTTC | TCTTCTACAT | TCAAAATTTT | 2359 |
|---|---|---|---|---|---|---|---|---|---|
| Ala | Asp | Gln | Leu | Leu | | | | | |
| | 770 | | | | | | | | |

| TACACCATAG | ATTTATGTCA | AATATATCAA | AATGAAATTT | CGAAA | 2404 |
|---|---|---|---|---|---|

( 2 ) INFORMATION FOR SEQ ID NO:44:

( i ) SEQUENCE CHARACTERISTICS:
        ( A ) LENGTH: 773 amino acids
        ( B ) TYPE: amino acid
        ( D ) TOPOLOGY: linear ( i i ) MOLECULE TYPE: protein ( x i ) SEQUENCE DESCRIPTION: SEQ ID NO:44:

| Met | Val | Lys | Glu | Ile | Ala | Ser | Trp | Leu | Leu | Ile | Leu | Ser | Met | Val | Val |
|---|---|---|---|---|---|---|---|---|---|---|---|---|---|---|---|
| 1 | | | | 5 | | | | | 10 | | | | | 15 | |

| Phe | Val | Ser | Pro | Val | Leu | Ala | Ile | Asn | Gly | Gly | Gly | Tyr | Pro | Arg | Cys |
|---|---|---|---|---|---|---|---|---|---|---|---|---|---|---|---|
| | | | 20 | | | | | 25 | | | | | 30 | | |

| Asn | Cys | Glu | Asp | Glu | Gly | Asn | Ser | Phe | Trp | Ser | Thr | Glu | Asn | Ile | Leu |
|---|---|---|---|---|---|---|---|---|---|---|---|---|---|---|---|
| | | 35 | | | | | 40 | | | | | 45 | | | |

| Glu | Thr | Gln | Arg | Val | Ser | Asp | Phe | Leu | Ile | Ala | Val | Ala | Tyr | Phe | Ser |
|---|---|---|---|---|---|---|---|---|---|---|---|---|---|---|---|
| | 50 | | | | | 55 | | | | | 60 | | | | |

| Ile | Pro | Ile | Glu | Leu | Leu | Tyr | Phe | Val | Ser | Cys | Ser | Asn | Val | Pro | Phe |
|---|---|---|---|---|---|---|---|---|---|---|---|---|---|---|---|
| 65 | | | | | 70 | | | | | 75 | | | | | 80 |

| Lys | Trp | Val | Leu | Phe | Glu | Phe | Ile | Ala | Phe | Ile | Val | Leu | Cys | Gly | Met |
|---|---|---|---|---|---|---|---|---|---|---|---|---|---|---|---|
| | | | | 85 | | | | | 90 | | | | | 95 | |

| Thr | His | Leu | Leu | His | Gly | Trp | Thr | Tyr | Ser | Ala | His | Pro | Phe | Arg | Leu |
|---|---|---|---|---|---|---|---|---|---|---|---|---|---|---|---|
| | | | 100 | | | | | 105 | | | | | 110 | | |

| Met | Met | Ala | Phe | Thr | Val | Phe | Lys | Met | Leu | Thr | Ala | Leu | Val | Ser | Cys |
|---|---|---|---|---|---|---|---|---|---|---|---|---|---|---|---|
| | | 115 | | | | | 120 | | | | | 125 | | | |

| Ala | Thr | Ala | Ile | Thr | Leu | Ile | Thr | Leu | Ile | Pro | Leu | Leu | Leu | Lys | Val |
|---|---|---|---|---|---|---|---|---|---|---|---|---|---|---|---|
| | 130 | | | | | 135 | | | | | 140 | | | | |

| Lys | Val | Arg | Glu | Phe | Met | Leu | Lys | Lys | Ala | His | Glu | Leu | Gly | Arg |
|---|---|---|---|---|---|---|---|---|---|---|---|---|---|---|
| 145 | | | | | 150 | | | | | 155 | | | | | 160 |

| Glu | Val | Gly | Leu | Ile | Leu | Ile | Lys | Lys | Glu | Thr | Gly | Phe | His | Val | Arg |
|---|---|---|---|---|---|---|---|---|---|---|---|---|---|---|---|

```
                       165                        170                         175
Met  Leu  Thr  Gln  Glu  Ile  Arg  Lys  Ser  Leu  Asp  Arg  His  Thr  Ile  Leu
               180                      185                      190

Tyr  Thr  Thr  Leu  Val  Glu  Leu  Ser  Lys  Thr  Leu  Gly  Leu  Gln  Asn  Cys
          195                      200                      205

Ala  Val  Trp  Met  Pro  Asn  Asp  Gly  Thr  Glu  Met  Asp  Leu  Thr  His
     210                      215                      220

Glu  Leu  Arg  Gly  Arg  Gly  Gly  Tyr  Gly  Gly  Cys  Ser  Val  Ser  Met  Glu
225                      230                      235                      240

Asp  Leu  Asp  Val  Val  Arg  Ile  Arg  Glu  Ser  Asp  Glu  Val  Asn  Val  Leu
                    245                      250                      255

Ser  Val  Asp  Ser  Ser  Ile  Ala  Arg  Ala  Ser  Gly  Gly  Gly  Gly  Asp  Val
               260                      265                      270

Ser  Glu  Ile  Gly  Ala  Val  Ala  Ala  Ile  Arg  Met  Pro  Met  Leu  Arg  Val
          275                      280                      285

Ser  Asp  Phe  Asn  Gly  Glu  Leu  Ser  Tyr  Ala  Ile  Leu  Val  Cys  Val  Leu
     290                      295                      300

Pro  Gly  Gly  Thr  Arg  Arg  Asp  Trp  Thr  Tyr  Gln  Glu  Ile  Glu  Ile  Val
305                      310                      315                      320

Lys  Val  Val  Ala  Asp  Gln  Val  Thr  Val  Ala  Leu  Asp  His  Ala  Ala  Val
                    325                      330                      335

Leu  Glu  Glu  Ser  Gln  Leu  Met  Arg  Glu  Lys  Leu  Ala  Glu  Gln  Asn  Arg
               340                      345                      350

Ala  Leu  Gln  Met  Ala  Lys  Arg  Asp  Ala  Leu  Arg  Ala  Ser  Gln  Ala  Arg
          355                      360                      365

Asn  Ala  Phe  Gln  Lys  Thr  Met  Ser  Glu  Gly  Met  Arg  Arg  Pro  Met  His
     370                      375                      380

Ser  Ile  Leu  Gly  Leu  Leu  Ser  Met  Ile  Gln  Asp  Glu  Lys  Leu  Ser  Asp
385                      390                      395                      400

Glu  Gln  Lys  Met  Ile  Val  Asp  Thr  Met  Val  Lys  Thr  Gly  Asn  Val  Met
                    405                      410                      415

Ser  Asn  Leu  Val  Gly  Asp  Ser  Met  Asp  Val  Pro  Asp  Gly  Arg  Phe  Gly
               420                      425                      430

Thr  Glu  Met  Lys  Pro  Phe  Ser  Leu  His  Arg  Thr  Ile  His  Glu  Ala  Ala
          435                      440                      445

Cys  Met  Ala  Arg  Cys  Leu  Cys  Leu  Cys  Asn  Gly  Ile  Arg  Phe  Leu  Val
     450                      455                      460

Asp  Ala  Glu  Lys  Ser  Leu  Pro  Asp  Asn  Val  Val  Gly  Asp  Glu  Arg  Arg
465                      470                      475                      480

Val  Phe  Gln  Val  Ile  Leu  His  Met  Val  Gly  Ser  Leu  Val  Lys  Pro  Arg
                    485                      490                      495

Lys  Arg  Gln  Glu  Gly  Ser  Ser  Leu  Met  Phe  Lys  Val  Leu  Lys  Glu  Arg
               500                      505                      510

Gly  Ser  Leu  Asp  Arg  Ser  Asp  His  Arg  Trp  Ala  Ala  Trp  Arg  Ser  Pro
          515                      520                      525

Ala  Ser  Ser  Ala  Asp  Gly  Asp  Val  Tyr  Ile  Arg  Phe  Glu  Met  Asn  Val
     530                      535                      540

Glu  Asn  Asp  Asp  Ser  Ser  Ser  Gln  Ser  Phe  Ala  Ser  Val  Ser  Ser  Arg
545                      550                      555                      560

Asp  Gln  Glu  Val  Gly  Asp  Val  Arg  Phe  Ser  Gly  Gly  Tyr  Gly  Leu  Gly
                    565                      570                      575

Gln  Asp  Leu  Ser  Phe  Gly  Val  Cys  Lys  Lys  Val  Val  Gln  Leu  Ile  His
               580                      585                      590
```

| | | | | | | | | | | | | | | |
|---|---|---|---|---|---|---|---|---|---|---|---|---|---|---|
| Gly | Asn | Ile | Ser | Val | Val | Pro | Gly | Ser | Asp | Gly | Ser | Pro | Glu | Thr | Met |
| | | 595 | | | | | 600 | | | | | 605 | | | |
| Ser | Leu | Leu | Leu | Arg | Phe | Arg | Arg | Arg | Pro | Ser | Ile | Ser | Val | His | Gly |
| | 610 | | | | | 615 | | | | | 620 | | | | |
| Ser | Ser | Glu | Ser | Pro | Ala | Pro | Asp | His | His | Ala | His | Pro | His | Ser | Asn |
| 625 | | | | | 630 | | | | | 635 | | | | | 640 |
| Ser | Leu | Leu | Arg | Gly | Leu | Gln | Val | Leu | Leu | Val | Asp | Thr | Asn | Asp | Ser |
| | | | | 645 | | | | | 650 | | | | | 655 | |
| Asn | Arg | Ala | Val | Thr | Arg | Lys | Leu | Leu | Glu | Lys | Leu | Gly | Cys | Asp | Val |
| | | | 660 | | | | | 665 | | | | | 670 | | |
| Thr | Ala | Val | Ser | Ser | Gly | Phe | Asp | Cys | Leu | Thr | Ala | Ile | Ala | Pro | Gly |
| | | 675 | | | | | 680 | | | | | 685 | | | |
| Ser | Ser | Ser | Pro | Ser | Thr | Ser | Phe | Gln | Val | Val | Val | Leu | Asp | Leu | Gln |
| | | 690 | | | | | 695 | | | | | 700 | | | |
| Met | Ala | Glu | Met | Asp | Gly | Tyr | Glu | Val | Ala | Met | Arg | Ile | Arg | Ser | Arg |
| 705 | | | | | 710 | | | | | 715 | | | | | 720 |
| Ser | Trp | Pro | Leu | Ile | Val | Ala | Thr | Thr | Val | Ser | Leu | Asp | Glu | Glu | Met |
| | | | | 725 | | | | | 730 | | | | | 735 | |
| Trp | Asp | Lys | Cys | Ala | Gln | Ile | Gly | Ile | Asn | Gly | Val | Val | Arg | Lys | Pro |
| | | | 740 | | | | | 745 | | | | | 750 | | |
| Val | Val | Leu | Arg | Ala | Met | Glu | Ser | Glu | Leu | Arg | Arg | Val | Leu | Leu | Gln |
| | | 755 | | | | | 760 | | | | | 765 | | | |
| Ala | Asp | Gln | Leu | Leu | | | | | | | | | | | |
| | | 770 | | | | | | | | | | | | | |

(2) INFORMATION FOR SEQ ID NO:45:

(i) SEQUENCE CHARACTERISTICS:
        (A) LENGTH: 3009 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: join(564..1469, 1565..1933, 2014..2280, 2359
            ..2486, 2577..2748)

(xi) SEQUENCE DESCRIPTION: SEQ ID NO:45:

```
ACTTTTAAAA TTTCTTTATT TCATTGTCAG AAAAAGAGAG CTAATAATAT TATTATTTAA      60

ATGTAACAAG TAGGCCTATA ACACGTGAAC TTCCCTCTTT GCAAAAAAAA AATCATCAAA     120

AACTTTTACC TCTCATTGGT TTCTTCTTTA TCACACTGTT ACGCTTGGAT TCTCATTTCT     180

TCAAGTTCAT AACGCTCGGA TCAATCAGGA AGACGAACTT GAACTTTCTT TTTTTCATCA     240

TTACCCAAAG CTATGAGGCT CACACCACCA ATACGTCCGC CGTCATGAAT CCTTCTCTTC     300

CAGGTACTGT GCCGTCTCGG GATAACAAAC TTTCTATTTA TTCTCTTCTG ATCGGATCTA     360

TCTATCGATG AAGATTGATT TCACTACTTT AGTAACATTT CATCTGATCG ATCTGTGTTG     420

TGTTATCGAG GAATCAATCT CATTTTGTAG ATTCAATTTT CTGGATAGAT TTTGTATCTC     480

TTTTCCATAG CTCTAGTCCA AATCTAGTCT CCACTGATAT CTGAGTTTTG TTGACCAGGT     540

CAACACAAGT CAGAGCTCCA AAA ATG GAG TCA TGC GAT TGT TTT GAG ACG          590
                          Met Glu Ser Cys Asp Cys Phe Glu Thr
                            1               5
```

| CAT | GTG | AAT | CAA | GAT | GAT | CTG | TTA | GTG | AAG | TAC | CAA | TAC | ATC | TCA | GAT | 638 |
|---|---|---|---|---|---|---|---|---|---|---|---|---|---|---|---|---|
| His | Val | Asn | Gln | Asp | Asp | Leu | Leu | Val | Lys | Tyr | Gln | Tyr | Ile | Ser | Asp | |
| 10 | | | | 15 | | | | | 20 | | | | | 25 | | |

| GCG | TTG | ATT | GCT | CTT | GCA | TAC | TTC | TCA | ATC | CCA | CTC | GAG | CTT | ATC | TAT | 686 |
|---|---|---|---|---|---|---|---|---|---|---|---|---|---|---|---|---|
| Ala | Leu | Ile | Ala | Leu | Ala | Tyr | Phe | Ser | Ile | Pro | Leu | Glu | Leu | Ile | Tyr | |

|  |  |  |  |  | 30 |  |  |  | 35 |  |  |  |  | 40 |  |  |
|---|---|---|---|---|---|---|---|---|---|---|---|---|---|---|---|---|
| TTC | GTG | CAA | AAG | TCT | GCT | TTC | TTC | CCT | TAC | AAA | TGG | GTG | CTT | ATG | CAG | 734 |
| Phe | Val | Gln | Lys | Ser | Ala | Phe | Phe | Pro | Tyr | Lys | Trp | Val | Leu | Met | Gln | |
| | | | 45 | | | | | 50 | | | | | 55 | | | |
| TTT | GGA | GCC | TTT | ATC | ATT | CTC | TGT | GGA | GCT | ACG | CAT | TTC | ATC | AAC | CTA | 782 |
| Phe | Gly | Ala | Phe | Ile | Ile | Leu | Cys | Gly | Ala | Thr | His | Phe | Ile | Asn | Leu | |
| | | 60 | | | | | 65 | | | | | 70 | | | | |
| TGG | ATG | TTC | TTC | ATG | CAT | TCC | AAA | GCC | GTT | GCC | ATT | GTC | ATG | ACT | ATT | 830 |
| Trp | Met | Phe | Phe | Met | His | Ser | Lys | Ala | Val | Ala | Ile | Val | Met | Thr | Ile | |
| | 75 | | | | | 80 | | | | | 85 | | | | | |
| GCT | AAA | GTC | TCT | TGC | GCG | GTT | GTG | TCG | TGT | GCT | ACC | GCG | TTG | ATG | TTG | 878 |
| Ala | Lys | Val | Ser | Cys | Ala | Val | Val | Ser | Cys | Ala | Thr | Ala | Leu | Met | Leu | |
| 90 | | | | | 95 | | | | | 100 | | | | | 105 | |
| GTT | CAT | ATT | ATT | CCT | GAT | CTT | CTC | AGT | GTT | AAG | AAC | AGG | GAA | TTG | TTT | 926 |
| Val | His | Ile | Ile | Pro | Asp | Leu | Leu | Ser | Val | Lys | Asn | Arg | Glu | Leu | Phe | |
| | | | | 110 | | | | | 115 | | | | | 120 | | |
| CTC | AAG | AAG | AAA | GCT | GAT | GAG | TTA | GAT | AGA | GAA | ATG | GGT | CTT | ATT | TTA | 974 |
| Leu | Lys | Lys | Lys | Ala | Asp | Glu | Leu | Asp | Arg | Glu | Met | Gly | Leu | Ile | Leu | |
| | | | 125 | | | | | 130 | | | | | 135 | | | |
| ACA | CAA | GAG | GAG | ACT | GGT | AGG | CAT | GTT | AGG | ATG | CTT | ACT | CAT | GGA | ATT | 1022 |
| Thr | Gln | Glu | Glu | Thr | Gly | Arg | His | Val | Arg | Met | Leu | Thr | His | Gly | Ile | |
| | | | 140 | | | | | 145 | | | | | 150 | | | |
| AGA | AGA | ACT | CTT | GAT | AGG | CAT | ACT | ATT | TTA | AGA | ACC | ACT | CTT | GTT | GAG | 1070 |
| Arg | Arg | Thr | Leu | Asp | Arg | His | Thr | Ile | Leu | Arg | Thr | Thr | Leu | Val | Glu | |
| | 155 | | | | | 160 | | | | | 165 | | | | | |
| CTT | GGT | AAA | ACT | CTT | TGT | CTT | GAG | GAA | TGT | GCG | TTG | TGG | ATG | CCT | TCT | 1118 |
| Leu | Gly | Lys | Thr | Leu | Cys | Leu | Glu | Glu | Cys | Ala | Leu | Trp | Met | Pro | Ser | |
| 170 | | | | | 175 | | | | | 180 | | | | | 185 | |
| CAA | AGT | GGT | TTA | TAT | TTG | CAG | CTT | TCT | CAT | ACT | TTG | AGT | CAT | AAA | ATA | 1166 |
| Gln | Ser | Gly | Leu | Tyr | Leu | Gln | Leu | Ser | His | Thr | Leu | Ser | His | Lys | Ile | |
| | | | | 190 | | | | | 195 | | | | | 200 | | |
| CAA | GTT | GGA | AGC | AGT | GTG | CCG | ATA | AAT | CTC | CCG | ATT | ATT | AAT | GAA | CTC | 1214 |
| Gln | Val | Gly | Ser | Ser | Val | Pro | Ile | Asn | Leu | Pro | Ile | Ile | Asn | Glu | Leu | |
| | | | 205 | | | | | 210 | | | | | 215 | | | |
| TTC | AAT | AGC | GCT | CAA | GCT | ATG | CAC | ATA | CCT | CAT | TCT | TGT | CCT | TTG | GCT | 1262 |
| Phe | Asn | Ser | Ala | Gln | Ala | Met | His | Ile | Pro | His | Ser | Cys | Pro | Leu | Ala | |
| | | 220 | | | | | 225 | | | | | 230 | | | | |
| AAG | ATT | GGG | CCT | CCG | GTT | GGG | AGA | TAT | TCA | CCT | CCT | GAG | GTT | GTT | TCT | 1310 |
| Lys | Ile | Gly | Pro | Pro | Val | Gly | Arg | Tyr | Ser | Pro | Pro | Glu | Val | Val | Ser | |
| | 235 | | | | | 240 | | | | | 245 | | | | | |
| GTC | CGT | GTT | CCT | CTT | TTA | CAT | CTC | TCT | AAT | TTC | CAA | GGC | AGT | GAC | TGG | 1358 |
| Val | Arg | Val | Pro | Leu | Leu | His | Leu | Ser | Asn | Phe | Gln | Gly | Ser | Asp | Trp | |
| 250 | | | | | 255 | | | | | 260 | | | | | 265 | |
| TCG | GAT | CTC | TCT | GGC | AAA | GGT | TAC | GCT | ATC | ATG | GTC | CTG | ATT | CTC | CCA | 1406 |
| Ser | Asp | Leu | Ser | Gly | Lys | Gly | Tyr | Ala | Ile | Met | Val | Leu | Ile | Leu | Pro | |
| | | | | 270 | | | | | 275 | | | | | 280 | | |
| ACC | GAT | GGT | GCA | AGA | AAA | TGG | AGA | GAC | CAT | GAG | TTA | GAG | CTT | GTA | GAA | 1454 |
| Thr | Asp | Gly | Ala | Arg | Lys | Trp | Arg | Asp | His | Glu | Leu | Glu | Leu | Val | Glu | |
| | | | 285 | | | | | 290 | | | | | 295 | | | |
| AAC | GTG | GCG | GAT | CAG | GTCCATCTCT | | TTACTTGTAT | | ATGTTTGGTT | | GTGTGTCAAG | | | | | 1509 |
| Asn | Val | Ala | Asp | Gln | | | | | | | | | | | | |
| | | | 300 | | | | | | | | | | | | | |

TTGCTTTACC AGCTTTTAGT GTTTTGTTTT GTCCCCTGAC TCTCACTTCA TTCAG GTG  1567
                                                             Val

| GCT | GTG | GCT | CTC | TCA | CAT | GCT | GCA | ATT | TTG | GAA | GAA | TCC | ATG | CAC | GCT | 1615 |
|---|---|---|---|---|---|---|---|---|---|---|---|---|---|---|---|---|
| Ala | Val | Ala | Leu | Ser | His | Ala | Ala | Ile | Leu | Glu | Glu | Ser | Met | His | Ala | |
| | | 305 | | | | | 310 | | | | | 315 | | | | |
| CGT | GAC | CAG | CTT | ATG | GAG | CAG | AAT | TTT | GCT | TTA | GAC | AAG | GCT | CGT | CAA | 1663 |
| Arg | Asp | Gln | Leu | Met | Glu | Gln | Asn | Phe | Ala | Leu | Asp | Lys | Ala | Arg | Gln | |
| 320 | | | | | 325 | | | | | 330 | | | | | 335 | |

-continued

| | |
|---|---|
| GAG GCT GAG ATG GCA GTA CAT GCT CGA AAT GAT TTC CTA GCT GTT ATG<br>Glu Ala Glu Met Ala Val His Ala Arg Asn Asp Phe Leu Ala Val Met<br>                      340                      345                      350 | 1711 |
| AAC CAC GAG ATG AGG ACA CCG ATG CAT GCC ATC ATC TCT CTT TCT TCT<br>Asn His Glu Met Arg Thr Pro Met His Ala Ile Ile Ser Leu Ser Ser<br>                  355                      360                      365 | 1759 |
| CTT CTC CTT GAG ACT GAG CTG TCT CCA GAG CAA AGA GTT ATG ATC GAG<br>Leu Leu Leu Glu Thr Glu Leu Ser Pro Glu Gln Arg Val Met Ile Glu<br>        370                      375                      380 | 1807 |
| ACA ATA CTG AAA AGC AGC AAT CTT GTG GCT ACA CTA ATC AGC GAC GTT<br>Thr Ile Leu Lys Ser Ser Asn Leu Val Ala Thr Leu Ile Ser Asp Val<br>        385                      390                      395 | 1855 |
| CTG GAT CTT TCG AGA TTG GAA GAT GGG AGC TTA CTC TTG GAA AAT GAA<br>Leu Asp Leu Ser Arg Leu Glu Asp Gly Ser Leu Leu Leu Glu Asn Glu<br>400                      405                      410                      415 | 1903 |
| CCA TTC AGT CTA CAA GCG ATC TTT GAA GAG GTAACTAAAT CCCCCTGATT<br>Pro Phe Ser Leu Gln Ala Ile Phe Glu Glu<br>                  420                      425 | 1953 |
| AACCAGTGAA GTCCATTATA TATGTCTTAC ATGAATAACA TGGGCGCTTT GAATCTGCAG | 2013 |
| GTC ATC TCT TTG ATA AAG CCA ATC GCA TCA GTG AAG AAA CTA TCA ACG<br>Val Ile Ser Leu Ile Lys Pro Ile Ala Ser Val Lys Lys Leu Ser Thr<br>                  430                      435                      440 | 2061 |
| AAT CTG ATT CTG TCT GCA GAC TTA CCA ACT TAT GCT ATT GGT GAT GAG<br>Asn Leu Ile Leu Ser Ala Asp Leu Pro Thr Tyr Ala Ile Gly Asp Glu<br>                  445                      450                      455 | 2109 |
| AAA CGT CTG ATG CAA ACA ATT CTT AAC ATC ATG GGC AAC GCT GTG AAA<br>Lys Arg Leu Met Gln Thr Ile Leu Asn Ile Met Gly Asn Ala Val Lys<br>        460                      465                      470 | 2157 |
| TTT ACT AAG GAA GGC TAC ATC TCC ATA ATA GCC TCT ATC ATG AAA CCC<br>Phe Thr Lys Glu Gly Tyr Ile Ser Ile Ile Ala Ser Ile Met Lys Pro<br>        475                      480                      485 | 2205 |
| GAG TCC TTA CAA GAA TTA CCA TCT CCA GAA TTT TTT CCA GTT CTC AGT<br>Glu Ser Leu Gln Glu Leu Pro Ser Pro Glu Phe Phe Pro Val Leu Ser<br>490                      495                      500                      505 | 2253 |
| GAC AGT CAC TTC TAC CTA TGT GTG CAG GTTAGACCCA ATCTACAAAT<br>Asp Ser His Phe Tyr Leu Cys Val Gln<br>                  510 | 2300 |
| TACTAAACTA CAAAGTTAAG CTTCTTACTG TGTTCTTACT GTTATAATCA TGGTGCAG | 2358 |
| GTG AAG GAC ACA GGG TGT GGA ATT CAC ACA CAA GAC ATT CCT TTG CTC<br>Val Lys Asp Thr Gly Cys Gly Ile His Thr Gln Asp Ile Pro Leu Leu<br>515                      520                      525                      530 | 2406 |
| TTT ACC AAA TTT GTA CAG CCT CGG ACC GGA ACT CAG AGG AAC CAT TCC<br>Phe Thr Lys Phe Val Gln Pro Arg Thr Gly Thr Gln Arg Asn His Ser<br>                  535                      540                      545 | 2454 |
| GGT GGA GGA CTC GGG CTA GCT CTC TGT AAA   CG GTAACAACCC<br>Gly Gly Gly Leu Gly Leu Ala Leu Cys Lys   Arg<br>                  550                              555 | 2496 |
| AAAAGTATAT ATAAGTTATA AGCAGATGGT GTTACAAATA GCTAAAGGC AAGTTTCTGT | 2556 |
| TGATGGATGT CTCTGGTTAG G TTT GTC GGG CTA ATG GGA GGA TAC ATG TGG<br>                                      Phe Val Gly Leu Met Gly Gly Tyr Met Trp<br>                                                      560                      565 | 2607 |
| ATA GAA AGT GAA GGC CTA GAG AAA GGC TGC ACA GCT TCG TTC ATC ATC<br>Ile Glu Ser Glu Gly Leu Glu Lys Gly Cys Thr Ala Ser Phe Ile Ile<br>            570                      575                      580 | 2655 |
| AGG CTT GGT ATC TGC AAC GGT CCA AGC AGT AGC AGT GGT TCA ATG GCG<br>Arg Leu Gly Ile Cys Asn Gly Pro Ser Ser Ser Ser Gly Ser Met Ala<br>585                      590                      595 | 2703 |
| CTA CAT CTT GCA GCT AAA TCA CAA ACC AGA CCG TGG AAC TGG TGATACTTAC | 2755 |

| Leu | His | Leu | Ala | Ala | Lys | Ser | Gln | Thr | Arg | Pro | Trp | Asn | Trp |
|-----|-----|-----|-----|-----|-----|-----|-----|-----|-----|-----|-----|-----|-----|
| 600 | | | | | 605 | | | | | 610 | | | |

```
GTTGGAAAGA  CTTGTATTGA  GGTGAGACTT  TTTAACTACA  CAGCAGCAAG  AGAAAGAAGA    2815

AAATACATGA  CCGGACGGTG  TGATCTAACT  TATTGGATTT  TGTTGGATGT  AATATGTAAA    2875

ATAAAAATCC  TATATACGGG  GAGAGGTACC  TTATCTGTTC  TCACTATATT  TTATTGAACA    2935

TTACTTTAGA  GAATATGTTT  TGGAATTCAC  TACTAAATAA  ACGATATAAA  TCTTCACGAA    2995

AAGAGCAACA  TTTT                                                          3009
```

( 2 ) INFORMATION FOR SEQ ID NO:46:

( i ) SEQUENCE CHARACTERISTICS:
    ( A ) LENGTH: 613 amino acids
    ( B ) TYPE: amino acid
    ( D ) TOPOLOGY: linear ( i i ) MOLECULE TYPE: protein ( x i ) SEQUENCE DESCRIPTION: SEQ ID NO:46:

```
Met  Glu  Ser  Cys  Asp  Cys  Phe  Glu  Thr  His  Val  Asn  Gln  Asp  Asp  Leu
 1              5                        10                       15

Leu  Val  Lys  Tyr  Gln  Tyr  Ile  Ser  Asp  Ala  Leu  Ile  Ala  Leu  Ala  Tyr
               20                       25                       30

Phe  Ser  Ile  Pro  Leu  Glu  Leu  Ile  Tyr  Phe  Val  Gln  Lys  Ser  Ala  Phe
              35                        40                       45

Phe  Pro  Tyr  Lys  Trp  Val  Leu  Met  Gln  Phe  Gly  Ala  Phe  Ile  Ile  Leu
     50                        55                       60

Cys  Gly  Ala  Thr  His  Phe  Ile  Asn  Leu  Trp  Met  Phe  Phe  Met  His  Ser
 65                       70                       75                       80

Lys  Ala  Val  Ala  Ile  Val  Met  Thr  Ile  Ala  Lys  Val  Ser  Cys  Ala  Val
                    85                       90                       95

Val  Ser  Cys  Ala  Thr  Ala  Leu  Met  Leu  Val  His  Ile  Ile  Pro  Asp  Leu
               100                      105                      110

Leu  Ser  Val  Lys  Asn  Arg  Glu  Leu  Phe  Leu  Lys  Lys  Ala  Asp  Glu
               115                      120                      125

Leu  Asp  Arg  Glu  Met  Gly  Leu  Ile  Leu  Thr  Gln  Glu  Glu  Thr  Gly  Arg
     130                      135                      140

His  Val  Arg  Met  Leu  Thr  His  Gly  Ile  Arg  Arg  Thr  Leu  Asp  Arg  His
145                           150                      155                 160

Thr  Ile  Leu  Arg  Thr  Thr  Leu  Val  Glu  Leu  Gly  Lys  Thr  Leu  Cys  Leu
                    165                      170                      175

Glu  Glu  Cys  Ala  Leu  Trp  Met  Pro  Ser  Gln  Ser  Gly  Leu  Tyr  Leu  Gln
               180                      185                      190

Leu  Ser  His  Thr  Leu  Ser  His  Lys  Ile  Gln  Val  Gly  Ser  Ser  Val  Pro
               195                      200                      205

Ile  Asn  Leu  Pro  Ile  Ile  Asn  Glu  Leu  Phe  Asn  Ser  Ala  Gln  Ala  Met
     210                      215                      220

His  Ile  Pro  His  Ser  Cys  Pro  Leu  Ala  Lys  Ile  Gly  Pro  Pro  Val  Gly
225                           230                      235                 240

Arg  Tyr  Ser  Pro  Pro  Glu  Val  Val  Ser  Val  Arg  Val  Pro  Leu  Leu  His
               245                      250                      255

Leu  Ser  Asn  Phe  Gln  Gly  Ser  Asp  Trp  Ser  Asp  Leu  Ser  Gly  Lys  Gly
               260                      265                      270

Tyr  Ala  Ile  Met  Val  Leu  Ile  Leu  Pro  Thr  Asp  Gly  Ala  Arg  Lys  Trp
               275                      280                      285

Arg  Asp  His  Glu  Leu  Glu  Leu  Val  Glu  Asn  Val  Ala  Asp  Gln  Val  Ala
```

|   |   |   |   |   |   |   | 290 |   |   |   |   | 295 |   |   |   |   | 300 |   |   |
|---|---|---|---|---|---|---|---|---|---|---|---|---|---|---|---|---|---|---|---|

Val Ala Leu Ser His Ala Ala Ile Leu Glu Glu Ser Met His Ala Arg
305                 310             315                 320

Asp Gln Leu Met Glu Gln Asn Phe Ala Leu Asp Lys Ala Arg Gln Glu
            325             330             335

Ala Glu Met Ala Val His Ala Arg Asn Asp Phe Leu Ala Val Met Asn
        340             345             350

His Glu Met Arg Thr Pro Met His Ala Ile Ile Ser Leu Ser Ser Leu
    355             360             365

Leu Leu Glu Thr Glu Leu Ser Pro Glu Gln Arg Val Met Ile Glu Thr
370             375             380

Ile Leu Lys Ser Ser Asn Leu Val Ala Thr Leu Ile Ser Asp Val Leu
385             390             395             400

Asp Leu Ser Arg Leu Glu Asp Gly Ser Leu Leu Leu Glu Asn Glu Pro
            405             410             415

Phe Ser Leu Gln Ala Ile Phe Glu Glu Val Ile Ser Leu Ile Lys Pro
            420             425             430

Ile Ala Ser Val Lys Lys Leu Ser Thr Asn Leu Ile Leu Ser Ala Asp
        435             440             445

Leu Pro Thr Tyr Ala Ile Gly Asp Glu Lys Arg Leu Met Gln Thr Ile
    450             455             460

Leu Asn Ile Met Gly Asn Ala Val Lys Phe Thr Lys Glu Gly Tyr Ile
465             470             475             480

Ser Ile Ile Ala Ser Ile Met Lys Pro Glu Ser Leu Gln Glu Leu Pro
            485             490             495

Ser Pro Glu Phe Phe Pro Val Leu Ser Asp Ser His Phe Tyr Leu Cys
        500             505             510

Val Gln Val Lys Asp Thr Gly Cys Gly Ile His Thr Gln Asp Ile Pro
        515             520             525

Leu Leu Phe Thr Lys Phe Val Gln Pro Arg Thr Gly Thr Gln Arg Asn
    530             535             540

His Ser Gly Gly Gly Leu Gly Leu Ala Leu Cys Lys Arg Phe Val Gly
545             550             555             560

Leu Met Gly Gly Tyr Met Trp Ile Glu Ser Glu Gly Leu Glu Lys Gly
            565             570             575

Cys Thr Ala Ser Phe Ile Ile Arg Leu Gly Ile Cys Asn Gly Pro Ser
        580             585             590

Ser Ser Ser Gly Ser Met Ala Leu His Leu Ala Ala Lys Ser Gln Thr
        595             600             605

Arg Pro Trp Asn Trp
610

( 2 ) INFORMATION FOR SEQ ID NO:47:

( i ) SEQUENCE CHARACTERISTICS:
        ( A ) LENGTH: 2314 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 224..2065

( x i ) SEQUENCE DESCRIPTION: SEQ ID NO:47:

```
AAAAAAATCA TCAAAAACTT TTACCTCTCA TTGGTTTCTT CTTTATCACA CTGTTACGCT      60

TGGATTCTCA TTTCTTCAAG TTCATAACGC TCGGATCAAT CAGGAAGACG AACTTGAACT     120
```

-continued

```
TTCTTTTTTT CATCATTACC CAAAGCTATG AGGCTCACAC CACCAATACG TCCGCCGTCA       180

TGAATCCTTC TCTTCCAGGT CAACACAAGT CAGAGCTCCA AAA ATG GAG TCA TGC        235
                                                 Met Glu Ser Cys
                                                  1

GAT TGT TTT GAG ACG CAT GTG AAT CAA GAT GAT CTG TTA GTG AAG TAC        283
Asp Cys Phe Glu Thr His Val Asn Gln Asp Asp Leu Leu Val Lys Tyr
 5               10                  15                      20

CAA TAC ATC TCA GAT GCG TTG ATT GCT CTT GCA TAC TTC TCA ATC CCA        331
Gln Tyr Ile Ser Asp Ala Leu Ile Ala Leu Ala Tyr Phe Ser Ile Pro
                 25                  30                      35

CTC GAG CTT ATC TAT TTC GTG CAA AAG TCT GCT TTC TTC CCT TAC AAA        379
Leu Glu Leu Ile Tyr Phe Val Gln Lys Ser Ala Phe Phe Pro Tyr Lys
                 40                  45                      50

TGG GTG CTT ATG CAG TTT GGA GCC TTT ATC ATT CTC TGT GGA GCT ACG        427
Trp Val Leu Met Gln Phe Gly Ala Phe Ile Ile Leu Cys Gly Ala Thr
                 55                  60                      65

CAT TTC ATC AAC CTA TGG ATG TTC TTC ATG CAT TCC AAA GCC GTT GCC        475
His Phe Ile Asn Leu Trp Met Phe Phe Met His Ser Lys Ala Val Ala
         70                  75                  80

ATT GTC ATG ACT ATT GCT AAA GTC TCT TGC GCG GTT GTG TCG TGT GCT        523
Ile Val Met Thr Ile Ala Lys Val Ser Cys Ala Val Val Ser Cys Ala
 85                  90                  95                 100

ACC GCG TTG ATG TTG GTT CAT ATT ATT CCT GAT CTT CTC AGT GTT AAG        571
Thr Ala Leu Met Leu Val His Ile Ile Pro Asp Leu Leu Ser Val Lys
                105                 110                     115

AAC AGG GAA TTG TTT CTC AAG AAG AAA GCT GAT GAG TTA GAT AGA GAA        619
Asn Arg Glu Leu Phe Leu Lys Lys Lys Ala Asp Glu Leu Asp Arg Glu
                120                 125                     130

ATG GGT CTT ATT TTA ACA CAA GAG GAG ACT GGT AGG CAT GTT AGG ATG        667
Met Gly Leu Ile Leu Thr Gln Glu Glu Thr Gly Arg His Val Arg Met
                135                 140                     145

CTT ACT CAT GGA ATT AGA AGA ACT CTT GAT AGG CAT ACT ATT TTA AGA        715
Leu Thr His Gly Ile Arg Arg Thr Leu Asp Arg His Thr Ile Leu Arg
        150                 155                     160

ACC ACT CTT GTT GAG CTT GGT AAA ACT CTT TGT CTT GAG GAA TGT GCG        763
Thr Thr Leu Val Glu Leu Gly Lys Thr Leu Cys Leu Glu Glu Cys Ala
165                 170                     175                 180

TTG TGG ATG CCT TCT CAA AGT GGT TTA TAT TTG CAG CTT TCT CAT ACT        811
Leu Trp Met Pro Ser Gln Ser Gly Leu Tyr Leu Gln Leu Ser His Thr
                185                 190                     195

TTG AGT CAT AAA ATA CAA GTT GGA AGC AGT GTG CCG ATA AAT CTC CCG        859
Leu Ser His Lys Ile Gln Val Gly Ser Ser Val Pro Ile Asn Leu Pro
                200                 205                     210

ATT ATT AAT GAA CTC TTC AAT AGC GCT CAA GCT ATG CAC ATA CCT CAT        907
Ile Ile Asn Glu Leu Phe Asn Ser Ala Gln Ala Met His Ile Pro His
                215                 220                     225

TCT TGT CCT TTG GCT AAG ATT GGG CCT CCG GTT GGG AGA TAT TCA CCT        955
Ser Cys Pro Leu Ala Lys Ile Gly Pro Pro Val Gly Arg Tyr Ser Pro
        230                 235                     240

CCT GAG GTT GTT TCT GTC CGT GTT CCT CTT TTA CAT CTC TCT AAT TTC       1003
Pro Glu Val Val Ser Val Arg Val Pro Leu Leu His Leu Ser Asn Phe
245                 250                     255                 260

CAA GGC AGT GAC TGG TCG GAT CTC TCT GGC AAA GGT TAC GCT ATC ATG       1051
Gln Gly Ser Asp Trp Ser Asp Leu Ser Gly Lys Gly Tyr Ala Ile Met
                265                 270                     275

GTC CTG ATT CTC CCA ACC GAT GGT GCA AGA AAA TGG AGA GAC CAT GAG       1099
Val Leu Ile Leu Pro Thr Asp Gly Ala Arg Lys Trp Arg Asp His Glu
                280                 285                     290

TTA GAG CTT GTA GAA AAC GTG GCG GAT CAG GTG GCT GTG GCT CTC TCA       1147
```

-continued

```
Leu Glu Leu Val Glu Asn Val Ala Asp Gln Val Ala Val Ala Leu Ser
    295             300             305

CAT GCT GCA ATT TTG GAA GAA TCC ATG CAC GCT CGT GAC CAG CTT ATG    1195
His Ala Ala Ile Leu Glu Glu Ser Met His Ala Arg Asp Gln Leu Met
310             315             320

GAG CAG AAT TTT GCT TTA GAC AAG GCT CGT CAA GAG GCT GAG ATG GCA    1243
Glu Gln Asn Phe Ala Leu Asp Lys Ala Arg Gln Glu Ala Glu Met Ala
325             330             335             340

GTA CAT GCT CGA AAT GAT TTC CTA GCT GTT ATG AAC CAC GAG ATG AGG    1291
Val His Ala Arg Asn Asp Phe Leu Ala Val Met Asn His Glu Met Arg
            345             350             355

ACA CCG ATG CAT GCC ATC ATC TCT CTT TCT TCT CTT CTC CTT GAG ACT    1339
Thr Pro Met His Ala Ile Ile Ser Leu Ser Ser Leu Leu Leu Glu Thr
            360             365             370

GAG CTG TCT CCA GAG CAA AGA GTT ATG ATC GAG ACA ATA CTG AAA AGC    1387
Glu Leu Ser Pro Glu Gln Arg Val Met Ile Glu Thr Ile Leu Lys Ser
        375             380             385

AGC AAT CTT GTG GCT ACA CTA ATC AGC GAC GTT CTG GAT CTT TCG AGA    1435
Ser Asn Leu Val Ala Thr Leu Ile Ser Asp Val Leu Asp Leu Ser Arg
    390             395             400

TTG GAA GAT GGG AGC TTA CTC TTG GAA AAT GAA CCA TTC AGT CTA CAA    1483
Leu Glu Asp Gly Ser Leu Leu Leu Glu Asn Glu Pro Phe Ser Leu Gln
405             410             415             420

GCG ATC TTT GAA GAG GTC ATC TCT TTG ATA AAG CCA ATC GCA TCA GTG    1531
Ala Ile Phe Glu Glu Val Ile Ser Leu Ile Lys Pro Ile Ala Ser Val
            425             430             435

AAG AAA CTA TCA ACG AAT CTG ATT CTG TCT GCA GAC TTA CCA ACT TAT    1579
Lys Lys Leu Ser Thr Asn Leu Ile Leu Ser Ala Asp Leu Pro Thr Tyr
            440             445             450

GCT ATT GGT GAT GAG AAA CGT CTG ATG CAA ACA ATT CTT AAC ATC ATG    1627
Ala Ile Gly Asp Glu Lys Arg Leu Met Gln Thr Ile Leu Asn Ile Met
        455             460             465

GGC AAC GCT GTG AAA TTT ACT AAG GAA GGC TAC ATC TCC ATA ATA GCC    1675
Gly Asn Ala Val Lys Phe Thr Lys Glu Gly Tyr Ile Ser Ile Ile Ala
    470             475             480

TCT ATC ATG AAA CCC GAG TCC TTA CAA GAA TTA CCA TCT CCA GAA TTT    1723
Ser Ile Met Lys Pro Glu Ser Leu Gln Glu Leu Pro Ser Pro Glu Phe
485             490             495             500

TTT CCA GTT CTC AGT GAC AGT CAC TTC TAC CTA TGT GTG CAG GTG AAG    1771
Phe Pro Val Leu Ser Asp Ser His Phe Tyr Leu Cys Val Gln Val Lys
            505             510             515

GAC ACA GGG TGT GGA ATT CAC ACA CAA GAC ATT CCT TTG CTC TTT ACC    1819
Asp Thr Gly Cys Gly Ile His Thr Gln Asp Ile Pro Leu Leu Phe Thr
        520             525             530

AAA TTT GTA CAG CCT CGG ACC GGA ACT CAG AGG AAC CAT TCC GGT GGA    1867
Lys Phe Val Gln Pro Arg Thr Gly Thr Gln Arg Asn His Ser Gly Gly
    535             540             545

GGA CTC GGG CTA GCT CTC TGT AAA CGG TTT GTC GGG CTA ATG GGA GGA    1915
Gly Leu Gly Leu Ala Leu Cys Lys Arg Phe Val Gly Leu Met Gly Gly
550             555             560

TAC ATG TGG ATA GAA AGT GAA GGC CTA GAG AAA GGC TGC ACA GCT TCG    1963
Tyr Met Trp Ile Glu Ser Glu Gly Leu Glu Lys Gly Cys Thr Ala Ser
565             570             575             580

TTC ATC ATC AGG CTT GGT ATC TGC AAC GGT CCA AGC AGT AGC AGT GGT    2011
Phe Ile Ile Arg Leu Gly Ile Cys Asn Gly Pro Ser Ser Ser Ser Gly
            585             590             595

TCA ATG GCG CTA CAT CTT GCA GCT AAA TCA CAA ACC AGA CCG TGG AAC    2059
Ser Met Ala Leu His Leu Ala Ala Lys Ser Gln Thr Arg Pro Trp Asn
        600             605             610

TGG TGATACTTAC GTTGGAAAGA CTTGTATTGA GGTGAGACTT TTTAACTACA        2112
```

-continued

```
Trp

CAGCAGCAAG  AGAAAGAAGA  AAATACATGA  CCGGACGGTG  TGATCTAACT  TATTGGATTT    2172

TGTTGGATGT  AATATGTAAA  ATAAAATCC   TATATACGGG  GAGAGGTACC  TTATCTGTTC    2232

TCACTATATT  TTATTGAACA  TTACTTTAGA  GAATATGTTT  TGGAATTCAC  TACTAAATAA    2292

ACGATATAAA  TCTTCACGAA  AA                                                2314
```

( 2 ) INFORMATION FOR SEQ ID NO:48:

( i ) SEQUENCE CHARACTERISTICS:
        ( A ) LENGTH: 613 amino acids
        ( B ) TYPE: amino acid
        ( D ) TOPOLOGY: linear ( i i ) MOLECULE TYPE: protein ( x i ) SEQUENCE DESCRIPTION: SEQ ID NO:48:

```
Met  Glu  Ser  Cys  Asp  Cys  Phe  Glu  Thr  His  Val  Asn  Gln  Asp  Asp  Leu
 1              5                        10                       15

Leu  Val  Lys  Tyr  Gln  Tyr  Ile  Ser  Asp  Ala  Leu  Ile  Ala  Leu  Ala  Tyr
              20                       25                       30

Phe  Ser  Ile  Pro  Leu  Glu  Leu  Ile  Tyr  Phe  Val  Gln  Lys  Ser  Ala  Phe
              35                       40                       45

Phe  Pro  Tyr  Lys  Trp  Val  Leu  Met  Gln  Phe  Gly  Ala  Phe  Ile  Ile  Leu
         50                       55                       60

Cys  Gly  Ala  Thr  His  Phe  Ile  Asn  Leu  Trp  Met  Phe  Phe  Met  His  Ser
 65                       70                       75                       80

Lys  Ala  Val  Ala  Ile  Val  Met  Thr  Ile  Ala  Lys  Val  Ser  Cys  Ala  Val
                   85                       90                       95

Val  Ser  Cys  Ala  Thr  Ala  Leu  Met  Leu  Val  His  Ile  Ile  Pro  Asp  Leu
              100                      105                      110

Leu  Ser  Val  Lys  Asn  Arg  Glu  Leu  Phe  Leu  Lys  Lys  Ala  Asp  Glu
              115                      120                      125

Leu  Asp  Arg  Glu  Met  Gly  Leu  Ile  Leu  Thr  Gln  Glu  Glu  Thr  Gly  Arg
         130                      135                      140

His  Val  Arg  Met  Leu  Thr  His  Gly  Ile  Arg  Arg  Thr  Leu  Asp  Arg  His
145                      150                      155                      160

Thr  Ile  Leu  Arg  Thr  Thr  Leu  Val  Glu  Leu  Gly  Lys  Thr  Leu  Cys  Leu
                   165                      170                      175

Glu  Glu  Cys  Ala  Leu  Trp  Met  Pro  Ser  Gln  Ser  Gly  Leu  Tyr  Leu  Gln
              180                      185                      190

Leu  Ser  His  Thr  Leu  Ser  His  Lys  Ile  Gln  Val  Gly  Ser  Ser  Val  Pro
              195                      200                      205

Ile  Asn  Leu  Pro  Ile  Ile  Asn  Glu  Leu  Phe  Asn  Ser  Ala  Gln  Ala  Met
         210                      215                      220

His  Ile  Pro  His  Ser  Cys  Pro  Leu  Ala  Lys  Ile  Gly  Pro  Pro  Val  Gly
225                      230                      235                      240

Arg  Tyr  Ser  Pro  Pro  Glu  Val  Val  Ser  Val  Arg  Val  Pro  Leu  Leu  His
                        245                      250                      255

Leu  Ser  Asn  Phe  Gln  Gly  Ser  Asp  Trp  Ser  Asp  Leu  Ser  Gly  Lys  Gly
              260                      265                      270

Tyr  Ala  Ile  Met  Val  Leu  Ile  Leu  Pro  Thr  Asp  Gly  Ala  Arg  Lys  Trp
              275                      280                      285

Arg  Asp  His  Glu  Leu  Glu  Leu  Val  Glu  Asn  Val  Ala  Asp  Gln  Val  Ala
         290                      295                      300

Val  Ala  Leu  Ser  His  Ala  Ala  Ile  Leu  Glu  Glu  Ser  Met  His  Ala  Arg
```

|     |     |     |     | 305 |     |     |     |     | 310 |     |     |     |     | 315 |     |     |     |     | 320 |
| --- | --- | --- | --- | --- | --- | --- | --- | --- | --- | --- | --- | --- | --- | --- | --- | --- | --- | --- | --- |
| Asp | Gln | Leu | Met | Glu | Gln | Asn | Phe | Ala | Leu | Asp | Lys | Ala | Arg | Gln | Glu |
|     |     |     |     | 325 |     |     |     |     | 330 |     |     |     |     | 335 |     |
| Ala | Glu | Met | Ala | Val | His | Ala | Arg | Asn | Asp | Phe | Leu | Ala | Val | Met | Asn |
|     |     |     | 340 |     |     |     |     | 345 |     |     |     |     | 350 |     |     |
| His | Glu | Met | Arg | Thr | Pro | Met | His | Ala | Ile | Ile | Ser | Leu | Ser | Ser | Leu |
|     |     | 355 |     |     |     |     | 360 |     |     |     |     | 365 |     |     |     |
| Leu | Leu | Glu | Thr | Glu | Leu | Ser | Pro | Glu | Gln | Arg | Val | Met | Ile | Glu | Thr |
|     | 370 |     |     |     |     | 375 |     |     |     |     | 380 |     |     |     |     |
| Ile | Leu | Lys | Ser | Ser | Asn | Leu | Val | Ala | Thr | Leu | Ile | Ser | Asp | Val | Leu |
| 385 |     |     |     |     | 390 |     |     |     |     | 395 |     |     |     |     | 400 |
| Asp | Leu | Ser | Arg | Leu | Glu | Asp | Gly | Ser | Leu | Leu | Leu | Glu | Asn | Glu | Pro |
|     |     |     |     | 405 |     |     |     |     | 410 |     |     |     |     | 415 |     |
| Phe | Ser | Leu | Gln | Ala | Ile | Phe | Glu | Glu | Val | Ile | Ser | Leu | Ile | Lys | Pro |
|     |     |     | 420 |     |     |     |     | 425 |     |     |     |     | 430 |     |     |
| Ile | Ala | Ser | Val | Lys | Lys | Leu | Ser | Thr | Asn | Leu | Ile | Leu | Ser | Ala | Asp |
|     |     | 435 |     |     |     |     | 440 |     |     |     |     | 445 |     |     |     |
| Leu | Pro | Thr | Tyr | Ala | Ile | Gly | Asp | Glu | Lys | Arg | Leu | Met | Gln | Thr | Ile |
|     | 450 |     |     |     |     | 455 |     |     |     |     | 460 |     |     |     |     |
| Leu | Asn | Ile | Met | Gly | Asn | Ala | Val | Lys | Phe | Thr | Lys | Glu | Gly | Tyr | Ile |
| 465 |     |     |     |     | 470 |     |     |     |     | 475 |     |     |     |     | 480 |
| Ser | Ile | Ile | Ala | Ser | Ile | Met | Lys | Pro | Glu | Ser | Leu | Gln | Glu | Leu | Pro |
|     |     |     |     | 485 |     |     |     |     | 490 |     |     |     |     | 495 |     |
| Ser | Pro | Glu | Phe | Phe | Pro | Val | Leu | Ser | Asp | Ser | His | Phe | Tyr | Leu | Cys |
|     |     |     | 500 |     |     |     |     | 505 |     |     |     |     | 510 |     |     |
| Val | Gln | Val | Lys | Asp | Thr | Gly | Cys | Gly | Ile | His | Thr | Gln | Asp | Ile | Pro |
|     |     | 515 |     |     |     |     | 520 |     |     |     |     | 525 |     |     |     |
| Leu | Leu | Phe | Thr | Lys | Phe | Val | Gln | Pro | Arg | Thr | Gly | Thr | Gln | Arg | Asn |
|     | 530 |     |     |     |     | 535 |     |     |     |     | 540 |     |     |     |     |
| His | Ser | Gly | Gly | Gly | Leu | Gly | Leu | Ala | Leu | Cys | Lys | Arg | Phe | Val | Gly |
| 545 |     |     |     |     | 550 |     |     |     |     | 555 |     |     |     |     | 560 |
| Leu | Met | Gly | Gly | Tyr | Met | Trp | Ile | Glu | Ser | Glu | Gly | Leu | Glu | Lys | Gly |
|     |     |     |     | 565 |     |     |     |     | 570 |     |     |     |     | 575 |     |
| Cys | Thr | Ala | Ser | Phe | Ile | Ile | Arg | Leu | Gly | Ile | Cys | Asn | Gly | Pro | Ser |
|     |     |     | 580 |     |     |     |     | 585 |     |     |     |     | 590 |     |     |
| Ser | Ser | Ser | Gly | Ser | Met | Ala | Leu | His | Leu | Ala | Ala | Lys | Ser | Gln | Thr |
|     |     | 595 |     |     |     |     | 600 |     |     |     |     | 605 |     |     |     |
| Arg | Pro | Trp | Asn | Trp |
|     | 610 |     |     |     |

( 2 ) INFORMATION FOR SEQ ID NO:49:

( i ) SEQUENCE CHARACTERISTICS:
        ( A ) LENGTH: 2405 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 288..2196

( x i ) SEQUENCE DESCRIPTION: SEQ ID NO:49:

| TTTTTTTTTT | GTCAAAAGCT | CGATGTAAAA | ATCCGATGGC | CACAAGCAAA | ACGACAGGTT | 60 |
| CCAACTTCAC | GGAGATTGTG | AAAATGGAGT | AGTAGTTCAG | TGAAGTAGTA | GATACTGAGA | 120 |
| TCGCATTCTC | CGGCGTCGTT | TTTCACATCG | AAATAGTCGT | GTAAAAAAAT | GAAAAAATTG | 180 |

```
CTGCGAGACA GGTATGTGTC GCAGCAGGAA ATAGCATCTT AAAGGAAGGA AGGAAGGAAA      240

CTCGAAAGTT ACTAAAAATT TTTGATTCTT TGGGACGAAA CGAGATA ATG GAA TCC        296
                                                    Met Glu Ser
                                                     1

TGT GAT TGC ATT GAG GCT TTA CTG CCA ACT GGT GAC CTG CTG GTT AAA        344
Cys Asp Cys Ile Glu Ala Leu Leu Pro Thr Gly Asp Leu Leu Val Lys
     5              10               15

TAC CAA TAC CTC TCA GAT TTC TTC ATT GCT GTA GCC TAC TTT TCC ATT        392
Tyr Gln Tyr Leu Ser Asp Phe Phe Ile Ala Val Ala Tyr Phe Ser Ile
 20              25              30                       35

CTG TTG GAG CTT ATT TAT TTT GTC CAC AAA TCT GCA TGC TTC CCA TAC        440
Leu Leu Glu Leu Ile Tyr Phe Val His Lys Ser Ala Cys Phe Pro Tyr
             40              45                       50

AGA TGG GTC CTC ATG CAA TTT GGT GCT TTT ATT GTG CTC TGT GGA GCA        488
Arg Trp Val Leu Met Gln Phe Gly Ala Phe Ile Val Leu Cys Gly Ala
             55              60              65

ACA CAC TTT ATT AGC TTG TGG ACC TTC TTT ATG CAC TCT AAG ACG GTC        536
Thr His Phe Ile Ser Leu Trp Thr Phe Phe Met His Ser Lys Thr Val
         70              75              80

GCT GTG GTT ATG ACC ATA TCA AAA ATG TTG ACA GCT GCC GTG TCC TGT        584
Ala Val Val Met Thr Ile Ser Lys Met Leu Thr Ala Ala Val Ser Cys
     85              90              95

ATC ACA GCT TTG ATG CTT GTT CAC ATT ATT CCT GAT TTG CTA AGT GTT        632
Ile Thr Ala Leu Met Leu Val His Ile Ile Pro Asp Leu Leu Ser Val
100              105             110                         115

AAA ACG CGA GAG TTG TTC TTG AAA ACT CGA GCT GAA GAG CTT GAC AAG        680
Lys Thr Arg Glu Leu Phe Leu Lys Thr Arg Ala Glu Glu Leu Asp Lys
                 120             125                         130

GAA ATG GGC CTA ATA ATA AGA CAA GAA GAA ACT GGC AGA CAT GTC AGG        728
Glu Met Gly Leu Ile Ile Arg Gln Glu Glu Thr Gly Arg His Val Arg
             135             140             145

ATG CTG ACT CAT GAG ATA AGA AGC ACA CTC GAC AGA CAC ACA ATC TTG        776
Met Leu Thr His Glu Ile Arg Ser Thr Leu Asp Arg His Thr Ile Leu
             150             155             160

AAG ACT ACT CTT GTG GAG CTA GGT AGG ACC TTA GAC CTG GCA GAA TGT        824
Lys Thr Thr Leu Val Glu Leu Gly Arg Thr Leu Asp Leu Ala Glu Cys
165             170                         175

GCT TTG TGG ATG CCA TGC CAA GGA GGC CTG ACT TTG CAA CTT TCC CAT        872
Ala Leu Trp Met Pro Cys Gln Gly Gly Leu Thr Leu Gln Leu Ser His
180             185             190                         195

AAT TTA AAC AAT CTA ATA CCT CTG GGA TCT ACT GTG CCA ATT AAT CTT        920
Asn Leu Asn Asn Leu Ile Pro Leu Gly Ser Thr Val Pro Ile Asn Leu
                 200             205             210

CCT ATT ATC AAT GAA ATT TTT AGT AGC CCT GAA GCA ATA CAA ATT CCA        968
Pro Ile Ile Asn Glu Ile Phe Ser Ser Pro Glu Ala Ile Gln Ile Pro
             215             220             225

CAT ACA AAT CCT TTG GCA AGG ATG AGG AAT ACT GTT GGT AGA TAT ATT       1016
His Thr Asn Pro Leu Ala Arg Met Arg Asn Thr Val Gly Arg Tyr Ile
         230             235             240

CCA CCA GAA GTA GTT GCT GTT CGT GTA CCG CTT TTA CAC CTC TCA AAT       1064
Pro Pro Glu Val Val Ala Val Arg Val Pro Leu Leu His Leu Ser Asn
245             250             255

TTT ACT AAT GAC TGG GCT GAA CTG TCT ACT AGA AGT TAT GCG GTT ATG       1112
Phe Thr Asn Asp Trp Ala Glu Leu Ser Thr Arg Ser Tyr Ala Val Met
260             265             270                         275

GTT CTG GTT CTC CCG ATG AAT GGC TTA AGA AAG TGG CGT GAA CAT GAG       1160
Val Leu Val Leu Pro Met Asn Gly Leu Arg Lys Trp Arg Glu His Glu
             280             285             290

TTA GAA CTT GTG CAA GTT GTC GCA GAT CAG GTT GCT GTC GCT CTT TCA       1208
Leu Glu Leu Val Gln Val Val Ala Asp Gln Val Ala Val Ala Leu Ser
```

```
                    295                          300                           305
CAT  GCT  GCA  ATT  TTA  GAA  GAT  TCC  ATG  CGA  GCC  CAT  GAT  CAG  CTC  ATG      1256
His  Ala  Ala  Ile  Leu  Glu  Asp  Ser  Met  Arg  Ala  His  Asp  Gln  Leu  Met
          310                      315                     320

GAA  CAG  AAT  ATT  GCT  TTG  GAT  GTA  GCT  CGA  CAA  GAA  GCA  GAG  ATG  GCC      1304
Glu  Gln  Asn  Ile  Ala  Leu  Asp  Val  Ala  Arg  Gln  Glu  Ala  Glu  Met  Ala
          325                      330                     335

ATC  CGT  GCA  CGT  AAC  GAC  TTC  CTT  GCT  GTG  ATG  AAC  CAT  GAA  ATG  AGA      1352
Ile  Arg  Ala  Arg  Asn  Asp  Phe  Leu  Ala  Val  Met  Asn  His  Glu  Met  Arg
340                      345                     350                          355

ACG  CCC  ATG  CAT  GCA  GTT  ATT  GCT  CTG  TGC  TCT  CTG  CTT  TTA  GAA  ACA      1400
Thr  Pro  Met  His  Ala  Val  Ile  Ala  Leu  Cys  Ser  Leu  Leu  Leu  Glu  Thr
                    360                     365                          370

GAC  TTA  ACT  CCA  GAG  CAG  AGA  GTT  ATG  ATT  GAG  ACC  ATA  TTG  AAG  AGC      1448
Asp  Leu  Thr  Pro  Glu  Gln  Arg  Val  Met  Ile  Glu  Thr  Ile  Leu  Lys  Ser
               375                      380                     385

AGC  AAT  CTT  CTT  GCA  ACA  CTG  ATA  AAT  GAT  GTT  CTA  GAT  CTT  TCT  AGA      1496
Ser  Asn  Leu  Leu  Ala  Thr  Leu  Ile  Asn  Asp  Val  Leu  Asp  Leu  Ser  Arg
          390                      395                     400

CTT  GAA  GAT  GGT  ATT  CTT  GAA  CTA  GAA  AAC  GGA  ACA  TTC  AAT  CTT  CAT      1544
Leu  Glu  Asp  Gly  Ile  Leu  Glu  Leu  Glu  Asn  Gly  Thr  Phe  Asn  Leu  His
     405                      410                     415

GGC  ATC  TTA  AGA  GAG  GCC  GTT  AAT  TTG  ATA  AAG  CCA  ATT  GCA  TCT  TTG      1592
Gly  Ile  Leu  Arg  Glu  Ala  Val  Asn  Leu  Ile  Lys  Pro  Ile  Ala  Ser  Leu
420                      425                     430                          435

AAG  AAA  TTA  TCT  ATA  ACT  CTT  GCT  TTG  GCT  CTG  GAT  TTA  CCT  ATT  CTT      1640
Lys  Lys  Leu  Ser  Ile  Thr  Leu  Ala  Leu  Ala  Leu  Asp  Leu  Pro  Ile  Leu
                    440                     445                          450

GCT  GTG  GGT  GAT  GCA  AAA  CGT  CTT  ATC  CAA  ACT  CTC  TTA  AAC  GTG  GTG      1688
Ala  Val  Gly  Asp  Ala  Lys  Arg  Leu  Ile  Gln  Thr  Leu  Leu  Asn  Val  Val
               455                      460                     465

GGA  AAT  GCT  GTG  AAG  TTC  ACT  AAA  GAA  GGA  CAT  ATT  TCA  ATT  GAG  GCT      1736
Gly  Asn  Ala  Val  Lys  Phe  Thr  Lys  Glu  Gly  His  Ile  Ser  Ile  Glu  Ala
          470                      475                     480

TCA  GTT  GCC  AAA  CCA  GAG  TAT  GCG  AGA  GAT  TGT  CAT  CCT  CCT  GAA  ATG      1784
Ser  Val  Ala  Lys  Pro  Glu  Tyr  Ala  Arg  Asp  Cys  His  Pro  Pro  Glu  Met
     485                      490                     495

TTC  CCT  ATG  CCA  AGT  GAT  GGC  CAG  TTT  TAT  TTG  CGT  GTC  CAG  GTT  AGA      1832
Phe  Pro  Met  Pro  Ser  Asp  Gly  Gln  Phe  Tyr  Leu  Arg  Val  Gln  Val  Arg
500                      505                     510                          515

GAT  ACT  GGG  TGT  GGA  ATT  AGC  CCA  CAA  GAT  ATA  CCA  CTA  GTA  TTC  ACC      1880
Asp  Thr  Gly  Cys  Gly  Ile  Ser  Pro  Gln  Asp  Ile  Pro  Leu  Val  Phe  Thr
                    520                     525                          530

AAA  TTT  GCA  GAG  TCA  CGG  CCT  ACG  TCA  AAT  CGA  AGT  ACT  GGA  GGG  GAA      1928
Lys  Phe  Ala  Glu  Ser  Arg  Pro  Thr  Ser  Asn  Arg  Ser  Thr  Gly  Gly  Glu
               535                      540                     545

GGT  CTA  GGG  CTT  GCC  ATT  TGG  AGA  CGA  TTT  ATT  CAA  CTT  ATG  AAA  GGT      1976
Gly  Leu  Gly  Leu  Ala  Ile  Trp  Arg  Arg  Phe  Ile  Gln  Leu  Met  Lys  Gly
          550                      555                     560

AAC  ATT  TGG  ATT  GAG  AGT  GAG  GGC  CCT  GGA  AAG  GGA  ACC  ACT  GTC  ACG      2024
Asn  Ile  Trp  Ile  Glu  Ser  Glu  Gly  Pro  Gly  Lys  Gly  Thr  Thr  Val  Thr
     565                      570                     575

TTT  GTA  GTG  AAA  CTC  GGA  ATC  TGT  CAC  CAT  CCA  AAT  GCA  TTA  CCT  CTG      2072
Phe  Val  Val  Lys  Leu  Gly  Ile  Cys  His  His  Pro  Asn  Ala  Leu  Pro  Leu
580                      585                     590                          595

CTA  CCT  ATG  CCT  CCC  AGA  GGC  AGA  TTG  AAC  AAA  GGT  AGC  GAT  GAT  CTC      2120
Leu  Pro  Met  Pro  Pro  Arg  Gly  Arg  Leu  Asn  Lys  Gly  Ser  Asp  Asp  Leu
                    600                     605                          610

TTC  AGG  TAT  AGA  CAG  TTC  CGT  GGA  GAT  GAT  GGT  GGG  ATG  TCT  GTG  AAT      2168
Phe  Arg  Tyr  Arg  Gln  Phe  Arg  Gly  Asp  Asp  Gly  Gly  Met  Ser  Val  Asn
```

|  | 615 | 620 | 625 |  |
|---|---|---|---|---|
| GCT CAA CGC TAT CAA AGA AGT ATG TAA A TGACAAAGG ACATTGGTGT | | | | 2216 |
| Ala Gln Arg Tyr Gln Arg Ser Met * | | | | |
|  | 630 | | 635 | |

```
GACAAAGAAC ATTAAATCAT GACTAGTGAA TTTGAGATTT CTTCACTGTT CTGTACACTC        2276

CAAATGGCAC AGTTTGTCTT GTAACTAACC TAATTCAATG CTCGTAAAGT GAGTACTGGA        2336

GTATCTTGAA AATGTAACTA TCGAATTTAT ACATCGAGCT TTTGACAAAA AAAAAAAAA        2396

AAAAAAAA                                                                 2405
```

( 2 ) INFORMATION FOR SEQ ID NO:50:

( i ) SEQUENCE CHARACTERISTICS:
    ( A ) LENGTH: 635 amino acids
    ( B ) TYPE: amino acid
    ( D ) TOPOLOGY: linear ( i i ) MOLECULE TYPE: protein ( x i ) SEQUENCE DESCRIPTION: SEQ ID NO:50:

```
Met Glu Ser Cys Asp Cys Ile Glu Ala Leu Leu Pro Thr Gly Asp Leu
 1               5                  10                  15

Leu Val Lys Tyr Gln Tyr Leu Ser Asp Phe Phe Ile Ala Val Ala Tyr
             20                  25                  30

Phe Ser Ile Leu Leu Glu Leu Ile Tyr Phe Val His Lys Ser Ala Cys
         35                  40                  45

Phe Pro Tyr Arg Trp Val Leu Met Gln Phe Gly Ala Phe Ile Val Leu
     50                  55                  60

Cys Gly Ala Thr His Phe Ile Ser Leu Trp Thr Phe Phe Met His Ser
 65                  70                  75                  80

Lys Thr Val Ala Val Val Met Thr Ile Ser Lys Met Leu Thr Ala Ala
             85                  90                  95

Val Ser Cys Ile Thr Ala Leu Met Leu Val His Ile Ile Pro Asp Leu
            100                 105                 110

Leu Ser Val Lys Thr Arg Glu Leu Phe Leu Lys Thr Arg Ala Glu Glu
            115                 120                 125

Leu Asp Lys Glu Met Gly Leu Ile Ile Arg Gln Glu Glu Thr Gly Arg
        130                 135                 140

His Val Arg Met Leu Thr His Glu Ile Arg Ser Thr Leu Asp Arg His
145                 150                 155                 160

Thr Ile Leu Lys Thr Thr Leu Val Glu Leu Gly Arg Thr Leu Asp Leu
                165                 170                 175

Ala Glu Cys Ala Leu Trp Met Pro Cys Gln Gly Gly Leu Thr Leu Gln
            180                 185                 190

Leu Ser His Asn Leu Asn Asn Leu Ile Pro Leu Gly Ser Thr Val Pro
        195                 200                 205

Ile Asn Leu Pro Ile Ile Asn Glu Ile Phe Ser Ser Pro Glu Ala Ile
    210                 215                 220

Gln Ile Pro His Thr Asn Pro Leu Ala Arg Met Arg Asn Thr Val Gly
225                 230                 235                 240

Arg Tyr Ile Pro Pro Glu Val Val Ala Val Arg Val Pro Leu Leu His
                245                 250                 255

Leu Ser Asn Phe Thr Asn Asp Trp Ala Glu Leu Ser Thr Arg Ser Tyr
            260                 265                 270

Ala Val Met Val Leu Val Leu Pro Met Asn Gly Leu Arg Lys Trp Arg
            275                 280                 285
```

-continued

| | | | | | | | | | | | | | | |
|---|---|---|---|---|---|---|---|---|---|---|---|---|---|---|
| Glu | His 290 | Glu | Leu | Glu | Leu | Val 295 | Gln | Val | Ala | Asp 300 | Gln | Val | Ala | Val |
| Ala 305 | Leu | Ser | His | Ala | Ala 310 | Ile | Leu | Glu | Asp | Ser 315 | Met | Arg | Ala | His | Asp 320 |
| Gln | Leu | Met | Glu | Gln 325 | Asn | Ile | Ala | Leu | Asp 330 | Val | Ala | Arg | Gln | Glu 335 | Ala |
| Glu | Met | Ala | Ile 340 | Arg | Ala | Arg | Asn | Asp 345 | Phe | Leu | Ala | Val | Met 350 | Asn | His |
| Glu | Met | Arg 355 | Thr | Pro | Met | His | Ala 360 | Val | Ile | Ala | Leu | Cys 365 | Ser | Leu | Leu |
| Leu | Glu 370 | Thr | Asp | Leu | Thr | Pro 375 | Glu | Gln | Arg | Val | Met 380 | Ile | Glu | Thr | Ile |
| Leu 385 | Lys | Ser | Ser | Asn | Leu 390 | Leu | Ala | Thr | Leu | Ile 395 | Asn | Asp | Val | Leu | Asp 400 |
| Leu | Ser | Arg | Leu | Glu 405 | Asp | Gly | Ile | Leu | Glu 410 | Leu | Glu | Asn | Gly | Thr 415 | Phe |
| Asn | Leu | His | Gly 420 | Ile | Leu | Arg | Glu | Ala 425 | Val | Asn | Leu | Ile | Lys 430 | Pro | Ile |
| Ala | Ser | Leu 435 | Lys | Lys | Leu | Ser | Ile 440 | Thr | Leu | Ala | Leu | Ala 445 | Leu | Asp | Leu |
| Pro | Ile 450 | Leu | Ala | Val | Gly | Asp 455 | Ala | Lys | Arg | Leu | Ile 460 | Gln | Thr | Leu | Leu |
| Asn 465 | Val | Val | Gly | Asn | Ala 470 | Val | Lys | Phe | Thr | Lys 475 | Glu | Gly | His | Ile | Ser 480 |
| Ile | Glu | Ala | Ser | Val 485 | Ala | Lys | Pro | Glu | Tyr 490 | Ala | Arg | Asp | Cys | His 495 | Pro |
| Pro | Glu | Met | Phe 500 | Pro | Met | Pro | Ser | Asp 505 | Gly | Gln | Phe | Tyr | Leu 510 | Arg | Val |
| Gln | Val | Arg 515 | Asp | Thr | Gly | Cys | Gly 520 | Ile | Ser | Pro | Gln | Asp 525 | Ile | Pro | Leu |
| Val | Phe 530 | Thr | Lys | Phe | Ala | Glu 535 | Ser | Arg | Pro | Thr | Ser 540 | Asn | Arg | Ser | Thr |
| Gly 545 | Gly | Glu | Gly | Leu | Gly 550 | Leu | Ala | Ile | Trp | Arg 555 | Arg | Phe | Ile | Gln | Leu 560 |
| Met | Lys | Gly | Asn | Ile 565 | Trp | Ile | Glu | Ser | Glu 570 | Gly | Pro | Gly | Lys | Gly 575 | Thr |
| Thr | Val | Thr | Phe 580 | Val | Val | Lys | Leu | Gly 585 | Ile | Cys | His | His | Pro 590 | Asn | Ala |
| Leu | Pro | Leu 595 | Leu | Pro | Met | Pro | Pro 600 | Arg | Gly | Arg | Leu | Asn 605 | Lys | Gly | Ser |
| Asp | Asp 610 | Leu | Phe | Arg | Tyr | Arg 615 | Gln | Phe | Arg | Gly | Asp 620 | Asp | Gly | Gly | Met |
| Ser 625 | Val | Asn | Ala | Gln | Arg 630 | Tyr | Gln | Arg | Ser | Met 635 | | | | | |